United States Patent
Hammer et al.

(10) Patent No.: US 12,053,380 B2
(45) Date of Patent: *Aug. 6, 2024

(54) ANCHORING OF A PROSTHETIC VALVE

(71) Applicant: CARDIOVALVE LTD., Or Yehuda (IL)

(72) Inventors: Tal Hammer, Ramat Gan (IL); Meni Iamberger, Kfar Saba (IL); Yaron Herman, Givat Ada (IL); Yuval Zipory, Modi'in (IL); Eran Hoffer, Yehud (IL); Michael Albitov, Kiryat Ono (IL); Natalia Kruglova, Ashdod (IL); Tal Reich, Moshav Moledet (IL); Ilia Hariton, Zichron Yaackov (IL); Aviram Baum, Tel Aviv (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/841,912

(22) Filed: Jun. 16, 2022

(65) Prior Publication Data
US 2022/0304804 A1   Sep. 29, 2022

Related U.S. Application Data

(63) Continuation of application No. 16/656,790, filed on Oct. 18, 2019, now Pat. No. 11,872,130, which is a (Continued)

(51) Int. Cl.
*A61F 2/24*   (2006.01)
*A61F 2/82*   (2013.01)

(52) U.S. Cl.
CPC .......... *A61F 2/2436* (2013.01); *A61F 2/2418* (2013.01); *A61F 2/2439* (2013.01); (Continued)

(58) Field of Classification Search
None
See application file for complete search history.

(56) References Cited

U.S. PATENT DOCUMENTS

| 3,604,488 A | 9/1971 | Wishart et al. |
| 3,656,185 A | 4/1972 | Carpentier |

(Continued)

FOREIGN PATENT DOCUMENTS

| CA | 2822801 | 8/2006 |
| CA | 2671966 | 6/2008 |

(Continued)

OTHER PUBLICATIONS

An Office Action dated Sep. 29, 2022, which issued during the prosecution of U.S. Appl. No. 17/010,886.
(Continued)

*Primary Examiner* — Ann Schillinger
(74) *Attorney, Agent, or Firm* — Sughrue Mion, PLLC

(57) ABSTRACT

A prosthetic valve includes a tubular valve body, snares, and an upstream support. A native valve of a heart of a subject is disposed between an atrium and a ventricle of the heart, and has an annulus and leaflets. The prosthetic valve is advanced to the heart while in a compressed state. The prosthetic valve is positioned within the heart such that the snares are disposed upstream of the annulus and leaflets. The snares are expanded radially outwardly upstream of the leaflets. Subsequently, the prosthetic valve is moved in a downstream direction such that the snares become disposed downstream of the leaflets. While the snares remain downstream of the leaflets, the upstream support is expanded within the atrium, and the upstream support is placed against an upstream surface of the annulus. Other embodiments are also described.

13 Claims, 38 Drawing Sheets

Related U.S. Application Data continuation of application No. 15/703,385, filed on Sep. 13, 2017, now Pat. No. 10,492,908, which is a continuation of application No. 15/329,920, filed as application No. PCT/IL2015/050792 on Jul. 30, 2015, now Pat. No. 10,524,910.

(60) Provisional application No. 62/030,715, filed on Jul. 30, 2014, provisional application No. 62/139,854, filed on Mar. 30, 2015.

(52) U.S. Cl.
CPC . *A61F 2002/828* (2013.01); *A61F 2220/0025* (2013.01); *A61F 2230/001* (2013.01); *A61F 2230/0067* (2013.01); *A61F 2250/0039* (2013.01)

(56) References Cited

U.S. PATENT DOCUMENTS

| | | |
|---|---|---|
| 3,840,018 A | 10/1974 | Heifetz |
| 3,874,388 A | 4/1975 | King et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,222,126 A | 9/1980 | Boretos et al. |
| 4,261,342 A | 4/1981 | Aranguren |
| 4,275,469 A | 6/1981 | Gabbay |
| 4,340,091 A | 7/1982 | Skelton et al. |
| 4,423,525 A | 1/1984 | Vallana et al. |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,853,986 A | 8/1989 | Allen |
| 4,892,541 A | 1/1990 | Alonso |
| 4,917,698 A | 4/1990 | Carpenter et al. |
| 4,961,738 A | 10/1990 | Mackin |
| 4,972,494 A | 11/1990 | White et al. |
| 4,994,077 A | 2/1991 | Dobben |
| 5,061,277 A | 10/1991 | Carpentier et al. |
| 5,078,739 A | 1/1992 | Martin |
| 5,089,006 A | 2/1992 | Stiles |
| 5,104,407 A | 4/1992 | Lam et al. |
| 5,108,420 A | 4/1992 | Marks |
| 5,201,757 A | 4/1993 | Heyn et al. |
| 5,201,880 A | 4/1993 | Wright |
| 5,258,008 A | 11/1993 | Wilk |
| 5,300,034 A | 4/1994 | Behnke |
| 5,306,296 A | 4/1994 | Wright et al. |
| 5,314,473 A | 5/1994 | Godin |
| 5,325,845 A | 7/1994 | Adair |
| 5,332,402 A | 7/1994 | Teitelbaum |
| 5,397,351 A | 3/1995 | Pavcnik et al. |
| 5,405,378 A | 4/1995 | Strecker |
| 5,443,500 A | 8/1995 | Sigwart |
| 5,450,860 A | 9/1995 | O'Connor |
| 5,473,812 A | 12/1995 | Morris et al. |
| 5,477,856 A | 12/1995 | Lundquist |
| 5,593,424 A | 1/1997 | Northrup III |
| 5,601,572 A | 2/1997 | Middleman et al. |
| 5,607,444 A | 3/1997 | Lam |
| 5,607,470 A | 3/1997 | Milo |
| 5,626,609 A | 5/1997 | Zvenyatsky et al. |
| 5,647,857 A | 7/1997 | Anderson et al. |
| 5,669,919 A | 9/1997 | Sanders et al. |
| 5,674,279 A | 10/1997 | Wright et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,713,948 A | 2/1998 | Uflacker |
| 5,716,370 A | 2/1998 | Williamson et al. |
| 5,716,397 A | 2/1998 | Myers |
| 5,716,417 A | 2/1998 | Girard et al. |
| 5,728,116 A | 3/1998 | Rosenman |
| 5,730,150 A | 3/1998 | Peppel et al. |
| 5,741,297 A | 4/1998 | Simon |
| 5,749,371 A | 5/1998 | Zadini et al. |
| 5,749,920 A | 5/1998 | Quiachon et al. |
| 5,765,682 A | 6/1998 | Bley et al. |
| 5,766,151 A | 6/1998 | Valley et al. |
| 5,776,140 A | 7/1998 | Cottone |
| 5,810,882 A | 9/1998 | Bolduc |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,868,777 A | 2/1999 | Lam |
| 5,873,906 A | 2/1999 | Lau et al. |
| 5,876,373 A | 3/1999 | Giba et al. |
| 5,906,619 A | 5/1999 | Olson et al. |
| 5,935,098 A | 8/1999 | Blaisdell et al. |
| 5,954,766 A | 9/1999 | Zadno-Azizi et al. |
| 5,957,949 A | 9/1999 | Leonhardt et al. |
| 5,957,953 A | 9/1999 | DiPoto et al. |
| 5,961,440 A | 10/1999 | Schweich et al. |
| 5,961,539 A | 10/1999 | Northrup, III et al. |
| 5,961,549 A | 10/1999 | Nguyen et al. |
| 5,980,565 A | 11/1999 | Jayaraman |
| 5,984,959 A | 11/1999 | Robertson |
| 6,010,530 A | 1/2000 | Goicoechea |
| 6,019,787 A | 2/2000 | Richard et al. |
| 6,042,554 A | 3/2000 | Rosenman |
| 6,042,607 A | 3/2000 | Williamson, IV |
| 6,045,497 A | 4/2000 | Schweich et al. |
| 6,050,936 A | 4/2000 | Schweich et al. |
| 6,059,715 A | 5/2000 | Schweich et al. |
| 6,059,827 A | 5/2000 | Fenton |
| 6,074,401 A | 6/2000 | Gardiner et al. |
| 6,074,417 A | 6/2000 | Peredo |
| 6,102,945 A | 8/2000 | Campbell |
| 6,106,550 A | 8/2000 | Magovern |
| 6,110,200 A | 8/2000 | Hinnenkamp |
| 6,113,612 A | 9/2000 | Swanson et al. |
| 6,120,534 A | 9/2000 | Ruiz |
| 6,126,686 A | 10/2000 | Badylak et al. |
| 6,143,024 A | 11/2000 | Campbell et al. |
| 6,152,937 A * | 11/2000 | Peterson .................. A61F 2/88 606/153 |
| 6,159,240 A | 12/2000 | Sparer |
| 6,165,119 A | 12/2000 | Schweich et al. |
| 6,165,183 A | 12/2000 | Kuehn et al. |
| 6,165,210 A | 12/2000 | Lau et al. |
| 6,174,332 B1 | 1/2001 | Loch |
| 6,183,411 B1 | 2/2001 | Mortier et al. |
| 6,187,020 B1 | 2/2001 | Zegdi et al. |
| 6,187,040 B1 | 2/2001 | Wright |
| 6,193,686 B1 | 2/2001 | Estrada et al. |
| 6,193,745 B1 | 2/2001 | Fogarty et al. |
| 6,315,784 B1 | 2/2001 | Djurovic |
| 6,217,610 B1 | 4/2001 | Carpentier et al. |
| 6,231,602 B1 | 5/2001 | Carpentier et al. |
| 6,251,092 B1 | 6/2001 | Qin et al. |
| 6,254,609 B1 | 7/2001 | Vrba et al. |
| 6,264,700 B1 | 7/2001 | Kilcoyne et al. |
| 6,271,278 B1 | 8/2001 | Park et al. |
| 6,287,339 B1 | 9/2001 | Vasquez et al. |
| 6,296,656 B1 | 10/2001 | Bolduc et al. |
| 6,312,465 B1 | 11/2001 | Griffin et al. |
| 6,319,281 B1 | 11/2001 | Patel |
| 6,332,893 B1 | 12/2001 | Mortier et al. |
| 6,334,873 B1 | 1/2002 | Lane et al. |
| 6,346,074 B1 | 2/2002 | Roth |
| 6,350,278 B1 | 2/2002 | Lenker et al. |
| 6,352,561 B1 | 3/2002 | Leopold et al. |
| 6,391,036 B1 | 5/2002 | Berg et al. |
| 6,398,758 B1 | 6/2002 | Jacobsen et al. |
| 6,402,780 B2 | 6/2002 | Williamson, IV |
| 6,406,420 B1 | 6/2002 | McCarthy et al. |

(56) References Cited

U.S. PATENT DOCUMENTS

| | | | |
|---|---|---|---|
| 6,406,493 B1 | 6/2002 | Tu et al. |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | Dimatteo et al. |
| 6,451,054 B1 | 9/2002 | Stevens |
| 6,454,799 B1 | 9/2002 | Schreck |
| 6,458,153 B1 | 10/2002 | Bailey et al. |
| 6,461,366 B1 | 10/2002 | Seguin |
| 6,470,892 B1 | 10/2002 | Forsell |
| 6,478,807 B1 | 11/2002 | Foreman et al. |
| 6,482,228 B1 | 11/2002 | Norred |
| 6,491,711 B1 | 12/2002 | Durcan |
| 6,503,274 B1 | 1/2003 | Howanec et al. |
| 6,511,491 B2 | 1/2003 | Grudem et al. |
| 6,524,338 B1 | 2/2003 | Gundry |
| 6,530,952 B2 | 3/2003 | Vesely |
| 6,533,772 B1 | 3/2003 | Sherts et al. |
| 6,537,314 B2 | 3/2003 | Langberg et al. |
| 6,540,782 B1 | 4/2003 | Snyders |
| 6,547,801 B1 | 4/2003 | Dargent et al. |
| 6,551,350 B1 | 4/2003 | Thornton et al. |
| 6,554,845 B1 | 4/2003 | Fleenor et al. |
| 6,558,396 B1 | 5/2003 | Inoue |
| 6,558,418 B2 | 5/2003 | Carpentier et al. |
| 6,564,805 B2 | 5/2003 | Garrison et al. |
| 6,565,603 B2 | 5/2003 | Cox |
| 6,569,196 B1 | 5/2003 | Vesely |
| 6,569,198 B1 | 5/2003 | Wilson et al. |
| 6,579,297 B2 | 6/2003 | Bicek et al. |
| 6,582,464 B2 | 6/2003 | Gabbay |
| 6,589,160 B2 | 7/2003 | Schweich et al. |
| 6,602,263 B1 | 8/2003 | Swanson et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,616,675 B1 | 9/2003 | Evard et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. et al. |
| 6,629,921 B1 | 10/2003 | Schweich et al. |
| 6,651,671 B1 | 11/2003 | Donlon et al. |
| 6,652,556 B1 | 11/2003 | VanTassel et al. |
| 6,669,724 B2 * | 12/2003 | Park ................ A61F 2/2418 623/1.24 |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,699,256 B1 | 3/2004 | Logan et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,456 B2 | 3/2004 | Langberg et al. |
| 6,711,444 B2 | 3/2004 | Koblish |
| 6,712,836 B1 * | 3/2004 | Berg ............... A61B 17/0057 606/213 |
| 6,716,244 B2 | 4/2004 | Klaco |
| 6,718,985 B2 | 4/2004 | Hlavka et al. |
| 6,719,781 B1 | 4/2004 | Kim |
| 6,719,786 B2 | 4/2004 | Ryan et al. |
| 6,719,788 B2 | 4/2004 | Cox |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,749,630 B2 | 6/2004 | McCarthy et al. |
| 6,752,813 B2 | 6/2004 | Goldfarb et al. |
| 6,755,857 B2 | 6/2004 | Peterson et al. |
| 6,764,310 B1 | 7/2004 | Ichihashi et al. |
| 6,764,510 B2 | 7/2004 | Vidlund et al. |
| 6,764,514 B1 | 7/2004 | Li et al. |
| 6,764,518 B2 | 7/2004 | Godin |
| 6,767,362 B2 | 7/2004 | Schreck |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,821,297 B2 | 11/2004 | Snyders |
| 6,830,585 B1 | 12/2004 | Artof et al. |
| 6,830,638 B2 | 12/2004 | Boylan et al. |
| 6,849,084 B2 | 2/2005 | Rabkin et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,884,257 B1 | 4/2005 | Cox |
| 6,893,459 B1 | 5/2005 | Macoviak |
| 6,893,460 B2 | 5/2005 | Spenser et al. |
| 6,908,482 B2 | 6/2005 | McCarthy et al. |
| 6,918,917 B1 | 7/2005 | Nguyen et al. |
| 6,926,715 B1 | 8/2005 | Hauck et al. |
| 6,926,730 B1 | 8/2005 | Nguyen et al. |
| 6,939,370 B2 | 9/2005 | Hartley et al. |
| 6,951,571 B1 | 10/2005 | Srivastava |
| 6,960,217 B2 | 11/2005 | Bolduc |
| 6,964,684 B2 | 11/2005 | Ortiz et al. |
| 6,964,686 B2 | 11/2005 | Gordon |
| 6,974,476 B2 | 12/2005 | McGuckin et al. |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,011,669 B2 | 3/2006 | Kimblad |
| 7,011,681 B2 | 3/2006 | Vesely |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,041,132 B2 | 5/2006 | Quijano et al. |
| 7,074,236 B2 | 7/2006 | Rabkin et al. |
| 7,077,850 B2 | 7/2006 | Kortenbach |
| 7,077,861 B2 | 7/2006 | Spence |
| 7,077,862 B2 | 7/2006 | Vidlund et al. |
| 7,087,064 B1 | 8/2006 | Hyde |
| 7,101,336 B2 | 9/2006 | Miller |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,137,184 B2 | 11/2006 | Schreck |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,656 B2 | 2/2007 | Khairkhahan |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,198,646 B2 | 4/2007 | Figulla et al. |
| 7,201,772 B2 * | 4/2007 | Schwammenthal .. A61F 2/2418 623/2.18 |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,252,682 B2 * | 8/2007 | Seguin ............... A61F 2/2403 623/2.18 |
| 7,261,686 B2 | 8/2007 | Couvillon, Jr. |

(56) References Cited

U.S. PATENT DOCUMENTS

| | | |
|---|---|---|
| 7,288,097 B2 | 10/2007 | Seguin |
| 7,288,111 B1 | 10/2007 | Holloway et al. |
| 7,294,148 B2 | 11/2007 | McCarthy |
| 7,297,150 B2 | 11/2007 | Cartledge et al. |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,316,716 B2 | 1/2008 | Egan |
| 7,329,279 B2 | 2/2008 | Haug et al. |
| 7,329,280 B2 | 2/2008 | Bolling et al. |
| 7,335,213 B1 | 2/2008 | Hyde et al. |
| 7,351,256 B2 | 4/2008 | Hojeibane et al. |
| 7,361,190 B2 | 4/2008 | Shoulian et al. |
| 7,364,588 B2 | 4/2008 | Mathis et al. |
| 7,374,571 B2 | 5/2008 | Pease et al. |
| 7,374,573 B2 | 5/2008 | Gabbay |
| 7,377,938 B2 | 5/2008 | Sarac et al. |
| 7,377,941 B2 | 5/2008 | Rhee et al. |
| 7,381,218 B2 | 6/2008 | Schreck |
| 7,381,219 B2 | 6/2008 | Salahieh et al. |
| 7,390,329 B2 | 6/2008 | Westra et al. |
| 7,404,824 B1 | 7/2008 | Webler et al. |
| 7,422,603 B2 | 9/2008 | Lane |
| 7,429,269 B2 | 9/2008 | Schwammenthal |
| 7,431,692 B2 | 10/2008 | Zollinger et al. |
| 7,442,204 B2 | 10/2008 | Schwammenthal |
| 7,442,207 B2 | 10/2008 | Rafiee |
| 7,445,630 B2 | 11/2008 | Lashinski et al. |
| 7,452,376 B2 | 11/2008 | Lim et al. |
| 7,455,677 B2 | 11/2008 | Vargas et al. |
| 7,455,688 B2 | 11/2008 | Furst et al. |
| 7,455,690 B2 | 11/2008 | Cartledge et al. |
| 7,462,162 B2 | 12/2008 | Phan et al. |
| 7,481,838 B2 | 1/2009 | Carpentier et al. |
| 7,485,142 B2 | 2/2009 | Milo |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,513,909 B2 | 4/2009 | Lane et al. |
| 7,524,331 B2 | 4/2009 | Birdsall |
| 7,527,646 B2 | 5/2009 | Rahdert et al. |
| 7,527,647 B2 | 5/2009 | Spence |
| 7,530,995 B2 | 5/2009 | Quijano et al. |
| 7,549,983 B2 | 6/2009 | Roue et al. |
| 7,556,632 B2 | 7/2009 | Zadno |
| 7,556,646 B2 | 7/2009 | Yang et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,582,111 B2 | 9/2009 | Krolik et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,597,711 B2 | 10/2009 | Drews et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,611,534 B2 | 11/2009 | Kapadia et al. |
| 7,618,449 B2 | 11/2009 | Tremulis et al. |
| 7,621,948 B2 | 11/2009 | Hermann et al. |
| 7,625,403 B2 | 12/2009 | Krivoruchko |
| 7,632,302 B2 | 12/2009 | Vreeman et al. |
| 7,632,303 B1 | 12/2009 | Stalker et al. |
| 7,635,329 B2 | 12/2009 | Goldfarb et al. |
| 7,635,386 B1 | 12/2009 | Gammie |
| 7,648,528 B2 | 1/2010 | Styrc |
| 7,655,015 B2 | 2/2010 | Goldfarb et al. |
| 7,666,204 B2 | 2/2010 | Thornton et al. |
| 7,682,319 B2 | 3/2010 | Martin |
| 7,682,369 B2 | 3/2010 | Seguin |
| 7,682,380 B2 | 3/2010 | Thornton et al. |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,708,775 B2 | 5/2010 | Rowe et al. |
| 7,717,952 B2 | 5/2010 | Case et al. |
| 7,717,955 B2 | 5/2010 | Lane et al. |
| 7,722,666 B2 | 5/2010 | Lafontaine |
| 7,731,741 B2 | 6/2010 | Eidenschink |
| 7,731,742 B2 | 6/2010 | Schlick et al. |
| 7,736,388 B2 | 6/2010 | Goldfarb et al. |
| 7,748,389 B2 | 7/2010 | Salahieh et al. |
| 7,753,922 B2 | 7/2010 | Starksen |
| 7,753,924 B2 | 7/2010 | Starksen et al. |
| 7,753,949 B2 | 7/2010 | Lamphere et al. |
| 7,758,595 B2 | 7/2010 | Allen et al. |
| 7,758,632 B2 | 7/2010 | Hojeibane et al. |
| 7,758,640 B2 | 7/2010 | Vesely |
| 7,771,467 B2 | 8/2010 | Svensson |
| 7,771,469 B2 | 8/2010 | Liddicoat |
| 7,776,080 B2 | 8/2010 | Bei et al. |
| 7,776,083 B2 | 8/2010 | Vesely |
| 7,780,726 B2 | 8/2010 | Seguin |
| 7,785,341 B2 | 8/2010 | Forster et al. |
| 7,799,069 B2 | 9/2010 | Bailey et al. |
| 7,803,181 B2 | 9/2010 | Furst et al. |
| 7,811,296 B2 | 10/2010 | Goldfarb et al. |
| 7,811,316 B2 | 10/2010 | Kalmann et al. |
| 7,824,442 B2 | 11/2010 | Salahieh et al. |
| 7,837,645 B2 | 11/2010 | Bessler et al. |
| 7,837,727 B2 * | 11/2010 | Goetz .................. A61F 2/2439 623/2.18 |
| 7,842,081 B2 | 11/2010 | Yadin |
| 7,850,725 B2 | 12/2010 | Vardi et al. |
| 7,871,368 B2 | 1/2011 | Zollinger et al. |
| 7,871,432 B2 | 1/2011 | Bergin |
| 7,871,433 B2 | 1/2011 | Lattouf |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,072 B2 | 5/2011 | Yang et al. |
| 7,947,075 B2 | 5/2011 | Goetz et al. |
| 7,951,195 B2 | 5/2011 | Antonsson et al. |
| 7,955,375 B2 | 6/2011 | Agnew |
| 7,955,377 B2 | 6/2011 | Melsheimer |
| 7,955,384 B2 | 6/2011 | Rafiee et al. |
| 7,959,666 B2 | 6/2011 | Salahieh et al. |
| 7,959,672 B2 | 6/2011 | Salahieh et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,988,725 B2 | 8/2011 | Gross et al. |
| 7,992,567 B2 | 8/2011 | Hirotsuka et al. |
| 7,993,368 B2 | 8/2011 | Gambale et al. |
| 7,993,392 B2 | 8/2011 | Righini et al. |
| 7,993,393 B2 | 8/2011 | Carpentier et al. |
| 7,993,397 B2 | 8/2011 | Lashinski |
| 8,002,825 B2 | 8/2011 | Letac et al. |
| 8,002,826 B2 | 8/2011 | Seguin |
| 8,012,201 B2 | 9/2011 | Lashinski et al. |
| 8,016,877 B2 | 9/2011 | Seguin et al. |
| 8,016,882 B2 | 9/2011 | Macoviak |
| 8,021,420 B2 | 9/2011 | Dolan |
| 8,021,421 B2 | 9/2011 | Fogarty et al. |
| 8,025,695 B2 | 9/2011 | Fogarty et al. |
| 8,029,518 B2 | 10/2011 | Goldfarb et al. |
| 8,029,557 B2 | 10/2011 | Sobrino-Serrano et al. |
| 8,029,564 B2 | 10/2011 | Johnson et al. |
| 8,034,103 B2 | 10/2011 | Burriesci |
| 8,034,104 B2 | 10/2011 | Carpentier et al. |
| 8,038,720 B2 | 10/2011 | Wallace et al. |
| 8,043,360 B2 | 10/2011 | McNamara et al. |

(56) References Cited

U.S. PATENT DOCUMENTS

| | | |
|---|---|---|
| 8,048,138 B2 | 11/2011 | Sulivan et al. |
| 8,048,140 B2 | 11/2011 | Purdy |
| 8,048,153 B2 | 11/2011 | Salahieh et al. |
| 8,052,592 B2 | 11/2011 | Goldfarb et al. |
| 8,052,741 B2 | 11/2011 | Bruszewski et al. |
| 8,052,749 B2 | 11/2011 | Salahieh et al. |
| 8,057,493 B2 | 11/2011 | Goldfarb et al. |
| 8,057,532 B2 | 11/2011 | Hoffman |
| 8,057,540 B2 | 11/2011 | Letac et al. |
| 8,062,355 B2 | 11/2011 | Figulla et al. |
| 8,062,359 B2 | 11/2011 | Marquez et al. |
| 8,070,708 B2 | 12/2011 | Rottenberg et al. |
| 8,070,800 B2 | 12/2011 | Lock et al. |
| 8,070,802 B2 | 12/2011 | Lamphere et al. |
| 8,070,804 B2 | 12/2011 | Hyde |
| 8,070,805 B2 | 12/2011 | Vidlund |
| 8,075,611 B2 | 12/2011 | Milwee et al. |
| 8,075,616 B2 | 12/2011 | Solem |
| 8,080,054 B2 | 12/2011 | Rowe |
| 8,083,793 B2 | 12/2011 | Lane et al. |
| D652,927 S | 1/2012 | Braido et al. |
| D653,341 S | 1/2012 | Braido et al. |
| 8,092,518 B2 | 1/2012 | Schreck |
| 8,092,520 B2 | 1/2012 | Quadri |
| 8,092,521 B2 | 1/2012 | Figulla et al. |
| 8,100,964 B2 | 1/2012 | Spence |
| 8,105,377 B2 | 1/2012 | Liddicoat |
| 8,109,996 B2 | 2/2012 | Stacchino et al. |
| 8,118,866 B2 | 2/2012 | Herrmann et al. |
| 8,123,800 B2 | 2/2012 | McCarthy |
| 8,123,801 B2 | 2/2012 | Milo |
| 8,323,334 B2 | 2/2012 | Deem et al. |
| 8,133,270 B2 | 3/2012 | Kheradvar et al. |
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,493 B2 | 3/2012 | Spence et al. |
| 8,142,494 B2 | 3/2012 | Rahdert et al. |
| 8,142,495 B2 | 3/2012 | Hasenkam et al. |
| 8,142,496 B2 | 3/2012 | Berreklouw |
| 8,142,497 B2 | 3/2012 | Friedman |
| 8,147,504 B2 | 4/2012 | Ino et al. |
| 8,147,542 B2 | 4/2012 | Maisano et al. |
| 8,152,844 B2 | 4/2012 | Rao |
| 8,157,852 B2 | 4/2012 | Bloom et al. |
| 8,157,853 B2 | 4/2012 | Laske et al. |
| 8,157,860 B2 | 4/2012 | McNamara et al. |
| 8,163,008 B2 | 4/2012 | Wilson et al. |
| 8,163,013 B2 | 4/2012 | Machold et al. |
| 8,163,014 B2 | 4/2012 | Lane et al. |
| D660,433 S | 5/2012 | Braido et al. |
| D660,967 S | 5/2012 | Braido et al. |
| 8,167,894 B2 | 5/2012 | Miles et al. |
| 8,167,932 B2 | 5/2012 | Bourang et al. |
| 8,167,935 B2 | 5/2012 | McGuckin, Jr. et al. |
| 8,172,896 B2 | 5/2012 | McNamara et al. |
| 8,172,898 B2 | 5/2012 | Alferness et al. |
| 8,177,836 B2 | 5/2012 | Lee et al. |
| 8,182,528 B2 | 5/2012 | Salahieh et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez-Duran |
| 8,211,169 B2 | 7/2012 | Lane et al. |
| 8,216,256 B2 | 7/2012 | Raschdorf, Jr. et al. |
| 8,216,301 B2 | 7/2012 | Bonhoeffer et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,226,711 B2 | 7/2012 | Mortier et al. |
| 8,231,670 B2 | 7/2012 | Salahieh et al. |
| 8,231,671 B2 | 7/2012 | Kim |
| 8,236,045 B2 | 8/2012 | Benichou et al. |
| 8,236,049 B2 | 8/2012 | Rowe et al. |
| 8,241,351 B2 | 8/2012 | Cabiri |
| 8,252,042 B2 | 8/2012 | McNamara et al. |
| 8,252,050 B2 | 8/2012 | Maisano et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,262,725 B2 | 9/2012 | Subramanian |
| 8,267,988 B2 | 9/2012 | Hamer et al. |
| 8,277,501 B2 | 10/2012 | Chalekian et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,298,280 B2 | 10/2012 | Yadin et al. |
| 8,303,608 B2 | 11/2012 | Goldfarb et al. |
| 8,303,653 B2 | 11/2012 | Bonhoeffer et al. |
| 8,308,798 B2 | 11/2012 | Pintor et al. |
| 8,313,525 B2 | 11/2012 | Tuval et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,333,777 B2 | 12/2012 | Schaller et al. |
| 8,337,541 B2 | 12/2012 | Quadri et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,348,999 B2 | 1/2013 | Kheradvar et al. |
| 8,349,002 B2 | 1/2013 | Milo |
| 8,353,956 B2 | 1/2013 | Miller et al. |
| 8,357,195 B2 | 1/2013 | Kuehn |
| 8,361,144 B2 | 1/2013 | Fish et al. |
| 8,366,767 B2 | 2/2013 | Zhang |
| 8,372,140 B2 | 2/2013 | Hoffman et al. |
| 8,377,119 B2 | 2/2013 | Drews et al. |
| 8,382,829 B1 | 2/2013 | Call et al. |
| 8,388,680 B2 | 3/2013 | Starksen et al. |
| 8,393,517 B2 | 3/2013 | Milo |
| 8,398,708 B2 | 3/2013 | Meiri et al. |
| 8,403,981 B2 | 3/2013 | Forster et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,425,593 B2 | 4/2013 | Braido et al. |
| 8,430,926 B2 | 4/2013 | Kirson |
| 8,430,934 B2 | 4/2013 | Das |
| 8,444,689 B2 | 5/2013 | Zhang |
| 8,449,599 B2 | 5/2013 | Chau et al. |
| 8,449,625 B2 | 5/2013 | Campbell et al. |
| 8,454,686 B2 | 6/2013 | Alkhatib |
| 8,460,365 B2 | 6/2013 | Haverkost et al. |
| 8,460,370 B2 | 6/2013 | Zakay et al. |
| 8,460,371 B2 | 6/2013 | Hlavka et al. |
| 8,474,460 B2 | 7/2013 | Barrett et al. |
| 8,475,491 B2 | 7/2013 | Milo |
| 8,480,732 B2 | 7/2013 | Subramanian |
| 8,500,800 B2 | 8/2013 | Maisano et al. |
| 8,500,821 B2 | 8/2013 | Sobrino-Serrano et al. |
| 8,512,400 B2 | 8/2013 | Tran et al. |
| 8,518,107 B2 | 8/2013 | Tsukashima et al. |
| 8,523,881 B2 | 9/2013 | Cabiri et al. |
| 8,523,940 B2 | 9/2013 | Richardson et al. |
| 8,529,431 B2 | 9/2013 | Baker et al. |
| 8,539,662 B2 | 9/2013 | Stacchino et al. |
| 8,540,767 B2 | 9/2013 | Zhang |
| 8,545,544 B2 | 10/2013 | Spenser et al. |
| 8,545,553 B2 | 10/2013 | Zipory et al. |
| 8,551,160 B2 | 10/2013 | Figulla et al. |
| 8,551,161 B2 | 10/2013 | Dolan |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,460 B2 | 11/2013 | Wilson et al. |
| 8,591,570 B2 | 11/2013 | Revuelta et al. |
| 8,591,576 B2 | 11/2013 | Hasenkam et al. |
| 8,608,797 B2 | 12/2013 | Gross et al. |
| 8,623,075 B2 | 1/2014 | Murray et al. |
| 8,623,080 B2 | 1/2014 | Fogarty et al. |

(56) References Cited

U.S. PATENT DOCUMENTS

| | | | |
|---|---|---|---|
| 8,628,569 B2 | 1/2014 | Benichou et al. |
| 8,628,570 B2 | 1/2014 | Seguin |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,652,204 B2 | 2/2014 | Quill et al. |
| 8,657,872 B2 | 2/2014 | Seguin |
| 8,663,322 B2 | 3/2014 | Keranen |
| 8,673,020 B2 | 3/2014 | Sobrino-Serrano et al. |
| 8,679,174 B2 | 3/2014 | Ottma et al. |
| 8,685,086 B2 | 4/2014 | Navia et al. |
| 8,690,939 B2 | 4/2014 | Miller et al. |
| 8,696,742 B2 | 4/2014 | Pintor et al. |
| 8,715,342 B2 | 5/2014 | Zipory et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,507 B2 | 5/2014 | Keranen |
| 8,740,920 B2 | 6/2014 | Goldfarb et al. |
| 8,747,460 B2 | 6/2014 | Tuval et al. |
| 8,771,345 B2 | 7/2014 | Tuval et al. |
| 8,778,021 B2 | 7/2014 | Cartledge |
| 8,784,472 B2 | 7/2014 | Eidenschink |
| 8,784,479 B2 | 7/2014 | Antonsson et al. |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,801,776 B2 | 8/2014 | House et al. |
| 8,808,366 B2 | 8/2014 | Braido et al. |
| 8,808,368 B2 | 8/2014 | Maisano et al. |
| 8,808,371 B2 | 8/2014 | Cartledge |
| 8,834,551 B2 * | 9/2014 | McGuckin, Jr. ...... A61F 2/2475 623/1.36 |
| 8,840,663 B2 | 9/2014 | Salahieh et al. |
| 8,840,664 B2 | 9/2014 | Karapetian et al. |
| 8,845,717 B2 | 9/2014 | Khairkhahan et al. |
| 8,845,722 B2 | 9/2014 | Gabbay |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,888,843 B2 | 11/2014 | Khairkhahan et al. |
| 8,894,702 B2 | 11/2014 | Quadri et al. |
| 8,900,294 B2 | 12/2014 | Paniagua et al. |
| 8,900,295 B2 | 12/2014 | Migliazza et al. |
| 8,906,083 B2 | 12/2014 | Obermiller et al. |
| 8,911,455 B2 | 12/2014 | Quadri et al. |
| 8,911,461 B2 | 12/2014 | Traynor et al. |
| 8,911,489 B2 | 12/2014 | Ben-Muvhar |
| 8,911,493 B2 | 12/2014 | Rowe et al. |
| 8,911,494 B2 | 12/2014 | Hammer et al. |
| 8,926,695 B2 | 1/2015 | Gross et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,042 B2 | 1/2015 | Miller et al. |
| 8,940,044 B2 | 1/2015 | Hammer et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,979,922 B2 | 3/2015 | Jayasinghe et al. |
| 8,986,370 B2 | 3/2015 | Annest |
| 8,986,373 B2 | 3/2015 | Chau et al. |
| 8,986,375 B2 | 3/2015 | Garde et al. |
| 8,992,599 B2 | 3/2015 | Thubrikar et al. |
| 8,992,604 B2 | 3/2015 | Gross et al. |
| 8,992,608 B2 | 3/2015 | Haug et al. |
| 8,998,982 B2 | 4/2015 | Richter et al. |
| 9,005,273 B2 | 4/2015 | Salahieh et al. |
| 9,011,468 B2 | 4/2015 | Ketai et al. |
| 9,011,520 B2 | 4/2015 | Miller et al. |
| 9,011,527 B2 | 4/2015 | Li et al. |
| 9,011,530 B2 | 4/2015 | Reich et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich et al. |
| 9,060,858 B2 | 6/2015 | Thornton et al. |
| 9,072,603 B2 * | 7/2015 | Tuval .................... A61F 2/2418 |
| 9,084,676 B2 | 7/2015 | Chau et al. |
| 9,095,434 B2 | 8/2015 | Rowe |
| 9,119,719 B2 | 9/2015 | Zipory et al. |
| 9,125,632 B2 | 9/2015 | Loulmet et al. |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,132,009 B2 | 9/2015 | Hacohen et al. |
| 9,138,312 B2 | 9/2015 | Tuval et al. |
| 9,155,619 B2 | 10/2015 | Liu et al. |
| 9,173,646 B2 | 11/2015 | Fabro |
| 9,173,659 B2 | 11/2015 | Bodewadt et al. |
| 9,173,738 B2 | 11/2015 | Murray et al. |
| 9,180,005 B1 | 11/2015 | Lashinski et al. |
| 9,180,009 B2 | 11/2015 | Majkrzak et al. |
| 9,192,472 B2 | 11/2015 | Gross et al. |
| 9,216,076 B2 | 12/2015 | Mitra et al. |
| 9,220,594 B2 | 12/2015 | Braido et al. |
| 9,226,820 B2 | 1/2016 | Braido et al. |
| 9,226,825 B2 | 1/2016 | Starksen et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,241,794 B2 | 1/2016 | Braido et al. |
| 9,248,014 B2 | 2/2016 | Lane et al. |
| 9,265,608 B2 | 2/2016 | Miller et al. |
| 9,277,994 B2 | 3/2016 | Miller et al. |
| 9,289,290 B2 | 3/2016 | Alkhatib et al. |
| 9,289,291 B2 | 3/2016 | Gorman et al. |
| 9,295,550 B2 | 3/2016 | Nguyen et al. |
| 9,295,551 B2 | 3/2016 | Straubinger et al. |
| 9,295,552 B2 | 3/2016 | McLean et al. |
| 9,301,836 B2 | 4/2016 | Buchbinder et al. |
| 9,308,087 B2 | 4/2016 | Lane et al. |
| 9,320,591 B2 | 4/2016 | Bolduc |
| D755,384 S | 5/2016 | Pesce et al. |
| 9,326,852 B2 | 5/2016 | Spenser |
| 9,326,876 B2 | 5/2016 | Acosta et al. |
| 9,345,573 B2 | 5/2016 | Nyuli et al. |
| 9,351,830 B2 | 5/2016 | Gross et al. |
| 9,358,107 B2 | 6/2016 | Nguyen et al. |
| 9,387,078 B2 | 7/2016 | Gross et al. |
| 9,393,110 B2 | 7/2016 | Levi et al. |
| 9,393,111 B2 * | 7/2016 | Ma ........................ A61F 2/2418 |
| 9,421,098 B2 | 8/2016 | Gifford et al. |
| 9,427,303 B2 | 8/2016 | Liddy et al. |
| 9,427,316 B2 | 8/2016 | Schweich, Jr. et al. |
| 9,439,757 B2 | 9/2016 | Wallace et al. |
| 9,445,893 B2 | 9/2016 | Vaturi |
| 9,463,102 B2 | 10/2016 | Kelly |
| 9,474,599 B2 | 10/2016 | Keränen |
| 9,474,638 B2 | 10/2016 | Robinson et al. |
| 9,480,559 B2 | 11/2016 | Vidlund et al. |
| 9,492,273 B2 | 11/2016 | Wallace et al. |
| 9,498,314 B2 | 11/2016 | Behan |

(56) References Cited

U.S. PATENT DOCUMENTS

| | | | |
|---|---|---|---|
| 9,498,332 B2 | 11/2016 | Hacohen et al. |
| 9,510,947 B2 | 12/2016 | Straubinger et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich et al. |
| 9,572,665 B2 | 2/2017 | Lane et al. |
| 9,597,182 B2 | 3/2017 | Straubinger et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,743,932 B2 | 8/2017 | Amplatz et al. |
| 9,763,657 B2 | 9/2017 | Hacohen et al. |
| 9,763,817 B2 | 9/2017 | Roeder |
| 9,770,256 B2 | 9/2017 | Cohen et al. |
| D800,908 S | 10/2017 | Hariton et al. |
| 9,788,941 B2 * | 10/2017 | Hacohen .............. A61F 2/2418 |
| 9,895,226 B1 | 2/2018 | Harari et al. |
| 9,901,443 B2 * | 2/2018 | Morriss ............... A61F 2/246 |
| 9,974,651 B2 | 5/2018 | Hariton et al. |
| 9,987,132 B1 | 6/2018 | Hariton et al. |
| 9,993,360 B2 | 6/2018 | Shalev et al. |
| 10,010,414 B2 | 7/2018 | Cooper et al. |
| 10,039,638 B2 | 8/2018 | Bruchman et al. |
| 10,045,845 B2 | 8/2018 | Hacohen et al. |
| 10,076,415 B1 | 9/2018 | Metchik et al. |
| 10,098,732 B1 | 10/2018 | Hariton et al. |
| 10,105,222 B1 | 10/2018 | Metchik et al. |
| 10,111,751 B1 | 10/2018 | Metchik et al. |
| 10,117,744 B2 * | 11/2018 | Ratz ................... A61F 2/2418 |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,143,552 B2 | 12/2018 | Wallace et al. |
| 10,149,761 B2 | 12/2018 | Granada et al. |
| 10,154,903 B2 | 12/2018 | Albitov et al. |
| 10,154,906 B2 | 12/2018 | Granada et al. |
| 10,159,570 B1 | 12/2018 | Metchik et al. |
| 10,182,908 B2 | 1/2019 | Tubishevitz et al. |
| 10,206,668 B2 | 2/2019 | Mcgoldrick et al. |
| 10,226,341 B2 | 3/2019 | Gross et al. |
| 10,231,831 B2 | 3/2019 | Hacohen |
| 10,231,837 B1 | 3/2019 | Metchik et al. |
| 10,238,493 B1 | 3/2019 | Metchik et al. |
| 10,245,143 B2 | 4/2019 | Gross et al. |
| 10,245,144 B1 | 4/2019 | Metchik et al. |
| 10,258,471 B2 | 4/2019 | Lutter et al. |
| 10,292,816 B2 | 5/2019 | Raanani et al. |
| 10,299,927 B2 * | 5/2019 | McLean ............... A61F 2/2418 |
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,335,278 B2 | 7/2019 | McLean et al. |
| 10,350,062 B2 | 7/2019 | Peterson et al. |
| 10,357,360 B2 | 7/2019 | Hariton et al. |
| 10,368,988 B2 * | 8/2019 | Jones ................. A61F 2/243 |
| 10,376,361 B2 | 8/2019 | Gross et al. |
| 10,390,952 B2 | 8/2019 | Hariton et al. |
| 10,426,610 B2 | 10/2019 | Hariton et al. |
| 10,426,614 B2 | 10/2019 | Hariton et al. |
| 10,449,047 B2 | 10/2019 | Hariton et al. |
| 10,456,256 B2 | 10/2019 | Braido et al. |
| 10,463,487 B2 | 11/2019 | Hariton et al. |
| 10,463,488 B2 | 11/2019 | Hariton et al. |
| 10,492,907 B2 | 12/2019 | Duffy |
| 10,492,908 B2 * | 12/2019 | Hammer ............... A61F 2/2436 |
| 10,507,105 B2 | 12/2019 | Hariton et al. |
| 10,507,108 B2 | 12/2019 | Delgado et al. |
| 10,507,109 B2 | 12/2019 | Metchik et al. |
| 10,512,456 B2 | 12/2019 | Hacohen et al. |
| 10,517,719 B2 | 12/2019 | Miller et al. |
| 10,524,792 B2 | 1/2020 | Hernandez et al. |
| 10,524,903 B2 | 1/2020 | Hariton et al. |
| 10,524,910 B2 | 1/2020 | Hammer et al. |
| 10,531,866 B2 | 1/2020 | Hariton et al. |
| 10,531,872 B2 | 1/2020 | Hacohen et al. |
| 10,537,426 B2 | 1/2020 | Iamberger et al. |
| 10,548,726 B2 | 2/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,595,997 B2 | 3/2020 | Metchik et al. |
| 10,610,358 B2 | 4/2020 | Vidlund et al. |
| 10,610,359 B2 | 4/2020 | Hacohen |
| 10,631,871 B2 | 4/2020 | Goldfarb et al. |
| 10,631,982 B2 | 4/2020 | Hammer et al. |
| 10,631,984 B2 | 4/2020 | Nyuli et al. |
| 10,646,342 B1 | 5/2020 | Marr et al. |
| 10,660,751 B2 | 5/2020 | Hacohen |
| 10,667,908 B2 | 6/2020 | Hariton et al. |
| 10,667,912 B2 | 6/2020 | Dixon et al. |
| 10,682,227 B2 | 6/2020 | Hariton et al. |
| 10,695,173 B2 | 6/2020 | Gross et al. |
| 10,695,177 B2 | 6/2020 | Hariton et al. |
| 10,702,385 B2 | 7/2020 | Hacohen |
| 10,722,354 B2 | 7/2020 | Cohen-Tzemach et al. |
| 10,722,360 B2 | 7/2020 | Hariton et al. |
| 10,736,742 B2 | 8/2020 | Hariton et al. |
| 10,758,342 B2 | 9/2020 | Chau et al. |
| 10,758,344 B2 | 9/2020 | Hariton et al. |
| 10,779,939 B2 | 9/2020 | Hariton et al. |
| 10,799,345 B2 | 10/2020 | Hariton et al. |
| 10,813,760 B2 | 10/2020 | Metchik et al. |
| 10,820,998 B2 | 11/2020 | Marr et al. |
| 10,835,377 B2 | 11/2020 | Hacohen et al. |
| 10,842,627 B2 | 11/2020 | Delgado et al. |
| 10,849,748 B2 | 12/2020 | Hariton et al. |
| 10,856,972 B2 | 12/2020 | Hariton et al. |
| 10,856,975 B2 | 12/2020 | Hariton et al. |
| 10,856,978 B2 | 12/2020 | Straubinger et al. |
| 10,864,078 B2 | 12/2020 | Hariton et al. |
| 10,874,514 B2 | 12/2020 | Dixon et al. |
| 10,881,511 B2 | 1/2021 | Hariton et al. |
| 10,888,422 B2 * | 1/2021 | Hariton ................. A61F 2/243 |
| 10,888,425 B2 | 1/2021 | Delgado et al. |
| 10,888,644 B2 | 1/2021 | Ratz et al. |
| 10,905,548 B2 | 2/2021 | Hariton et al. |
| 10,905,549 B2 | 2/2021 | Hariton et al. |
| 10,905,552 B2 | 2/2021 | Dixon et al. |
| 10,905,554 B2 | 2/2021 | Cao |
| 10,918,481 B2 | 2/2021 | Hariton et al. |
| 10,918,483 B2 | 2/2021 | Metchik et al. |
| 10,925,595 B2 | 2/2021 | Hacohen et al. |
| 10,925,732 B2 | 2/2021 | Delgado et al. |
| 10,945,843 B2 | 3/2021 | Delgado et al. |
| 10,945,844 B2 | 3/2021 | McCann et al. |
| 10,952,850 B2 | 3/2021 | Hariton et al. |
| 10,959,846 B2 | 3/2021 | Marr et al. |
| 10,973,636 B2 | 4/2021 | Hariton et al. |
| 10,993,809 B2 | 5/2021 | McCann et al. |
| 11,065,114 B2 | 7/2021 | Raanani et al. |
| 11,065,117 B2 | 7/2021 | Zeng |
| 11,083,582 B2 | 8/2021 | McCann et al. |
| 11,135,059 B2 | 10/2021 | Hammer et al. |
| 11,147,672 B2 | 10/2021 | McCann et al. |
| 11,179,240 B2 | 11/2021 | Delgado et al. |
| 11,246,704 B2 | 2/2022 | Hariton et al. |
| 11,291,545 B2 * | 4/2022 | Hacohen ............. A61B 17/122 |
| 11,291,546 B2 | 4/2022 | Gross et al. |
| 11,291,547 B2 | 4/2022 | Gross et al. |
| 11,291,844 B2 | 4/2022 | Gross |
| 11,304,804 B2 | 4/2022 | Hariton et al. |
| 11,304,805 B2 | 4/2022 | Hariton et al. |
| 11,304,806 B2 | 4/2022 | Hariton et al. |
| 11,318,014 B2 | 5/2022 | Hariton et al. |
| 11,318,015 B2 | 5/2022 | Hariton et al. |
| 11,337,802 B2 | 5/2022 | Hariton et al. |
| 11,337,803 B2 | 5/2022 | Hariton et al. |
| 11,337,804 B2 | 5/2022 | Hariton et al. |
| 11,389,297 B2 | 7/2022 | Franklin et al. |
| 11,426,155 B2 | 8/2022 | Hacohen et al. |
| 11,517,429 B2 | 12/2022 | Gross et al. |

(56) References Cited

U.S. PATENT DOCUMENTS

| | | |
|---|---|---|
| 11,517,436 B2 | 12/2022 | Hacohen |
| 2001/0002445 A1 | 5/2001 | Vesely |
| 2001/0005787 A1 | 6/2001 | Oz et al. |
| 2001/0021872 A1 | 9/2001 | Bailey et al. |
| 2001/0021874 A1 | 9/2001 | Carpentier et al. |
| 2001/0044656 A1 | 11/2001 | Williamson et al. |
| 2001/0056295 A1 | 12/2001 | Solem |
| 2002/0013571 A1 | 1/2002 | Goldfarb et al. |
| 2002/0022862 A1 | 2/2002 | Grafton et al. |
| 2002/0029080 A1 | 3/2002 | Mortier et al. |
| 2002/0032481 A1 | 3/2002 | Gabbay |
| 2002/0042621 A1 | 4/2002 | Liddicoat et al. |
| 2002/0082525 A1 | 6/2002 | Oslund et al. |
| 2002/0087048 A1 | 7/2002 | Brock et al. |
| 2002/0099436 A1 | 7/2002 | Thornton et al. |
| 2002/0103532 A1 | 8/2002 | Langberg et al. |
| 2002/0151916 A1 | 10/2002 | Muramatsu et al. |
| 2002/0151961 A1 | 10/2002 | Lashinski et al. |
| 2002/0151970 A1 | 10/2002 | Garrison et al. |
| 2002/0169358 A1 | 11/2002 | Mortier et al. |
| 2002/0173841 A1 | 11/2002 | Ortiz et al. |
| 2002/0177894 A1 | 11/2002 | Acosta et al. |
| 2002/0177904 A1 | 11/2002 | Huxel et al. |
| 2002/0198586 A1 | 12/2002 | Inoue |
| 2003/0009236 A1 | 1/2003 | Godin |
| 2003/0018358 A1 | 1/2003 | Saadat |
| 2003/0036791 A1 | 2/2003 | Philipp et al. |
| 2003/0050693 A1 | 3/2003 | Quijano et al. |
| 2003/0050694 A1 | 3/2003 | Yang et al. |
| 2003/0060846 A1 | 3/2003 | Egnelov et al. |
| 2003/0060875 A1 | 3/2003 | Wittens |
| 2003/0069635 A1 | 4/2003 | Cartledge |
| 2003/0074052 A1 | 4/2003 | Besselink |
| 2003/0074059 A1 | 4/2003 | Nguyen et al. |
| 2003/0078465 A1 | 4/2003 | Pai et al. |
| 2003/0078653 A1 | 4/2003 | Vesely et al. |
| 2003/0083742 A1 | 5/2003 | Spence et al. |
| 2003/0100943 A1 | 5/2003 | Bolduc |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0130731 A1 | 7/2003 | Vidlund et al. |
| 2003/0158578 A1 | 8/2003 | Pantages et al. |
| 2003/0167062 A1 | 9/2003 | Gambale et al. |
| 2003/0171760 A1 | 9/2003 | Gambale |
| 2003/0191528 A1 | 10/2003 | Quijano et al. |
| 2003/0199974 A1 | 10/2003 | Lee et al. |
| 2003/0204195 A1 | 10/2003 | Keane et al. |
| 2003/0229350 A1 | 12/2003 | Kay |
| 2003/0229395 A1 | 12/2003 | Cox |
| 2003/0233142 A1 | 12/2003 | Morales et al. |
| 2004/0010272 A1 | 1/2004 | Manetakis et al. |
| 2004/0019377 A1 | 1/2004 | Taylor et al. |
| 2004/0024451 A1 | 2/2004 | Johnson et al. |
| 2004/0030382 A1 | 2/2004 | St. Goar et al. |
| 2004/0039414 A1 | 2/2004 | Carley et al. |
| 2004/0039436 A1 | 2/2004 | Spenser et al. |
| 2004/0039442 A1 | 2/2004 | St. Goar et al. |
| 2004/0049207 A1 | 3/2004 | Goldfarb et al. |
| 2004/0059413 A1 | 3/2004 | Argento |
| 2004/0092962 A1 | 5/2004 | Thornton et al. |
| 2004/0093060 A1 | 5/2004 | Seguin et al. |
| 2004/0122448 A1 | 6/2004 | Levine |
| 2004/0122503 A1 | 6/2004 | Campbell et al. |
| 2004/0122514 A1 | 6/2004 | Fogarty et al. |
| 2004/0127982 A1 | 7/2004 | Machold et al. |
| 2004/0127983 A1 | 7/2004 | Mortier et al. |
| 2004/0133220 A1 | 7/2004 | Lashinski et al. |
| 2004/0133267 A1 | 7/2004 | Lane |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0143315 A1 | 7/2004 | Bruun et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153146 A1 | 8/2004 | Lashinski et al. |
| 2004/0172046 A1 | 9/2004 | Hlavka et al. |
| 2004/0176788 A1 | 9/2004 | Opolski |
| 2004/0176839 A1 | 9/2004 | Huynh et al. |
| 2004/0181287 A1 | 9/2004 | Gellman |
| 2004/0186558 A1 | 9/2004 | Pavcnik et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0236354 A1 | 11/2004 | Seguin |
| 2004/0236419 A1 | 11/2004 | Milo |
| 2004/0249433 A1 | 12/2004 | Freitag |
| 2004/0249453 A1 | 12/2004 | Cartledge et al. |
| 2004/0260317 A1 | 12/2004 | Bloom et al. |
| 2004/0260389 A1 | 12/2004 | Case et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0021056 A1 | 1/2005 | St. Goar et al. |
| 2005/0027305 A1 | 2/2005 | Shiu et al. |
| 2005/0027348 A1 | 2/2005 | Case et al. |
| 2005/0038494 A1 | 2/2005 | Eidenschink |
| 2005/0055038 A1 | 3/2005 | Kelleher et al. |
| 2005/0055086 A1 | 3/2005 | Stobie |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075726 A1 | 4/2005 | Svanidze et al. |
| 2005/0075727 A1 | 4/2005 | Wheatley |
| 2005/0075731 A1 | 4/2005 | Artof et al. |
| 2005/0080430 A1 | 4/2005 | Wright et al. |
| 2005/0080474 A1 | 4/2005 | Andreas et al. |
| 2005/0085900 A1 | 4/2005 | Case et al. |
| 2005/0085903 A1 | 4/2005 | Lau |
| 2005/0090827 A1 | 4/2005 | Gedebou |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137681 A1 | 6/2005 | Shoemaker et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1* | 6/2005 | Salahieh ............... A61F 2/2427 623/1.36 |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137695 A1 | 6/2005 | Salahieh et al. |
| 2005/0137697 A1 | 6/2005 | Salahieh et al. |
| 2005/0137699 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0182483 A1 | 8/2005 | Osborne et al. |
| 2005/0182486 A1 | 8/2005 | Gabbay |
| 2005/0187613 A1 | 8/2005 | Bolduc et al. |
| 2005/0192596 A1 | 9/2005 | Jugenheimer et al. |
| 2005/0197695 A1 | 9/2005 | Stacchino et al. |
| 2005/0197696 A1 | 9/2005 | Gomez Duran |
| 2005/0203549 A1 | 9/2005 | Realyvasquez |
| 2005/0203606 A1 | 9/2005 | VanCamp |
| 2005/0203618 A1 | 9/2005 | Sharkawy et al. |

(56) References Cited

U.S. PATENT DOCUMENTS

| | | |
|---|---|---|
| 2005/0216039 A1 | 9/2005 | Lederman |
| 2005/0216079 A1 | 9/2005 | MaCoviak |
| 2005/0222665 A1 | 10/2005 | Aranyi |
| 2005/0222678 A1 | 10/2005 | Lashinski et al. |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0256532 A1 | 11/2005 | Nayak et al. |
| 2005/0256566 A1 | 11/2005 | Gabbay |
| 2005/0267478 A1 | 12/2005 | Corradi et al. |
| 2005/0267573 A9 | 12/2005 | Macoviak et al. |
| 2005/0273138 A1 | 12/2005 | To et al. |
| 2005/0288776 A1 | 12/2005 | Shaoulian et al. |
| 2005/0288778 A1 | 12/2005 | Shaoulian et al. |
| 2005/0288781 A1 | 12/2005 | Moaddeb et al. |
| 2006/0004439 A1 | 1/2006 | Spenser et al. |
| 2006/0004442 A1 | 1/2006 | Spenser et al. |
| 2006/0004443 A1 | 1/2006 | Liddicoat et al. |
| 2006/0004469 A1 | 1/2006 | Sokel |
| 2006/0015171 A1 | 1/2006 | Armstrong |
| 2006/0020275 A1 | 1/2006 | Goldfarb et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025855 A1 | 2/2006 | Lashinski et al. |
| 2006/0025858 A1 | 2/2006 | Alameddine |
| 2006/0030885 A1 | 2/2006 | Hyde |
| 2006/0041189 A1 | 2/2006 | Vancaillie |
| 2006/0041319 A1 | 2/2006 | Taylor et al. |
| 2006/0052867 A1 | 3/2006 | Revuelta et al. |
| 2006/0052868 A1 | 3/2006 | Mortier |
| 2006/0058871 A1 | 3/2006 | Zakay et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0089627 A1 | 4/2006 | Burnett et al. |
| 2006/0095009 A1 | 5/2006 | Lampropoulos et al. |
| 2006/0106423 A1 | 5/2006 | Weisel et al. |
| 2006/0111773 A1 | 5/2006 | Rittgers et al. |
| 2006/0116750 A1 | 6/2006 | Herbert et al. |
| 2006/0116757 A1 | 6/2006 | Lashinski et al. |
| 2006/0122692 A1 | 6/2006 | Gilad et al. |
| 2006/0129166 A1 | 6/2006 | Lavelle |
| 2006/0135964 A1 | 6/2006 | Vesley |
| 2006/0149280 A1 | 7/2006 | Harvine et al. |
| 2006/0149360 A1 | 7/2006 | Schwammenthal et al. |
| 2006/0149368 A1 | 7/2006 | Spence |
| 2006/0155357 A1 | 7/2006 | Melsheimer |
| 2006/0161250 A1 | 7/2006 | Shaw |
| 2006/0161265 A1 | 7/2006 | Levine et al. |
| 2006/0047297 A1 | 8/2006 | Case |
| 2006/0178700 A1 | 8/2006 | Quinn |
| 2006/0178740 A1 | 8/2006 | Stacchino et al. |
| 2006/0184203 A1 | 8/2006 | Martin et al. |
| 2006/0184240 A1 | 8/2006 | Jimenez et al. |
| 2006/0184242 A1 | 8/2006 | Lichtenstein |
| 2006/0190036 A1 | 8/2006 | Wendel et al. |
| 2006/0190038 A1 | 8/2006 | Carley et al. |
| 2006/0195134 A1 | 8/2006 | Crittenden |
| 2006/0195183 A1 * | 8/2006 | Navia ............... A61F 2/2418 623/2.11 |
| 2006/0195184 A1 | 8/2006 | Lane et al. |
| 2006/0201519 A1 | 9/2006 | Frazier et al. |
| 2006/0212111 A1 | 9/2006 | Case et al. |
| 2006/0216404 A1 | 9/2006 | Seyler et al. |
| 2006/0229708 A1 | 10/2006 | Powell et al. |
| 2006/0241622 A1 | 10/2006 | Zergiebel |
| 2006/0241656 A1 | 10/2006 | Starksen et al. |
| 2006/0241745 A1 | 10/2006 | Solem |
| 2006/0241748 A1 | 10/2006 | Lee et al. |
| 2006/0247680 A1 | 11/2006 | Amplatz et al. |
| 2006/0247763 A1 | 11/2006 | Slater |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0271175 A1 | 11/2006 | Woolfson |
| 2006/0282150 A1 | 12/2006 | Olson et al. |
| 2006/0282161 A1 | 12/2006 | Huyn et al. |
| 2006/0287661 A1 | 12/2006 | Bolduc et al. |
| 2006/0287716 A1 | 12/2006 | Banbury et al. |
| 2006/0287719 A1 | 12/2006 | Rowe et al. |
| 2007/0001627 A1 | 1/2007 | Lin et al. |
| 2007/0008018 A1 | 1/2007 | Nagashima et al. |
| 2007/0016286 A1 | 1/2007 | Herrmann et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027528 A1 | 2/2007 | Agnew |
| 2007/0027533 A1 | 2/2007 | Douk |
| 2007/0027536 A1 | 2/2007 | Mihaljevic et al. |
| 2007/0027549 A1 | 2/2007 | Godin |
| 2007/0038221 A1 | 2/2007 | Fine et al. |
| 2007/0038293 A1 | 2/2007 | St. et al. |
| 2007/0038295 A1 | 2/2007 | Case et al. |
| 2007/0043435 A1 | 2/2007 | Seguin et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0055340 A1 | 3/2007 | Pryor |
| 2007/0056346 A1 | 3/2007 | Spenser et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0078510 A1 | 4/2007 | Ryan |
| 2007/0080188 A1 | 4/2007 | Spence et al. |
| 2007/0083168 A1 | 4/2007 | Whiting et al. |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0197858 A1 | 8/2007 | Goldfarb et al. |
| 2007/0198077 A1 | 8/2007 | Cully et al. |
| 2007/0198082 A1 | 8/2007 | Kapadia et al. |
| 2007/0198097 A1 | 8/2007 | Zegdi |
| 2007/0208550 A1 | 9/2007 | Cao et al. |
| 2007/0213582 A1 | 9/2007 | Zollinger et al. |
| 2007/0213810 A1 | 9/2007 | Newhauser et al. |
| 2007/0213813 A1 | 9/2007 | Von Segesser et al. |
| 2007/0219558 A1 | 9/2007 | Deutsch |
| 2007/0219630 A1 | 9/2007 | Chu |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0233239 A1 | 10/2007 | Navia et al. |
| 2007/0239208 A1 | 10/2007 | Crawford |
| 2007/0239265 A1 | 10/2007 | Birdsall et al. |
| 2007/0239272 A1 | 10/2007 | Navia et al. |
| 2007/0239273 A1 | 10/2007 | Allen |
| 2007/0244546 A1 | 10/2007 | Francis |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0270943 A1 | 11/2007 | Solem et al. |
| 2007/0276437 A1 | 11/2007 | Call et al. |

(56) References Cited

U.S. PATENT DOCUMENTS

| | | |
|---|---|---|
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004688 A1 | 1/2008 | Spenser et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Mackoviak et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086138 A1 | 4/2008 | Stone et al. |
| 2008/0086164 A1 | 4/2008 | Rowe et al. |
| 2008/0086203 A1 | 4/2008 | Roberts |
| 2008/0086204 A1 | 4/2008 | Rankin |
| 2008/0091257 A1 | 4/2008 | Andreas et al. |
| 2008/0091261 A1 | 4/2008 | Long et al. |
| 2008/0097523 A1 | 4/2008 | Bolduc et al. |
| 2008/0097595 A1 | 4/2008 | Gabbay |
| 2008/0132989 A1 | 6/2008 | Snow et al. |
| 2008/0140003 A1 | 6/2008 | Bei et al. |
| 2008/0140116 A1 | 6/2008 | Bonutti |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195126 A1 | 8/2008 | Solem |
| 2008/0195200 A1 | 8/2008 | Vidlund et al. |
| 2008/0200980 A1 | 8/2008 | Robin et al. |
| 2008/0208265 A1 | 8/2008 | Frazier et al. |
| 2008/0208328 A1 | 8/2008 | Antocci et al. |
| 2008/0208330 A1 | 8/2008 | Keranen |
| 2008/0208332 A1 | 8/2008 | Lamphere et al. |
| 2008/0221672 A1 | 9/2008 | Lamphere et al. |
| 2008/0234813 A1 | 9/2008 | Heuser |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0294234 A1 | 11/2008 | Hartley et al. |
| 2008/0294248 A1 | 11/2008 | Yang et al. |
| 2008/0300629 A1 | 12/2008 | Surti |
| 2009/0005863 A1 | 1/2009 | Goetz et al. |
| 2009/0036966 A1 | 2/2009 | O'Connor et al. |
| 2009/0043153 A1 | 2/2009 | Zollinger et al. |
| 2009/0043381 A1 | 2/2009 | Macoviak et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082844 A1 | 3/2009 | Zacharias et al. |
| 2009/0088836 A1 | 4/2009 | Bishop et al. |
| 2009/0088837 A1 | 4/2009 | Gillinov et al. |
| 2009/0099554 A1 | 4/2009 | Forster et al. |
| 2009/0099650 A1 | 4/2009 | Bolduc et al. |
| 2009/0099653 A1 | 4/2009 | Suri et al. |
| 2009/0105794 A1 | 4/2009 | Ziarno et al. |
| 2009/0105816 A1 | 4/2009 | Olsen et al. |
| 2009/0112159 A1 | 4/2009 | Slattery et al. |
| 2009/0125098 A1 | 5/2009 | Chuter |
| 2009/0125102 A1 | 5/2009 | Cartledge |
| 2009/0149872 A1 | 6/2009 | Gross et al. |
| 2009/0157175 A1 | 6/2009 | Benichou |
| 2009/0163934 A1 | 6/2009 | Raschdorf, Jr. et al. |
| 2009/0177274 A1 | 6/2009 | Scorsin et al. |
| 2009/0171363 A1 | 7/2009 | Chocron |
| 2009/0171439 A1 | 7/2009 | Nissl |
| 2009/0177266 A1 | 7/2009 | Powell et al. |
| 2009/0177277 A1 | 7/2009 | Milo |
| 2009/0177278 A1 | 7/2009 | Spence |
| 2009/0192601 A1 | 7/2009 | Rafiee et al. |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0241656 A1 | 10/2009 | Jacquemin |
| 2009/0248143 A1 | 10/2009 | Laham |
| 2009/0248148 A1 | 10/2009 | Shaolian et al. |
| 2009/0254103 A1 | 10/2009 | Deustch |
| 2009/0259306 A1 | 10/2009 | Rowe |
| 2009/0259307 A1 | 10/2009 | Gross et al. |
| 2009/0264859 A1 | 10/2009 | Mas |
| 2009/0264994 A1 | 10/2009 | Saadat |
| 2009/0264995 A1 | 10/2009 | Subramanian |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0287304 A1 | 11/2009 | Dahlgren et al. |
| 2009/0299409 A1 | 12/2009 | Coe et al. |
| 2009/0299449 A1 | 12/2009 | Styrc |
| 2009/0306768 A1 | 12/2009 | Quardi |
| 2009/0319037 A1 | 12/2009 | Rowe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0022823 A1 | 1/2010 | Goldfarb et al. |
| 2010/0023117 A1 | 1/2010 | Yoganathan et al. |
| 2010/0023118 A1 | 1/2010 | Medlock et al. |
| 2010/0023120 A1 | 1/2010 | Holecek et al. |
| 2010/0030014 A1 | 2/2010 | Ferrazzi |
| 2010/0036479 A1 | 2/2010 | Hill et al. |
| 2010/0036484 A1 | 2/2010 | Hariton et al. |
| 2010/0042147 A1 | 2/2010 | Janovsky et al. |
| 2010/0049306 A1 | 2/2010 | House et al. |
| 2010/0049313 A1 | 2/2010 | Alon et al. |
| 2010/0063542 A1 | 3/2010 | Van der Burg et al. |
| 2010/0063550 A1 | 3/2010 | Felix et al. |
| 2010/0063586 A1 | 3/2010 | Hasenkam et al. |
| 2010/0069852 A1 | 3/2010 | Kelley |
| 2010/0076499 A1 | 3/2010 | McNamara et al. |
| 2010/0076548 A1 | 3/2010 | Konno |
| 2010/0082094 A1 | 4/2010 | Quadri et al. |
| 2010/0094248 A1 | 4/2010 | Nguyen et al. |
| 2010/0100167 A1 | 4/2010 | Bortlein et al. |
| 2010/0114180 A1 | 5/2010 | Rock |
| 2010/0114299 A1 | 5/2010 | Ben-Muvhar et al. |
| 2010/0121349 A1 | 5/2010 | Meier |
| 2010/0130992 A1 | 5/2010 | Machold et al. |
| 2010/0131054 A1 | 5/2010 | Tuval et al. |
| 2010/0137979 A1 | 6/2010 | Tuval et al. |
| 2010/0152845 A1 | 6/2010 | Bloom et al. |
| 2010/0160958 A1 | 6/2010 | Clark |
| 2010/0161036 A1 | 6/2010 | Pintor et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168845 A1 | 7/2010 | Wright |
| 2010/0174358 A1 | 7/2010 | Rabkin et al. |
| 2010/0174363 A1 | 7/2010 | Castro |
| 2010/0179574 A1 | 7/2010 | Longoria et al. |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0185277 A1 | 7/2010 | Braido et al. |
| 2010/0198347 A1 | 8/2010 | Zakay et al. |

(56) References Cited

U.S. PATENT DOCUMENTS

| | | |
|---|---|---|
| 2010/0217382 A1* | 8/2010 | Chau .................. A61F 2/2436 623/2.12 |
| 2010/0222810 A1 | 9/2010 | DeBeer et al. |
| 2010/0228285 A1 | 9/2010 | Miles et al. |
| 2010/0234935 A1 | 9/2010 | Bashiri et al. |
| 2010/0234940 A1 | 9/2010 | Dolan |
| 2010/0249908 A1 | 9/2010 | Chau et al. |
| 2010/0249915 A1 | 9/2010 | Zhang |
| 2010/0249917 A1 | 9/2010 | Zhang |
| 2010/0249920 A1 | 9/2010 | Bolling et al. |
| 2010/0256737 A1 | 10/2010 | Pollock et al. |
| 2010/0262232 A1 | 10/2010 | Annest |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0280606 A1 | 11/2010 | Naor |
| 2010/0286628 A1 | 11/2010 | Gross |
| 2010/0286767 A1 | 11/2010 | Zipory et al. |
| 2010/0305475 A1 | 12/2010 | Hinchliffe et al. |
| 2010/0312333 A1 | 12/2010 | Navia et al. |
| 2010/0324595 A1 | 12/2010 | Linder et al. |
| 2010/0331971 A1 | 12/2010 | Keränen et al. |
| 2011/0004210 A1 | 1/2011 | Johnson et al. |
| 2011/0004227 A1 | 1/2011 | Goldfarb et al. |
| 2011/0004296 A1 | 1/2011 | Lutter et al. |
| 2011/0004298 A1 | 1/2011 | Lee et al. |
| 2011/0004299 A1 | 1/2011 | Navia et al. |
| 2011/0011917 A1 | 1/2011 | Loulmet |
| 2011/0015729 A1 | 1/2011 | Jimenez et al. |
| 2011/0015731 A1 | 1/2011 | Carpentier et al. |
| 2011/0015739 A1 | 1/2011 | Cheung et al. |
| 2011/0021985 A1 | 1/2011 | Spargias |
| 2011/0022165 A1 | 1/2011 | Oba et al. |
| 2011/0178597 A9 | 1/2011 | Navia et al. |
| 2011/0026208 A1 | 2/2011 | Otsuro et al. |
| 2011/0029066 A1 | 2/2011 | Gilad et al. |
| 2011/0029067 A1 | 2/2011 | Mcguckin, Jr. et al. |
| 2011/0029072 A1* | 2/2011 | Gabbay ............... A61F 2/2418 623/2.37 |
| 2011/0035000 A1 | 2/2011 | Nieminen et al. |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0066231 A1 | 3/2011 | Cartledge et al. |
| 2011/0066233 A1 | 3/2011 | Thornton et al. |
| 2011/0067770 A1 | 3/2011 | Pederson et al. |
| 2011/0071626 A1 | 3/2011 | Wright et al. |
| 2011/0077730 A1 | 3/2011 | Fentster |
| 2011/0082538 A1 | 4/2011 | Dahlgren et al. |
| 2011/0087146 A1 | 4/2011 | Ryan et al. |
| 2011/0087322 A1 | 4/2011 | Letac et al. |
| 2011/0093002 A1 | 4/2011 | Rucker et al. |
| 2011/0093063 A1 | 4/2011 | Schreck |
| 2011/0098525 A1 | 4/2011 | Kermode et al. |
| 2011/0098802 A1 | 4/2011 | Braido et al. |
| 2011/0098805 A1 | 4/2011 | Dwork et al. |
| 2011/0106245 A1 | 5/2011 | Miller et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0113768 A1 | 5/2011 | Bauer et al. |
| 2011/0118830 A1 | 5/2011 | Liddicoat et al. |
| 2011/0118832 A1 | 5/2011 | Punjabi |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1* | 6/2011 | Chau .................. A61F 2/2427 623/2.37 |
| 2011/0137409 A1 | 6/2011 | Yang et al. |
| 2011/0137410 A1 | 6/2011 | Hacohen |
| 2011/0144703 A1 | 6/2011 | Krause et al. |
| 2011/0144742 A1 | 6/2011 | Madrid et al. |
| 2011/0166636 A1 | 7/2011 | Rowe |
| 2011/0166649 A1 | 7/2011 | Gross et al. |
| 2011/0172784 A1 | 7/2011 | Richter |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0202130 A1 | 8/2011 | Cartledge et al. |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0230941 A1 | 9/2011 | Markus |
| 2011/0230961 A1 | 9/2011 | Langer et al. |
| 2011/0238088 A1 | 9/2011 | Bodluc et al. |
| 2011/0238094 A1 | 9/2011 | Thomas et al. |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Weimeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257433 A1 | 10/2011 | Walker |
| 2011/0257633 A1 | 10/2011 | Cartledge et al. |
| 2011/0257721 A1 | 10/2011 | Tabor |
| 2011/0257728 A1 | 10/2011 | Kuehn |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy |
| 2011/0270276 A1 | 11/2011 | Rothstein et al. |
| 2011/0271967 A1 | 11/2011 | Mortier et al. |
| 2011/0276062 A1 | 11/2011 | Bolduc |
| 2011/0276128 A1 | 11/2011 | Cao et al. |
| 2011/0282361 A1 | 11/2011 | Miller et al. |
| 2011/0282438 A1 | 11/2011 | Drews et al. |
| 2011/0282439 A1 | 11/2011 | Thill et al. |
| 2011/0282440 A1 | 11/2011 | Cao |
| 2011/0283514 A1 | 11/2011 | Fogarty et al. |
| 2011/0288435 A1 | 11/2011 | Christy et al. |
| 2011/0288632 A1 | 11/2011 | White |
| 2011/0288634 A1 | 11/2011 | Tuval et al. |
| 2011/0288635 A1 | 11/2011 | Miller et al. |
| 2011/0295354 A1 | 12/2011 | Bueche et al. |
| 2011/0295363 A1 | 12/2011 | Girard et al. |
| 2011/0301498 A1 | 12/2011 | Maenhout et al. |
| 2011/0301688 A1 | 12/2011 | Dolan |
| 2011/0301698 A1 | 12/2011 | Miller et al. |
| 2011/0301701 A1 | 12/2011 | Padala et al. |
| 2011/0301702 A1 | 12/2011 | Rust et al. |
| 2011/0306916 A1 | 12/2011 | Nitzan et al. |
| 2011/0307049 A1 | 12/2011 | Kao |
| 2011/0313452 A1 | 12/2011 | Carley et al. |
| 2011/0313515 A1 | 12/2011 | Quadri et al. |
| 2011/0319988 A1 | 12/2011 | Schankereli et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0016468 A1 | 1/2012 | Robin et al. |
| 2012/0022557 A1 | 1/2012 | Cabiri et al. |
| 2012/0022629 A1 | 1/2012 | Perera et al. |

(56) References Cited

U.S. PATENT DOCUMENTS

| | | |
|---|---|---|
| 2012/0022633 A1 | 1/2012 | Olson et al. |
| 2012/0022637 A1 | 1/2012 | Ben-Movhar et al. |
| 2012/0022639 A1* | 1/2012 | Hacohen .............. A61F 2/2436 |
| | | 623/2.11 |
| 2012/0022640 A1 | 1/2012 | Gross et al. |
| 2012/0022644 A1 | 1/2012 | Reich et al. |
| 2012/0035703 A1 | 2/2012 | Lutter et al. |
| 2012/0035712 A1 | 2/2012 | Maisano et al. |
| 2012/0035713 A1 | 2/2012 | Lutter et al. |
| 2012/0035722 A1 | 2/2012 | Tuval et al. |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053680 A1 | 3/2012 | Bolling et al. |
| 2012/0053682 A1 | 3/2012 | Kovalsky et al. |
| 2012/0053688 A1 | 3/2012 | Fogarty et al. |
| 2012/0059337 A1 | 3/2012 | Eilat |
| 2012/0059454 A1 | 3/2012 | Millwee et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078355 A1 | 3/2012 | Zipory et al. |
| 2012/0078357 A1 | 3/2012 | Conklin |
| 2012/0078359 A1 | 3/2012 | Li et al. |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089022 A1 | 4/2012 | House et al. |
| 2012/0089223 A1 | 4/2012 | Nguyen et al. |
| 2012/0095552 A1 | 4/2012 | Spence et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0109155 A1 | 5/2012 | Robinson et al. |
| 2012/0123511 A1 | 5/2012 | Brown |
| 2012/0123529 A1 | 5/2012 | Levi et al. |
| 2012/0123530 A1 | 5/2012 | Carpentier et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0136436 A1 | 5/2012 | Cabiri et al. |
| 2012/0143323 A1 | 6/2012 | Hasenkam et al. |
| 2012/0150218 A1 | 6/2012 | Sandgren et al. |
| 2012/0150290 A1 | 6/2012 | Gabbay |
| 2012/0158021 A1 | 6/2012 | Morrill |
| 2012/0165915 A1 | 6/2012 | Melsheimer et al. |
| 2012/0165930 A1 | 6/2012 | Gifford, III et al. |
| 2012/0179086 A1 | 7/2012 | Shank et al. |
| 2012/0179244 A1 | 7/2012 | Schankereli et al. |
| 2012/0191182 A1 | 7/2012 | Hauser et al. |
| 2012/0197292 A1 | 8/2012 | Chin-Chen et al. |
| 2012/0197388 A1 | 8/2012 | Khairkhahan et al. |
| 2012/0215303 A1 | 8/2012 | Quadri et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0277845 A1 | 11/2012 | Bowe |
| 2012/0283757 A1 | 11/2012 | Miller et al. |
| 2012/0283824 A1 | 11/2012 | Lutter et al. |
| 2012/0290062 A1 | 11/2012 | McNamara et al. |
| 2012/0296349 A1 | 11/2012 | Smith et al. |
| 2012/0296360 A1 | 11/2012 | Norris et al. |
| 2012/0296417 A1 | 11/2012 | Hill et al. |
| 2012/0296418 A1 | 11/2012 | Bonyuet et al. |
| 2012/0296419 A1 | 11/2012 | Richardson |
| 2012/0300063 A1 | 11/2012 | Majkrzak et al. |
| 2012/0303116 A1* | 11/2012 | Gorman, III .......... A61F 2/2436 |
| | | 623/2.11 |
| 2012/0123531 A1 | 12/2012 | Tsukashima et al. |
| 2012/0310328 A1 | 12/2012 | Olson et al. |
| 2012/0310330 A1 | 12/2012 | Buchbinder et al. |
| 2012/0323313 A1 | 12/2012 | Seguin |
| 2012/0323316 A1 | 12/2012 | Chau et al. |
| 2012/0323317 A1 | 12/2012 | Karapetian et al. |
| 2012/0330408 A1 | 12/2012 | Hillukka et al. |
| 2012/0330410 A1 | 12/2012 | Hammer et al. |
| 2012/0330411 A1 | 12/2012 | Gross et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0023758 A1 | 1/2013 | Fabro |
| 2013/0030519 A1 | 1/2013 | Tran et al. |
| 2013/0030522 A1 | 1/2013 | Rowe et al. |
| 2013/0035759 A1 | 2/2013 | Gross et al. |
| 2013/0041204 A1 | 2/2013 | Heilman et al. |
| 2013/0041451 A1 | 2/2013 | Patterson et al. |
| 2013/0046373 A1 | 2/2013 | Cartledge et al. |
| 2013/0066341 A1 | 3/2013 | Ketai et al. |
| 2013/0066342 A1 | 3/2013 | Dell et al. |
| 2013/0079872 A1 | 3/2013 | Gallagher |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0116779 A1 | 5/2013 | Weber |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0123910 A1 | 5/2013 | Cartledge et al. |
| 2013/0131791 A1 | 5/2013 | Hlavka et al. |
| 2013/0131792 A1 | 5/2013 | Miller et al. |
| 2013/0138068 A1 | 5/2013 | Hu et al. |
| 2013/0144381 A1 | 6/2013 | Quadri et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0178930 A1 | 7/2013 | Straubinger et al. |
| 2013/0190857 A1 | 7/2013 | Mitra et al. |
| 2013/0190861 A1 | 7/2013 | Chau et al. |
| 2013/0190863 A1 | 7/2013 | Call et al. |
| 2013/0190866 A1 | 7/2013 | Zipory et al. |
| 2013/0197622 A1 | 8/2013 | Mitra et al. |
| 2013/0197632 A1 | 8/2013 | Kovach et al. |
| 2013/0204361 A1 | 8/2013 | Adams et al. |
| 2013/0211501 A1 | 8/2013 | Buckley et al. |
| 2013/0211508 A1 | 8/2013 | Lane et al. |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0245742 A1 | 9/2013 | Norris |
| 2013/0253643 A1 | 9/2013 | Rolando et al. |
| 2013/0261737 A1 | 10/2013 | Costello |
| 2013/0261738 A1 | 10/2013 | Clague et al. |
| 2013/0268069 A1 | 10/2013 | Zakai et al. |
| 2013/0274870 A1 | 10/2013 | Lombardi et al. |
| 2013/0274873 A1 | 10/2013 | Delaloye et al. |
| 2013/0282059 A1 | 10/2013 | Ketai et al. |
| 2013/0289711 A1 | 10/2013 | Liddy et al. |
| 2013/0289718 A1 | 10/2013 | Tsukashima et al. |
| 2013/0289740 A1 | 10/2013 | Liddy et al. |
| 2013/0297013 A1 | 11/2013 | Klima et al. |
| 2013/0304093 A1 | 11/2013 | Serina et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2013/0325118 A1 | 12/2013 | Cartledge |
| 2013/0331929 A1 | 12/2013 | Mitra et al. |
| 2014/0000112 A1 | 1/2014 | Braido et al. |
| 2014/0005767 A1 | 1/2014 | Glazier et al. |
| 2014/0005778 A1 | 1/2014 | Buchbinder et al. |
| 2014/0018911 A1 | 1/2014 | Zhou et al. |
| 2014/0018914 A1 | 1/2014 | Zipory et al. |
| 2014/0018915 A1 | 1/2014 | Biadillah et al. |
| 2014/0031928 A1 | 1/2014 | Murphy et al. |

(56) References Cited

U.S. PATENT DOCUMENTS

| | | |
|---|---|---|
| 2014/0046430 A1 | 2/2014 | Shaw |
| 2014/0052237 A1 | 2/2014 | Lane et al. |
| 2014/0067050 A1 | 3/2014 | Costello et al. |
| 2014/0067054 A1 | 3/2014 | Chau et al. |
| 2014/0081376 A1 | 3/2014 | Burkart et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0099726 A1 | 4/2014 | Heller |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |
| 2014/0135799 A1 | 5/2014 | Henderson |
| 2014/0135894 A1 | 5/2014 | Norris et al. |
| 2014/0135895 A1 | 5/2014 | Andress et al. |
| 2014/0142619 A1 | 5/2014 | Serina et al. |
| 2014/0142681 A1 | 5/2014 | Norris |
| 2014/0142688 A1 | 5/2014 | Duffy et al. |
| 2014/0142695 A1 | 5/2014 | Gross et al. |
| 2014/0148849 A1 | 5/2014 | Serina et al. |
| 2014/0148891 A1 | 5/2014 | Johnson |
| 2014/0148898 A1 | 5/2014 | Gross et al. |
| 2014/0155783 A1 | 6/2014 | Starksen et al. |
| 2014/0163668 A1 | 6/2014 | Rafiee |
| 2014/0163670 A1 | 6/2014 | Alon et al. |
| 2014/0163690 A1 | 6/2014 | White |
| 2014/0172069 A1 | 6/2014 | Roeder et al. |
| 2014/0172077 A1 | 6/2014 | Bruchman et al. |
| 2014/0172082 A1 | 6/2014 | Bruchman et al. |
| 2014/0188108 A1 | 7/2014 | Goodine et al. |
| 2014/0188140 A1 | 7/2014 | Meier et al. |
| 2014/0188210 A1 | 7/2014 | Beard et al. |
| 2014/0188215 A1 | 7/2014 | Hlavka et al. |
| 2014/0188221 A1 | 7/2014 | Chung et al. |
| 2014/0194970 A1 | 7/2014 | Chobotov |
| 2014/0194976 A1 | 7/2014 | Starksen et al. |
| 2014/0194981 A1 | 7/2014 | Menk et al. |
| 2014/0194983 A1 | 7/2014 | Kovalsky et al. |
| 2014/0207231 A1 | 7/2014 | Hacohen et al. |
| 2014/0214157 A1 | 7/2014 | Börtlein et al. |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0275757 A1 | 9/2014 | Goodwin et al. |
| 2014/0276648 A1 | 9/2014 | Hammer et al. |
| 2014/0277358 A1 | 9/2014 | Slazas |
| 2014/0277409 A1 | 9/2014 | Börtlein et al. |
| 2014/0277411 A1 | 9/2014 | Börtlein et al. |
| 2014/0277412 A1 | 9/2014 | Börtlein et al. |
| 2014/0277413 A1 | 9/2014 | Richter et al. |
| 2014/0277417 A1 | 9/2014 | Schraut et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0324164 A1 | 10/2014 | Gross et al. |
| 2014/0329225 A1 | 11/2014 | Morin |
| 2014/0331475 A1 | 11/2014 | Duffy et al. |
| 2014/0336744 A1 | 11/2014 | Tani et al. |
| 2014/0343668 A1 | 11/2014 | Zipory et al. |
| 2014/0343670 A1 | 11/2014 | Bakis et al. |
| 2014/0350662 A1 | 11/2014 | Vaturi |
| 2014/0350670 A1 | 11/2014 | Keränen |
| 2014/0358222 A1 | 12/2014 | Gorman, III et al. |
| 2014/0358224 A1 | 12/2014 | Tegels et al. |
| 2014/0378331 A1 | 12/2014 | Morin |
| 2014/0379006 A1 | 12/2014 | Sutherland et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0012087 A1 | 1/2015 | Miller et al. |
| 2015/0018940 A1 | 1/2015 | Quill et al. |
| 2015/0018944 A1 | 1/2015 | O'connell et al. |
| 2015/0032205 A1 | 1/2015 | Matheny |
| 2015/0045880 A1 | 2/2015 | Hacohen |
| 2015/0045881 A1 | 2/2015 | Lim |
| 2015/0051697 A1 | 2/2015 | Spence et al. |
| 2015/0073544 A1 | 3/2015 | Gorman, III et al. |
| 2015/0081014 A1 | 3/2015 | Gross et al. |
| 2015/0094802 A1 | 4/2015 | Buchbinder et al. |
| 2015/0105855 A1 | 4/2015 | Cabiri et al. |
| 2015/0119970 A1 | 4/2015 | Nakayama et al. |
| 2015/0127097 A1 | 5/2015 | Neumann et al. |
| 2015/0142100 A1 | 5/2015 | Morriss et al. |
| 2015/0142103 A1 | 5/2015 | Vidlund |
| 2015/0148894 A1 | 5/2015 | Damm et al. |
| 2015/0148896 A1 | 5/2015 | Karapetian et al. |
| 2015/0157457 A1 | 6/2015 | Hacohen |
| 2015/0157458 A1 | 6/2015 | Thambar et al. |
| 2015/0164640 A1 | 6/2015 | McLean et al. |
| 2015/0173896 A1 | 6/2015 | Richter et al. |
| 2015/0173897 A1 | 6/2015 | Raanani et al. |
| 2015/0182336 A1 | 7/2015 | Zipory et al. |
| 2015/0196390 A1 | 7/2015 | Ma et al. |
| 2015/0196393 A1 | 7/2015 | Vidlund et al. |
| 2015/0216661 A1 | 8/2015 | Hacohen et al. |
| 2015/0230924 A1 | 8/2015 | Miller et al. |
| 2015/0238313 A1 | 8/2015 | Spence et al. |
| 2015/0238315 A1 | 8/2015 | Rabito et al. |
| 2015/0245934 A1 | 9/2015 | Lombardi et al. |
| 2015/0250588 A1 | 9/2015 | Yang et al. |
| 2015/0272730 A1 | 10/2015 | Melnick et al. |
| 2015/0272731 A1 | 10/2015 | Racchini et al. |
| 2015/0272734 A1 | 10/2015 | Sheps et al. |
| 2015/0282964 A1 | 10/2015 | Beard et al. |
| 2015/0305903 A1 | 10/2015 | Kitaoka |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0342736 A1 | 12/2015 | Rabito et al. |
| 2015/0351903 A1* | 12/2015 | Morriss ............... A61F 2/2418 623/2.11 |
| 2015/0351904 A1* | 12/2015 | Cooper ............... A61F 2/2418 623/2.1 |
| 2015/0351906 A1 | 12/2015 | Hammer et al. |
| 2015/0359629 A1 | 12/2015 | Ganesan et al. |
| 2015/0359631 A1 | 12/2015 | Sheahan et al. |
| 2016/0008129 A1 | 1/2016 | Siegel |
| 2016/0030165 A1 | 2/2016 | Mitra et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0089482 A1 | 3/2016 | Siegenthaler |
| 2016/0095700 A1 | 4/2016 | Righini |
| 2016/0100939 A1 | 4/2016 | Armstrong et al. |
| 2016/0106537 A1 | 4/2016 | Christianson et al. |
| 2016/0106539 A1 | 4/2016 | Buchbinder et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0125160 A1 | 5/2016 | Heneghan et al. |
| 2016/0157862 A1 | 6/2016 | Hernandez et al. |
| 2016/0175095 A1 | 6/2016 | Dienno et al. |
| 2016/0184098 A1 | 6/2016 | Vaturi |

(56) References Cited

U.S. PATENT DOCUMENTS

| | | |
|---|---|---|
| 2016/0200773 A1 | 7/2016 | Morin |
| 2016/0213473 A1 | 7/2016 | Hacohen et al. |
| 2016/0220367 A1 | 8/2016 | Barrett |
| 2016/0228244 A1 | 8/2016 | Cerf et al. |
| 2016/0228247 A1 | 8/2016 | Maimon et al. |
| 2016/0242902 A1 | 8/2016 | Morriss et al. |
| 2016/0245802 A1 | 8/2016 | Morin et al. |
| 2016/0258939 A1 | 9/2016 | Morin et al. |
| 2016/0262885 A1 | 9/2016 | Sandstrom et al. |
| 2016/0266089 A1 | 9/2016 | Morin et al. |
| 2016/0270911 A1 | 9/2016 | Ganesan et al. |
| 2016/0296330 A1 | 10/2016 | Hacohen |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0324640 A1 | 11/2016 | Gifford et al. |
| 2016/0331526 A1 | 11/2016 | Schweich et al. |
| 2016/0331527 A1 | 11/2016 | Vidlund et al. |
| 2016/0338706 A1 | 11/2016 | Rowe |
| 2016/0367360 A1 | 12/2016 | Cartledge et al. |
| 2016/0367368 A1 | 12/2016 | Vidlund et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0049435 A1 | 2/2017 | Sauer et al. |
| 2017/0056166 A1 | 3/2017 | Ratz et al. |
| 2017/0056169 A1 | 3/2017 | Johnson et al. |
| 2017/0056171 A1 | 3/2017 | Cooper et al. |
| 2017/0065407 A1 | 3/2017 | Hacohen et al. |
| 2017/0065411 A1 | 3/2017 | Grundeman et al. |
| 2017/0074855 A1 | 3/2017 | Morin et al. |
| 2017/0100236 A1 | 4/2017 | Robertson et al. |
| 2017/0128205 A1 | 5/2017 | Tamir et al. |
| 2017/0135816 A1 | 5/2017 | Lashinski et al. |
| 2017/0143938 A1 | 5/2017 | Ogle et al. |
| 2017/0165054 A1 | 6/2017 | Benson et al. |
| 2017/0189174 A1 | 7/2017 | Braido et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0224323 A1 | 8/2017 | Rowe et al. |
| 2017/0231757 A1 | 8/2017 | Gassler |
| 2017/0231759 A1 | 8/2017 | Geist et al. |
| 2017/0231760 A1 | 8/2017 | Lane et al. |
| 2017/0231766 A1 | 8/2017 | Hariton et al. |
| 2017/0234850 A1 | 8/2017 | Morin |
| 2017/0239048 A1 | 8/2017 | Goldfarb et al. |
| 2017/0252159 A1 | 9/2017 | Hacohen et al. |
| 2017/0266003 A1 | 9/2017 | Hammer et al. |
| 2017/0281337 A1 | 10/2017 | Campbell |
| 2017/0325948 A1 | 11/2017 | Wallace et al. |
| 2017/0333183 A1 | 11/2017 | Backus |
| 2017/0333187 A1 | 11/2017 | Hariton et al. |
| 2017/0349940 A1 | 12/2017 | Morin et al. |
| 2017/0360426 A1 | 12/2017 | Hacohen et al. |
| 2017/0367823 A1 | 12/2017 | Hariton et al. |
| 2018/0000580 A1 | 1/2018 | Wallace et al. |
| 2018/0014930 A1 | 1/2018 | Hariton et al. |
| 2018/0014932 A1 | 1/2018 | Hammer et al. |
| 2018/0021129 A1 | 1/2018 | Peterson et al. |
| 2018/0023114 A1 | 1/2018 | Morin et al. |
| 2018/0023115 A1 | 1/2018 | Morin et al. |
| 2018/0028215 A1 | 2/2018 | Cohen |
| 2018/0028311 A1 | 2/2018 | Hacohen |
| 2018/0049873 A1 | 2/2018 | Manash et al. |
| 2018/0055628 A1 | 3/2018 | Patel et al. |
| 2018/0055629 A1 | 3/2018 | Oba et al. |
| 2018/0055630 A1 | 3/2018 | Patel et al. |
| 2018/0098850 A1 | 4/2018 | Rafiee et al. |
| 2018/0116790 A1 | 5/2018 | Ratz et al. |
| 2018/0116843 A1 | 5/2018 | Schreck et al. |
| 2018/0125644 A1 | 5/2018 | Conklin |
| 2018/0132999 A1 | 5/2018 | Perouse |
| 2018/0133003 A1 | 5/2018 | Levi |
| 2018/0147059 A1 | 5/2018 | Hammer et al. |
| 2018/0153687 A1 | 6/2018 | Hariton et al. |
| 2018/0153689 A1 | 6/2018 | Maimon et al. |
| 2018/0153695 A1 | 6/2018 | Cunningham et al. |
| 2018/0153696 A1 | 6/2018 | Albitov et al. |
| 2018/0161159 A1 | 6/2018 | Lee et al. |
| 2018/0177593 A1 | 6/2018 | Hariton et al. |
| 2018/0177594 A1 | 6/2018 | Patel et al. |
| 2018/0185148 A1 | 7/2018 | Hariton et al. |
| 2018/0206982 A1 | 7/2018 | Haivatov et al. |
| 2018/0206983 A1 | 7/2018 | Noe et al. |
| 2018/0214263 A1 | 8/2018 | Rolando et al. |
| 2018/0243086 A1 | 8/2018 | Barbarino et al. |
| 2018/0250126 A1 | 9/2018 | O'connor et al. |
| 2018/0250130 A1 | 9/2018 | Hariton et al. |
| 2018/0250147 A1 | 9/2018 | Syed |
| 2018/0256323 A1 | 9/2018 | Hariton et al. |
| 2018/0256325 A1 | 9/2018 | Hariton et al. |
| 2018/0271654 A1 | 9/2018 | Hariton et al. |
| 2018/0271655 A1 | 9/2018 | Hariton et al. |
| 2018/0280136 A1 | 10/2018 | Hariton et al. |
| 2018/0289479 A1 | 10/2018 | Hariton et al. |
| 2018/0296333 A1 | 10/2018 | Dixon et al. |
| 2018/0296336 A1 | 10/2018 | Cooper et al. |
| 2018/0296341 A1 | 10/2018 | Noe et al. |
| 2018/0325671 A1 | 11/2018 | Abunassar et al. |
| 2018/0338829 A1 | 11/2018 | Hariton et al. |
| 2018/0338830 A1 | 11/2018 | Hariton et al. |
| 2018/0338831 A1 | 11/2018 | Hariton et al. |
| 2018/0344457 A1 | 12/2018 | Gross et al. |
| 2018/0344490 A1 | 12/2018 | Fox et al. |
| 2018/0353294 A1 | 12/2018 | Calomeni et al. |
| 2018/0360457 A1 | 12/2018 | Ellis et al. |
| 2019/0000613 A1 | 1/2019 | Delgado et al. |
| 2019/0008640 A1 | 1/2019 | Cooper et al. |
| 2019/0015093 A1 | 1/2019 | Hacohen et al. |
| 2019/0015200 A1 | 1/2019 | Delgado et al. |
| 2019/0021852 A1 | 1/2019 | Delgado et al. |
| 2019/0021857 A1 | 1/2019 | Hacohen et al. |
| 2019/0038404 A1 | 2/2019 | Iamberger et al. |
| 2019/0038405 A1 | 2/2019 | Iamberger et al. |
| 2019/0046314 A1 | 2/2019 | Levi et al. |
| 2019/0053895 A1 | 2/2019 | Levi |
| 2019/0053896 A1 | 2/2019 | Adamek-bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0069998 A1 | 3/2019 | Hacohen |
| 2019/0076244 A1 | 3/2019 | Yohanan et al. |
| 2019/0083242 A1 | 3/2019 | Hariton et al. |
| 2019/0083243 A1 | 3/2019 | Hariton et al. |
| 2019/0083244 A1 | 3/2019 | Hariton et al. |
| 2019/0083245 A1 | 3/2019 | Hariton et al. |
| 2019/0083246 A1 | 3/2019 | Hariton et al. |
| 2019/0083247 A1 | 3/2019 | Hariton et al. |
| 2019/0083248 A1 | 3/2019 | Hariton et al. |
| 2019/0083249 A1 | 3/2019 | Hariton et al. |
| 2019/0083250 A1 | 3/2019 | Hariton et al. |
| 2019/0083251 A1 | 3/2019 | Hariton et al. |
| 2019/0083252 A1 | 3/2019 | Hariton et al. |
| 2019/0083253 A1 | 3/2019 | Hariton et al. |
| 2019/0083254 A1 | 3/2019 | Hariton et al. |
| 2019/0083261 A1 | 3/2019 | Perszyk et al. |
| 2019/0083262 A1 | 3/2019 | Hariton et al. |
| 2019/0083263 A1 | 3/2019 | Hariton et al. |
| 2019/0105153 A1 | 4/2019 | Barash et al. |
| 2019/0117391 A1 | 4/2019 | Humair |
| 2019/0167423 A1 | 6/2019 | Hariton et al. |
| 2019/0175339 A1 | 6/2019 | Vidlund |
| 2019/0175342 A1 | 6/2019 | Hariton et al. |
| 2019/0183639 A1 | 6/2019 | Moore |
| 2019/0183644 A1 | 6/2019 | Hacohen |
| 2019/0192295 A1 | 6/2019 | Spence et al. |
| 2019/0216602 A1 | 7/2019 | Lozonschi |
| 2019/0231525 A1 | 8/2019 | Hariton et al. |

(56) References Cited

U.S. PATENT DOCUMENTS

| | | |
|---|---|---|
| 2019/0240010 A1 | 8/2019 | Hacohen |
| 2019/0254818 A1 | 8/2019 | Quill et al. |
| 2019/0262507 A1 | 8/2019 | Adamek-bowers et al. |
| 2019/0321172 A1 | 10/2019 | Gross et al. |
| 2019/0328519 A1 | 10/2019 | Hariton et al. |
| 2019/0336280 A1 | 11/2019 | Naor |
| 2019/0343627 A1 | 11/2019 | Hariton et al. |
| 2019/0350701 A1 | 11/2019 | Adamek-bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2019/0388223 A1 | 12/2019 | Hariton et al. |
| 2020/0000449 A1 | 1/2020 | Goldfarb et al. |
| 2020/0000579 A1 | 1/2020 | Manash et al. |
| 2020/0000580 A1 | 1/2020 | Hacohen |
| 2020/0015964 A1 | 1/2020 | Noe et al. |
| 2020/0030098 A1 | 1/2020 | Delgado et al. |
| 2020/0038181 A1 | 2/2020 | Hariton et al. |
| 2020/0046496 A1 | 2/2020 | Hammer et al. |
| 2020/0046497 A1 | 2/2020 | Hariton et al. |
| 2020/0054335 A1 | 2/2020 | Hernandez et al. |
| 2020/0054451 A1 | 2/2020 | Hariton et al. |
| 2020/0060818 A1 | 2/2020 | Geist et al. |
| 2020/0069424 A1 | 3/2020 | Hariton et al. |
| 2020/0078002 A1 | 3/2020 | Hacohen et al. |
| 2020/0113677 A1 | 4/2020 | McCann et al. |
| 2020/0113689 A1 | 4/2020 | McCann et al. |
| 2020/0113692 A1 | 4/2020 | McCann et al. |
| 2020/0129294 A1 | 4/2020 | Hariton et al. |
| 2020/0138567 A1 | 5/2020 | Marr et al. |
| 2020/0146671 A1 | 5/2020 | Hacohen et al. |
| 2020/0146824 A1 | 5/2020 | Hammer et al. |
| 2020/0163760 A1 | 5/2020 | Hariton et al. |
| 2020/0163761 A1 | 5/2020 | Hariton et al. |
| 2020/0205969 A1 | 7/2020 | Hacohen |
| 2020/0214832 A1 | 7/2020 | Metchik et al. |
| 2020/0237512 A1 | 7/2020 | McCann et al. |
| 2020/0246136 A1 | 8/2020 | Marr et al. |
| 2020/0246140 A1 | 8/2020 | Hariton et al. |
| 2020/0253600 A1 | 8/2020 | Darabian |
| 2020/0261094 A1 | 8/2020 | Goldfarb et al. |
| 2020/0281721 A1 | 9/2020 | Hariton et al. |
| 2020/0297486 A1 | 9/2020 | Hariton et al. |
| 2020/0306037 A1 | 10/2020 | Siegel et al. |
| 2020/0315786 A1 | 10/2020 | Metchik et al. |
| 2020/0315797 A1 | 10/2020 | Hariton et al. |
| 2020/0330221 A1 | 10/2020 | Hacohen |
| 2020/0330227 A1 | 10/2020 | Hacohen |
| 2020/0337842 A1 | 10/2020 | Metchik et al. |
| 2020/0360139 A1 | 11/2020 | Hammer et al. |
| 2020/0390546 A1 | 12/2020 | Hariton et al. |
| 2020/0390548 A1 | 12/2020 | Hariton et al. |
| 2020/0397573 A1 | 12/2020 | Hariton et al. |
| 2021/0085455 A1 | 3/2021 | Bateman et al. |
| 2021/0085457 A1 | 3/2021 | Hariton et al. |
| 2021/0093449 A1 | 4/2021 | Hariton et al. |
| 2021/0106419 A1 | 4/2021 | Abunassar |
| 2021/0113331 A1 | 4/2021 | Quadri et al. |
| 2021/0137680 A1 | 5/2021 | Kizuka et al. |
| 2021/0145578 A1 | 5/2021 | Hariton et al. |
| 2021/0169467 A1 | 6/2021 | Hacohen et al. |
| 2021/0196461 A1 | 7/2021 | Hariton et al. |
| 2021/0259835 A1 | 8/2021 | Tyler, II et al. |
| 2021/0330456 A1 | 10/2021 | Hacohen et al. |
| 2021/0361422 A1 | 11/2021 | Gross et al. |
| 2021/0361426 A1 | 11/2021 | Hacohen |
| 2021/0393402 A1 | 12/2021 | Hammer et al. |
| 2021/0401573 A1 | 12/2021 | Gross et al. |
| 2022/0000612 A1 | 1/2022 | Hacohen |
| 2022/0023036 A1 | 1/2022 | Levi et al. |
| 2022/0061984 A1 | 3/2022 | Humair et al. |
| 2022/0105238 A1 | 4/2022 | Reimer et al. |
| 2022/0151779 A1 | 5/2022 | Pintor |

FOREIGN PATENT DOCUMENTS

| | | |
|---|---|---|
| CN | 101653365 | 2/2010 |
| CN | 103974674 | 8/2014 |
| CN | 103997990 | 8/2014 |
| CN | 105324091 | 2/2016 |
| EP | 0170262 | 2/1986 |
| EP | 06/14342 | 9/1994 |
| EP | 10/06905 | 6/2000 |
| EP | 0954257 | 8/2000 |
| EP | 1258437 | 11/2002 |
| EP | 1264582 | 12/2002 |
| EP | 0871417 | 10/2003 |
| EP | 1266641 | 10/2004 |
| EP | 1034753 | 2/2005 |
| EP | 1258232 | 1/2006 |
| EP | 1637092 | 3/2006 |
| EP | 1990014 | 11/2008 |
| EP | 1562522 | 12/2008 |
| EP | 1420723 | 1/2009 |
| EP | 1903991 | 9/2009 |
| EP | 1418865 | 10/2009 |
| EP | 2119399 | 11/2009 |
| EP | 1531762 | 4/2010 |
| EP | 1450733 | 2/2011 |
| EP | 2 446 915 A1 | 5/2012 |
| EP | 2088965 | 11/2012 |
| EP | 2641569 | 9/2013 |
| EP | 1768630 | 1/2015 |
| EP | 1861045 | 3/2015 |
| EP | 1465555 | 5/2015 |
| EP | 2349124 | 10/2018 |
| EP | 2739214 | 10/2018 |
| EP | 3417813 | 12/2018 |
| EP | 3583922 | 12/2019 |
| EP | 3270825 | 4/2020 |
| EP | 2485795 | 9/2020 |
| IL | 223448 | 12/2012 |
| JP | S53152790 | 12/1978 |
| KR | 20010046894 | 6/2001 |
| WO | 92/05093 | 4/1992 |
| WO | 93/10714 | 6/1993 |
| WO | 96/39963 | 12/1996 |
| WO | 96/40344 | 12/1996 |
| WO | 97/01369 | 1/1997 |
| WO | 98/46149 | 10/1998 |
| WO | 1998/043557 | 10/1998 |
| WO | 1999/030647 | 6/1999 |
| WO | 00/22981 | 4/2000 |
| WO | 2000-047139 | 8/2000 |
| WO | 01/26586 | 4/2001 |
| WO | 01/56457 | 8/2001 |
| WO | 2001-062189 | 8/2001 |
| WO | 01/82832 | 11/2001 |
| WO | 02/085250 | 10/2002 |
| WO | 02/085251 | 10/2002 |
| WO | 02/085252 | 10/2002 |
| WO | 2003/020179 | 3/2003 |
| WO | 2003/028558 | 4/2003 |
| WO | 03/047467 | 6/2003 |
| WO | 2003/049647 | 6/2003 |
| WO | 2003/105667 | 12/2003 |
| WO | 2004/028399 | 4/2004 |
| WO | 04/103434 | 12/2004 |
| WO | 2004/108191 | 12/2004 |
| WO | 05/021063 | 3/2005 |
| WO | 05/046488 | 5/2005 |
| WO | 2005/062931 | 7/2005 |
| WO | 2005/107650 | 11/2005 |
| WO | 2006/007389 | 1/2006 |
| WO | 2006/007401 | 1/2006 |
| WO | 06/012013 | 2/2006 |
| WO | 06/012038 | 2/2006 |
| WO | 06/054930 | 5/2006 |
| WO | 2006/065212 | 6/2006 |
| WO | 2006/070372 | 7/2006 |
| WO | 06/086434 | 8/2006 |
| WO | 2006/089236 | 8/2006 |
| WO | 2006/091163 | 8/2006 |

(56) References Cited

FOREIGN PATENT DOCUMENTS

| | | |
|---|---|---|
| WO | 06/097931 | 9/2006 |
| WO | 06/105084 | 10/2006 |
| WO | 2006/113906 | 10/2006 |
| WO | 06/116558 | 11/2006 |
| WO | 2006/128193 | 11/2006 |
| WO | 07/011799 | 1/2007 |
| WO | 2007/030063 | 3/2007 |
| WO | 2007/047488 | 4/2007 |
| WO | 2007/059252 | 5/2007 |
| WO | 07/121314 | 10/2007 |
| WO | 07/136783 | 11/2007 |
| WO | 07/136981 | 11/2007 |
| WO | 08/013915 | 1/2008 |
| WO | 2008/014144 | 1/2008 |
| WO | 2008/029296 | 3/2008 |
| WO | 2008/031103 | 3/2008 |
| WO | 2008/058940 | 5/2008 |
| WO | 08/068756 | 6/2008 |
| WO | 2008/070797 | 6/2008 |
| WO | 2008/103722 | 8/2008 |
| WO | 2009/026563 | 2/2009 |
| WO | 09/033469 | 3/2009 |
| WO | 09/053497 | 4/2009 |
| WO | 2009/080801 | 7/2009 |
| WO | 2009/091509 | 7/2009 |
| WO | 2009/130631 | 10/2009 |
| WO | 10/004546 | 1/2010 |
| WO | 2010/000454 | 1/2010 |
| WO | 2010/005827 | 1/2010 |
| WO | 2010/006627 | 1/2010 |
| WO | 2010/006905 | 1/2010 |
| WO | 2010/027485 | 3/2010 |
| WO | 2010/037141 | 4/2010 |
| WO | 2010/044851 | 4/2010 |
| WO | 2010/045297 | 4/2010 |
| WO | 2010/057262 | 5/2010 |
| WO | 2010/073246 | 7/2010 |
| WO | 2010/081033 | 7/2010 |
| WO | 2010/085649 | 7/2010 |
| WO | 2010/121076 | 10/2010 |
| WO | 2010/128502 | 11/2010 |
| WO | 2010/128503 | 11/2010 |
| WO | 2010/150178 | 12/2010 |
| WO | 2011/025972 | 3/2011 |
| WO | 2011/051942 | 5/2011 |
| WO | 2011/057087 | 5/2011 |
| WO | 2011/067770 | 6/2011 |
| WO | 2011/069048 | 6/2011 |
| WO | 2011/072084 | 6/2011 |
| WO | 2011/089401 | 7/2011 |
| WO | 2011/089601 | 7/2011 |
| WO | 2011/106137 | 9/2011 |
| WO | 2011/111047 | 9/2011 |
| WO | 01/87190 | 11/2011 |
| WO | 2011/137531 | 11/2011 |
| WO | 2011-143263 | 11/2011 |
| WO | 2011/144351 | 11/2011 |
| WO | 2011/148374 | 12/2011 |
| WO | 2011/154942 | 12/2011 |
| WO | 2012/011108 | 1/2012 |
| WO | 2012/014201 | 2/2012 |
| WO | 2012/024428 | 2/2012 |
| WO | 2012/036740 | 3/2012 |
| WO | 2012/048035 | 4/2012 |
| WO | 2012/068541 | 5/2012 |
| WO | 2012/127309 | 9/2012 |
| WO | 2012/176195 | 12/2012 |
| WO | 2012/177942 | 12/2012 |
| WO | 2012/178115 | 12/2012 |
| WO | 2013/021374 | 2/2013 |
| WO | 2013/021375 | 2/2013 |
| WO | 2013/021384 | 2/2013 |
| WO | 2013/028387 | 2/2013 |
| WO | 2013/059743 | 4/2013 |
| WO | 2013/059747 | 4/2013 |
| WO | 2013/069019 | 5/2013 |
| WO | 2013/072496 | 5/2013 |
| WO | 2013/078497 | 6/2013 |
| WO | 2013/088327 | 6/2013 |
| WO | 2013/114214 | 8/2013 |
| WO | 2013/128436 | 9/2013 |
| WO | 2013/175468 | 11/2013 |
| WO | 2014/022124 | 2/2014 |
| WO | 2014/064694 | 5/2014 |
| WO | 2014/064695 | 5/2014 |
| WO | 2014/076696 | 5/2014 |
| WO | 2014/087402 | 6/2014 |
| WO | 2014/115149 | 7/2014 |
| WO | 2014/121275 | 8/2014 |
| WO | 2014/121280 | 8/2014 |
| WO | 2014/144937 | 9/2014 |
| WO | 2014/145338 | 9/2014 |
| WO | WO-2014145338 A1 * 9/2014 ........... A61F 2/2418 |
| WO | 2014/164364 | 10/2014 |
| WO | 2014/194178 | 12/2014 |
| WO | 2014/195786 | 12/2014 |
| WO | 2015/059699 | 4/2015 |
| WO | 2015/173794 | 11/2015 |
| WO | 2015/191923 | 12/2015 |
| WO | 2016/016899 | 2/2016 |
| WO | 2016/093877 | 6/2016 |
| WO | 2016/098104 | 6/2016 |
| WO | 2016/125160 | 8/2016 |
| WO | 2016/150806 | 9/2016 |
| WO | 2016/183526 | 11/2016 |
| WO | 2017/223486 | 12/2017 |
| WO | 2018/025260 | 2/2018 |
| WO | 2018/025263 | 2/2018 |
| WO | 2018/029680 | 2/2018 |
| WO | 2018/039631 | 3/2018 |
| WO | 2018/106837 | 6/2018 |
| WO | 2018/112429 | 6/2018 |
| WO | 2018/118717 | 6/2018 |
| WO | 2018/131042 | 7/2018 |
| WO | 2018/131043 | 7/2018 |
| WO | 2019/026059 | 2/2019 |
| WO | 2019/027507 | 2/2019 |
| WO | 2019/030753 | 2/2019 |
| WO | 2019/077595 | 4/2019 |
| WO | 2019/086958 | 5/2019 |
| WO | 2019/116369 | 6/2019 |
| WO | 2019/138400 | 7/2019 |
| WO | 2019/195860 | 10/2019 |
| WO | 2019/202579 | 10/2019 |
| WO | 2020/058972 | 3/2020 |
| WO | 2020/167677 | 8/2020 |
| WO | 2021/156866 | 8/2021 |
| WO | 2021/186424 | 9/2021 |
| WO | 2022/046568 | 3/2022 |
| WO | 2022/061017 | 3/2022 |

OTHER PUBLICATIONS

An Office Action dated Sep. 29, 2022, which issued during the prosecution of U.S. Appl. No. 16/656,790.
An Office Action dated Nov. 2, 2022, which issued during the prosecution of U.S. Appl. No. 17/004,693.
An Office Action dated Nov. 28, 2022, which issued during the prosecution of U.S. Appl. No. 17/141,853.
An Office Action dated Oct. 19, 2022, which issued during the prosecution of U.S. Appl. No. 17/875,589.
An Office Action dated Oct. 26, 2022, which issued during the prosecution of U.S. Appl. No. 16/746,489.
An Office Action dated Nov. 23. 2012, which issued during the prosecution of U.S. Appl. No. 13/033,852.
An Office Action dated Dec. 31. 2012, which issued during the prosecution of U.S. Appl. No. 13/044,694.
An Office Action dated Feb. 6, 2013, which issued during the prosecution of U.S. Appl. No. 13/412,814.
Langer F et al., "RING plus STRING: Papillary muscle repositioning as an adjunctive repair technique for ischemic mitral regurgitation," J Thorac Cardiovasc Surg 133:247-9, Jan. 2007.

(56) References Cited

OTHER PUBLICATIONS

Langer F et al., "RING+STRING: Successful repair technique for ischemic mitral regurgitation with severe leaflet tethering," Circulation 120[suppl 1]: S85-S91, Sep. 2009.
"Transcatheter Valve-in-Valve Implantation for Failed Bioprosthetic Heart Valves", J Webb et al., Circulation. Apr. 2010; 121: 1848-1857.
Jansen, J., Willeke, S., Reul, H. and Rum, G. (1992), Detachable Shape-Memory Sewing Ring for Heart Valves. Artificial Organs, 16:294-297. 1992 (an abstract).
Alexander S. Geha, et al., Replacement of degenerated mitral and aortic bioprostheses without explanation Ann Thorac Surg. Jun. 2001; 72:1509-1514.
An International Search Report and a Written Opinion both dated Oct. 13, 2011 which issued during the prosecution of Applicant's PCT/IL11/00231.
An Office Action dated Jul. 1, 2016, which issued during the prosecution of U.S. Appl. No. 14/161,921.
An International Search Report and a Written Opinion both dated Dec. 5, 2011, which issued during the prosecution of Applicant's PCT/IL11/00582.
An Office Action dated May 29, 2012, which issued during the prosecution of U.S. Appl. No. 12/840,463.
U.S. Appl. No. 61/555,160, filed Nov. 3, 2011.
U.S. Appl. No. 61/525,281, filed Aug. 19, 2011.
U.S. Appl. No. 61/537,276, filed Sep. 21, 2011.
U.S. Appl. No. 61/515,372, filed Aug. 5, 2011.
U.S. Appl. No. 61/492,449, filed Jun. 2, 2011.
U.S. Appl. No. 61/588,892, filed Jan. 20, 2012.
An International Search Report and a Written Opinion both dated Feb. 6, 2013, which issued during the prosecution of Applicant's PCT/IL12/00292.
An International Search Report and a Written Opinion both dated Feb. 6, 2013, which issued during the prosecution of Applicant's PCT/IL12/00293.
An Office Action dated Nov. 28, 2012, which issued during the prosecution of U.S. Appl. No. 12/961,721.
An Office Action dated Feb. 15, 2013, which issued during the prosecution of U.S. Appl. No. 12/840,463.
An Office Action dated Feb. 10, 2014, which issued during the prosecution of U.S. Appl. No. 13/033,852.
An Office Action dated Sep. 19, 2014, which issued during the prosecution of U.S. Appl. No. 13/044,694.
An International Search Report and a Written Opinion both dated Sep. 4, 2014 which issued during the prosecution of Applicant's PCT/IL2014/050087.
Invitation to Pay Additional Fees dated Jun. 12, 2014 PCT/IL2014/050087.
An Office Action dated Jun. 17, 2014, which issued during the prosecution of U.S. Appl. No. 12/961,721.
An Office Action dated Jul. 3, 2014, which issued during the prosecution of U.S. Appl. No. 13/033,852.
An Office Action dated May 23, 2014, which issued during the prosecution of U.S. Appl. No. 13/412,814.
Dominique Himbert; Mitral Regurgitation and Stenosis from Bioprosthesis and Annuloplasty Failure: Transcatheter approaches and outcomes, 24 pages Oct. 28, 2013.
An International Search Report and a Written Opinion both dated Mar. 17, 2014 which issued during the prosecution of Applicant's PCT/IL2013/050937.
An International Preliminary Report on patentabilty dated Dec. 2, 2013, which issued during the prosecution of Applicant's PCT/IL11/00582.
An Office Action dated Sep. 12, 2013, which issued during the prosecution of U.S. Appl. No. 13/412,814.
An Office Action dated Aug. 2, 2013, which issued during the prosecution of U.S. Appl. No. 13/033,852.
An International Preliminary Report on patentabilty dated Sep. 11, 2012, which issued during the prosecution of Applicant's PCT/IL2011/000231.
An Office Action dated Jul. 2, 2014, which issued during the prosecution of U.S. Appl. No. 13/811,308.
An Office Action dated Jan. 20, 2016, which issued during the prosecution of U.S. Appl. No. 14/161,921.
An Office Action dated Jul. 23, 2013, which issued during the prosecution of U.S. Appl. No. 12/961,721.
An Office Action dated Jul. 18, 2013, which issued during the prosecution of U.S. Appl. No. 13/044,694.
An Office Action dated Nov. 8, 2013, which issued during the prosecution of U.S. Appl. No. 12/840,463.
An Office Action dated Jun. 4, 2014, which issued during the prosecution of U.S. Appl. No. 12/840,463.
An Office Action dated Aug. 13, 2012, which issued during the prosecution of U.S. Appl. No. 13/044,694.
An Office Action dated Jul. 2, 2012, which issued during the prosecution of U.S. Appl. No. 13/033,852.
An Office Action dated Feb. 3, 2014, which issued during the prosecution of U.S. Appl. No. 13/811,308.
An International Preliminary Report on patentabilty dated Feb. 11, 2014, which issued during the prosecution of Applicant's PCT/IL12/00292.
An International Preliminary Report on patentabilty dated Feb. 11, 2014, which issued during the prosecution of Applicant's PCT/IL12/00293.
A Notice of Allowance dated Aug. 15, 2014, which issued during the prosecution of U.S. Appl. No. 13/412,814.
An Office Action dated Aug. 14. 2012, which issued during the prosecution of U.S. Appl. No. 12/961,721.
U.S. Appl. No. 61/283,819, filed Dec. 8, 2009.
Notice of Allowance dated Apr. 8, 2016, which issued during the prosecution of U.S. Appl. No. 14/237,258.
U.S. Appl. No. 61/756,034, filed Jan. 24, 2013.
U.S. Appl. No. 61/756,049, filed Jan. 24, 2013.
An International Preliminary Report on Patentability dated Jan. 31, 2017, which issued during the prosecution of Applicant's PCT/IL2015/050792.
U.S. Appl. No. 62/372,861, filed Aug. 10, 2016.
Notice of Allowance dated Aug. 13, 2018, which issued during the prosecution of U.S. Appl. No. 15/995,597.
Notice of Allowance dated Apr. 20, 2018, which issued during the prosecution of U.S. Appl. No. 15/878,206.
An Office Action dated Dec. 10, 2015, which issued during the prosecution of U.S. Appl. No. 14/237,258.
An International Preliminary Report on Patentability dated Jul. 28, 2015, which issued during the prosecution of Applicant's PCT/IL2014/050087
An Office Action dated Nov. 27, 2015, which issued during the prosecution of U.S. Appl. No. 14/626,267.
An Office Action dated Jan. 21, 2016, which issued during the prosecution of U.S. Appl. No. 14/237,264.
An Office Action dated Jan. 30, 2015, which issued during the prosecution of UK Patent Application No. 1413474.6.
An International Search Report and a Written Opinion both dated May 30, 2016, which issued during the prosecution of Applicant's PCT/IL2016/050125.
An Office Action dated Sep. 26, 2016, which issued during the prosecution of U.S. Appl. No. 14/763,004.
An Office Action dated Jan. 18, 2017, which issued during the prosecution of U.S. Appl. No. 14/626,267.
An Office Action dated Feb. 7, 2017, which issued during the prosecution of U.S. Appl. No. 14/689,608.
An Office Action dated Feb. 8, 2017, which issued during the prosecution of UK Patent Application No. 1613219.3.
An Office Action together dated Feb. 10, 2017, which issued during the prosecution of European Patent Application No. 12821522.5.
International Search Report and a Written Opinion both dated Oct. 27, 2015, during the prosecution of Applicant's PCT/IL2015/050792.
European Search Report dated Feb. 18. 2015, which issued during the prosecution of Applicant's European App No. 12821522.5.
Saturn Project—a novel solution for transcatheter heart valve replacement specifically designed to address clinical therapeutic needs on mitral valve: Dec. 2016.

(56) References Cited

OTHER PUBLICATIONS

Righini presentation EuroPCR May 2015 (Saturn)—(downloaded from: https://www.pcronline.com/Cases-resourcesimages/Resources/Course-videos-slides/2015/Cardiovascularinnovation-pipeline-Mitral-and-tricuspid-valve-interventions).
An Advisory Action dated Apr. 2, 2018, which issued during the prosecution of U.S. Appl. No. 14/763,004.
An Office Action dated Jul. 26, 2018, which issued during the prosecution of U.S. Appl. No. 15/872,501.
An Office Action dated May 4, 2018, which issued during the prosecution of U.S. Appl. No. 15/872,501.
An Office Action dated Apr. 20, 2018, which issued during the prosecution of U.S. Appl. No. 15/886,517.
An Office Action dated Aug. 9, 2018, which issued during the prosecution of U.S. Appl. No. 15/899,858.
An Office Action dated Aug. 9, 2018, which issued during the prosecution of U.S. Appl. No. 15/902,403.
An Office Action dated Jun. 28, 2018, which issued during the prosecution of Design U.S. Appl. No. 29/635,658.
An Office Action dated Jun. 28, 2018, which issued during the prosecution of Design U.S. Appl. No. 29/635,661.
Georg Lutter, MD, et al, "Percutaneous Valve Replacement: Current State and Future Prospects", The Annals of Thoracic Surgery, vol. 78, pp. 2199-2206, Dec. 2004.
An Office Action dated Jun. 6, 2018, which issued during the prosecution of UK Patent Application No. 1720803.4.
An International Search Report and a Written Opinion both dated Jun. 20, 2018, which issued during the prosecution of Applicant's PCT/IL2018/050024.
An Office Action dated Jun. 18, 2018, which issued during the prosecution of UK Patent Application No. 1800399.6.
An Office Action dated Oct. 23, 2017, which issued during the prosecution of U.S. Appl. No. 14/763,004.
An Office Action dated Dec. 7, 2017, which issued during the prosecution of U.S. Appl. No. 15/213,791.
Interview Summary dated Feb. 8, 2018, which issued during the prosecution of U.S. Appl. No. 15/213,791.
An Office Action dated Feb. 7, 2018, which issued during the prosecution of U.S. Appl. No. 15/197,069.
An International Search Report and a Written Opinion both dated Nov. 24, 2017, which issued during the prosecution of Applicant's PCT/IL2017/050873.
An Office Action dated Jan. 5, 2018, which issued during the prosecution of U.S. Appl. No. 15/541,783.
An Office Action dated Feb. 2, 2018, which issued during the prosecution of U.S. Appl. No. 15/329,920.
An Invitation to pay additional fees dated Jan. 2, 2018, which issued during the prosecution of Applicant's PCT/IL2017/050849.
An Invitation to pay additional fees dated Sep. 29, 2017, which issued during the prosecution of Applicant's PCT/IL2017/050873.
European Search Report dated Jun. 29, 2017, which issued during the prosecution of Applicant's European App No. 11809374.9.
An Invitation to pay additional fees dated Oct. 11, 2018, which issued during the prosecution of Applicant's PCT/IL2018/050725.
An Office Action dated Dec. 4, 2018, which issued during the prosecution of U.S. Appl. No. 16/045,059.
An Office Action together with the English translation dated Nov. 5, 2018 which issued during the prosecution of Chinese Patent Application No. 201680008328.5.
Notice of Allowance dated Sep. 25, 2018, which issued during the prosecution of U.S. Appl. No. 15/188,507.
European Search Report dated Sep. 26, 2018 which issued during the prosecution of Applicant's European App No. 18186784.7.
An Office Action dated Jun. 30, 2015, which issued during the prosecution of U.S. Appl. No. 14/522,987.
Notice of Allowance dated Dec. 13. 2013, which issued during the prosecution of U.S. Appl. No. 13/675,119.
An International Preliminary Report on Patentability dated Aug. 8, 2017, which issued during the prosecution of Applicant's PCT/IL2016/050125.

An Office Action dated Jan. 17, 2018, which issued during the prosecution of U.S. Appl. No. 14/763,004.
An Office Action dated Mar. 25, 2015, which issued during the prosecution of U.S. Appl. No. 12/840,463.
An Office Action dated Feb. 25, 2016, which issued during the prosecution of U.S. Appl. No. 14/522,987.
An Office Action dated Apr. 13, 2016, which issued during the prosecution of U.S. Appl. No. 14/626,267.
An Office Action dated Aug. 28, 2015, which issued during the prosecution of U.S. Appl. No. 14/237,264.
Maisano (2015) TCR presentation re Cardiovalve.
Notice of Allowance dated Sep. 29, 2016, which issued during the prosecution of U.S. Appl. No. 14/442,541.
Notice of Allowance dated May 10, 2016, which issued during the prosecution of U.S. Appl. No. 14/237,258.
Notice of Allowance dated May 20, 2016, which issued during the prosecution of U.S. Appl. No. 14/237,258.
An International Preliminary Report on Patentability dated May 19, 2015, which issued during the prosecution of Applicant's PCT/IL2013/050937.
Dusan Pavcnik, MD, PhD2, et al; "Development and Initial Experimental Evaluation of a Prosthetic Aortic Valve for Transcatheter Placement", Cardiovascular Radiology. Radiology Apr. 1992, vol. 183, pp. 151-154.
Notice of Allowance dated Oct. 16, 2013, which issued during the prosecution of U.S. Appl. No. 13/675,119.
Notice of Allowance dated Feb. 11, 2015, which issued during the prosecution of U.S. Appl. No. 13/033,852.
Notice of Allowance dated May 5, 2015, which issued during the prosecution of U.S. Appl. No. 12/840,463.
Notice of Allowance dated Mar. 10, 2015, which issued during the prosecution of U.S. Appl. No. 13/811,308.
Notice of Allowance dated July 1, 2016, which issued during the prosecution of U.S. Appl. No. 14/442,541.
An Office Action dated Mar. 25, 2019, which issued during the prosecution of European Patent Application No. 14710060.6.
An International Search Report and a Written Opinion both dated Nov. 9, 2018, which issued during the prosecution of Applicant's PCT/IL2018/050869.
An International Search Report and a Written Opinion both dated Dec. 5, 2018, which issued during the prosecution of Applicant's PCT/IL2018/050725.
An International Search Report and a Written Opinion both dated Apr. 25. 2019, which issued during the prosecution of Applicant's PCT/IL2019/050142.
An International Preliminary Report on Patentability dated Feb. 12. 2019, which issued during the prosecution of Applicant's PCT/IL2017/050873.
An Office Action dated Sep. 13, 2019, which issued during the prosecution of U.S. Appl. No. 16/460,313.
An Office Action dated Nov. 26, 2019, which issued during the prosecution of U.S. Appl. No. 16/532,945.
An Office Action dated Aug. 16, 2019, which issued during the prosecution of U.S. Appl. No. 15/668,659.
An Office Action dated Nov. 1, 2019, which issued during the prosecution of U.S. Appl. No. 15/872,501.
An Office Action dated Jun. 14, 2019, which issued during the prosecution of U.S. Appl. No. 15/703,385.
An Office Action dated Oct. 4, 2019, which issued during the prosecution of U.S. Appl. No. 16/183,140.
An Office Action dated Jun. 13, 2019, which issued during the prosecution of U.S. Appl. No. 16/388,038.
An International Preliminary Report on Patentability dated Feb. 4, 2020, which issued during the prosecution of Applicant's PCT/IL2018/050725.
An International Search Report and a Written Opinion both dated Jan. 25. 2019, which issued during the prosecution of Applicant's PCT/IL2018/051122.
An International Search Report and a Written Opinion both dated May 13, 2019, which issued during the prosecution of Applicant's PCT/IL2018/051350.

(56) References Cited

OTHER PUBLICATIONS

An International Preliminary Report on Patentability dated Feb. 5, 2019, which issued during the prosecution of Applicant's PCT/IL2017/050849.
An Office Action dated Oct. 25, 2018, which issued during the prosecution of U.S. Appl. No. 14/763,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
An Office Action dated Aug. 1, 2019, which issued during the prosecution of U.S. Appl. No. 15/668,559.
An Office Action dated Jun. 19, 2019, which issued during the prosecution of U.S. Appl. No. 15/682,789.
Notice of Allowance dated Jan. 13, 2020, which issued during the prosecution of U.S. Appl. No. 15/956,956.
An Office Action dated Jun. 25. 2019, which issued during the prosecution of U.S. Appl. No. 15/329,920.
An Office Action dated May 16, 2019, which issued during the prosecution of U.S. Appl. No. 15/433,547.
U.S. Appl. No. 62/560,384, filed Sep. 19, 2017.
U.S. Appl. No. 62/112,343, filed Feb. 5, 2015.
An International Preliminary Report on Patentability dated Feb. 11. 2020. which issued during the prosecution of Applicant's PCT/IL2018/050869.
An International Preliminary Report on Patentability dated Oct. 20, 2020, which issued during the prosecution of Applicant's PCT/IL2019/050142.
An Office Action dated Jan. 6, 2020, which issued during the prosecution of U.S. Appl. No. 16/660,231.
An Office Action dated Dec. 31, 2019, which issued during the prosecution of U.S. Appl. No. 16/183,140.
Notice of Allowance dated Apr. 24, 2019, which issued during the prosecution of U.S. Appl. No. 16/045,059.
An Office Action dated Jan. 14, 2020, which issued during the prosecution of U.S. Appl. No. 16/284,331.
European Search Report dated Mar. 5, 2020 which issued during the prosecution of Applicant's European App No. 17752184.6.
European Search Report dated Mar. 4, 2020 which issued during the prosecution of Applicant's European App No. 16706913.7.
Notice of Allowance dated Mar. 12, 2020, which issued during the prosecution of U.S. Appl. No. 16/460,313.
An Office Action dated Jan. 9, 2020, which issued during the prosecution of U.S. Appl. No. 15/600,190.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.
Notice of Allowance dated Jan. 16, 2020, which issued during the prosecution of U.S. Appl. No. 16/532,945.
Notice of Allowance dated Aug. 19, 2020, which issued during the prosecution of U.S. Appl. No. 16/637,166.
Notice of Allowance dated Jul. 27, 2020, which issued during the prosecution of U.S. Appl. No. 16/637,166.
Notice of Allowance dated Jun. 23, 2020, which issued during the prosecution of U.S. Appl. No. 16/637,166.
Notice of Allowance dated May 7, 2020, which issued during the prosecution of U.S. Appl. No. 16/637,166.
Sündermann, Simon H., et al. "Feasibility of the Engager™ aortic transcatheter valve system using a flexible over-the-wire design." European Journal of Cardio-Thoracic Surgery 42.4 (2012): e48-e52.

An Office Action summarized English translation and Search Report dated Jul. 3, 2020, which issued during the prosecution of Chinese Patent Application No. 201780061210.3.
Serruys, P. W., Piazza, N., Cribier, A., Webb, J., Laborde, J. C., & de Jaegere, P. (Eds.). (2009). Transcatheter aortic valve implantation: tips and tricks to avoid failure. CRC Press.—Screenshots from Google Books downloaded from: https://books.google.co.il/books?id=FLzLBQAAQBAJ&lpg=PA198&ots=soqWrDH-y_&dq=%20%22Edwards%20SAPIEN%22&lr&pg=PA20#v=onepage&q=%22Edwards%20SAPIEN%22&f=false ; Downloaded on Jun. 18, 2020.
An International Search Report and a Written Opinion both dated Jun. 24, 2020, which issued during the prosecution of Applicant's PCT/IL2019/051398.
An Office Action dated Jul. 14, 2020, which issued during the prosecution of U.S. Appl. No. 16/324,339.
Notice of Allowance dated Aug. 28, 2020, which issued during the prosecution of U.S. Appl. No. 16/324,339.
Notice of Allowance dated Jul. 29, 2020, which issued during the prosecution of U.S. Appl. No. 16/132,937.
An Office Action dated Jul. 29, 2020, which issued during the prosecution of U.S. Appl. No. 16/269,328.
Notice of Allowance dated Aug. 26, 2020, which issued during the prosecution of U.S. Appl. No. 16/269,328.
An Office Action dated Aug. 7, 2020, which issued during the prosecution of U.S. Appl. No. 15/668,659.
Tchetche, D. and Nicolas M. Van Mieghem: "New-generation TAVI devices: description and specifications" EuroIntervention, 2014, No. 10:U90-U100.
An Office Action dated Aug. 23, 2019, which issued during the prosecution of U.S. Appl. No. 15/600,190.
Symetis S.A.: "ACURATE neo™ Aortic Bioprosthesis for Implantation using the ACURATE neo™ TA Transapical Delivery System in Patients with Severe Aortic Stenosis," Clinical Investigation Plan, Protocol No. 2015-01, Vs. No. 2, 2015:1-76.
Notice of Allowance dated Sep. 10, 2020, which issued during the prosecution of U.S. Appl. No. 15/600,190.
Notice of Allowance dated Sep. 10, 2020, which issued during the prosecution of U.S. Appl. No. 16/324,339.
Notice of Allowance dated Oct. 19, 2020, which issued during the prosecution of U.S. Appl. No. 16/324,339.
Notice of Allowance dated Sep. 21, 2020, which issued during the prosecution of U.S. Appl. No. 16/269,328.
Notice of Allowance dated Oct. 28, 2020, which issued during the prosecution of U.S. Appl. No. 16/269,328.
Notice of Allowance dated Jan. 16, 2020, which issued during the prosecution of U.S. Appl. No. 15/872,501.
An Office Action dated May 11, 2020, which issued during the prosecution of U.S. Appl. No. 16/811,732.
An Office Action dated Sep. 24, 2020, which issued during the prosecution of U.S. Appl. No. 16/811,732.
Notice of Allowance dated Mar. 29, 2017, which issued during the prosecution of U.S. Appl. No. 14/161,921.
Agarwal et al. International Cardiology Perspective Functional Tricuspid Regurgitation, Circ Cardiovasc Interv 2009;2;2;565-573 (2009).
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri, "The edge-to-edge repair of the mitral valve," [Abstract] 6th Annual NewEra Cardiac Care: Innovation & Technology, Heart Surgery Forum pp. 103. (2000).
Alfieri et al."Novel Suture Device for Beating-Heart Mitral Leaflet Approximation", Ann Thorac Surg. 2002, 74:1488-1493.
Alfieri et al., "The edge to edge technique," The European Association for Cardio-Thoracic Surgery 14th Annual Meeting Oct. 7-11, Book of Procees. (2000).
Amplatzer Cardiac Plug brochure (English pages), AGA Medical Corporation (Plymouth, MN) (copyright 2008-2010, downloaded Jan. 11, 2011).

(56) References Cited

OTHER PUBLICATIONS

Amplatzer® Cribriform Occluder. A patient guide to Percutaneous, Transcatheter, Atrial Septal Defect Closuer, AGA Medical Corporation, Apr. 2008.
Amplatzer® Septal Occluder. A patient guide to the Non-Surgical Closuer of the Atrial Septal Defect Using the Amplatzer Septal Occluder System, AGA Medical Corporation, Apr. 2008.
Brennan, Jennifer, 510(k) Summary of safety and effectiveness, Jan. 2008.
Dictionary.com definition of "lock", Jul. 29, 2013.
Dang NC et al. "Simplified Placement of Multiple Artificial Mitral Valve Chords," The Heart Surgery Forum #2005-1005, 8 (3) (2005).
Maisano, The double-orifice technique as a standardized approach to treat mitral . . . , European Journal of Cardio-thoracic Surgery 17 (2000) 201-205.
"Two dimensional real-time ultrasonic imaging of the heart and great vessels", Mayo Clin Proc. vol. 53:271-303, 1978.
Odell JA et al., "Early Results o4yf a Simplified Method of Mitral Valve Annuloplasty," Circulation 92:150-154 (1995).
O'Reilly S et al., "Heart valve surgery pushes the envelope," Medtech Insight 8(3):73, 99-108 (2006).
Swain CP et al., "An endoscopically deliverable tissue-transfixing device for securing biosensors in the gastrointestinal tract," Gastrointestinal Endoscopy 40(6): 730-734 (1994).
An Invitation to pay additional fees dated Jan. 31, 2014, which issued during the prosecution of Applicant's PCT/IL2013/050860.
U.S. Appl. No. 62/030,715, filed Jul. 30, 2014.
U.S. Appl. No. 62/139,854, filed Mar. 30, 2015.
U.S. Appl. No. 61/312,412, filed Mar. 10, 2010.
An Invitation to pay additional fees dated Jan. 31, 2014, which issued during the prosecution of Applicant's PCT/IL2013/050861.
An International Preliminary Report on Patentability dated Dec. 23, 2013, which issued during the prosecution of Applicant's PCT/IL2012/000250.
An International Preliminary Report on Patentability dated Sep. 18, 2007, which issued during the prosecution of Applicant's PCT/IL2006/000342.
An International Preliminary Report on Patentability dated Jun. 5, 2012, which issued during the prosecution of Applicant's PCT/IL2010/001024.
An International Preliminary Report on Patentability dated Apr. 28, 2015, which issued during the prosecution of Applicant's PCT/IL2013/050861.
An International Preliminary Report on Patentability dated Apr. 26, 2016, which issued during the prosecution of Applicant's PCT/IL2014/050914.
An International Preliminary Report on Patentability dated Jun. 10, 2009, which issued during the prosecution of Applicant's PCT/IL07/01503.
An International Preliminary Report on Patentability dated Dec. 18, 2010. which issued during the prosecution of Applicant's PCT/IL09/00593.
An International Preliminary Report on Patentability dated Jun. 29, 2011, which issued during the prosecution of Applicant's PCT/IL2009/001209.
Notice of Allowance dated Aug. 18, 2017, which issued during the prosecution of U.S. Appl. No. 14/689,608.
Notice of Allowance dated Jul. 6, 2017, which issued during the prosecution of U.S. Appl. No. 14/689,608.
Notice of Allowance dated May 22, 2017, which issued during the prosecution of U.S. Appl. No. 14/689,608.
An Office Action dated Apr. 21, 2017, which issued during the prosecution of U.S. Appl. No. 15/213,791.
An Office Action dated Sep. 29, 2017, which issued during the prosecution of U.S. Appl. No. 15/197,069.
An International Preliminary Report on Patentability dated Nov. 9, 2011, which issued during the prosecution of Applicant's PCT/IL2010/000357.
An International Preliminary Report on Patentability dated Nov. 9, 2011 which issued during the prosecution of Applicant's PCT/IL2010/000358.
An International Preliminary Report on Patentability dated Nov. 27, 2012, which issued during the prosecution of Applicant's PCT/IL2011/000404.
An International Preliminary Report on Patentability dated Feb. 4, 2014, which issued during the prosecution of Applicant's PCT/IL2011/000446.
An International Preliminary Report on Patentability dated Jan. 29, 2013, which issued during the prosecution of Applicant's PCT/IL2011/000600.
An International Preliminary Report on Patentability dated Dec. 23, 2014, which issued during the prosecution of Applicant's PCT/IL2012/050451.
A Notice of Allowance dated Jul. 30. 2015, which issued during the prosecution of U.S. Appl. No. 13/319,007.
An Office Action dated Sep. 29, 2014, which issued during the prosecution of U.S. Appl. No. 13/504,870.
An Office Action dated 13, 2015, which during the prosecution of U.S. Appl. No. 13/707,013.
An Office Action dated Mar. 23, 2015, which issued during the prosecution of U.S. Appl. No. 13/707,013.
Notice of Allowance dated Mar. 25, 2015, which issued during the prosecution of U.S. Appl. No. 13/749,153.
An Office Action dated Oct. 3, 2014, which issued during the prosecution of U.S. Appl. No. 13/749,53.
Notice of Allowance dated May 22, 2015, which issued during the prosecution of U.S. Appl. No. 13/749,153.
Notice of Allowance dated Aug. 3, 2015, which issued during the prosecution of U.S. Appl. No. 13/749,153.
An Office Action dated Dec. 19, 2013, which issued during the prosecution of U.S. Appl. No. 14/027,934.
An Office Action dated Jun. 11, 2014, which issued during the prosecution of U.S. Appl. No. 14/027,934.
An Office Action dated Aug. 22, 2014, which issued during the prosecution of U.S. Appl. No. 14/027,934.
An Office Action dated Apr. 2, 2015, which issued during the prosecution of U.S. Appl. No. 14/027,934.
An Office Action dated Jan. 5, 2016, which issued during the prosecution of U.S. Appl. No. 14/027,934
An Office Action dated Jan. 5, 2016, which issued during the prosecution of U.S. Appl. No. 14/084,426.
An Office Action dated Mar. 16, 2015, which issued during the prosecution of U.S. Appl. No. 14/084,426.
An Office Action dated Jan. 6, 2016, which issued during the prosecution of U.S. Appl. No. 14/128,756.
An Office Action dated May 11, 2016, which issued during the prosecution of U.S. Appl. No. 14/128,756.
Notice of Allowance dated Oct. 20, 2015, which issued during the prosecution of U.S. Appl. No. 12/996,954.
Notice of Allowance dated Feb. 19, 2014, which issued during the prosecution of U.S. Appl. No. 12/795,192.
An Office Action dated Jul. 20, 2012, which issued during the prosecution of U.S. Appl. No. 12/843,412.
An Office Action dated Mar. 27, 2013, which issued during the prosecution of U.S. Appl. No. 12/843,412.
A Restriction Requirement dated May 1, 2012, which issued during the prosecution of U.S. Appl. No. 12/843,412.
A Notice of Allowance dated May 2, 2013, which issued during the prosecution of U.S. Appl. No. 12/843,412.
A Restriction Requirement dated Nov. 19, 2012, which issued during the prosecution of U.S. Appl. No. 12/926,673.
An Office Action dated Feb. 12, 2013, which issued during the prosecution of U.S. Appl. No. 12/926,673.
An Office Action dated Oct. 22, 2013, which issued during the prosecution of U.S. Appl. No. 12/926,673.
A Notice of Allowance dated Jan. 7, 2014, which issued during the prosecution of U.S. Appl. No. 12/926,673.
An Office Action dated Oct. 9, 2013, which issued during the prosecution of U.S. Appl. No. 12/996,954.
An Office Action dated Mar. 24, 2015, which issued during the prosecution of U.S. Appl. No. 12/996,954.

(56) References Cited

OTHER PUBLICATIONS

An Office Action dated Oct. 5, 2012, which issued during the prosecution of U.S. Appl. No. 12/996,954.
Notice of Allowance dated Jul. 7, 2015, which issued during the prosecution of U.S. Appl. No. 12/996,954.
An Office Action dated Nov. 16, 2018, which issued during the prosecution of U.S. Appl. No. 16/042,028.
An International Search Report with Written Opinion both dated Feb. 2, 2012, which issued during the prosecution of Applicant's PCT/IL2011/000600.
An International Search Report together with Written Opinion both dated Mar. 30, 2011, which issued during the prosecution of Applicant's PCT/IL2010/001024.
An International Search Report and A Written Opinion both dated Feb. 10, 2011, which issued during the prosecution of Applicant's PCT/IL10/00890.
An Office Action dated May 28, 2015, which issued during the prosecution of U.S. Appl. No. 14/128,756.
An Office Action dated Sep. 6, 2018, which issued during the prosecution of U.S. Appl. No. 15/994,022.
An Office Action dated Sep. 7, 2018, which issued during the prosecution of U.S. Appl. No. 15/995,725.
An Office Action dated Nov. 26, 2018, which issued during the prosecution of U.S. Appl. No. 16/040,831.
An Office Action dated Jul. 11, 2018, which issued during the prosecution of U.S. Appl. No. 15/978,494.
An Office Action dated Nov. 23, 2018, which issued during the prosecution of U.S. Appl. No. 16/041,208.
An Office Action dated Jun. 15, 2018, which issued during the prosecution of U.S. Appl. No. 15/970,314.
An Office Action dated. Oct. 12, 2018, which issued during the prosecution of U.S. Appl. No. 15/970,314.
An Office Action dated Jul. 26, 2018, which issued during the prosecution of U.S. Appl. No. 15/979,686.
An Office Action dated Sep. 10, 2018, which issued during the prosecution of U.S. Appl. No. 16/008,618.
An International Preliminary Report on Patentability dated Apr. 28, 2015, which issued during the prosecution of Applicant's PCT/IL2013/050860.
An Office Action dated Apr. 22, 2019, which issued during the prosecution of U.S. Appl. No. 15/668,559.
Notice of Allowance dated Aug. 30, 2019, which issued during the prosecution of U.S. Appl. No. 15/682,789.
Notice of Allowance dated Mar. 29, 2019, which issued during the prosecution of U.S. Appl. No. 15/541,783.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
An Advisory Action dated Dec. 13, 2013, which issued during the prosecution of U.S. Appl. No. 12/961,721.
An Office Action dated Aug. 7, 2015, which issued during the prosecution of U.S. Appl. No. 14/128,756.
An Office Action dated May 19, 2011, which issued during the prosecution of U.S. Appl. No. 12/706,868.
An Office Action dated Sep. 1, 2011, which issued during the prosecution of U.S. Appl. No. 12/706,868.
An Office Action dated May 30, 2012, which issued during the prosecution of U.S. Appl. No. 12/706,868.
A Notice of Allowance dated Sep. 18, 2012, which issued during the prosecution of U.S. Appl. No. 12/706,868.
Restriction Requirement dated May 5, 2011, which issued during the prosecution of U.S. Appl. No. 12/706,868.
A Restriction Requirement dated Mar. 30, 2012, which issued during the prosecution of U.S. Appl. No. 12/785,717.
An Office Action dated Oct. 5, 2020, which issued during the prosecution of Canadian Patent Application No. 2,973,940.
An Office Action dated Nov. 30, 2020, which issued during the prosecution of U.S. Appl. No. 16/138,129.
An Office Action summarized English translation and Search Report dated Nov. 25, 2020, which issued during the prosecution of Chinese Patent Application No. 201910449820.1.
Notice of Allowance dated Nov. 19, 2020, which issued during the prosecution of U.S. Appl. No. 16/318,025.
An Office Action dated Aug. 2, 2011, which issued during the prosecution of U.S. Appl. No. 12/435,291.
Notice of Allowance dated Dec. 7, 2011, which issued during the prosecution of U.S. Appl. No. 12/435,291.
An Office Action dated Apr. 6, 2010, which issued during the prosecution of Applicant's U.S. Appl. No. 12/484,512.
An Office Action dated Oct. 6, 2010, which issued during the prosecution of Applicant's U.S. Appl. No. 12/484,512.
Notice of Allowance dated Apr. 20, 2011, which issued during the prosecution of U.S. Appl. No. 12/484,512.
Notice of Allowance dated Mar. 23, 2011, which issued during the prosecution of U.S. Appl. No. 12/484,512.
An Office Action dated Jan. 27, 2012, which issued during the prosecution of U.S. Appl. No. 12/548,991.
An Office Action dated Aug. 6, 2012, which issued during the prosecution of U.S. Appl. No. 12/548,991.
An Advisory Action dated Sep. 6, 2012 which issued during the prosecution of U.S. Appl. No. 12/548,991.
Notice of Allowance dated Jun. 23, 2014, which issued during the prosecution of U.S. Appl. No. 12/548,991.
A Restriction Requirement dated Nov. 14, 2011 which issued during the prosecution of U.S. Appl. No. 12/548,991.
Amendment, Terminal Disclaimer and Extension dated Jun. 27, 2012, which issued during the prosecution of U.S. Appl. No. 12/548,991.
A Restriction Requirement dated Jul. 5, 2012, which issued during the prosecution of U.S. Appl. No. 12/563,930.
An Office Action dated Apr. 2, 2013, which issued during the prosecution of U.S. Appl. No. 12/785,717.
An Office Action dated Dec. 27, 2013, which issued during the prosecution of U.S. Appl. No. 12/785,717.
An Office Action dated Nov. 5, 2012, which issued during the prosecution of U.S. Appl. No. 12/795,026.
An Office Action dated May 10, 2012, which issued during the prosecution of U.S. Appl. No. 12/795,026.
Notice of Allowance dated Nov. 13, 2014, which issued during the prosecution of U.S. Appl. No. 12/795,026.
Notice of Allowance dated Dec. 24, 2014, which issued during the prosecution of U.S. Appl. No. 12/795,026.
A Restriction Requirement dated Jan. 6, 2012, which issued during the prosecution of U.S. Appl. No. 12/795,026.
A Restriction Requirement dated Sep. 14, 2012, which issued during the prosecution of U.S. Appl. No. 12/795,192.
An Office Action dated Aug. 15, 2013, which issued during the prosecution of U.S. Appl. No. 12/795,192.
An Office Action dated Jan. 17, 2013, which issued during the prosecution of U.S. Appl. No. 12/795,192.
Notice of Allowance dated Nov. 19, 2013, which issued during the prosecution of U.S. Appl. No. 12/795,192.
A Notice of Allowance dated Jun. 26, 2012, which issued during the prosecution of U.S. Appl. No. 12/608,316.
An Office Action dated Nov. 14. 2011, which issued during the prosecution of U.S. Appl. No. 12/608,316.
A Restriction Requirement dated Apr. 1, 2011, which issued during the prosecution of U.S. Appl. No. 12/608,316.
An Office Action dated Jul. 6, 2012, which issued during the prosecution of U.S. Appl. No. 12/692,061.
An Office Action dated Jan. 23, 2012, which issued during the prosecution of U.S. Appl. No. 12/692,061.
An Office Action dated Mar. 9, 2012, which issued during the prosecution of U.S. Appl. No. 12/689,635.
An Office Action dated Nov. 30, 2012, which issued during the prosecution of U.S. Appl. No. 12/689,635.
A Notice of Allowance dated May 22, 2013, which issued during the prosecution of U.S. Appl. No. 12/689,635.
Restriction Requirement dated Nov. 14, 2011, which issued during the prosecution of U.S. Appl. No. 12/689,635.

(56) References Cited

OTHER PUBLICATIONS

An Office Action dated May 6, 2013, which issued during the prosecution of U.S. Appl. No. 12/689,693.
An Office Action dated Feb. 3, 2014, which issued during the prosecution of U.S. Appl. No. 12/689,693.
Notice of Allowance dated Jun. 11, 2014, which issued during the prosecution of U.S. Appl. No. 12/689,693.
A Restriction Requirement dated Sep. 17, 2012, which issued during the prosecution of U.S. Appl. No. 12/689,693.
A Notice of Allowance dated Sep. 3, 2014, which issued during the prosecution of U.S. Appl. No. 12/689,693.
European Search Report dated Jul. 8, 2016, which issued during the prosecution of Applicant's European App No. 13849843.1.
A Supplementary European Search Report dated Dec. 4, 2012, which issued during the prosecution of European Patent Application No. EP09834225.6.
A Supplementary European Search Report dated Mar. 28, 2013, which issued during the prosecution of European Patent Application No. EP 1077 2091.4.
Search Report in European Patent Application 10772090.6 dated Jan. 17, 2014.
Supplementary European Search Report dated Oct. 23, 2014 which issued during the prosecution of Applicant's European App No. 10826224.7.
Notice of Allowance dated May 6, 2016, which issued during the prosecution of U.S. Appl. No. 14/667,090.
Notice of Allowance dated Apr. 12, 2016, which issued during the prosecution of U.S. Appl. No. 14/667,090.
An Office Action dated Jun. 7, 2013 which issued during the prosecution of U.S. Appl. No. 13/141,606.
An Office Action dated Jun. 13, 2014, which issued during the prosecution of U.S. Appl. No. 13/141,606.
Notice of Allowance dated Sep. 29, 2014, which issued during the prosecution of U.S. Appl. No. 13/141,606.
An Office Action dated Feb. 4, 2013 which issued during the prosecution of U.S. Appl. No. 13/141,606.
An English translation of an Office Action dated Apr. 23, 2014 which issued during the prosecution of Chinese Patent Application No. 201080059948.4.
Communication dated Jul. 25, 2014, issued by the State Intellectual Property Office of the P.R. of China in counterpart Application No. 200980157331.3.
An International Search Report and a Written Opinion both dated Jan. 25, 2016, which issued during the prosecution of Applicant's PCT/IL2015/051027.
An International Search Report dated May 19, 2011, which issued during the prosecution of Applicant's PCT/IL2011/00064.
An International Search Report and a Written Opinion both dated Feb. 22, 2013, which issued during the prosecution of Applicant's PCT/IL201/050451.
An International Search Report & Written Opinion both dated Mar. 21, 2014, which issued during the prosecution of Applicant's PCT/IL13/50992.
An International Search Report and Written Opinion both dated Apr. 9, 2014, which issued during the prosecution of Applicant's PCT/IL13/50860.
An International Search Report and a Written Opinion both dated Apr. 15, 2014, which issued during the prosecution of Applicant's PCT/IL2013/050861.
An International Search Report & Written Opinion both dated May 12, 2015, which issued during the prosecution of Applicant's PCT/IL2014/050914.
An International Search Report and a Written Opinion both dated May 30, 2007, which issued during the prosecution of Applicant's PCT/IL2006/000342.
An International Search Report and a Written Opinion both dated Jun. 10, 2010, which issued during the prosecution of Applicant's PCT/IL09/01209.
An International Search Report and a Written Opinion both dated Aug. 17, 2010. which issued during the prosecution of Applicant's PCT/IL10/00357.
An International Search Report & Written Opinion both dated Sep. 8, 2009, which issued during the prosecution of Applicant's PCT/IL09/00593.
An International Search Report and a Written Opinion both dated Sep. 12, 2008, which issued during the prosecution of Applicant's PCT/IL07/01503.
An International Search Report and Written Opinion dated Nov. 8, 2010, which issued during the prosecution of Applicant's PCT/IL2010/000358.
An International Search Report and a Written Opinion both dated Nov. 23, 2011, which issued during the prosecution of Applicant's PCT/IL2011/000446.
Supplementary European Search Report dated Sep. 25, 2015, which issued during the prosecution of Applicant's European App No. 09794095.1.
A Supplementary European Search Report dated Feb. 1, 2011, which issued during the prosecution of European Patent Application No. EP 07849540.
An English translation of an Office Action dated Dec. 12, 2013 which issued during the prosecution of Chinese Patent Application No. 200980157331.3.
Communication regarding amended claims filed dated Dec. 27, 2012, regarding European App No. 11792047.0.
An Office Action dated Mar. 23, 2015, which issued during the prosecution of European Patent Application No. EP 09834225.6.
An English translation of an Office Action dated Jul. 17, 2015 which issued during the prosecution of Chinese Patent Application No. 201080059948.4.
An English translation of an Office Action dated Dec. 16, 2015 which issued during the prosecution of Chinese Patent Application No. 201080059948.4.
Communication from the European Patent Office dated Jun. 11, 2015, which issued during the prosecution of European Patent Application No. 11811934.
A communication from the European Patent Office dated Sep. 28, 2011 which issued during the prosecution of European Application No. 09834225.6.
A communication from the European Patent Office dated Oct. 19, 2012 which issued during the prosecution of European Application No. 11792047.0.
An Office Action dated Oct. 23, 2012, which issued during the prosecution of Japanese Patent Application No. 2009-539871.
An English Translation of an Office Action dated Nov. 24, 2015, which issued during the prosecution of Israel Patent Application No. 223448. (the relevant part only).
Notice of Allowance dated Nov. 17, 2015, which issued during the prosecution of U.S. Appl. No. 14/486,226.
Notice of Allowance dated Jan. 29, 2016, which issued during the prosecution of U.S. Appl. No. 14/551,951.
An Office Action dated Jun. 18, 2015, which issued during the prosecution of U.S. Appl. No. 14/551,951.
An Office Action dated Jan. 4, 2016, which issued during the prosecution of U.S. Appl. No. 14/589,100.
An Office Action dated May 4, 2016, which issued during the prosecution of U.S. Appl. No. 14/589,100.
An International Search Report and a Written Opinion both dated Nov. 14, 2011, which issued during the prosecution of Applicant's PCT/IL2011/000404.
An International Search Report and a Written Opinion both dated Dec. 6, 2012 which issued during the prosecution of Applicant's PCT/IL2012/000250.
A Notice of Allowance dated Apr. 3, 2013, which issued during the prosecution of U.S. Appl. No. 12/563,930.
An Office Action dated Aug. 24, 2012, which issued during the prosecution of U.S. Appl. No. 12/563,930.
An Office Action dated Dec. 29, 2011, which issued during the prosecution of U.S. Appl. No. 12/563,952.
A Restriction Requirement dated Oct. 27, 2011, which issued during the prosecution of U.S. Appl. No. 12/563,952.

(56) References Cited

OTHER PUBLICATIONS

A Notice of Allowance dated May 24, 2012, which issued during the prosecution of U.S. Appl. No. 12/563,952.
An Office Action dated Apr. 1, 2013 which issued during the prosecution of U.S. Appl. No. 13/167,476.
An Office Action dated Nov. 21, 2013, which issued during the prosecution of U.S. Appl. No. 13/167,476.
An Advisory Action dated Feb. 4, 2014, which issued during the prosecution of U.S. Appl. No. 13/167,476.
A Restriction Requirement dated Oct. 25, 2012 which issued during the prosecution of U.S. Appl. No. 13/167,444.
An Office Action dated Jan. 17, 2013, which issued during the prosecution of U.S. Appl. No. 13/167,444.
An Office Action dated Aug. 26, 2014 which issued during the prosecution of U.S. Appl. No. 13/167,444.
An Office Action dated Aug. 23, 2013 which issued during the prosecution of U.S. Appl. No. 13/167,444.
Notice of Allowance dated Nov. 12, 2015, which issued during the prosecution of U.S. Appl. No. 13/319,007.
Notice of Allowance dated Jan. 7, 2016, which issued during the prosecution of U.S. Appl. No. 13/319,007.
An Office Action dated Oct. 2, 2013, which issued during the prosecution of U.S. Appl. No. 13/167,492.
A Restriction Requirement dated Nov. 2, 2012, which issued during the prosecution of U.S. Appl. No. 13/167,492.
An Office Action dated Feb. 14, 2013 which issued during the prosecution of U.S. Appl. No. 13/167,492.
Notice of Allowance dated Nov. 7, 2014, which issued during the prosecution of U.S. Appl. No. 13/167,492.
An Office Action dated Jun. 10, 2014, which issued during the prosecution of U.S. Appl. No. 13/167,492.
Notice of Allowance dated Dec. 9, 2014, which issued during the prosecution of U.S. Appl. No. 13/167,476.
Notice of Allowance dated Jan. 22, 2015, which issued during the prosecution of U.S. Appl. No. 13/167,444.
An International Preliminary Report on Patentability dated May 1, 2012, which issued during the prosecution of Applicant's PCT/IL2010/000890.
An International Preliminary Report on Patentability dated Jun. 9, 2015, which issued during the prosecution of Applicant's PCT/IL2013/050992.
U.S. Appl. No. 60/873,075, filed Dec. 5, 2006.
U.S. Appl. No. 60/902,146, filed Feb. 16, 2007.
An Office Action dated Mar. 29, 2018, which issued during the prosecution of U.S. Appl. No. 12/961,721.
Notice of Allowance dated Sep. 17, 2014, which issued during the prosecution of U.S. Appl. No. 12/961,721.
An Office Action dated Oct. 1, 2015, which issued during the prosecution of U.S. Appl. No. 14/141,228.
A Restriction Requirement dated Jun. 2, 2014, which issued during the prosecution of U.S. Appl. No. 13/319,030.
An Office Action dated Oct. 14, 2014, which issued during the prosecution of U.S. Appl. No. 13/319,030.
An Office Action dated Jun. 18, 2015, which issued during the prosecution of U.S. Appl. No. 13/319,030.
An Office Action dated May 3, 2016, which issued during the prosecution of U.S. Appl. No. 13/319,030.
Notice of Allowance dated Dec. 30, 2016, which issued during the prosecution of U.S. Appl. No. 13/319,030.
An Office Action dated Apr. 7, 2015, which issued during the prosecution of U.S. Appl. No. 13/319,007.
An Office Action dated Apr. 8, 2016, which issued during the prosecution of U.S. Appl. No. 14/141,228.
An Office Action dated Oct. 5, 2015, which issued during the prosecution of U.S. Appl. No. 14/246,417.
An Office Action dated Apr. 7, 2016, which issued during the prosecution of U.S. Appl. No. 14/242,151.
An Office Action dated May 23, 2016, which issued during the prosecution of U.S. Appl. No. 14/209,171.
An Office Action dated Jul. 20, 2016, which issued during the prosecution of U.S. Appl. No. 14/246,417.
An Office Action dated Jun. 14, 2016, which issued during the prosecution of U.S. Appl. No. 14/273,155.
An Office Action dated Jun. 17, 2016, which issued during the prosecution of U.S. Appl. No. 14/357,040.
An Office Action dated Mar. 24, 2015, which issued during the prosecution of U.S. Appl. No. 14/486,226.
U.S. Appl. No. 61/001,013, filed Oct. 29, 2007.
U.S. Appl. No. 61/132,295, filed Jun. 16, 2008.
U.S. Appl. No. 61/265,936, filed Dec. 2, 2009.
U.S. Appl. No. 61/283,445, filed Dec. 2, 2009.
U.S. Appl. No. 61/207,908, filed Feb. 17, 2009.
U.S. Appl. No. 61/733,979, filed Dec. 6, 2012.
U.S. Appl. No. 61/717,303, filed Oct. 23, 2012.
U.S. Appl. No. 61/820,979, filed May 8, 2013.
U.S. Appl. No. 61/745,848, filed Dec. 6, 2012.
U.S. Appl. No. 61/555,570, filed Nov. 4, 2011.
U.S. Appl. No. 61/557,082, filed Nov. 8, 2011.
U.S. Appl. No. 60/662,616, filed Mar. 17, 2005.
U.S. Appl. No. 60/700,542, filed Jul. 18, 2005.
U.S. Appl. No. 61/782,121, filed Mar. 14, 2013.
European Search Report dated Jul. 15, 2016, which issued during the prosecution of Applicant's European App No. 13849947.0.
European Search Report dated Nov. 4, 2015, which issued during the prosecution of European Patent Application No. EP 1077 2091.4.
Search Report in European Patent Application 10826224.7 dated Nov. 16, 2015.
Supplementary European Search Report dated Dec. 23, 2014 which issued during the prosecution of Applicant's European App No. 10834311.
Supplementary European Search Report dated Jan. 21, 2014 which issued during the prosecution of Applicant's European App No. 11 78 6226.
A Supplementary European Search Report dated Jan. 20, 2015, which issued during the prosecution of European Patent Application No. 12803037.6.
Supplementary European Search Report dated Aug. 4, 2014 which issued during the prosecution of Applicant's European App No. 11 81 1934.6.
European Search Report dated Jun. 24, 2016, which issued during the prosecution of European Patent Application No. EP 12847363.
Supplementary European Search Report dated Apr. 29, 2015, which issued during the prosecution of Applicant's European App No. 14200202.
An Office Action dated Dec. 16, 2013, which issued during the prosecution of U.S. Appl. No. 13/666,262.
An Office Action dated Dec. 18, 2013, which issued during the prosecution of U.S. Appl. No. 13/666,141.
Notice of Allowance dated Jun. 25, 2014, which issued during the prosecution of U.S. Appl. No. 13/666,262.
A Notice of Allowance dated Feb. 2, 2015, which issued during the prosecution of U.S. Appl. No. 13/504,870.
Notice of Allowance dated Aug. 19, 2013, which issued during the prosecution of U.S. Appl. No. 11/908,906.
An Office Action dated Jun. 8, 2012, which issued during the prosecution of U.S. Appl. No. 11/908,906.
An Office Action dated Dec. 21, 2013, which issued during the prosecution of U.S. Appl. No. 11/908,906.
A Restriction Requirement dated Aug. 5, 2011, which issued during the prosecution of U.S. Appl. No. 11/908,906.
An Office Action dated Sep. 16, 2009 which issued during the prosecution of U.S. Appl. No. 11/950,930.
Notice of Allowance dated Sep. 12, 2014, which issued during the prosecution of U.S. Appl. No. 11/950,930.
An Office Action dated Aug. 5, 2010 which issued during the prosecution of U.S. Appl. No. 11/950,930.
An Office Action dated Feb. 17, 2010 which issued during the prosecution of U.S. Appl. No. 11/950,930.
A Restriction Requirement dated Apr. 19, 2010 which issued during the prosecution of U.S. Appl. No. 12/341,960.

(56) References Cited

OTHER PUBLICATIONS

An Office Action dated Sep. 28, 2011, which issued during the prosecution of U.S. Appl. No. 12/437,103.
An Office Action dated Jun. 13, 2012, which issued during the prosecution of U.S. Appl. No. 12/437,103.
A Restriction Requirement dated Jul. 12, 2011, which issued during the prosecution of U.S. Appl. No. 12/437,103.
Notice of Allowance dated Mar. 6, 2014, which issued during the prosecution of U.S. Appl. No. 12/437,103.
Notice of Allowance dated Dec. 20, 2013, which issued during the prosecution of U.S. Appl. No. 12/437,103.
Notice of Allowance dated Apr. 27, 2012, which issued during the prosecution of U.S. Appl. No. 12/341,960.
An Office Action dated Mar. 29, 2011, which issued during the prosecution of U.S. Appl. No. 12/341,960.
An Office Action dated Aug. 4, 2010, which issued during the prosecution of U.S. Appl. No. 12/341,960.
An Interview Summary dated Jul. 27, 2011, which issued during the prosecution of U.S. Appl. No. 12/341,960.
Notice of Allowance dated Aug. 21, 2019, which issued during the prosecution of U.S. Appl. No. 15/703,385.
Notice of Allowance dated Oct. 16, 2019, which issued during the prosecution of U.S. Appl. No. 15/703,385.
Notice of Allowance dated Dec. 24, 2020, which issued during the prosecution of U.S. Appl. No. 15/668,659.
Notice of Allowance dated Oct. 21, 2020, which issued during the prosecution of U.S. Appl. No. 15/668,659.
Declaration of Ivan Vesely, Ph.D., In Support of Petition for Inter PartesReview of U.S. Pat. No. 7,563,267—dated May 29, 2019.
U.S. Appl. No. 60/128,690, filed Apr. 9, 1999.
U.S. Appl. No. 60/613,867, filed Sep. 27, 2004.
An Office Action dated Dec. 24, 2020, which issued during the prosecution of U.S. Appl. No. 16/144,054.
An Office Action dated Feb. 2, 2021, which issued during the prosecution of U.S. Appl. No. 16/811,732.
An Office Action dated Jan. 13. 2021, which issued during the prosecution of European Patent Application No. 15751089.2.
An Office Action together with an English summary dated Mar. 3, 2021, which issued during the prosecution of Chinese Patent Application No. 201780047391.4.
Declaration of Dr. Ivan Vesely, Ph.D. in Support of Petition for Inter Partes Review of U.S. Pat. No. 10,226,341—dated Dec. 17, 2020.
Petition for Inter Partes Review of U.S. Pat. No. 10,226,341 and Exhibits 1001-1013—dated Dec. 29, 2020.
Batista, Randas JV, et al. "Partial left ventriculectomy to treat end-stage heart disease." The Annals of thoracic surgery 64.3 (1997): 634-638.
Beall Jr, Arthur C., et al. "Clinical experience with a dacron velour-covered teflon-disc mitral-valve prosthesis." The Annals of thoracic surgery 5.5 (1968): 402-410.
Kalbacher, D., et al. "1000 MitraClip™ procedures: Lessons learnt from the largest single-centre experience worldwide." (2019): 3137-3139.
Maisano, F., et al. "The edge-to-edge technique: a simplified method to correct mitral insufficiency." European journal of cardio-thoracic surgery 13.3 (1998): 240-246.
Fucci, C., et al. "Improved results with mitral valve repair using new surgical techniques." European journal of cardio-thoracic surgery 9.11 (1995): 621-627.
Notice of Allowance dated Nov. 19, 2019, which issued during the prosecution of U.S. Appl. No. 15/668,559.
Mitral Valve Academic Research Consortium. "Clinical Trial Design Principles and Endpoint Definitions for Transcatheter Mitral Valve Repair and Replacement: Part 1: Clinical Trial Design Principles a Consensus Document from the Mitral Valve Academic Research Consortium." Journal of the American College of Cardiology 66.3 (2015): 278-307.
An Office Action dated Aug. 29, 2018, which issued during the prosecution of U.S. Appl. No. 15/329,920.
An Office Action dated May 8, 2018, which issued during the prosecution of U.S. Appl. No. 15/902,403.
An Office Action dated May 11, 2018, which issued during the prosecution of U.S. Appl. No. 15/899,858.
Notice of Allowance dated Oct. 5, 2018, which issued during the prosecution of U.S. Appl. No. 15/886,517.
Notice of Allowance dated Jul. 19, 2019, which issued during the prosecution of U.S. Appl. No. 15/899,858.
Notice of Allowance dated Nov. 16, 2020, which issued during the prosecution of U.S. Appl. No. 16/324,339.
Notice of Allowance dated Apr. 27, 2020, which issued during the prosecution of U.S. Appl. No. 16/591,330.
An Advisory Action dated Jan. 2, 2020, which issued during the prosecution of U.S. Appl. No. 15/668,659.
Notice of Allowance dated Oct. 17, 2019, which issued during the prosecution of U.S. Appl. No. 15/329,920.
An Office Action dated Dec. 31, 2019, which issued during the prosecution of U.S. Appl. No. 16/591,330.
Notice of Allowance dated Feb. 9, 2021, which issued during the prosecution of U.S. Appl. No. 16/937,216.
An Advisory Action dated Nov. 18, 2020, which issued during the prosecution of U.S. Appl. No. 16/811,732.
An International Search Report and a Written Opinion both dated Mar. 27, 2018, which issued during the prosecution of Applicant's PCT/IL2017/050849.
Notice of Allowance dated Jun. 11, 2021, which issued during the prosecution of U.S. Appl. No. 16/811,732.
Notice of Allowance dated Jul. 16, 2021, which issued during the prosecution of U.S. Appl. No. 16/811,732.
Patent Trial and Appeal Board Decision Granting Institution in U.S. Pat. No. 10,226,341—Dated Jul. 20, 2021.
European Search Report dated Jun. 10, 2021 which issued during the prosecution of Applicant's European App No. 21157988.3.
Notice of Allowance dated Nov. 19, 2018, which issued during the prosecution of U.S. Appl. No. 15/197,069.
Poirier, Nancy C., et al. "A novel repair for patients with atrioventricular septal defect requiring reoperation for left atrioventricular valve regurgitation." European journal of cardio-thoracic surgery 18.1 (2000): 54-61.
An Office Action dated Mar. 29, 2021, which issued during the prosecution of U.S. Appl. No. 16/738,516.
Ando, Tomo, et al. "Iatrogenic ventricular septal defect following transcatheter aortic valve replacement: a systematic review." Heart, Lung and Circulation 25.10 (2016): 968-974.
Urena, Marina, et al. "Transseptal transcatheter mitral valve replacement using balloon-expandable transcatheter heart valves: a step-by-step approach." JACC: Cardiovascular Interventions 10.19 (2017): 1905-1919.
An English summary of an Official Action dated Mar. 29, 2021, which issued during the prosecution of Chinese Patent Application No. 201780061210.3.
An International Search Report and a Written Opinion both dated Jan. 28, 2020, which issued during the prosecution of Applicant's PCT/IL2019/051031.
An International Preliminary Report on Patentability dated Mar. 9, 2021, which issued during the prosecution of Applicant's PCT/IL2019/051031.
An Office Action dated May 4, 2021, which issued during the prosecution of U.S. Appl. No. 16/636,204.
Notice of Allowance dated May 17, 2021, which issued during the prosecution of U.S. Appl. No. 16/138,129.
Notice of Allowance dated Jun. 4, 2021, which issued during the prosecution of U.S. Appl. No. 16/802,353.
An Office Action dated May 12, 2021, which issued during the prosecution of Canadian Patent Application No. 2,973,940.
Petition for Inter Partes Review of U.S. Pat. No. 10,702,385—dated Jun. 4, 2021.
Declaration of Ivan Vesely, Ph.D. In Support of Petition for Inter Partes Review of U.S. Pat. No. 10,702,385—dated Jun. 4, 2021.
Notice of Allowance dated Oct. 30, 2018, which issued during the prosecution of U.S. Appl. No. 15/197,069.

(56) References Cited

OTHER PUBLICATIONS

An International Search Report and a Written Opinion both dated Jul. 12, 2021, which issued during the prosecution of Applicant's PCT/IL2021/050132.
Notice of Allowance dated Oct. 3, 2019, which issued during the prosecution of U.S. Appl. No. 15/691,032.
An Office Action dated Sep. 6, 2018, which issued during the prosecution of U.S. Appl. No. 15/213,791.
Condado, José Antonio, et al. "Percutaneous edge-to-edge mitral valve repair: 2-year follow-up in the first human case." Catheterization and cardiovascular interventions 67.2 (2006): 323-325.
Notice of Allowance dated Mar. 18, 2020, which issued during the prosecution of U.S. Appl. No. 16/284,331.
Feldman, Ted, et al. "Percutaneous mitral repair with the MitraClip system: safety and midterm durability in the initial EVEREST (Endovascular Valve Edge-to-Edge REpair Study) cohort." Journal of the American College of Cardiology 54.8 (2009): 686-694.
Notice of Allowance dated Nov. 21, 2018, which issued during the prosecution of U.S. Appl. No. 15/213,791.
Notice of Allowance dated Jul. 3, 2019, which issued during the prosecution of U.S. Appl. No. 15/691,032.
IPR2021-00383 Petitioners' Authorized Reply to Patent Owner's Preliminary Response dated May 27, 2021.
Exhibit 1014—Transcript of proceedings held May 20, 2021 (*Edwards Lifesciences* vs. *Cardiovalve*).
Exhibit 1015—Facilitate, Meriam-Webster.com, https://www.merriamwebster.com/dictionary/facilitate (visited May 26, 2021).
Patent Owner's Authorized Surreply to Petitioner's Reply to Patent Owner's Preliminary Response dated Jun. 4, 2021(*Lifesciences* vs. *Cardiovalve*).
An Invitation to pay additional fees dated May 19, 2021, which issued during the prosecution of Applicant's PCT/IL2021/050132.
An Office Action dated Aug. 18, 2021, which issued during the prosecution of U.S. Appl. No. 17/210,183.
An Office Action dated Sep. 9, 2021, which issued during the prosecution of U.S. Appl. No. 16/768,909.
An Office Action dated Sep. 15, 2021, which issued during the prosecution of U.S. Appl. No. 16/135,599.
An Office Action dated Oct. 14, 2021, which issued during the prosecution of U.S. Appl. No. 16/680,739.
An Office Action dated Oct. 21, 2021, which issued during the prosecution of U.S. Appl. No. 17/335,845.
European Search Report dated Oct. 11, 2021 which issued during the prosecution of Applicant's European App No. 21176010.3.
Fann, James I., et al. "Beating heart catheter-based edge-to-edge mitral valve procedure in a porcine model: efficacy and healing response." Circulation 110.8 (2004): 988-993.
IPR2021-00383 Patent Owner's Contingent Motion to Amend Under 37 C.F.R. §42.121 dated Oct. 13, 2021.
IPR2021-00383 Patent Owner's Response Pursuant to 37 C.F.R. §42.120 dated Oct. 13, 2021.
IPR2021-00383 Second Declaration of Dr. Michael Sacks dated Oct. 13, 2021.
An Ofice Action dated Oct. 21, 2021, which issued during the prosecution of U.S. Appl. No. 17/306,231.
Maisano, Francesco, et al. "The evolution from surgery to percutaneous mitral valve interventions: the role of the edge-to-edge technique." Journal of the American College of Cardiology 58.21 (2011): 2174-2182.
An Office Action dated Nov. 6, 2015, which issued during the prosecution of U.S. Appl. No. 14/626,267.
An Office Action dated Jan. 26, 2022, which issued during the prosecution of U.S. Appl. No. 16/888,210.
IPR2021-00383 Deposition of Dr. Ivan Vesely, dated Sep. 22, 2021.
Cardiovalve Exhibit 2009—Percutaneous Mitral Leaflet Repair: MitraClip® Therapy for Mitral Regurgitation (2012).
Feldman, Ted, et al. "Percutaneous mitral valve repair using the edge-to-edge technique: six-month results of the EVEREST Phase I Clinical Trial." Journal of the American College of Cardiology 46.11 (2005): 2134-2140.
An Office Action summarized English translation and Search Report dated Oct. 8, 2021, which issued during the prosecution of Chinese Patent Application No. 201780061210.3.
An Office Action dated Nov. 4, 2021, which issued during the prosecution of U.S. Appl. No. 17/366,711.
An Office Action summarized English translation and Search Report dated Aug. 12, 2021, which issued during the prosecution of Chinese Patent Application No. 201880058940.2.
An Office Action dated Nov. 25, 2021, which issued during the prosecution of European Patent Application No. 18826823.9.
IPR2021-01051 Institution decision dated Dec. 10, 2021.
Notice of Allowance dated Dec. 7, 2021, which issued during the prosecution of U.S. Appl. No. 17/394,807.
Notice of Allowance dated Dec. 6, 2021, which issued during the prosecution of U.S. Appl. No. 16/738,516.
Notice of Allowance dated Dec. 29, 2021, which issued during the prosecution of U.S. Appl. No. 17/210,183.
IPR2021-00383 Petitioners' Reply to Patent Owner's Response dated Jan. 5, 2022.
IPR2021-00383 Petitioners' Opposition to Patent Owner's Contingent Motion to Amend dated Jan. 5, 2022.
An Office Action dated Sep. 22, 2021, which issued during the prosecution of European Patent Application No. 20714289.4.
Summary of Examination Notice dated Jan. 6, 2022, which issued during the prosecution of Chinese Patent Application No. 201880064313.X.
An Office Action dated Jan. 12, 2022, which issued during the prosecution of U.S. Appl. No. 17/101,787.
Notice of Allowance dated Jun. 20, 2017, which issued during the prosecution of U.S. Appl. No. 14/626,267.
Notice of Allowance dated Oct. 20, 2021, which issued during the prosecution of U.S. Appl. No. 16/636,204.
Notice of Allowance dated Jan. 31, 2022, which issued during the prosecution of U.S. Appl. No. 17/479,418.
An Office Action dated Jan. 13, 2022, which issued during the prosecution of U.S. Appl. No. 17/473,472.
An Office Action dated Apr. 11, 2022, which issued during the prosecution of U.S. Appl. No. 17/473,472.
IPR2021-00383 Preliminary Guidance dated Jan. 31, 2022.
An Office Action dated Mar. 18, 2022, which issued during the prosecution of U.S. Appl. No. 16/746,489.
Notice of Allowance dated Mar. 22, 2022, which issued during the prosecution of U.S. Appl. No. 17/366,711.
Notice of Allowance dated Mar. 4, 2022, which issued during the prosecution of U.S. Appl. No. 16/768,909.
An Office Action dated Dec. 9, 2021, which issued during the prosecution of U.S. Appl. No. 16/135,969.
An Office Action dated Jan. 24, 2022, which issued during the prosecution of U.S. Appl. No. 16/135,466.
U.S. Appl. No. 63/120,808, filed Dec. 3, 2020.
An Advisory Action dated Apr. 9, 2019, which issued during the prosecution of U.S. Appl. No. 15/970,314.
An Advisory Action dated Mar. 13, 2019, which issued during the prosecution of U.S. Appl. No. 15/979,686.
An Advisory Action dated Jul. 8, 2019, which issued during the prosecution of U.S. Appl. No. 15/995,725.
An Office Action dated Nov. 16, 2018, which issued during the prosecution of U.S. Appl. No. 16/042,129.
An Office Action dated Jul. 22, 2020, which issued during the prosecution of U.S. Appl. No. 16/135,447.
IPR2021-01051 Preliminary Guidance Patent Owner's Motion to Amend dated Jun. 24, 2022.
EX Parte Quayle dated May 2, 2022, which issued during the prosecution of U.S. Appl. No. 16/879,952.
An International Search Report and a Written Opinion both dated May 3, 2022, which issued during the prosecution of Applicant's PCT/IL2021/051433.
An Office Action together with an English Summary dated May 7, 2022 which issued during the prosecution of Chinese Patent Application No. 201880058940.2.
Notice of Allowance dated May 4, 2022, which issued during the prosecution of U.S. Appl. No. 16/680,739.

(56) References Cited

OTHER PUBLICATIONS

An Office Action dated Jun. 28, 2022, which issued during the prosecution of U.S. Appl. No. 16/135,969.
An Office Action dated Jul. 8, 2022, which issued during the prosecution of U.S. Appl. No. 16/144,054.
An Advisory Action dated Jan. 2, 2020, which issued during the prosecution of U.S. Appl. No. 16/041,208.
Notice of Allowance dated Apr. 30, 2020, which issued during the prosecution of U.S. Appl. No. 15/970,314.
Notice of Allowance dated Feb. 28, 2022, which issued during the prosecution of U.S. Appl. No. 16/135,599.
Notice of Allowance dated Jan. 10, 2022, which issued during the prosecution of U.S. Appl. No. 16/135,599.
Notice of Allowance dated May 26, 2021, which issued during the prosecution of U.S. Appl. No. 16/135,599.
Notice of Allowance dated Feb. 2, 2022, which issued during the prosecution of U.S. Appl. No. 16/135,619.
Notice of Allowance dated Feb. 15, 2022, which issued during the prosecution of U.S. Appl. No. 16/135,619.
Notice of Allowance dated May 12, 2021, which issued during the prosecution of U.S. Appl. No. 16/135,619.
Notice of Allowance dated May 19, 2021, which issued during the prosecution of U.S. Appl. No. 16/135,619.
Notice of Allowance dated Feb. 2, 2022, which issued during the prosecution of U.S. Appl. No. 16/135,663.
Notice of Allowance dated Feb. 16, 2022, which issued during the prosecution of U.S. Appl. No. 16/135,663.
Notice of Allowance dated Sep. 16, 2020, which issued during the prosecution of U.S. Appl. No. 16/135,770.
Notice of Allowance dated Feb. 4, 2022, which issued during the prosecution of U.S. Appl. No. 16/135,447.
Notice of Allowance dated Mar. 24, 2022, which issued during the prosecution of U.S. Appl. No. 16/135,447.
Notice of Allowance dated Mar. 14, 2022, which issued during the prosecution of U.S. Appl. No. 16/135,505.
Notice of Allowance dated Mar. 16, 2021, which issued during the prosecution of U.S. Appl. No. 16/135,505.
Notice of Allowance dated Jun. 15, 2020, which issued during the prosecution of U.S. Appl. No. 16/135,843.
Notice of Allowance dated Jun. 23, 2020, which issued during the prosecution of U.S. Appl. No. 16/135,843.
Notice of Allowance dated Aug. 24, 2021, which issued during the prosecution of U.S. Appl. No. 16/135,979.
Notice of Allowance dated Dec. 24, 2021, which issued during the prosecution of U.S. Appl. No. 16/135,979.
Notice of Allowance dated Feb. 22, 2022, which issued during the prosecution of U.S. Appl. No. 16/135,979.
Notice of Allowance dated Mar. 17, 2021, which issued during the prosecution of U.S. Appl. No. 16/135,979.
Notice of Allowance dated Feb. 8, 2022, which issued during the prosecution of U.S. Appl. No. 16/136,074.
Advisory Action dated Feb. 3, 2021, which issued during the prosecution of U.S. Appl. No. 16/135,505.
Advisory Action dated Jan. 14, 2021, which issued during the prosecution of U.S. Appl. No. 16/135,663.
Advisory Action dated Dec. 15, 2020, which issued during the prosecution of U.S. Appl. No. 16/135,969.
Advisory Action dated Jul. 14, 2020, which issued during the prosecution of U.S. Appl. No. 16/520,289.
Notice of Allowance dated Mar. 8, 2019, which issued during the prosecution of U.S. Appl. No. 15/978,494.
Notice of Allowance dated May 22, 2019, which issued during the prosecution of U.S. Appl. No. 15/979,686.
Notice of Allowance dated Apr. 11, 2019, which issued during the prosecution of U.S. Appl. No. 15/994,022.
Notice of Allowance dated Feb. 12, 2020, which issued during the prosecution of U.S. Appl. No. 15/995,725.
Notice of Allowance dated May 1, 2020, which issued during the prosecution of U.S. Appl. No. 15/995,725.
Notice of Allowance dated Aug. 1, 2019, which issued during the prosecution of U.S. Appl. No. 16/008,618.
Notice of Allowance dated Nov. 13, 2019, which issued during the prosecution of U.S. Appl. No. 16/008,618.
Notice of Allowance dated Aug. 28, 2019, which issued during the prosecution of U.S. Appl. No. 16/040,831.
Notice of Allowance dated Dec. 10, 2019, which issued during the prosecution of U.S. Appl. No. 16/040,831.
Notice of Allowance dated Jan. 23, 2020, which issued during the prosecution of U.S. Appl. No. 16/041,208.
Notice of Allowance dated Mar. 5, 2020, which issued during the prosecution of U.S. Appl. No. 16/041,208.
Notice of Allowance dated May 6, 2020, which issued during the prosecution of U.S. Appl. No. 16/041,208.
Notice of Allowance dated Jun. 27, 2019, which issued during the prosecution of U.S. Appl. No. 16/042,028.
Notice of Allowance dated Jul. 3, 2019, which issued during the prosecution of U.S. Appl. No. 16/042,129.
Notice of Allowance dated Feb. 16, 2022, which issued during the prosecution of U.S. Appl. No. 16/136,074.
Notice of Allowance dated Jul. 30, 2021, which issued during the prosecution of U.S. Appl. No. 16/136,074.
Notice of Allowance dated Sep. 24, 2021, which issued during the prosecution of U.S. Appl. No. 16/136,074.
Notice of Allowance dated Dec. 23, 2021, which issued during the prosecution of U.S. Appl. No. 16/136,082.
Notice of Allowance dated Feb. 28, 2022, which issued during the prosecution of U.S. Appl. No. 16/136,082.
An Office Action dated Jun. 20, 2019, which issued during the prosecution of U.S. Appl. No. 15/970,314.
An Office Action dated Nov. 21, 2019, which issued during the prosecution of U.S. Appl. No. 15/970,314.
An Office Action dated Dec. 21, 2018, which issued during the prosecution of U.S. Appl. No. 15/978,494.
An Office Action dated Dec. 28, 2018, which issued during the prosecution of U.S. Appl. No. 15/979,686.
An Office Action dated Feb. 12, 2019, which issued during the prosecution of U.S. Appl. No. 15/994,022.
An Office Action dated Feb. 13, 2019, which issued during the prosecution of U.S. Appl. No. 15/995,725.
An Office Action dated Oct. 22, 2019, which issued during the prosecution of U.S. Appl. No. 15/995,725.
An Office Action dated Apr. 19, 2019, which issued during the prosecution of U.S. Appl. No. 16/008,618.
An Office Action dated Feb. 14, 2019, which issued during the prosecution of U.S. Appl. No. 16/008,618.
An Office Action dated Jun. 19, 2019, which issued during the prosecution of U.S. Appl. No. 16/040,831.
An Office Action dated Sep. 30, 2021, which issued during the prosecution of U.S. Appl. No. 16/135,447.
An Office Action dated Mar. 10, 2021, which issued during the prosecution of U.S. Appl. No. 16/135,447.
An Office Action dated Aug. 15, 2019, which issued during the prosecution of U.S. Appl. No. 16/041,208.
An Office Action dated Jun. 21, 2021, which issued during the prosecution of U.S. Appl. No. 16/135,447.
An Office Action dated Apr. 3, 2020, which issued during the prosecution of U.S. Appl. No. 16/135,466.
An Office Action dated Mar. 27, 2020, which issued during the prosecution of U.S. Appl. No. 16/135,505.
An Office Action dated Sep. 8, 2021, which issued during the prosecution of U.S. Appl. No. 16/135,505.
An Office Action dated Sep. 29, 2020, which issued during the prosecution of U.S. Appl. No. 16/135,505.
An Office Action dated Aug. 11, 2020, which issued during the prosecution of U.S. Appl. No. 16/135,619.
An Office Action dated Dec. 21, 2020, which issued during the prosecution of U.S. Appl. No. 16/135,619.
An Office Action dated Apr. 10, 2020, which issued during the prosecution of U.S. Appl. No. 16/135,663.
An Office Action dated Jun. 28, 2021, which issued during the prosecution of U.S. Appl. No. 16/135,663.

(56) References Cited

OTHER PUBLICATIONS

An Office Action dated Mar. 8, 2021, which issued during the prosecution of U.S. Appl. No. 16/135,663.
An Office Action dated Sep. 23, 2020, which issued during the prosecution of U.S. Appl. No. 16/135,663.
An Office Action dated Mar. 16, 2020, which issued during the prosecution of U.S. Appl. No. 16/135,770.
An Office Action dated Dec. 10, 2020, which issued during the prosecution of U.S. Appl. No. 16/135,599.
An Office Action dated Jun. 1, 2020, which issued during the prosecution of U.S. Appl. No. 16/135,599.
An Office Action dated Mar. 5, 2020, which issued during the prosecution of U.S. Appl. No. 16/135,843.
An Office Action dated Apr. 9, 2020, which issued during the prosecution of U.S. Appl. No. 16/135,969.
An Office Action dated Jan. 14, 2021, which issued during the prosecution of U.S. Appl. No. 16/135,969.
An Office Action dated May 28, 2021, which issued during the prosecution of U.S. Appl. No. 16/135,969.
An Office Action dated Sep. 9, 2020, which issued during the prosecution of U.S. Appl. No. 16/135,969.
An Office Action dated Mar. 20, 2020, which issued during the prosecution of U.S. Appl. No. 16/135,979.
An Office Action dated Oct. 20, 2020, which issued during the prosecution of U.S. Appl. No. 16/135,979.
An Office Action dated Mar. 6, 2020, which issued during the prosecution of U.S. Appl. No. 16/136,074.
An Office Action dated Mar. 19, 2021, which issued during the prosecution of U.S. Appl. No. 16/136,074.
An Office Action dated Sep. 8, 2020, which issued during the prosecution of U.S. Appl. No. 16/136,074.
An Office Action dated Jan. 25, 2021, which issued during the prosecution of U.S. Appl. No. 16/136,082.
An Office Action dated Jun. 1, 2020, which issued during the prosecution of U.S. Appl. No. 16/136,082.
An Office Action dated Mar. 16, 2020, which issued during the prosecution of U.S. Appl. No. 16/136,110.
An Office Action dated Mar. 12, 2020, which issued during the prosecution of U.S. Appl. No. 16/136,123.
An Office Action dated Mar. 10, 2020, which issued during the prosecution of U.S. Appl. No. 16/136,150.
An Office Action dated Apr. 7, 2020, which issued during the prosecution of U.S. Appl. No. 16/520,289.
An Office Action dated Oct. 7, 2019, which issued during the prosecution of U.S. Appl. No. 16/520,289.
An Office Action dated Oct. 23, 2019, which issued during the prosecution of U.S. Appl. No. 16/559,365.
An Office Action dated Dec. 12, 2019, which issued during the prosecution of U.S. Appl. No. 16/585,349.
An Office Action dated Jul. 16, 2020, which issued during the prosecution of U.S. Appl. No. 16/678,355.
An Office Action dated Mar. 18, 2020, which issued during the prosecution of U.S. Appl. No. 16/740,659.
Notice of Allowance dated Aug. 11, 2020, which issued during the prosecution of U.S. Appl. No. 16/136,110.
Notice of Allowance dated Sep. 30, 2020, which issued during the prosecution of U.S. Appl. No. 16/136,123.
IPR2021-00383 Final Written Decision Determining All Challenged Claims Unpatentable Denying Patent Owner's Contingent Motion to Amend Granting-in-Part and Denying-in-Part Petitioner's Motion to Strike Denying Patent Owner's Motion to Exclude dated Jul. 18, 2022
Notice of Allowance dated Aug. 26, 2020, which issued during the prosecution of U.S. Appl. No. 16/136,150.
Notice of Allowance dated Dec. 10, 2020, which issued during the prosecution of U.S. Appl. No. 16/136,150.
Notice of Allowance dated Aug. 22, 2019, which issued during the prosecution of U.S. Appl. No. 16/507,357.
Notice of Allowance dated Dec. 11, 2019, which issued during the prosecution of U.S. Appl. No. 16/507,357.
Notice of Allowance dated Dec. 16, 2020, which issued during the prosecution of U.S. Appl. No. 16/520,289.
Notice of Allowance dated Sep. 17, 2020, which issued during the prosecution of U.S. Appl. No. 16/520,289.
Notice of Allowance dated Mar. 25, 2020, which issued during the prosecution of U.S. Appl. No. 16/559,365.
Notice of Allowance dated May 6, 2020, which issued during the prosecution of U.S. Appl. No. 16/559,365.
Notice of Allowance dated Jul. 23, 2020, which issued during the prosecution of U.S. Appl. No. 16/585,349.
Notice of Allowance dated Nov. 2, 2020, which issued during the prosecution of U.S. Appl. No. 16/585,349.
Notice of Allowance dated Aug. 5, 2020, which issued during the prosecution of U.S. Appl. No. 16/660,231.
Notice of Allowance dated Nov. 18, 2020, which issued during the prosecution of U.S. Appl. No. 16/660,231.
Notice of Allowance dated Dec. 7, 2020, which issued during the prosecution of U.S. Appl. No. 16/678,355.
Notice of Allowance dated Feb. 24, 2020, which issued during the prosecution of U.S. Appl. No. 16/730,090.
Notice of Allowance dated May 6, 2020, which issued during the prosecution of U.S. Appl. No. 16/730,090.
Notice of Allowance dated Oct. 15, 2020, which issued during the prosecution of U.S. Appl. No. 16/740,659.
European Search Report dated Mar. 20, 2023 which issued during the prosecution of Applicant's European App No. 22204764.9.
Notice of Allowance dated Apr. 6, 2023, which issued during the prosecution of U.S. Appl. No. 16/746,489.
An Office Action dated Apr. 14, 2023, which issued during the prosecution of U.S. Appl. No. 16/144,054.
An Office Action dated May 15, 2023, which issued during the prosecution of U.S. Appl. No. 16/656,790.
An Office Action dated May 16, 2023, which issued during the prosecution of U.S. Appl. No. 17/114,771.
An Office Action dated May 17, 2023, which issued during the prosecution of U.S. Appl. No. 17/466,785.
An Office Action dated May 25, 2023, which issued during the prosecution of U.S. Appl. No. 17/397,235.
An Office Action dated Mar. 3, 2023, which issued during the prosecution of European Patent Application No. 17 751 143.3.
An Office Action dated Mar. 20, 2023, which issued during the prosecution of U.S. Appl. No. 17/181,722.
An Office Action dated Jul. 27, 2022, which issued during the prosecution of U.S. Appl. No. 16/881,350.
An Office Action dated Sep. 21, 2022, which issued during the prosecution of U.S. Appl. No. 16/776,581.
An Office Action dated Jul. 20, 2022, which issued during the prosecution of U.S. Appl. No. 17/101,787.
An Office Action dated Sep. 16, 2022, which issued during the prosecution of U.S. Appl. No. 16/135,466.
An Office Action dated Aug. 1, 2022, which issued during the prosecution of European Patent Application No. 18826823.9.
European Search Report dated Sep. 6, 2022 which issued during the prosecution of Applicant's European App No. 22161862.2.
IPR2021-01051 Petitioners' Reply to Preliminary Guidance dated Aug. 2, 2022.
IPR2021-01051 Patent Owner's Sur-Reply to Petitioners' Reply to Preliminary Guidance dated Aug. 23, 2022.
An Office Action dated Aug. 5, 2022, which issued during the prosecution of U.S. Appl. No. 16/760,147.
An Office Action dated Sep. 8, 2022, which issued during the prosecution of U.S. Appl. No. 16/896,858.
Notice of Allowance dated Sep. 20, 2023, which issued during the prosecution of U.S. Appl. No. 17/839,538.
An Office Action dated Oct. 13, 2023, which issued during the prosecution of U.S. Appl. No. 17/181,722.
Grounds of Opposition to European Patent No. EP 2 948 103, filed Sep. 6, 2023.
An Office Action dated Aug. 31, 2023, which issued during the prosecution of U.S. Appl. No. 17/397,235.
An Office Action dated Sep. 8, 2023, which issued during the prosecution of U.S. Appl. No. 18/216,391.

(56) References Cited

OTHER PUBLICATIONS

An Office Action dated Sep. 8, 2023, which issued during the prosecution of U.S. Appl. No. 18/218,419.
Opposition to European Patent No. EP 2 948 103, filed Sep. 6, 2023.
An International Search Report and a Written Opinion both dated Aug. 23, 2023, 2023, which issued during the prosecution of Applicant's PCT/IL2023/050586.
An Office Action dated Aug. 3, 2023, which issued during the prosecution of U.S. Appl. No. 17/683,875.
An International Search Report and a Written Opinion both dated Sep. 13, 2023, which issued during the prosecution of Applicant's PCT/IL2023/050587.

* cited by examiner

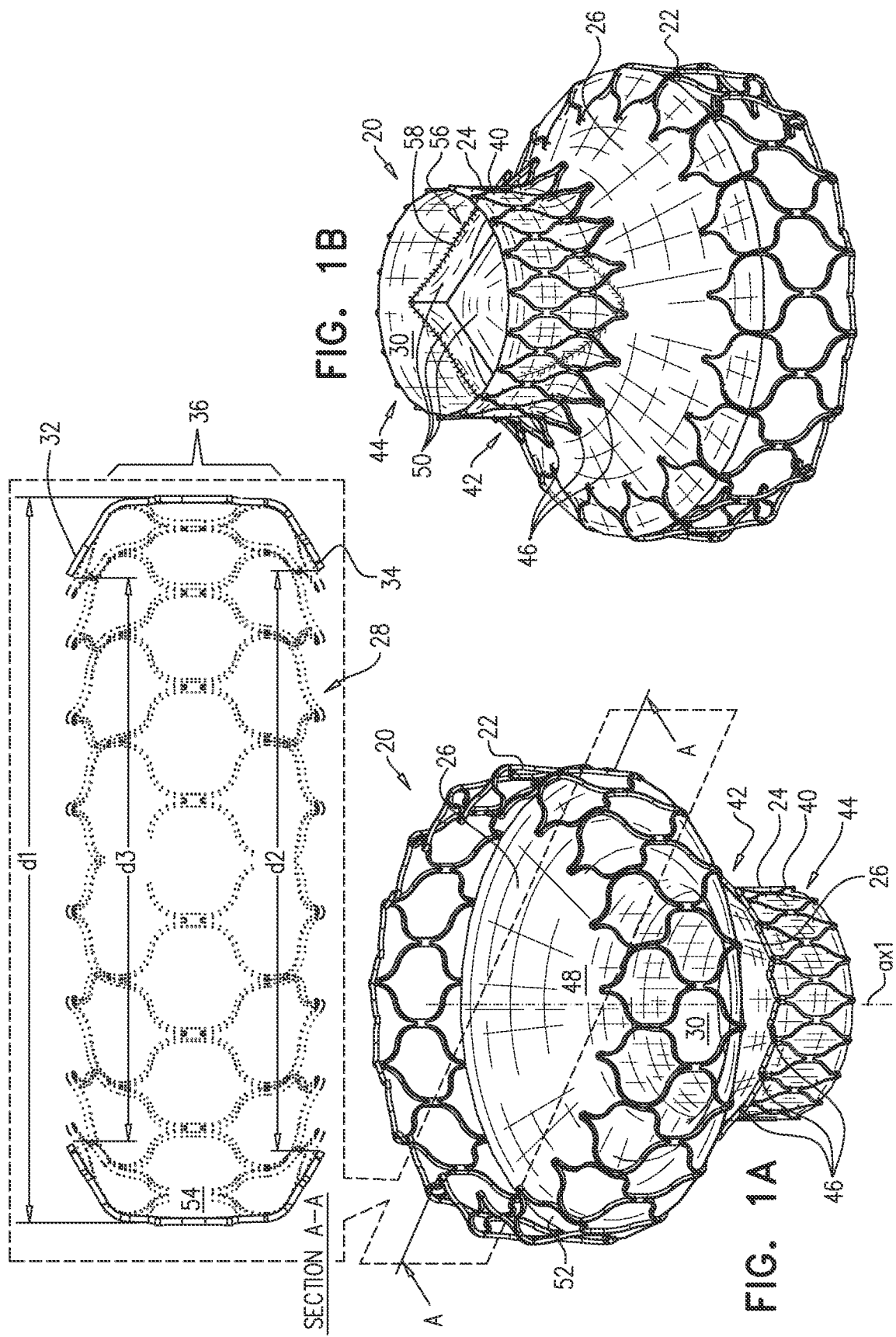

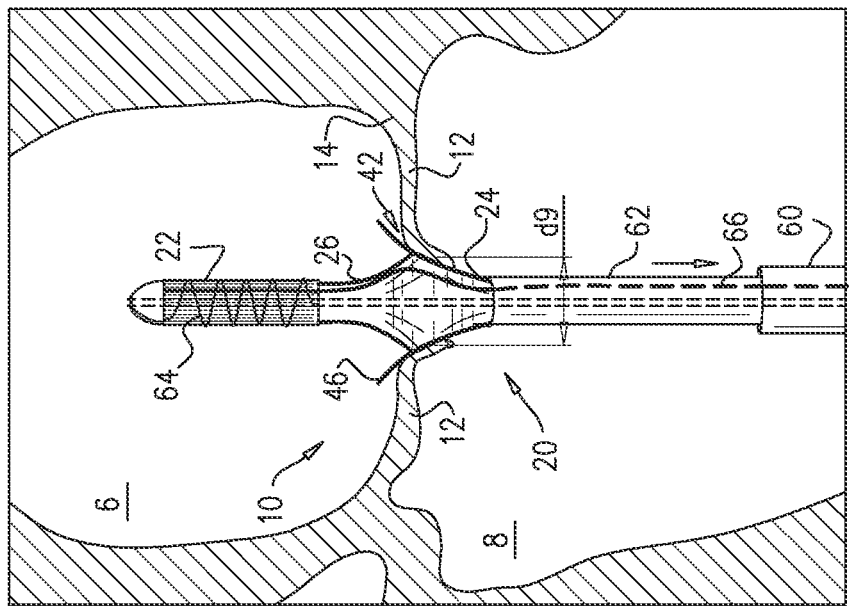
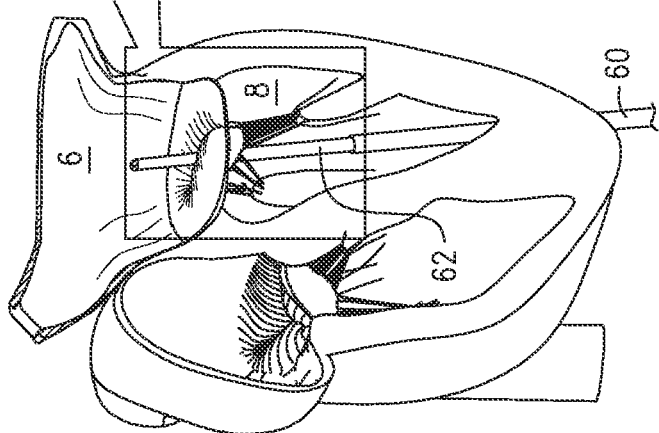

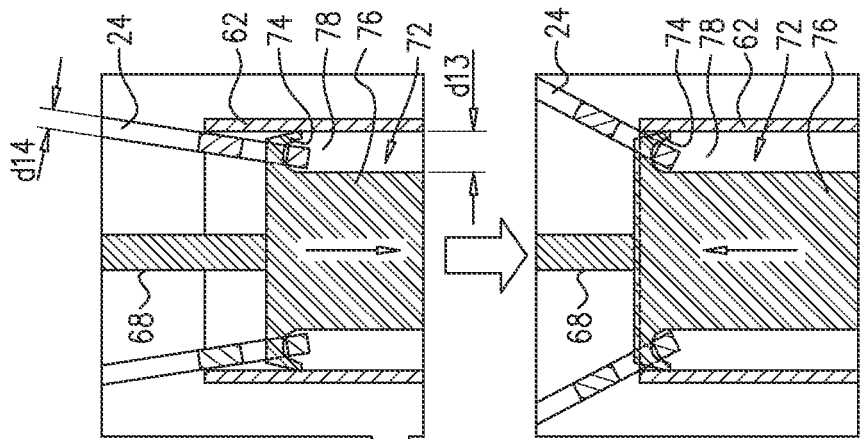
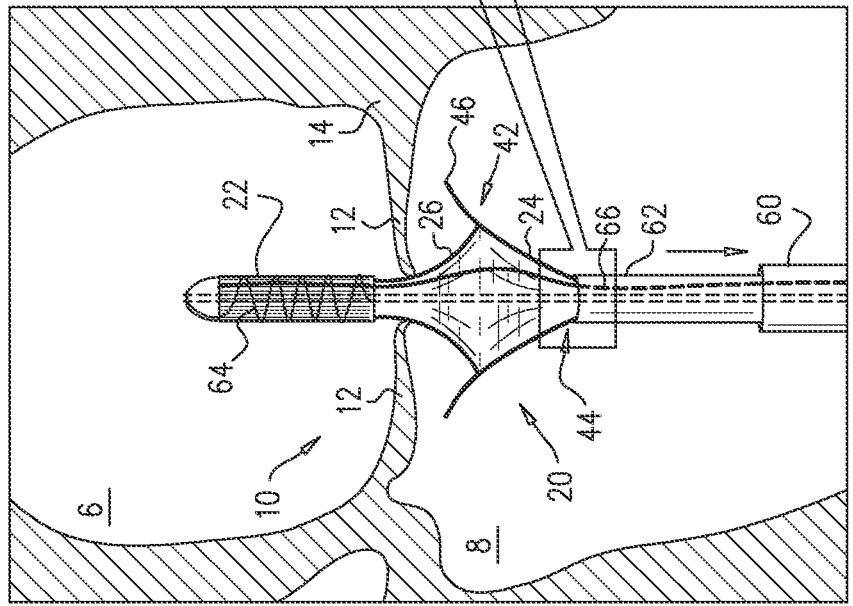
FIG. 4C
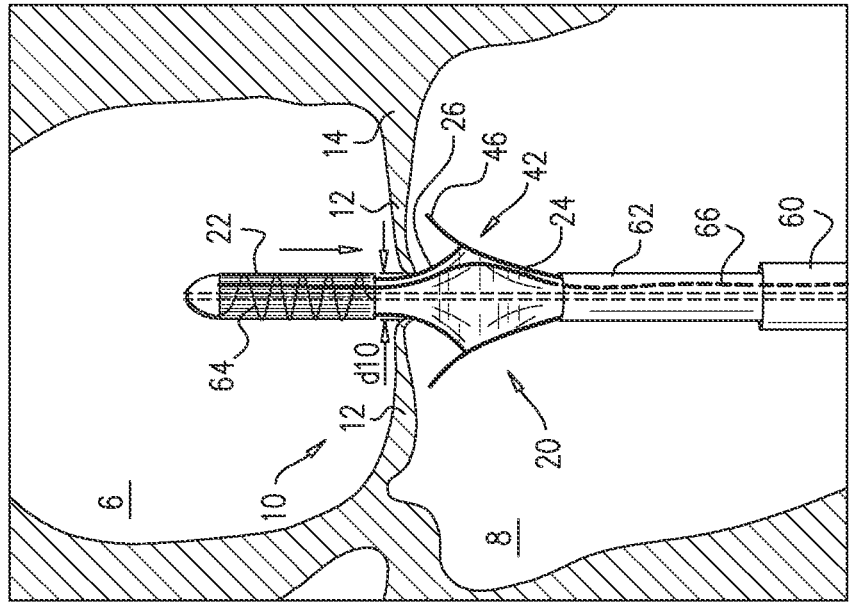
FIG. 4D

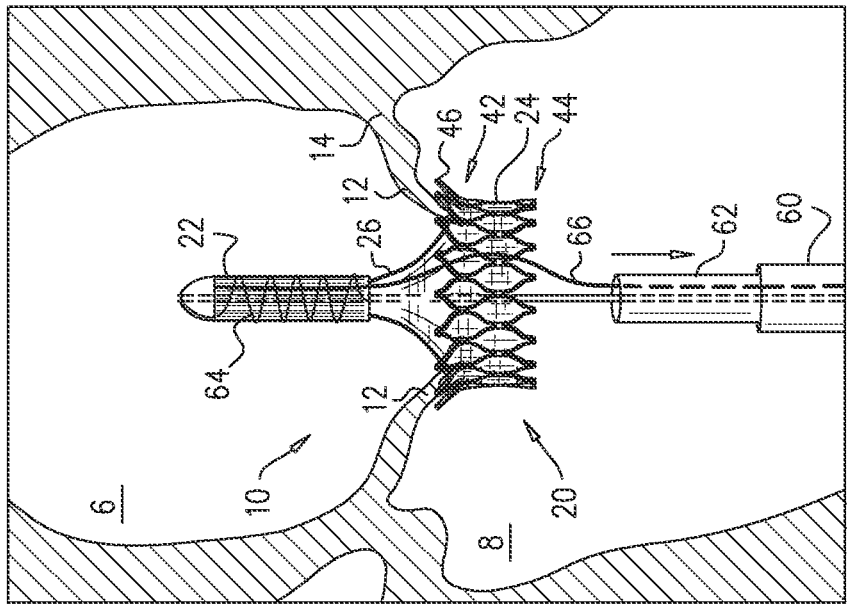
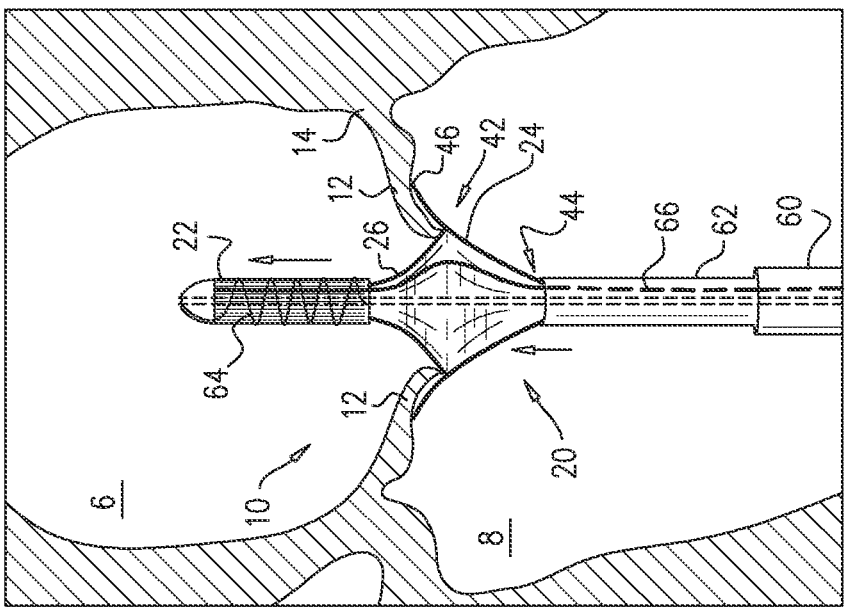

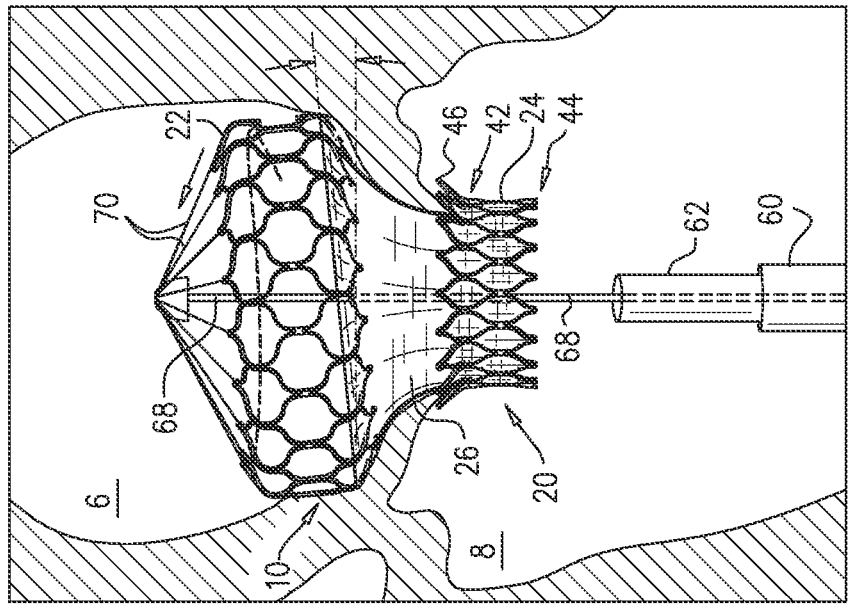
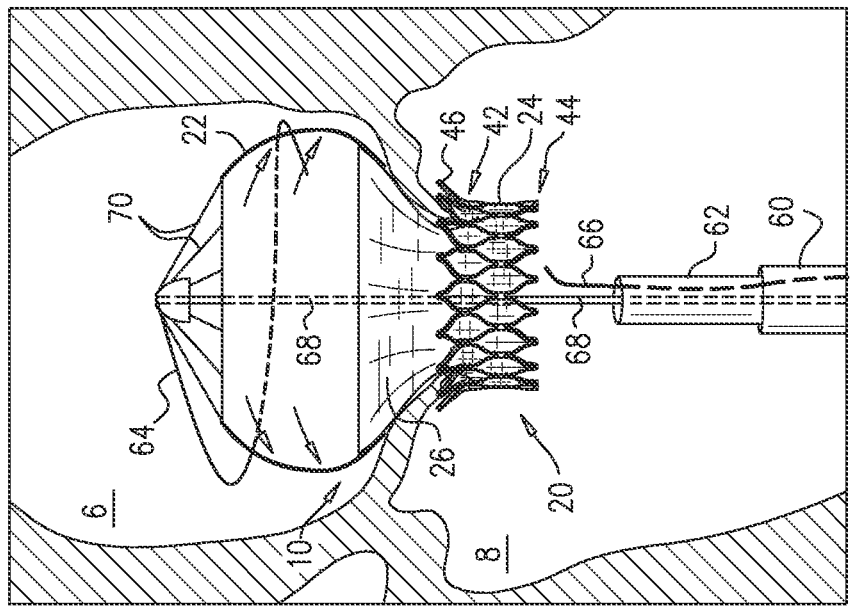

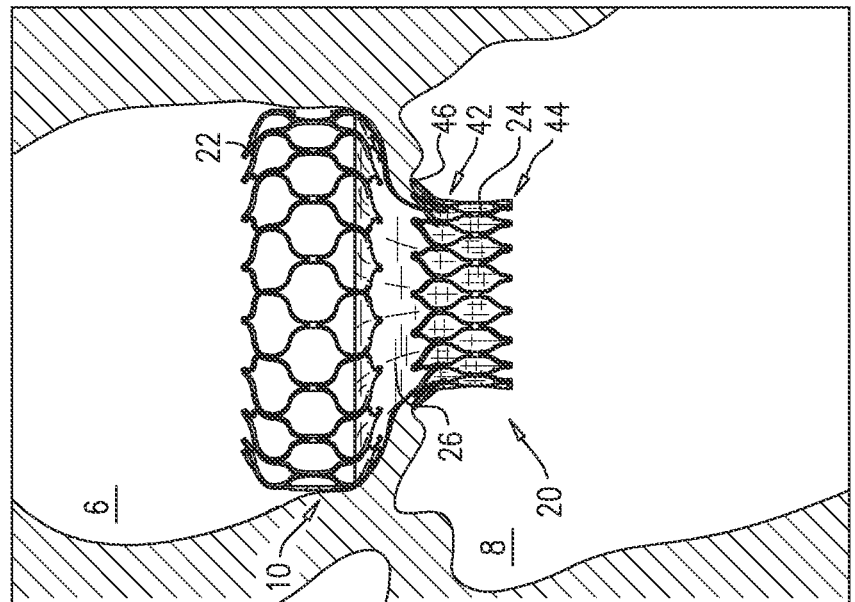
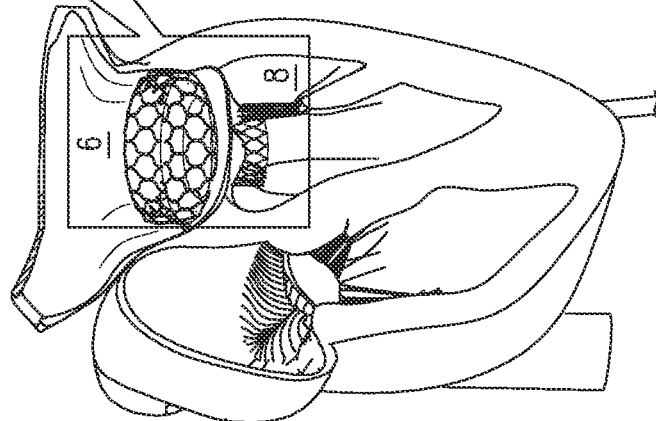
FIG. 4J
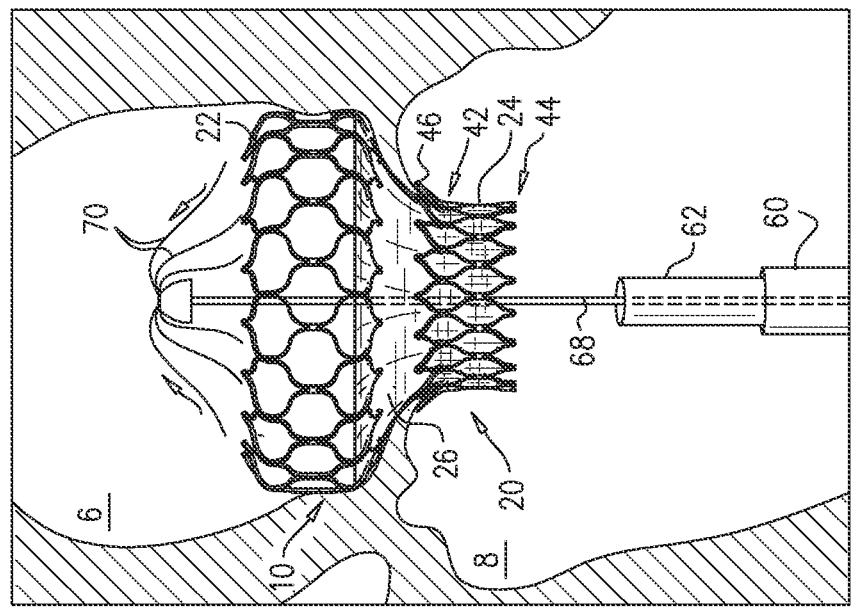
FIG. 4I

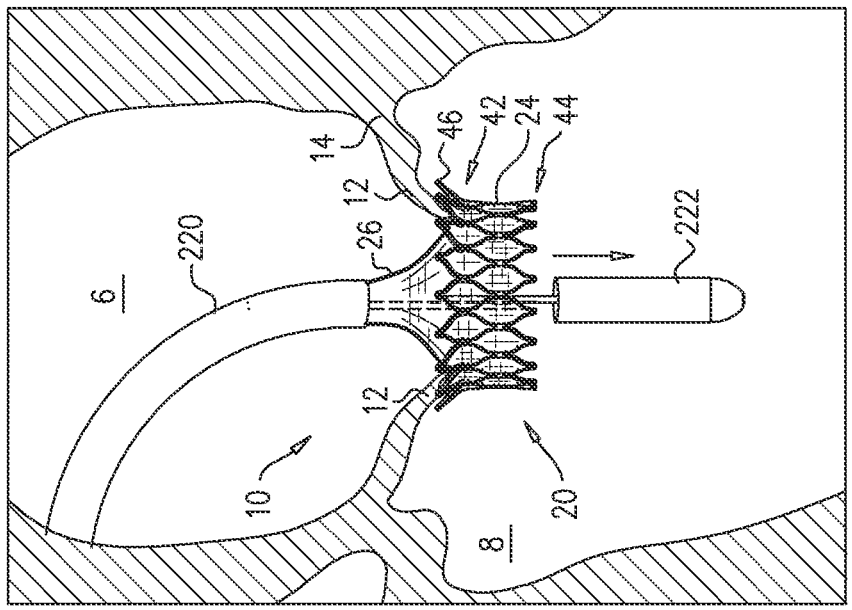
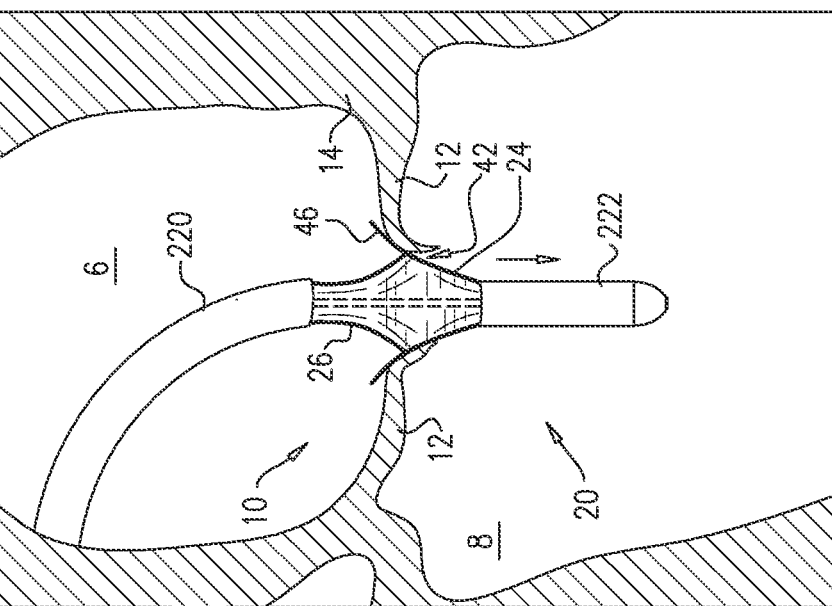
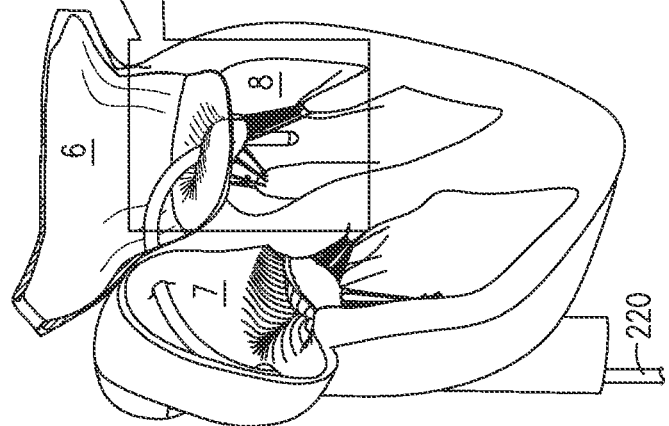

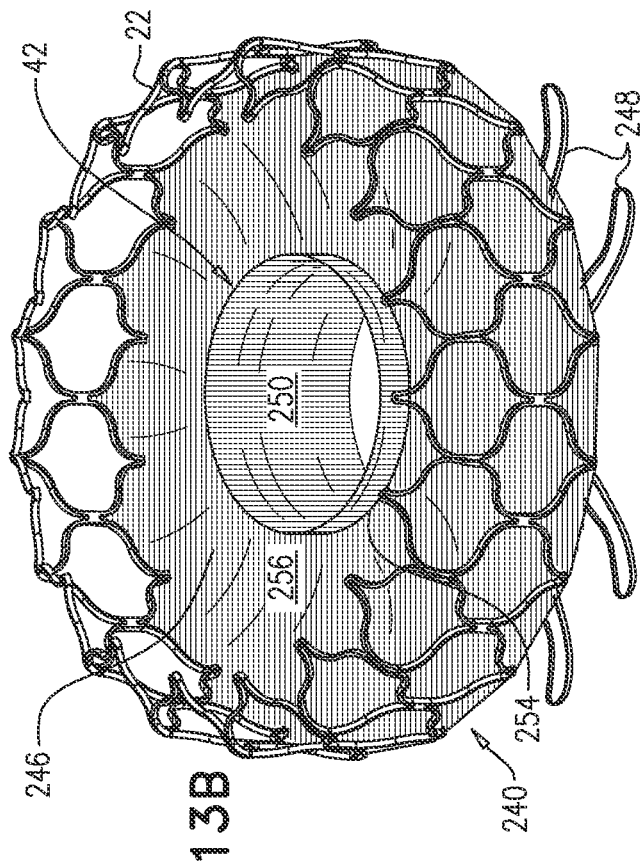
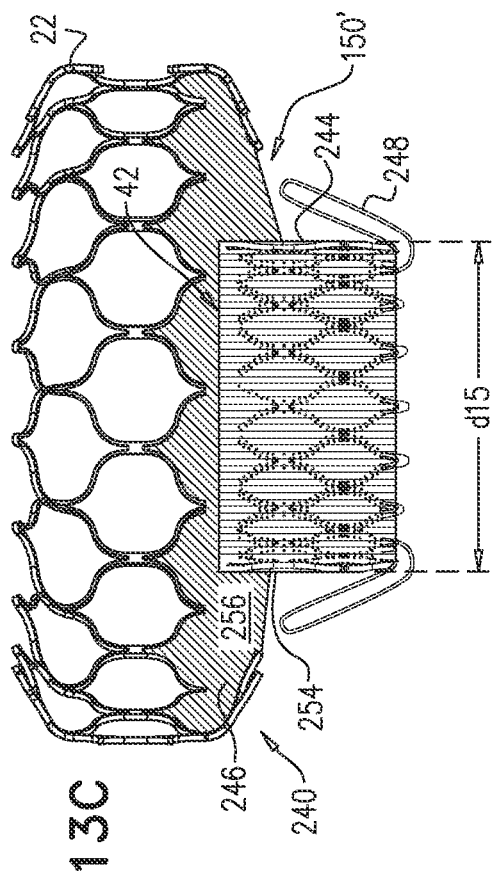
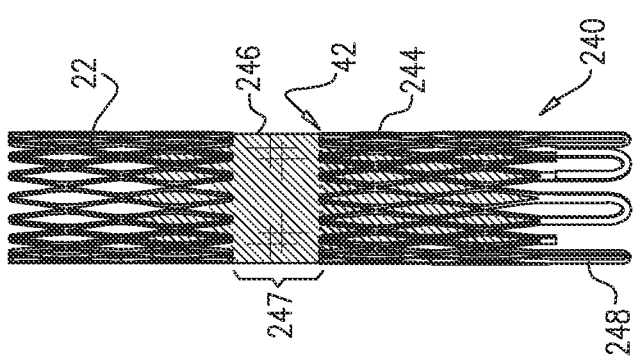
FIG. 13B
FIG. 13C
FIG. 13A

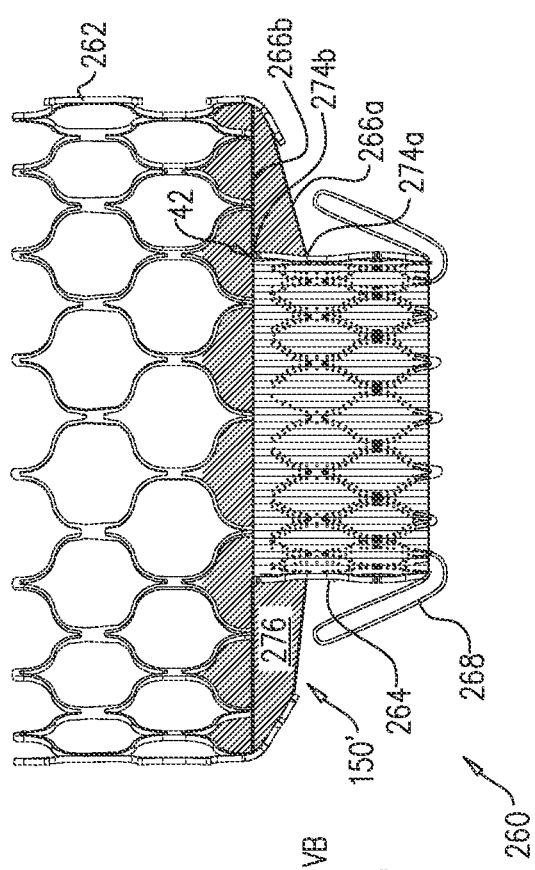
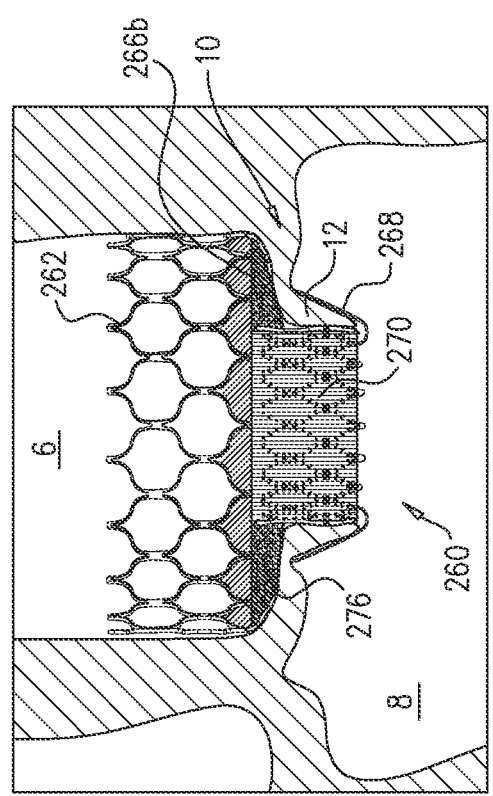
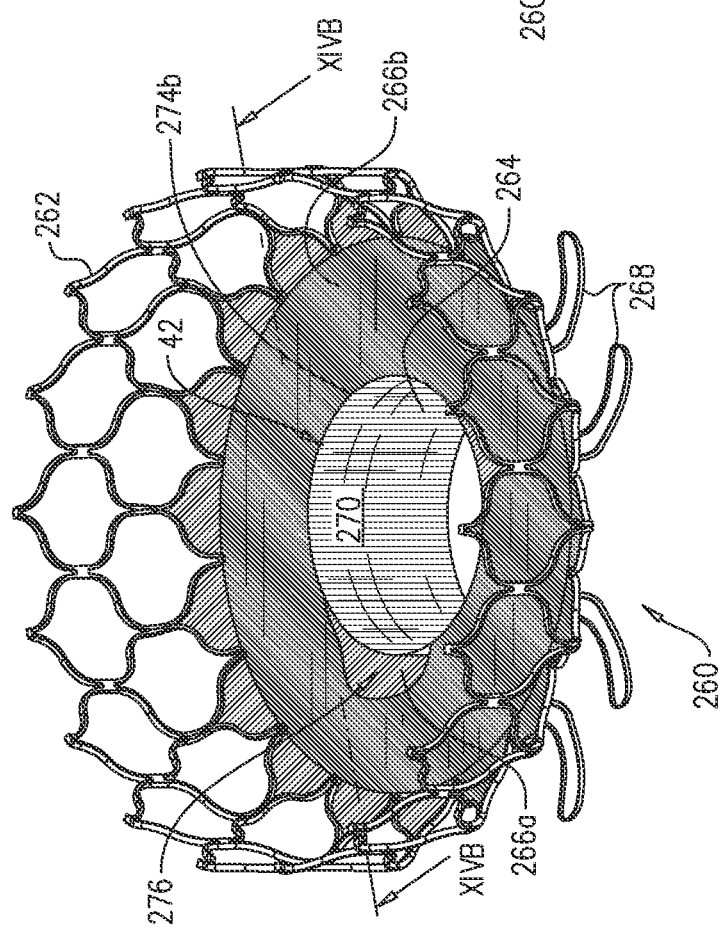
FIG. 14B
FIG. 14C
FIG. 14A

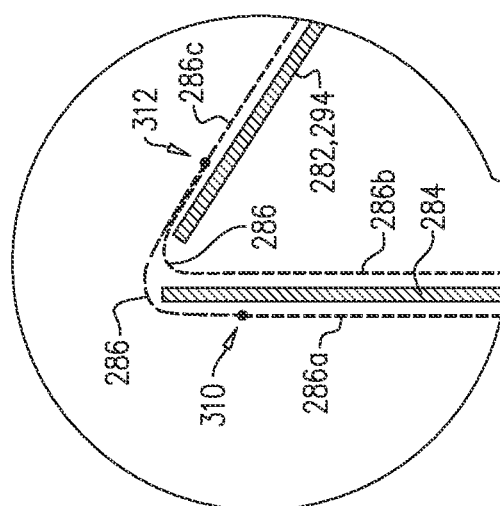
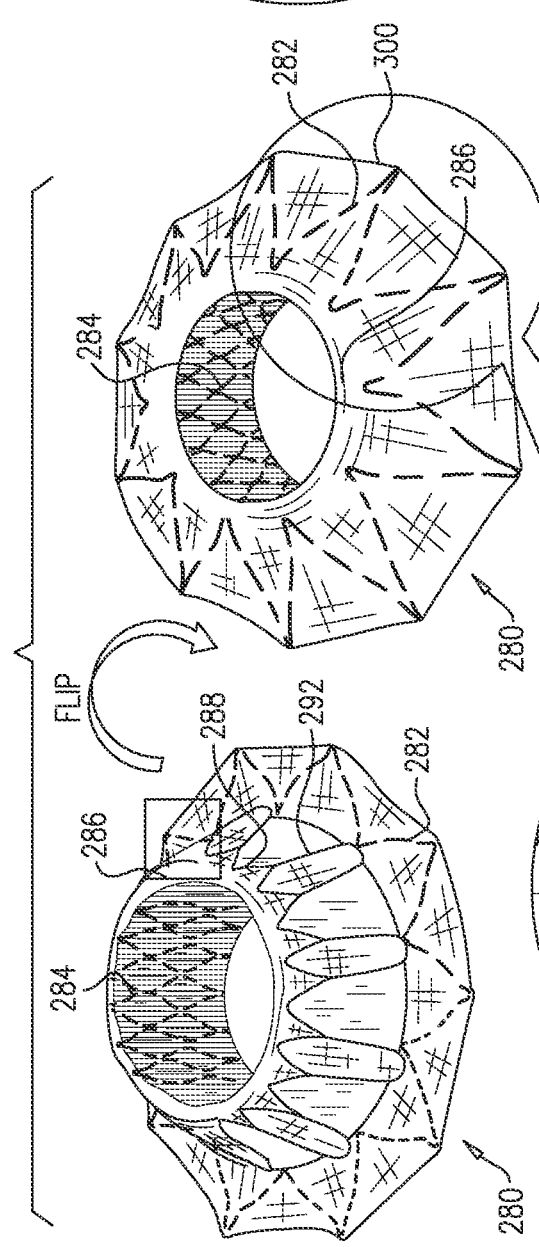
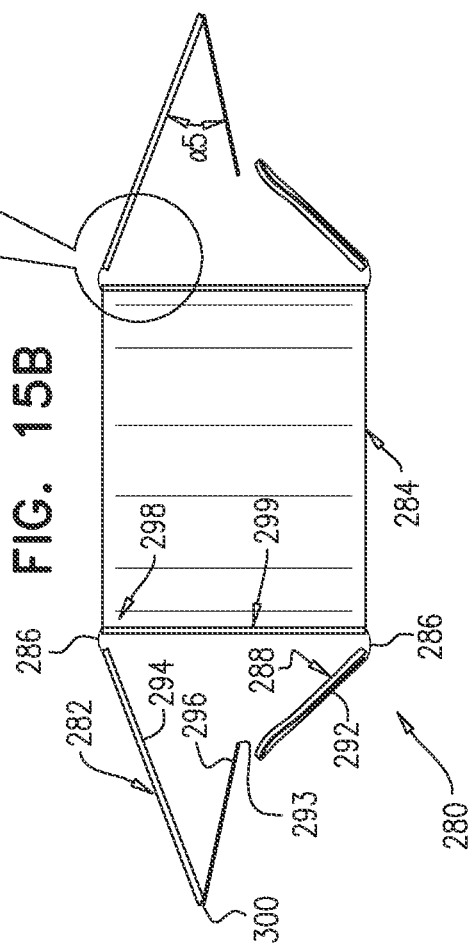
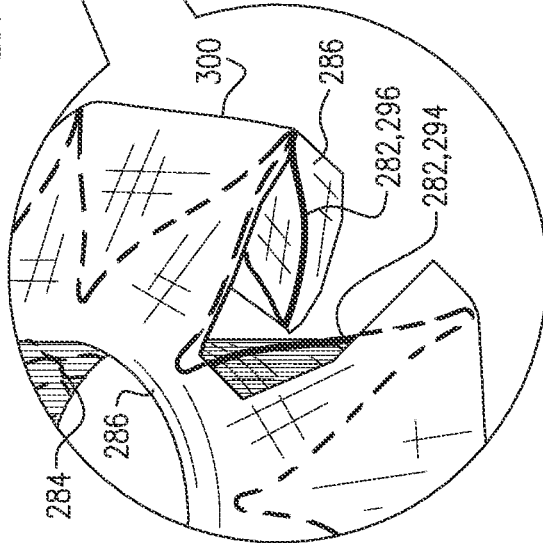

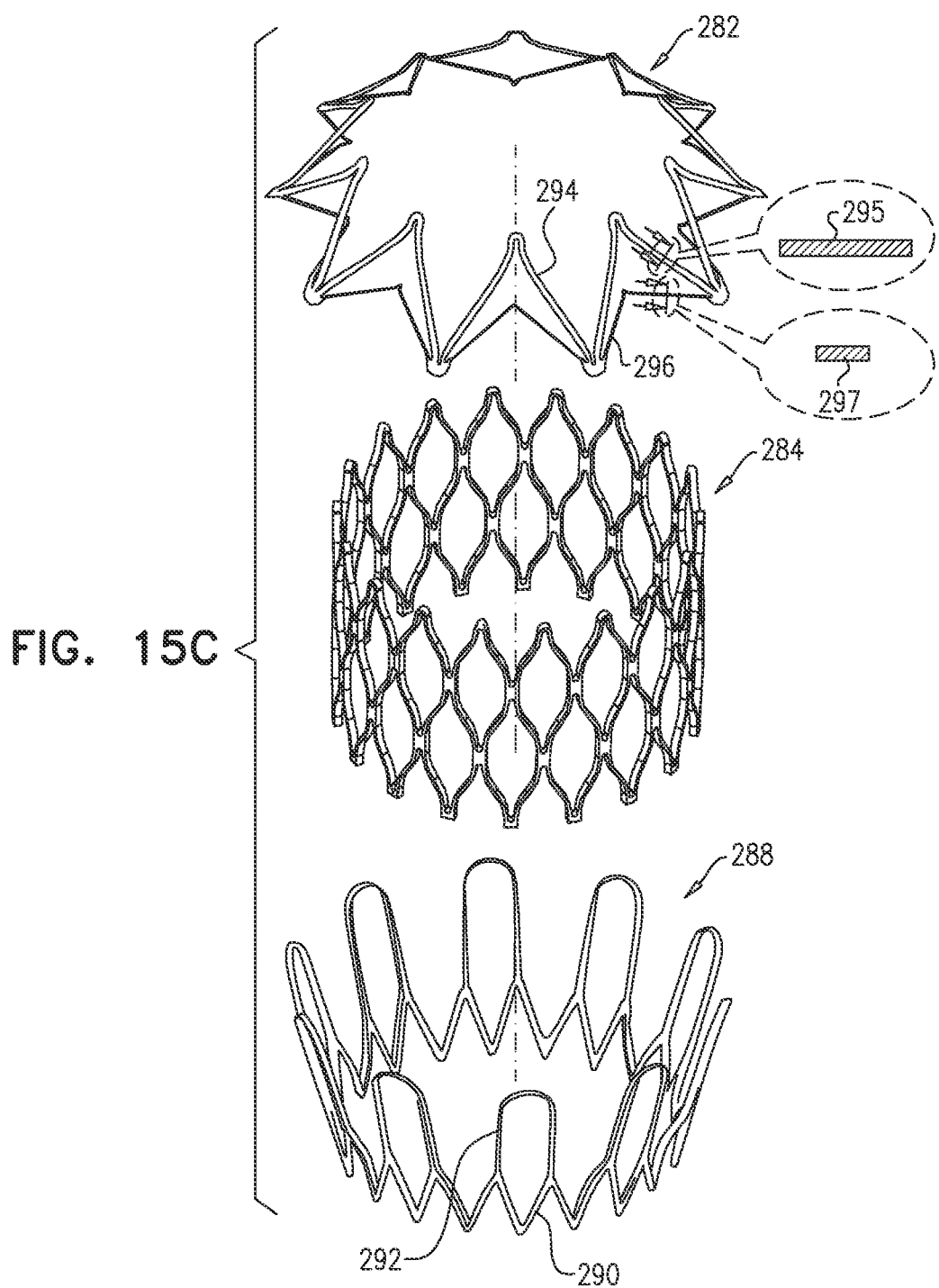

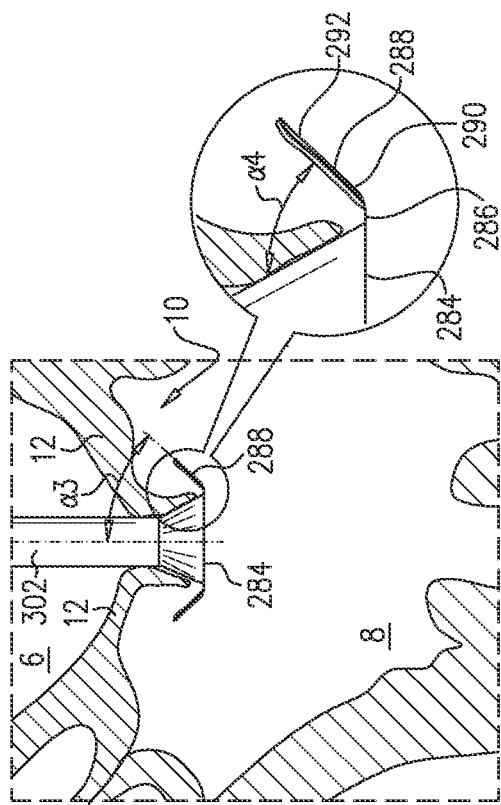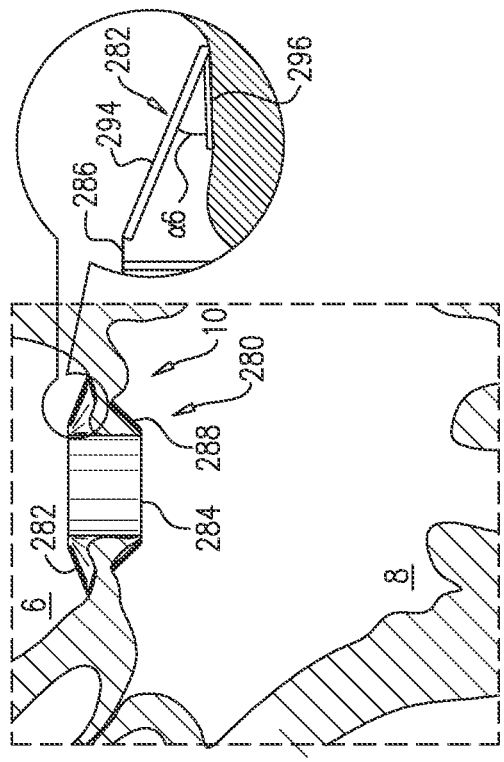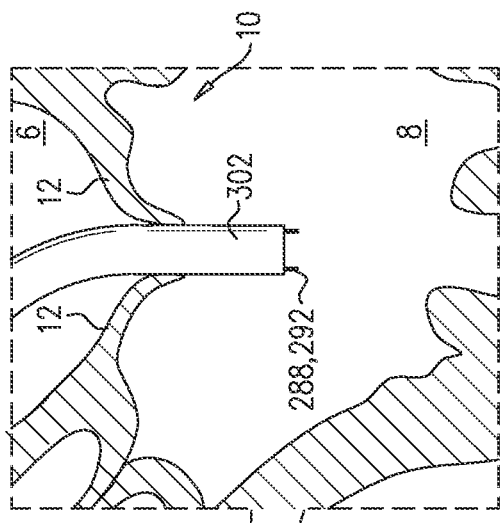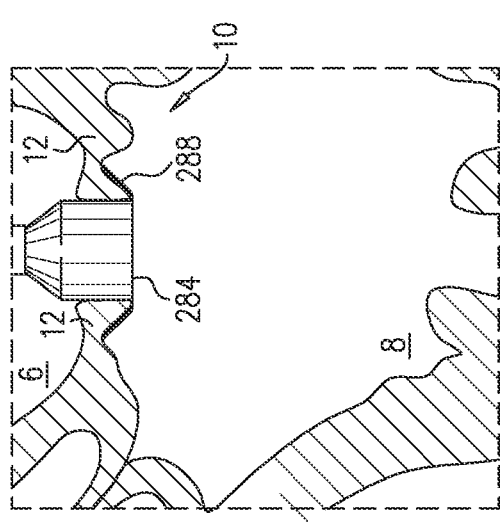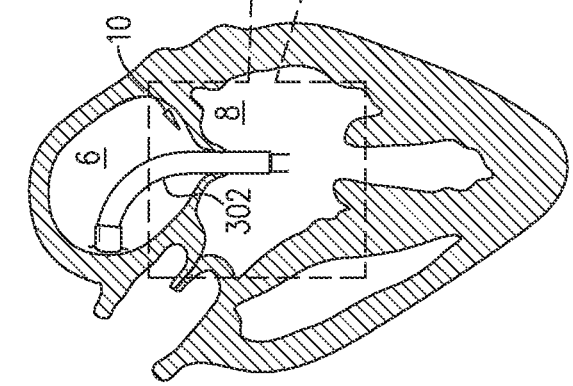

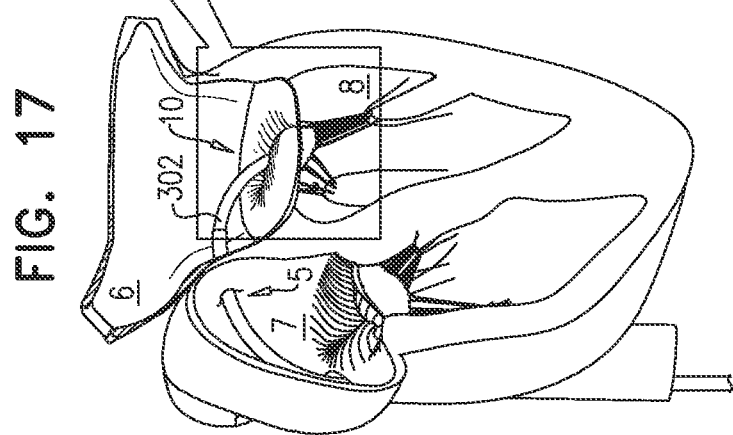
FIG. 17
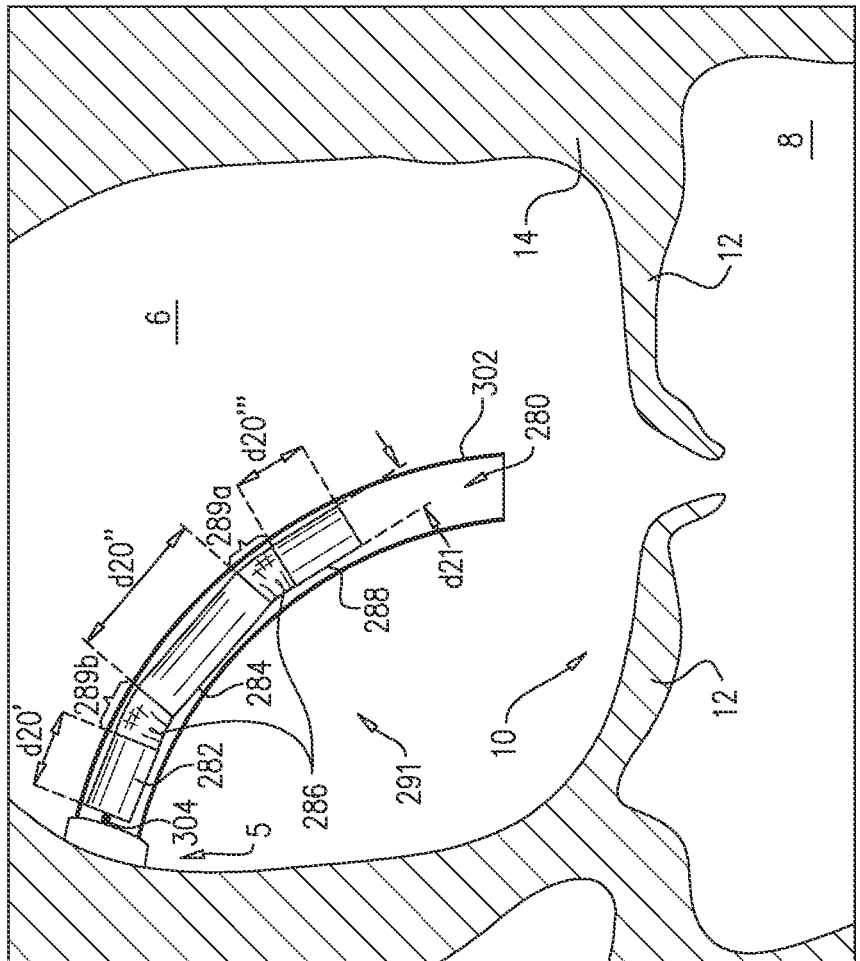

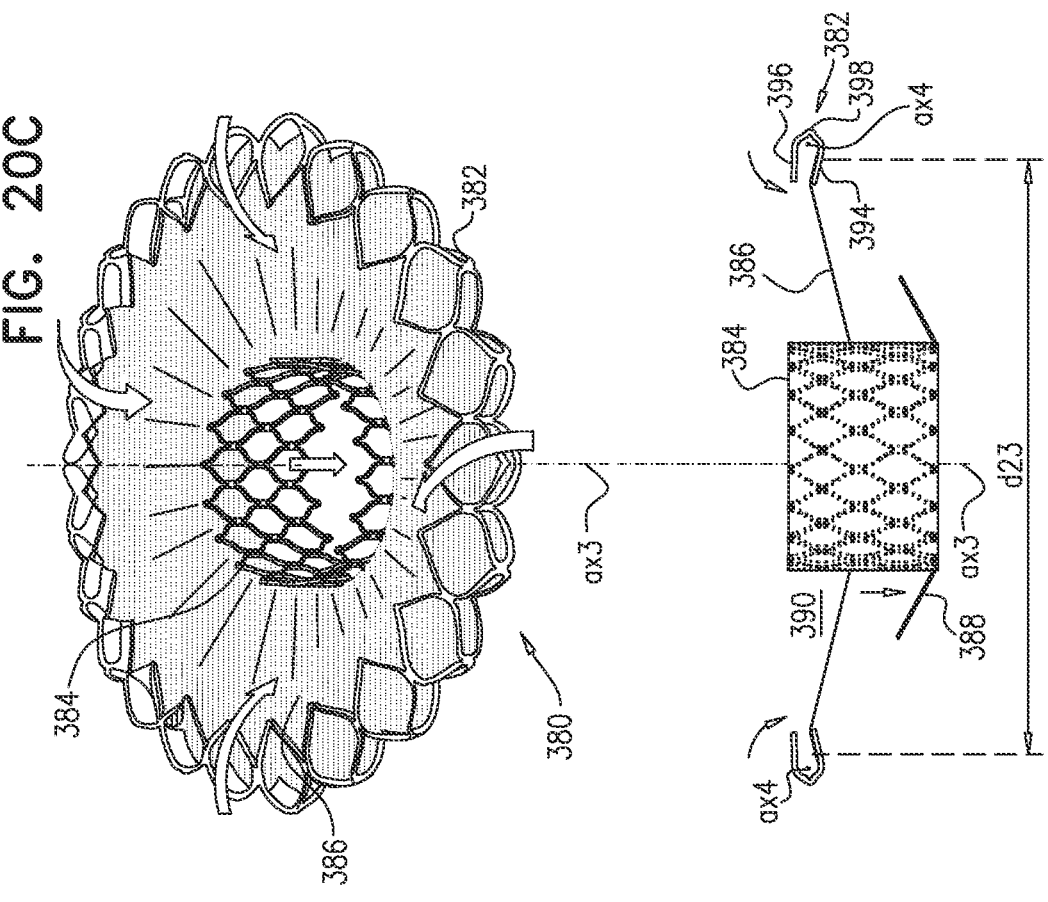
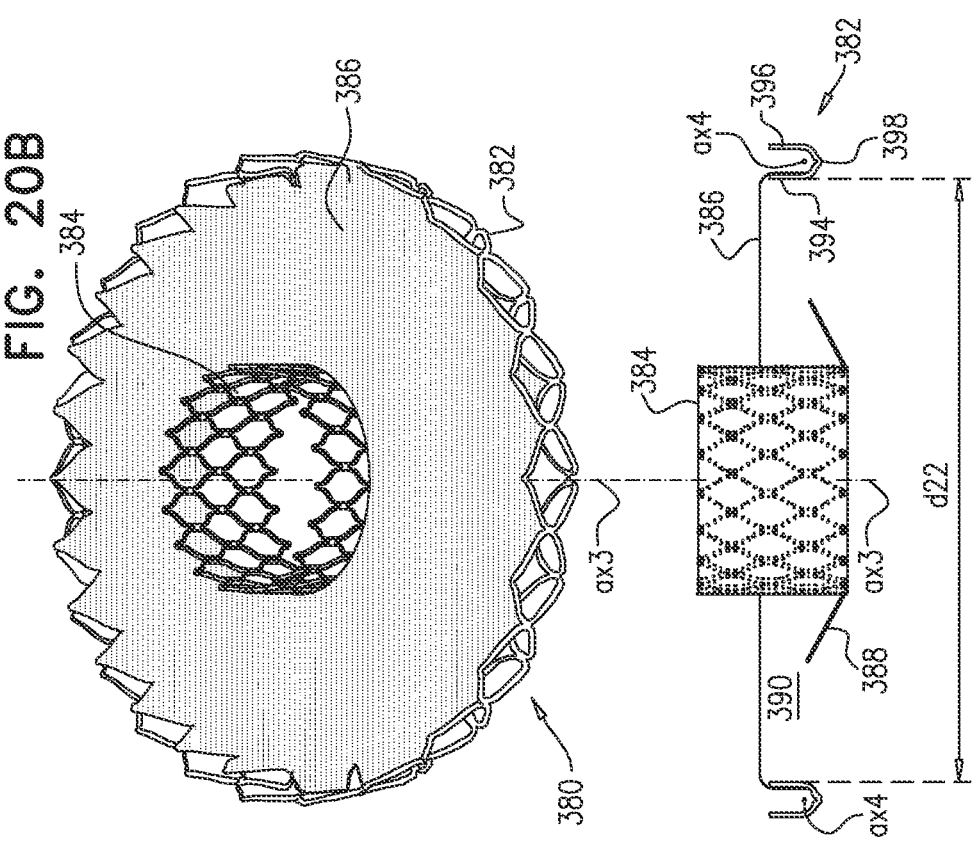

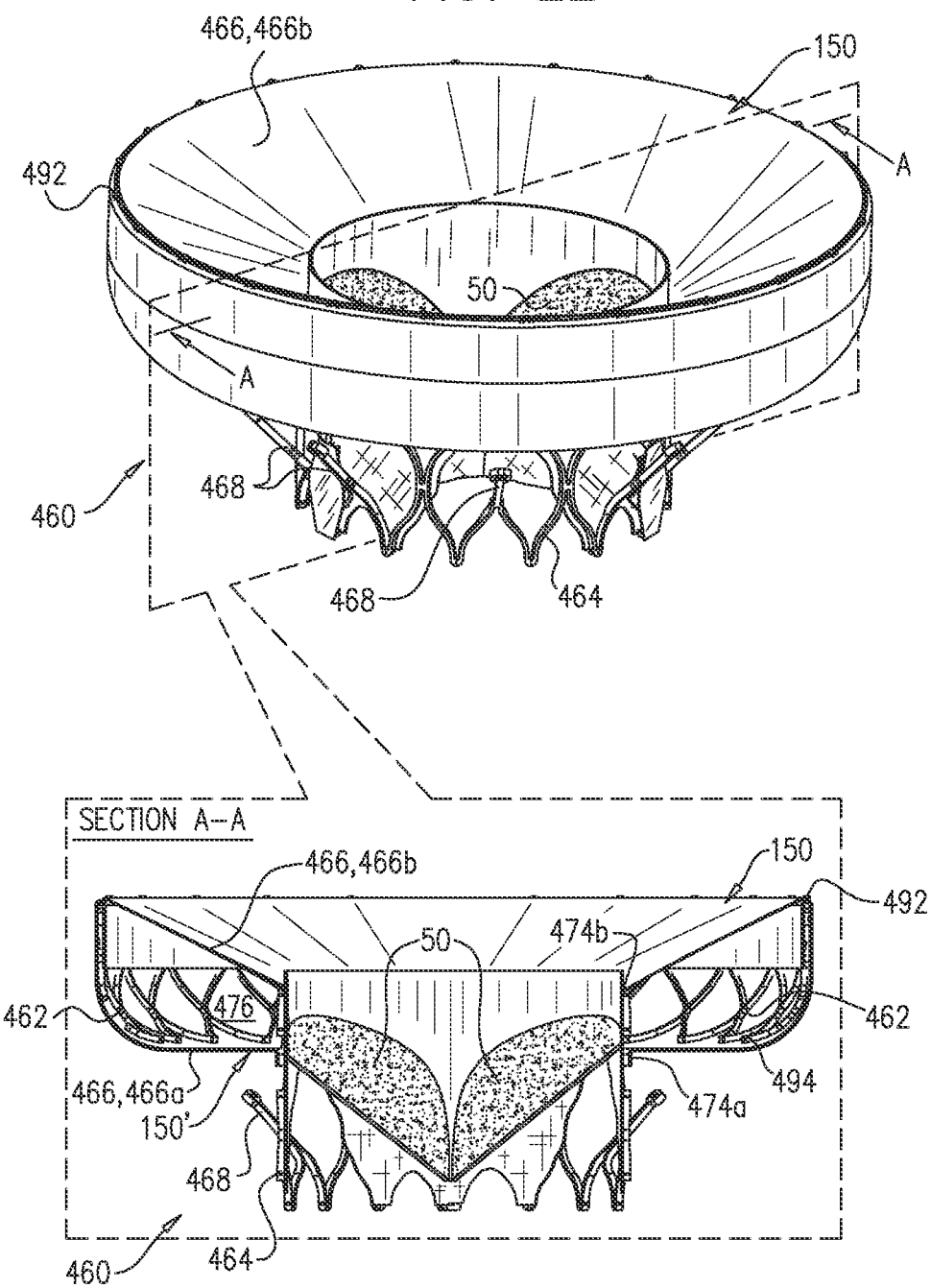

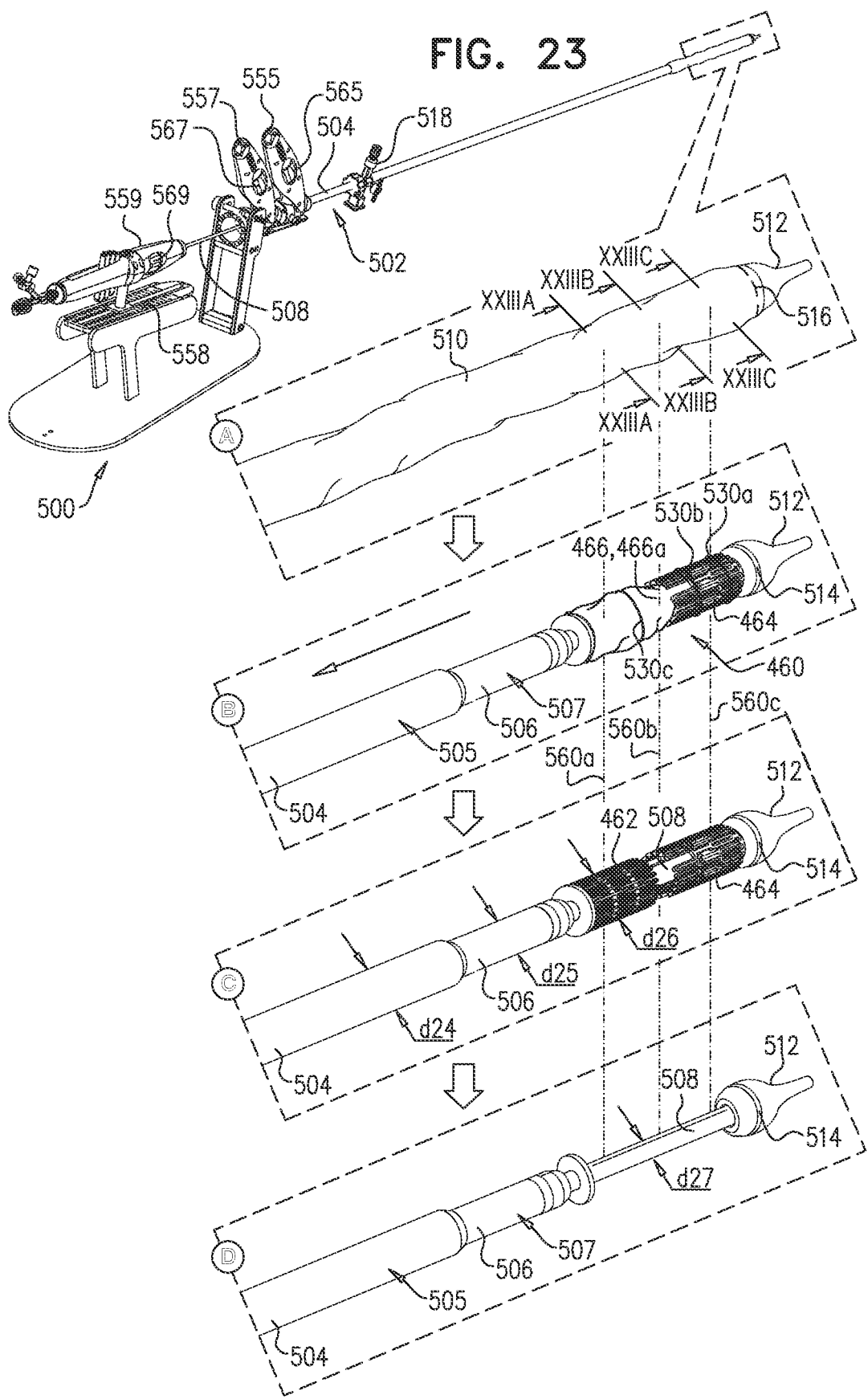

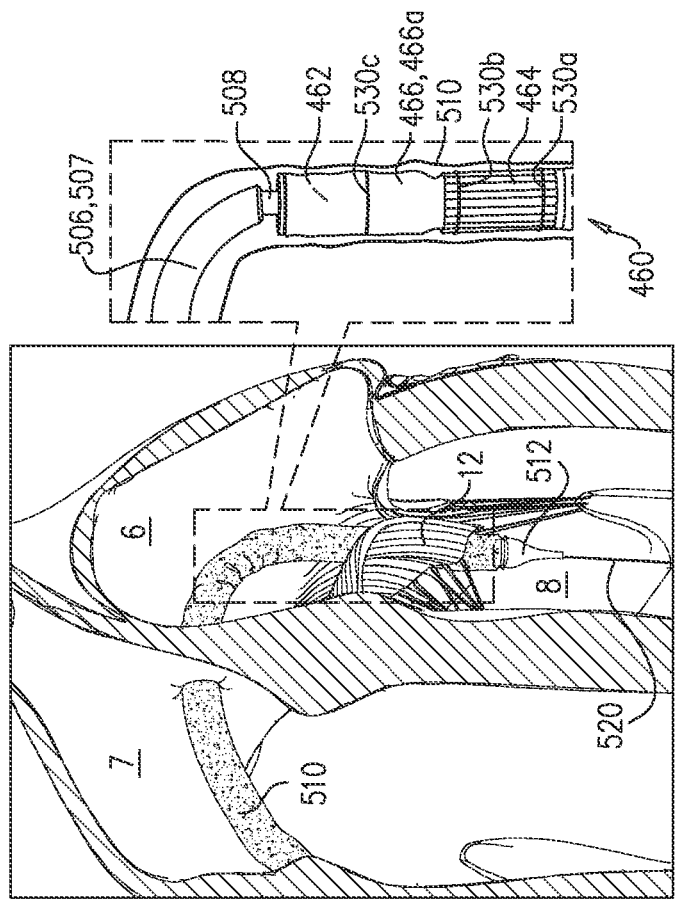
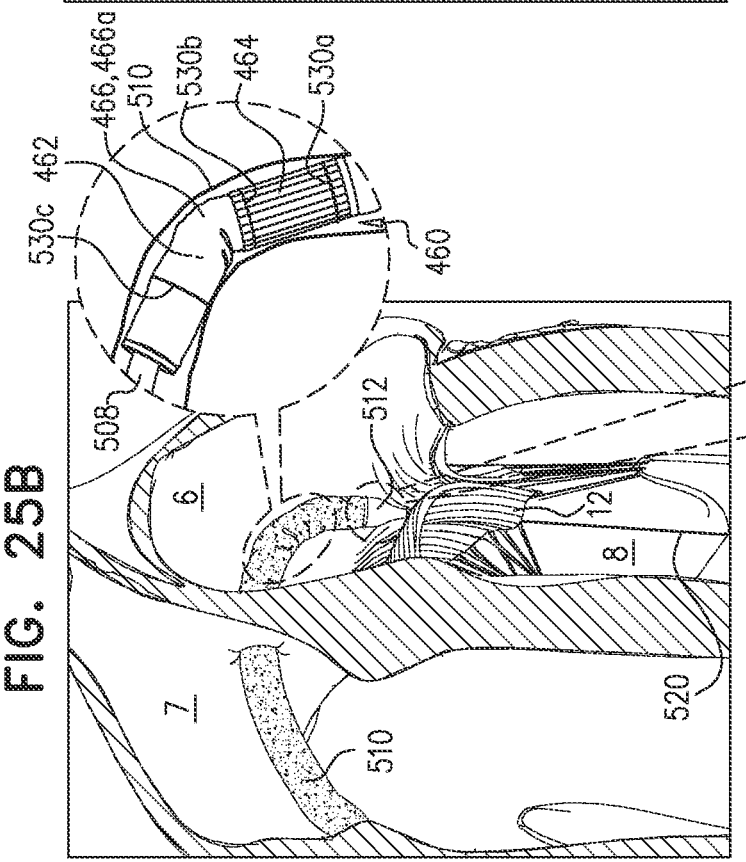
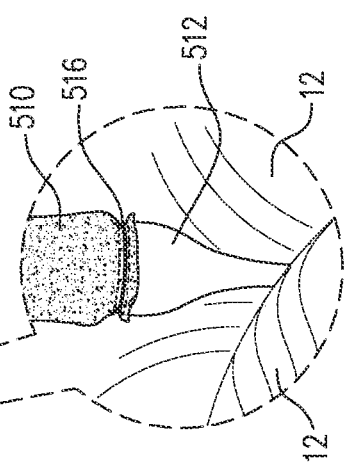
FIG. 25B
FIG. 25C

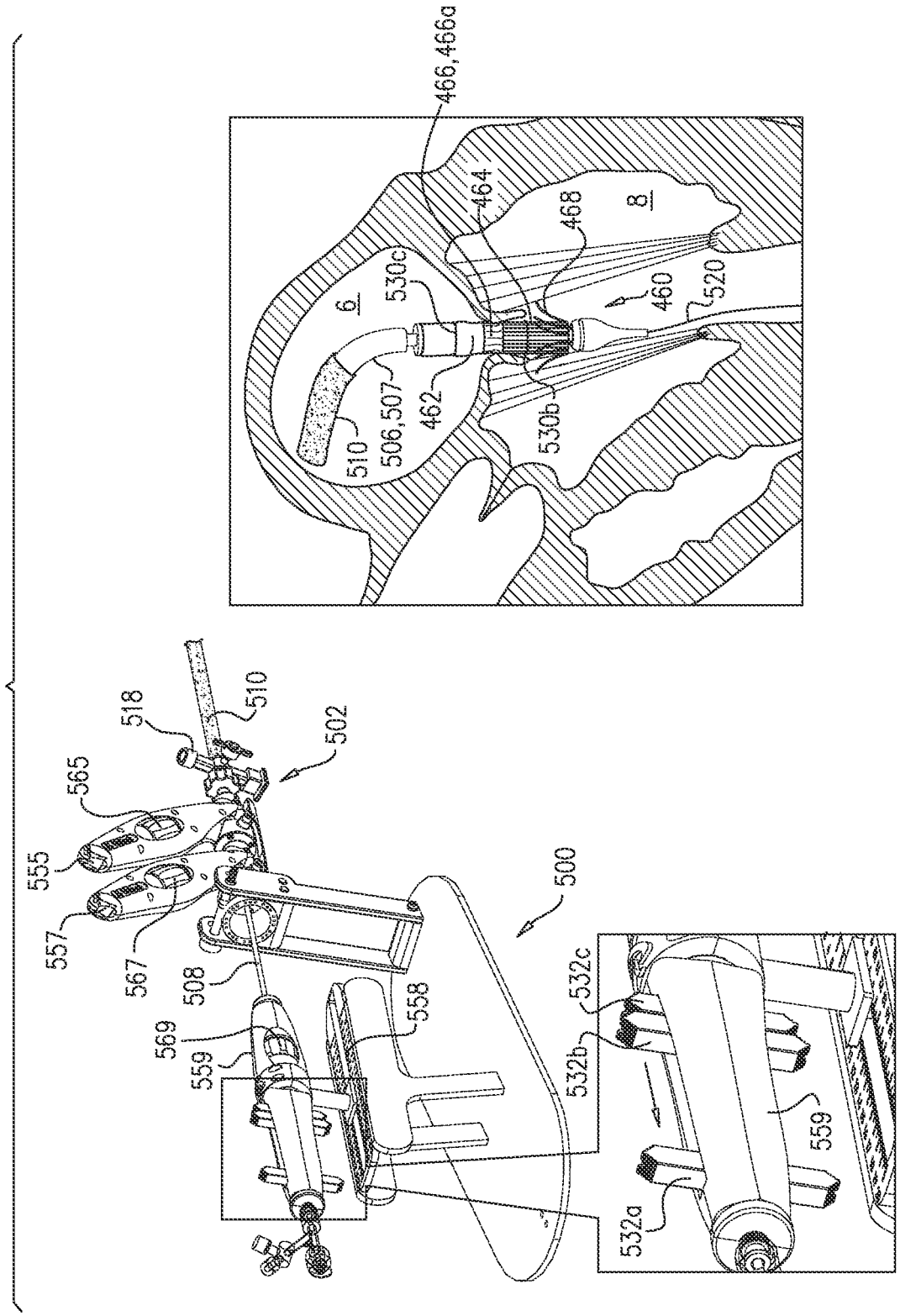

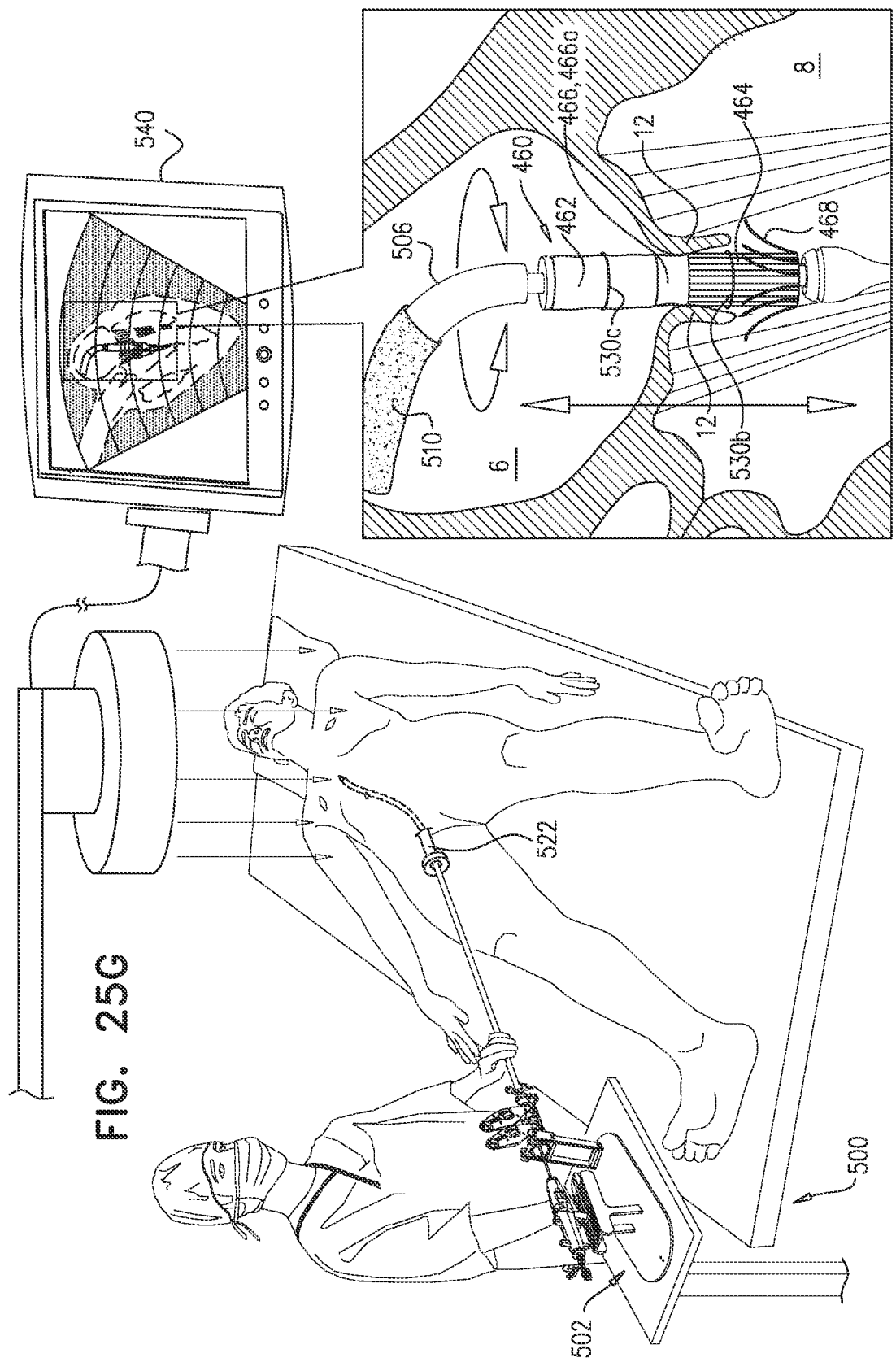

ANCHORING OF A PROSTHETIC VALVE

CROSS-REFERENCES TO RELATED APPLICATIONS

The present application is a Continuation of U.S. patent application Ser. No. 16/656,790 to Hammer et al., filed Oct. 18, 2019, which published as US 2020/0046496, and which is a Continuation of U.S. patent application Ser. No. 15/703, 385 to Hammer et al., filed Sep. 13, 2017, which issued as U.S. Pat. No. 10,492,908, and which is a Continuation of U.S. patent application Ser. No. 15/329,920 to Hammer et al., filed Jan. 27, 2017, which issued as U.S. Pat. No. 10,524,910, and which is the US National Phase of PCT application IL2015/050792 to Hammer et al., filed Jul. 30, 2015, and entitled "Articulatable prosthetic valve," which published as WO 2016/016899, and which claims priority from:

(i) U.S. Provisional Patent Application 62/030,715 to Hammer et al., filed Jul. 30, 2014, and entitled "Prosthetic valve with crown"; and (ii) U.S. Provisional Patent Application 62/139,854 to Hammer et al., filed Mar. 30, 2015, and entitled "Prosthetic valve with crown."

The present application is related to (i) PCT patent application IL2014/050087 to Hammer et al., filed Jan. 23, 2014, entitled "Ventricularly-anchored prosthetic valves", which published as WO 2014/115149, and (ii) U.S. patent application Ser. No. 14/763,004 to Hammer et al., entitled "Ventricularly-anchored prosthetic valves" (now abandoned), which is a US National Phase of PCT IL2014/050087.

All of the above are incorporated herein by reference.

FIELD OF THE INVENTION

Some applications of the present invention relate in general to valve replacement. More specifically, some applications of the present invention relate to prosthetic cardiac valves and techniques for implantation thereof.

BACKGROUND

Dilation of the annulus of a heart valve, such as that caused by ischemic heart disease, prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

For some applications, prosthetic heart valve implants are described that comprise an upstream frame, a downstream frame that is distinct from the upstream frame, and a flexible sheet that connects and provides fluid communication between the upstream and downstream frames. For some applications, snares are alternatively or additionally coupled to the valve frame by a flexible sheet.

The implants described are typically secured to tissue of a native heart valve by sandwiching the tissue between elements of the implant, such as between frames or frame components. The sandwiching is typically facilitated by elastic coupling between the frames or frame components. The elastic coupling may be provided by the flexible sheet, or may be provided by other means, such as by one or more of the frames, or by an additional elastic member.

There are therefore provided, in accordance with some applications of the invention, the following inventive concepts:

1. Apparatus, for use with a valve of a heart of a subject, the apparatus including:
   a rod, transfemorally advanceable to the heart, and having a distal portion;
   an implant, including:
     a first frame, compressed around a first longitudinal site of the distal portion
     a second frame, compressed around a third longitudinal site of the distal portion,
     a valve member, disposed within the second frame, and
     a flexible sheet, coupling the first frame to the second frame, and disposed around a second longitudinal site of the distal portion, the second longitudinal site being between the first longitudinal site and the third longitudinal site; and
   an extracorporeal controller, coupled to a proximal portion of the rod, and operably coupled to the distal portion of the rod such that operating the extracorporeal controller bends the distal portion of the rod at at least the second longitudinal site causing articulation between the first frame and the second frame.

2. The apparatus according to inventive concept 1, further including a sheath, disposed over the implant, and being sufficiently flexible to passively bend in response to the bending of the rod and the articulation between the first frame and the second frame.

3. Apparatus, for use with a valve of a heart of a subject, the apparatus including:
   a rod, transfemorally advanceable to the heart, and having a distal portion;
   a prosthetic valve, including:
     a first frame, compressed around the distal portion,
     a second frame, compressed around the distal portion in tandem with the first frame, and articulatably coupled to the first frame, and
     a valve member, disposed within the second frame; and
   an extracorporeal controller, coupled to a proximal portion of the rod, and operably coupled to the distal portion of the rod such that operating the extracorporeal controller bends the distal portion of the rod at at least the second longitudinal site causing articulation between the first frame and the second frame.

4. The apparatus according to inventive concept 3, further including a sheath, disposed over the implant, and being sufficiently flexible to passively bend in response to the bending of the rod and the articulation between the first frame and the second frame.

5. An implant, for use with a subject, the apparatus including:
   a first frame having a compressed state in which the frame is transluminally advanceable into the subject, and having a tendency to radially expand from the compressed state toward an expanded state;
   a flexible sheet; and
   a second frame coupled, via the flexible sheet, to the first frame, in tandem with the first frame, along a longitudinal axis of the implant,
   wherein the coupling of the second frame to the first frame via the flexible sheet is such that the radial expansion of the first frame pulls the second frame longitudinally into the first frame by pulling the sheet radially outward.

6. An implant, for use with a subject, the apparatus including:
 a first frame having a compressed state in which the frame is transluminally advanceable into the subject, and having a tendency to radially expand from the compressed state toward an expanded state; and
 a second frame distinct from the first frame, and coupled to the first frame in tandem with the first frame along a longitudinal axis of the implant,
 wherein the coupling of the second frame to the first frame is such that a radially outward force of the first frame during its expansion is converted into a longitudinal force that pulls the second frame into the first frame.

7. Apparatus, including:
 a delivery tool including:
 a first catheter,
 a second catheter extending through the first catheter, and
 one or more extracorporeal controllers, coupled to a proximal end of at least one of the first catheter and the second catheter; and
 an implant, including a first frame articulatably coupled to a second frame, and coupled to a distal portion of the delivery tool, distal to a distal end of the first catheter and to a distal end of the second catheter,
 wherein the one or more extracorporeal controllers are actuatable to transition the apparatus between:
 a first state in which the first catheter and the second catheter are straight, and the first frame is articulated with respect to the second frame, and
 a second state in which a distal portion of at least one of the first catheter and the second catheter is bent, and the first frame is collinear with the second frame.

8. Apparatus for use with a native valve of a heart of a subject, the apparatus including:
 a support frame, having a compressed state, and an expanded state in which the support frame defines an opening therethrough, and is dimensioned to be placed against an upstream surface of the native valve such that the opening is disposed over an orifice defined by the native valve;
 a flexible sheet; and
 a valve frame:
 having a compressed state, and an expanded state in which the valve frame defines a lumen therethrough, including a valve member disposed within the lumen, and
 coupled to the support frame via the flexible sheet such that when the support frame is in its expanded state, and the valve frame is in its expanded state, at least part of the lumen is disposed within the opening, and the valve frame is not in contact with the support frame.

9. The apparatus according to inventive concept 8, wherein the apparatus is configured such that when the valve frame is in its expanded state and the support frame is in its expanded state, the flexible sheet extends radially outward from the valve frame to the support frame.

10. The apparatus according to inventive concept 8, wherein the apparatus is configured such that, when the valve frame is in its expanded state and the support frame is in its expanded state, the valve frame does not apply a radially-expansive force to the support frame.

11. The apparatus according to inventive concept 8, wherein the opening has an opening diameter, and the valve frame has a generally tubular body that defines the lumen, and in the expanded state of the valve frame, the tubular body has a body diameter that is less than 75 percent as great as the opening diameter.

12. The apparatus according to any one of inventive concepts 8-11, wherein the apparatus has a compressed state in which (i) the support frame is in its compressed state, (ii) the valve frame is in its compressed state, and (iii) the support frame and the valve frame are disposed collinearly with respect to each other, and are articulatable with respect to each other.

13. The apparatus according to inventive concept 12, wherein:
 the valve frame is coupled to the support frame via a flexible sheet, and
 the apparatus is configured such that:
 when the valve frame is in its expanded state and the support frame is in its expanded state, the sheet extends radially outward from the valve frame to the support frame, and
 when the valve frame is in its compressed state and the support frame is in its compressed state, the support frame and the valve frame are articulatably coupled to each other via the sheet, and the apparatus defines an articulation zone in which the sheet, but neither the valve frame nor the support frame, is disposed.

14. The apparatus according to inventive concept 13, wherein:
 the apparatus includes an implant including the support frame, the valve frame, and the sheet, and further includes a delivery tool, and
 the apparatus has a delivery state in which (i) the support frame is in its compressed state, and is coupled to a distal portion of the delivery tool, and (ii) the valve frame is in its compressed state, and is coupled to the distal portion of the delivery tool in tandem with the support frame, the apparatus is bendable at the articulation zone.

15. The apparatus according to inventive concept 14, wherein the delivery tool includes a rod, the distal portion of the delivery tool is a distal portion of the rod, and in the delivery state, the support frame and the valve frame both circumscribe the distal portion of the rod.

16. The apparatus according to inventive concept 15, wherein the delivery tool includes an extracorporeal controller, operably coupled to the distal portion of the rod such that in the delivery state, operating the extracorporeal controller bends the distal portion of the rod, causing articulation between the valve frame and the support frame.

17. Apparatus including an implant, the implant being percutaneously implantable, and including:
 a first frame;
 a second frame; and
 a plurality of flexible sheets including at least a first flexible sheet and a second flexible sheet, at least the first sheet coupling the first frame to the second frame, and the plurality of flexible sheets being coupled to the first frame and the second frame such that a closed chamber is disposed between the first sheet and the second sheet, and at least one of the sheets being at least partially blood-permeable.

18. The apparatus according to inventive concept 17, wherein the chamber circumscribes at least part of the second frame, and at least part of the first frame circumscribes the chamber.

19. The apparatus according to inventive concept 17, wherein at least one of the sheets is configured to promote blood coagulation within the chamber.

20. The apparatus according to any one of inventive concepts 17-19, wherein the second frame includes a prosthetic valve frame, dimensioned to be positioned through a native heart valve of a subject, and wherein the first frame includes an upstream support, configured to be placed against an upstream surface of the heart valve.

21. Apparatus including an implant, the implant being percutaneously implantable, and including:
   a metallic frame; and
   a closed chamber:
   having a toroid shape, and
   defined by a fabric that is at least partially blood-permeable, and is coupled to the metallic frame,
   wherein the toroid shape is describable as a result of revolving, about an axis, a cross-section of the chamber in which:
   the chamber is delimited by a boundary of the fabric, and
   at least a portion of the boundary does not contact the metallic frame.

22. The apparatus according to inventive concept 21, wherein at at least one position of the revolution, at least part of the boundary contacts the metallic frame.

23. The apparatus according to inventive concept 21, wherein at every position of the revolution, at least part of the boundary contacts the metallic frame.

24. Apparatus for use with a native atrioventricular valve of a heart of a subject, the apparatus including:
   a prosthetic valve frame:
   having an upstream end and a downstream end,
   having a compressed state for percutaneous delivery to the heart, and
   being intracorporeally expandable into an expanded state thereof in which the valve frame defines a lumen therethrough;
   a plurality of prosthetic leaflets, coupled to the prosthetic valve frame so as to facilitate downstream movement of blood of the subject through the lumen;
   an upstream support:
   having a compressed state for percutaneous delivery to the heart, and
   being intracorporeally expandable into an expanded state thereof in which the upstream support is configured to be placed against an upstream surface of the native valve, and has an inner edge that defines an opening; and
   a flexible sheet that couples the upstream support to the valve frame, the apparatus:
   having a central longitudinal axis extending from an upstream end of the apparatus to a downstream end of the apparatus,
   having a first state in which the valve frame is in the compressed state of the valve frame, and the upstream support is in the compressed state of the upstream support, and the flexible sheet couples the valve frame to the upstream support in a manner in which movement of the apparatus toward a second state thereof pulls the valve frame longitudinally in an upstream direction such that the upstream end of the valve frame is disposed longitudinally upstream of the opening.

25. The apparatus according to inventive concept 24, wherein the flexible sheet couples the valve frame to the upstream support in a manner in which expansion of the upstream support toward the expanded state thereof pulls the valve frame longitudinally in an upstream direction such that the upstream end of the valve frame is disposed longitudinally upstream of the opening.

26. The apparatus according to inventive concept 24, wherein in the compressed state of the apparatus, the flexible sheet extends longitudinally between the valve frame and the upstream support, and articulatably couples the valve frame to the upstream support.

27. The apparatus according to any one of inventive concepts 24-26, wherein in the expanded state of the apparatus, the prosthetic valve frame has a diameter that is smaller than a diameter of the opening, and the flexible sheet is annular, and provides fluid sealing between the upstream support and the valve frame.

28. The apparatus according to inventive concept 27, wherein:
   the flexible sheet includes a first flexible sheet,
   the apparatus further includes a second flexible sheet, and
   in the expanded state of the apparatus:
   the first flexible sheet extends radially inward from the upstream support and is circumferentially attached to the valve frame at a first longitudinal site of the valve frame, and
   the second flexible sheet is annular, extends radially inward from the upstream support, and is circumferentially attached to the valve frame at a second longitudinal site of the valve frame that is closer to the upstream end of the valve frame than is the first longitudinal site.

29. The apparatus according to inventive concept 28, wherein the second longitudinal site is at the upstream end of the valve frame.

30. The apparatus according to inventive concept 28, wherein the second longitudinal site is at least 3 mm closer to the upstream end of the valve frame than is the first longitudinal site.

31. The apparatus according to inventive concept 28, wherein in the expanded state of the apparatus, the apparatus defines a chamber between the first flexible sheet and the second flexible sheet, and the apparatus is configured to encourage tissue growth within the chamber.

32. Apparatus, including:
   a first catheter, dimensioned for transfemoral and transseptal advancement into a left atrium of a heart of a subject, and having a lumen that has an internal diameter;
   a second catheter, having an external diameter that is smaller than the internal diameter, the second catheter being sufficiently long to extend through the first catheter such that a steerable distal portion of the second catheter extends out of a distal end of the first catheter; and
   an prosthetic valve, having a compressed state in which the implant is transfemorally and transseptally advanceable into the left atrium by the first catheter and the second catheter, and in which a width of the implant is greater than the internal diameter.

33. Apparatus for use with a heart of a subject, the apparatus including:
   a prosthetic valve, including a plurality of prosthetic leaflets, and a plurality of metallic struts disposed around the leaflets; and
   a delivery tool,
   wherein the apparatus has a delivery state in which:
   the apparatus is percutaneously advanceable to the heart along a longitudinal axis of the apparatus,
   a first cross-section through the apparatus shows concentric layers including, respectively, from inside outwardly: polymer, fabric, metal, and polytetrafluoroethylene (PTFE),
   a second cross-section through the apparatus shows concentric layers including, respectively, from inside outwardly: polymer, fabric, and PTFE, without a metal layer between the polymer and the fabric of the second cross-section, or between the fabric and the PTFE of the second cross-section, and a third cross-section through the apparatus shows concentric layers including, respectively, from inside outwardly: polymer, pericardial tissue, metal, and PTFE,
wherein the second cross-section is disposed longitudinally between the first cross-section and the third cross section.

34. The apparatus according to inventive concept 33, wherein the first cross-section shows another concentric layer including fabric between the layer including metal and the layer including PTFE.

35. The apparatus according to inventive concept 33, wherein the third cross-section shows another concentric layer including fabric between the layer including pericardial tissue and the layer including metal.

36. The apparatus according to inventive concept 33, wherein, for each cross-section, the layer including polymer is a component of the delivery tool.

37. The apparatus according to inventive concept 33, wherein, for each cross-section, the layer including PTFE is a component of the delivery tool.

38. The apparatus according to inventive concept 33, wherein, for each cross-section, the layer including metal is a component of the implant.

39. The apparatus according to inventive concept 33, wherein, for each cross-section, the layer including fabric is a component of the implant.

40. The apparatus according to inventive concept 33, wherein the second cross-section shows concentric layers including, respectively, from inside outwardly: polymer, fabric, and PTFE, without struts between the polymer and the fabric of the second cross-section, or between the fabric and the PTFE of the second cross-section.

41. The apparatus according to any one of inventive concepts 33-40, wherein the second cross-section shows concentric layers including, respectively, from inside outwardly: polymer, fabric, and PTFE, without any metal between the polymer and the fabric of the second cross-section, or between the fabric and the PTFE of the second cross-section.

42. Apparatus for use with a heart of a subject, the apparatus including:
a prosthetic valve, including a plurality of prosthetic leaflets, and a plurality of metallic struts disposed around the leaflets; and
a delivery tool,
wherein the apparatus has a delivery state in which:
the apparatus is percutaneously advanceable to the heart along a longitudinal axis of the apparatus,
a first cross-section through the apparatus shows concentric layers including, respectively, from inside outwardly: polymer, fabric, metal, and a material 100-300 microns thick,
a second cross-section through the apparatus shows concentric layers including, respectively, from inside outwardly: polymer, fabric, and the material 100-300 microns thick, without a metal layer between the polymer and the fabric of the second cross-section, or between the fabric and the material 100-300 microns thick of the second cross-section, and
a third cross-section through the apparatus shows concentric layers including, respectively, from inside outwardly: polymer, pericardial tissue, metal, and the material 100-300 microns thick,
wherein the second cross-section is disposed longitudinally between the first cross-section and the third cross section.

43. A method for use with a valve of a heart of a subject, the method including:
transfemorally advancing to the heart a rod and an implant compressed around a distal portion of the rod, the implant including a first frame, a second frame, a valve member disposed within the second frame, and a flexible sheet coupling the first frame to the second frame, wherein the first frame and the second frame are in tandem;
subsequently, articulating the second frame with respect to the first frame by bending the distal portion of the rod by operating an extracorporeal controller; and
subsequently, implanting the implant at the valve such that at least part of the first frame is disposed on a first side of the valve and at least part of the second frame is disposed on a second side of the valve.

44. The method according to inventive concept 43, wherein advancing the implant includes advancing the implant while a sheath is disposed over the implant, and wherein the step of articulating includes articulating the second frame with respect to the first frame by bending the rod such that the sheath passively bends in response to the articulation.

45. A method for use with a body of a subject, the method including:
percutaneously delivering into the body an implant in a compressed state, the implant:
having a longitudinal axis, and
including a first frame, a flexible sheet, and a second frame coupled, via the flexible sheet, to the first frame in tandem along the longitudinal axis; and
subsequently, radially expanding the first frame such that the first frame pulls the second frame longitudinally into the first frame by pulling the sheet radially outward.

46. A method, including:
transluminally advancing an implant to a heart of a subject while the implant is disposed within a sheath, the implant including (i) an expandable valve frame in a compressed state, (ii) a valve member disposed within the valve frame, and (iii) a plurality of snares coupled to the valve frame;
subsequently, entirely unsheathing the valve frame and the snares from the sheath;
subsequently, extending the snares radially outward from the valve frame while retaining the valve frame in the compressed state; and
subsequently, expanding the valve frame radially outward.

47. A method, including:
transluminally advancing an implant to a heart of a subject, the implant including (i) a valve frame at a downstream portion of the implant, (ii) a valve member disposed within the valve frame, (iii) a flexible sheet, and (iv) a support frame at an upstream portion of the implant, coupled to the valve frame via the flexible sheet, wherein the valve frame and the support frame are constrained in respective compressed states during the advancing; and
within the heart, (i) releasing the valve frame such that the valve frame automatically expands from its compressed state, while (ii) maintaining the support frame in its compressed state such that the support frame limits expansion of an upstream portion of the valve frame via tension on the sheet.

48. The method according to inventive concept 47, wherein maintaining the support frame in its compressed state includes maintaining the support frame in its compressed state such that, via tension on the sheet, the support frame limits expansion of the upstream portion of the valve frame more than expansion of a downstream portion of the valve frame.

49. A method, including:
   using a delivery tool, percutaneously advancing toward a heart of a subject a prosthetic valve implant coupled to a distal portion of the delivery tool, the implant including a first frame coupled to a second frame;
   subsequently, articulating the first frame with respect to the second frame by bending the distal portion of the delivery tool;
   subsequently, reducing the articulation of the first frame with respect to the second frame by reducing the bending of the distal portion of the delivery tool; and
   subsequently, implanting the implant in the heart of the subject.

50. The method according to inventive concept 49, further including, between the step of articulating the first frame and the step of implanting, bending another portion of the delivery tool, the other portion being proximal to the distal portion.

51. A method for use with a mitral valve disposed between a left atrium and a left ventricle of a heart of a subject, the method including:
   transfemorally and transseptally advancing an implant into the left atrium, the implant including:
      a support frame, shaped to define an opening therethrough, and
      a valve frame, (i) coupled to the support frame via a flexible sheet, (ii) shaped to define a lumen therethrough, and (iii) including a plurality of prosthetic leaflets disposed within the lumen;
   placing the support frame against an upstream surface of the valve; and
   placing at least part of the lumen within the opening, without placing the valve frame in contact with the support frame.

52. The method according to inventive concept 51, wherein the placing at least the part of the lumen within the opening includes positioning, within the opening, at least part of each leaflet of the plurality of leaflets.

53. The method according to inventive concept 51, wherein the valve frame is coupled to the support frame via a flexible sheet, and placing at least the part of the lumen within the opening includes placing at least the part of the lumen within the opening such that the flexible sheet extends radially outward from the valve frame to the support frame.

54. The method according to inventive concept 51, wherein the valve frame is coupled to the support frame via a flexible sheet, and placing at least the part of the lumen within the opening includes longitudinally pulling at least the part of the lumen into the opening by tensioning the sheet by radially expanding the support frame such that the support frame applies tension to the sheet.

55. The method according to inventive concept 51, wherein placing at least the part of the lumen within the opening includes placing at least the part of the lumen within the opening such that the valve frame does not apply a radially-expansive force to the support frame.

56. The method according to inventive concept 51, wherein the opening has an opening diameter, a tubular body of the valve frame defines the lumen, and the method further includes expanding the tubular body such that the tubular body has a body diameter that is less than 75 percent as great as the opening diameter.

57. The method according to any one of inventive concepts 51-56, wherein advancing the implant includes, while the support frame is in a compressed state thereof, and the valve frame is in a compressed state thereof and is coupled to the support frame, articulating the valve frame with respect to the support frame.

58. The method according to inventive concept 51, wherein advancing the implant includes advancing the implant while the implant is in a compressed state in which the support frame and the valve frame are both compressed, and are coupled in tandem.

59. The method according to inventive concept 58, wherein:
   the valve frame is coupled to the support frame via a flexible sheet which provides an articulation zone between the valve frame and the support frame while the implant is in its compressed state, and
   advancing the implant includes:
      advancing the implant while the implant is (i) in its compressed state and (ii) disposed around a rod of a delivery tool, and
      articulating the implant at the articulation zone by operating an extracorporeal controller to bend the rod.

60. Apparatus, including:
   a sealed product container; and
   an implant including a first frame, a flexible sheet, a second frame coupled to the first frame via the flexible sheet, and a valve member disposed within the second frame, wherein:
      the implant is disposed within the sealed product container,
      the first frame is constrained in a compressed state in which the first frame is dimensioned for percutaneous advancement into a subject, and
      the second frame is in an expanded state in which the second frame defines a lumen therethrough, the valve member is disposed within the lumen, and the second frame is not dimensioned for percutaneous advancement into the subject.

61. The apparatus according to inventive concept 60, further including a crimping tool, dimensioned to receive the second frame in the expanded state, and configured to compress the second frame such that the second frame is dimensioned for percutaneous advancement into the subject.

62. A method for use with an implant that includes a first frame coupled to a second frame, and a valve member disposed within the second frame, the method including:
   while the second frame is coupled to the first frame, compressing the second frame into a compressed state for percutaneous advancement into a subject;
   without compressing the first frame, percutaneously advancing the implant into the subject; and
   expanding the first frame and the second frame inside the subject.

63. The method according to inventive concept 62, wherein the first frame is coupled to the second frame by a flexible sheet, and wherein expanding the first frame and the second frame includes expanding the first frame and the second frame such that the expansion increases tension in the flexible sheet.

64. Apparatus for use with a native valve of a heart of a subject, the apparatus including:
   a valve body:
      including (1) a first frame shaped to define a lumen therethrough, and (2) a valve member disposed within the lumen,
      having a compressed state in which the first frame has a first diameter, and
      having an expanded state in which the first frame has a second diameter that is greater than the first diameter;
   an upstream support:

configured to be placed against an upstream surface of the native valve,
including a second frame,
having a compressed state, and
having an expanded state in which the second frame is annular, has an inner perimeter that defines an opening through the second frame, and has an outer perimeter;
one or more snares, configured to protrude radially outward from the second frame, and to ensnare leaflets of the native valve; and
a flexible sheet that couples the upstream support and the one or more snares to the valve body.

65. Apparatus for use with a native valve of a heart of a subject, the apparatus including:
a valve body, shaped to define a lumen and including a valve member disposed within the lumen, having a compressed state in which the valve body has a first diameter, and having an expanded state in which the first frame has a second diameter that is greater than the first diameter;
a snare frame, including a plurality of snares, configured to engage leaflets of the native valve; and
a flexible sheet that couples the valve body to the snare frame.

66. The apparatus according to inventive concept 65, wherein:
the apparatus includes an implant that includes the valve body, the snare frame and the flexible sheet,
the apparatus further includes a delivery tube,
the implant has a compressed state for percutaneous delivery to the native valve while disposed inside the delivery tube, and
in the compressed state the implant has an articulation zone, between the valve body and the snare frame, in which the flexible sheet is disposed, and at which the snare frame is articulatable with respect to the valve body.

67. The apparatus according to inventive concept 66, wherein in the compressed state the snares are disposed further from the valve body than is the articulation zone.

68. The apparatus according to any one of inventive concepts 66-67, wherein the snare frame is deployable from the delivery tube while the valve body remains disposed within the delivery tube, and the coupling of the snare frame to the valve body by the flexible sheet facilitates expansion of the snare frame into an expanded state thereof while the valve body remains compressed within the delivery tube.

69. The apparatus according to inventive concept 68, wherein the implant is configured such that, while the snare frame is in the expanded state thereof, expansion of the valve body into an expanded state thereof increases a rigidity of coupling between the valve body and the snare frame.

70. The apparatus according to inventive concept 68, wherein:
in the compressed state the snares are disposed closer to a downstream end of the implant than is the articulation zone, and
the snare frame is configured such that upon deployment of the snare frame from the delivery tube, the snare frame automatically inverts such that the snares become disposed further from the downstream end of the implant than is the articulation zone.

71. Apparatus for use at a native valve of a heart of a subject, the apparatus including an implant, the implant:
including an upstream frame; a downstream frame; a valve frame that defines a lumen; and a one-way valve member disposed within the lumen,
having an expanded state in which the one-way valve member facilitates one-way movement of fluid through the lumen, and
having a compressed state in which the valve frame is disposed collinearly between the upstream frame and the downstream frame, and is articulatably coupled to both the upstream frame and the downstream frame.

72. The apparatus according to inventive concept 71, wherein in the compressed state:
the upstream frame defines a first rigid segment,
the valve frame defines a second rigid segment,
the downstream frame defines a third rigid segment, and
the implant defines:
a first articulation zone longitudinally separating the first rigid segment from the second rigid segment by at least 1.5 mm, and
a second articulation zone longitudinally separating the second rigid segment from the third rigid by at least 1.5 mm.

73. The apparatus according to inventive concept 71, wherein in the compressed state of the implant, no individual rigid segment has a length that is greater than 22 mm.

74. The apparatus according to inventive concept 71, wherein the implant, in its compressed state, has a length of at least 30 mm.

75. The apparatus according to inventive concept 71, wherein, in the compressed state of the implant, a sum of (i) a length of the first rigid segment, (ii) a length of the second rigid segment, and (iii) a length of the third rigid segment, is at least 35 mm.

76. The apparatus according to any one of inventive concepts 71-75, wherein the valve frame is articulatably coupled to both the upstream frame and the downstream frame by a flexible sheet.

77. The apparatus according to inventive concept 76, wherein the sheet provides fluid sealing between the upstream frame and the valve frame.

78. The apparatus according to inventive concept 77, wherein the sheet provides fluid sealing between the valve frame and the downstream frame.

79. The apparatus according to any one of inventive concepts 71-75, further including a delivery tool, reversibly couplable to the implant, and configured to advance the implant to the heart while the implant is in its compressed state.

80. The apparatus according to inventive concept 79, wherein while the implant is in its compressed state, and is coupled to the delivery tool, the downstream frame is disposed distally to the valve frame, and the upstream frame is disposed proximally to the valve frame.

81. The apparatus according to any one of inventive concepts 71-75, further including a catheter, transluminally advanceable to the heart, and through which the implant, in its compressed state, is advanceable to the heart.

82. The apparatus according to inventive concept 81, wherein the catheter is capable of forming a bend having a radius of curvature of less than 13 mm, and the implant, in its compressed state, is advanceable through the bend.

83. The apparatus according to inventive concept 81, wherein:
the catheter has an internal diameter through which the implant, in its compressed state, is advanceable to the heart, and in its compressed state, the implant has a length of at least 25 mm, and a greatest width that is at least 75 percent of the internal diameter of the catheter.

84. A method for use with a valve of a heart of a subject, the method including:
providing an implant that includes:
a valve frame having an expanded state in which the valve frame is generally cylindrical, has a central longitudinal axis, and defines a lumen along the axis;
a plurality of leaflets disposed within the lumen, and
a plurality of snares coupled to the valve frame;
percutaneously delivering the implant through a catheter to the heart while the valve frame is in a compressed state;
while at least a portion of the valve frame remains disposed within the catheter, deploying the snares from a distal end of the catheter such that the snares protrude radially outward and form (i) a first angle with the axis, and (ii) a second angle with the valve frame;
subsequently, engaging tissue of the native valve using the snares; and
subsequently, by deploying more of the valve frame from the catheter, reducing the second angle by at least 50 percent, while not changing the first angle by more than 10 percent.

85. Apparatus, including:
a percutaneously-advanceable delivery tube; and
an implant, having a compressed state in which the implant is advanceable through the delivery tube, and including:
a valve frame having (i) a compressed state in which the valve frame is advanceable through the delivery tube, and (ii) an expanded state in which the valve frame is generally cylindrical and has a central longitudinal axis, and defines a lumen along the axis,
a plurality of leaflets disposed within the lumen, and
a snare frame:
shaped to define a plurality of snares,
having (i) a compressed state in which the snare frame is advanceable through the delivery tube, and (ii) an expanded state in which the snares protrude radially outward, and
coupled to the valve frame such that a first angle between the snares and the axis is independent of a second angle between the snares and the valve frame.

86. A method, including:
providing (i) an implant that includes a first frame, a second frame, and an elastic coupling between the first frame and the second frame, and (ii) a transluminally-advanceable delivery tool;
coupling the second frame to the delivery tool by compressing the second frame against the delivery tool;
stretching the elastic coupling by increasing a distance between the first frame and the second frame subsequently to coupling the second frame to the delivery tool.

87. The method according to inventive concept 86, wherein increasing the distance includes increasing the distance using the delivery tool.

88. The method according to inventive concept 86, further including coupling the first frame to the delivery tool by compressing the first frame against the delivery tool.

89. The method according to any one of inventive concepts 86-88, further including transluminally advancing the implant through a catheter, while the implant is coupled to the delivery tool.

90. The method according to inventive concept 89, wherein transluminally advancing the implant includes transluminally advancing the implant subsequently to the step of stretching.

91. The method according to inventive concept 89, wherein transluminally advancing the implant includes transluminally advancing the implant prior to the step of stretching.

92. The method according to any one of inventive concepts 86-88, wherein the first frame is coupled to a first connector of the delivery tool, and coupling the second frame to the delivery tool includes coupling the second frame to a second connector of the delivery tool.

93. The method according to inventive concept 92, further including coupling the first frame to the first connector by compressing the first frame against the delivery tool.

94. The method according to inventive concept 92, wherein increasing the distance includes increasing the distance by increasing a distance between the first connector of the delivery tool and the second connector of the delivery tool.

95. Apparatus including a frame, the frame including:
a first plurality of struts, arranged to define a first annular portion;
a second plurality of struts, narrower and more flexible than the first plurality of struts, arranged to define a second annular portion, the second annular portion being coupled to the first annular portion at a perimeter of the frame, such that in an unconstrained state of the frame, an angle is defined between the first annular portion and the second annular portion;
the frame being configured such that (i) the angle is reducible by applying a deforming force to the frame, and (ii) the angle automatically increases upon subsequent removal of the deforming force.

96. The apparatus according to inventive concept 95, wherein the first annular portion defines a flexible sector that is more flexible than other portions of the first annular portion.

97. The apparatus according to inventive concept 95, wherein each strut of the first plurality of struts has a transverse cross-sectional area of 0.25-1 mm^2, and each strut of the second plurality of struts has a transverse cross-sectional area of 0.04-0.2 mm^2.

98. The apparatus according to inventive concept 95, wherein the perimeter of the frame defines a frame diameter of 50-70 mm.

99. The apparatus according to inventive concept 95, wherein in the unconstrained state of the frame, the angle is 45-90 degrees.

100. The apparatus according to any one of inventive concepts 95-99, wherein the first plurality of struts are arranged in a circumferentially-repeating chevron pattern.

101. The apparatus according to inventive concept 100, wherein the second plurality of struts are arranged in a circumferentially-repeating chevron pattern.

102. The apparatus according to inventive concept 100, wherein the second plurality of struts are individual rods that protrude radially inward from the perimeter of the frame.

103. Apparatus for use with a native atrioventricular valve of a heart of a subject, the apparatus including:
a prosthetic valve frame having an upstream end and a downstream end, and defining a lumen therebetween;
a plurality of prosthetic leaflets, coupled to the prosthetic valve frame so as to facilitate downstream movement of blood of the subject through the lumen; and an upstream support:
  having an upper annular portion, and a lower annular portion circumferentially coupled to the upper annular portion, and
  coupled to the prosthetic valve frame such that:
    the upper annular portion extends radially outward from a first longitudinal site of the prosthetic valve frame toward a perimeter of the upstream support, and
    the lower annular portion extends radially inward from the upper annular portion toward a second longitudinal site of the prosthetic valve frame, the second longitudinal site being downstream of the first longitudinal site.

104. The apparatus according to inventive concept 103, wherein the upper annular portion extends, from the first longitudinal site, radially outward in a downstream direction.

105. The apparatus according to inventive concept 103, wherein the lower annular portion extends, from the upper annular portion, radially inward in a downstream direction.

106. The apparatus according to inventive concept 103, wherein the lower annular portion does not contact the valve frame.

107. The apparatus according to inventive concept 103, wherein the lower annular portion is more flexible that the upper annular portion.

108. The apparatus according to any one of inventive concepts 103-107, wherein the lower annular portion is articulatably coupled to the upper annular portion.

109. Apparatus for use with a native valve of a heart of a subject, the apparatus including:
  a prosthetic valve, shaped to define a lumen therethrough, and configured to be placed at the native valve, and
  a prosthetic valve support:
    having a generally toroid shape that has an axis of revolution,
    configured to be placed against an annulus of the native valve, and
    configured, and coupled to the prosthetic valve, such that:
      in response to tension applied to the prosthetic valve by moving the prosthetic valve support away from the prosthetic valve, the prosthetic valve support moves into a constrained state by rolling about the axis of revolution in a first direction, and
      in response to removal of the tension, the prosthetic valve support moves away from the constrained state by rolling about the axis of revolution in a second direction that is opposite to the first direction.

110. The apparatus according to inventive concept 109, wherein the toroid shape of the prosthetic valve support defines an opening through the prosthetic valve support, and in a relaxed state of the apparatus, at least part of the lumen is disposed within the opening.

111. The apparatus according to inventive concept 109, wherein the prosthetic valve support defines at least one ring, and is configured such that (i) a diameter of the ring is reduced as the frame rolls in the first direction, and (ii) the diameter of the ring is increased as the frame rolls in the second direction.

112. The apparatus according to any one of inventive concepts 109-111, wherein the axis of revolution circumscribes a central longitudinal axis of the support frame, and the generally toroid shape is describable as a result of moving a U-shape along the axis of revolution.

113. A method for use with a valve of a heart of a subject, the method including:
  transluminally advancing an implant to the heart, the implant including:
    a support frame having a generally toroidal shape, the toroidal shape being describable as a result of moving revolving a plane geometric figure along an axis of revolution that circumscribes a central longitudinal axis of the support frame,
    a valve frame, shaped to define a lumen therethrough, and including a plurality of prosthetic leaflets disposed within the lumen, and
    a flexible sheet that couples the support frame to the valve frame;
  placing the support frame against an upstream surface of the valve such that the support frame circumscribes an orifice defined by the valve; and
  causing the support frame to move the valve frame in an upstream direction by releasing the valve frame such that the support frame rolls about the axis of revolution.

114. Apparatus for use with a heart of a subject, the apparatus including:
  a prosthetic valve frame:
    having an upstream end and a downstream end,
    having a compressed state for percutaneous delivery to the heart,
    being intracorporeally expandable into an expanded state, and
    defining a lumen therethrough;
  a plurality of prosthetic leaflets, coupled to the prosthetic valve frame so as to facilitate one-way downstream movement of blood of the subject through the lumen;
  a support frame:
    having a compressed state for percutaneous delivery to the heart,
    being intracorporeally expandable into a generally toroid shape dimensioned to be placed against an upstream surface of a valve of the heart such that the support frame circumscribes an orifice defined by the valve, the toroid shape (i) being describable as a result of revolving a plane geometric figure about a central longitudinal axis of the support frame, and (ii) defining an opening through the support frame, and
    in the toroid shape:
      having a first state in which the plane geometrical figure is in a first orientation with respect to the opening,
      being movable by a force into a constrained state in which the plane geometrical figure is in a second orientation with respect to the opening, and
      being configured to automatically move from the constrained state toward the first state upon removal of the force; and
  a flexible sheet, coupling the support frame to the prosthetic valve frame, and coupled to the support frame such that the force is applicable to the support frame by tensioning the sheet.

115. The apparatus according to inventive concept 114, wherein the flexible sheet is shaped to define a channel between the opening and the lumen.

116. Apparatus for use with a native valve of a heart of a subject, the apparatus including:
  a prosthetic valve frame:
    having an upstream end and a downstream end,
    having a compressed state for percutaneous delivery to the heart,
    being configured to be delivered to the native valve such that at least the downstream end is disposed in a ventricle downstream of the valve, being intracorporeally expandable into an expanded state, and defining a lumen therethrough;

a plurality of prosthetic leaflets, coupled to the prosthetic valve frame so as to facilitate one-way downstream movement of blood of the subject through the lumen; and a support frame:

having a compressed state for percutaneous delivery to the heart, being intracorporeally expandable into a generally toroid shape that defines an opening and is dimensioned to be placed against an upstream surface of the valve, with the opening over an orifice defined by the valve, coupled to the prosthetic valve frame, and configured such that:

while (i) the support frame is in the generally toroid shape and is disposed against the upstream surface of the valve, and (ii) at least the downstream end of the prosthetic valve frame is disposed in the ventricle, in response to a force applied to the support frame by downstream movement of the prosthetic valve frame, the support frame moves into a constrained state by rolling inward toward the orifice, and in response to releasing the force, the support frame automatically moves away from the constrained state by rolling outward away from the orifice.

117. The apparatus according to inventive concept 116, wherein the support frame is coupled to the prosthetic valve frame such that there is fluid communication between the opening and the lumen.

118. Apparatus for use at a native valve of a heart of a subject, the apparatus including:

an upstream frame:

having a generally toroid shape, having an upstream end, a downstream end, and a mid portion therebetween, being wider at the mid portion than at the upstream end or the downstream end, and defining an opening at the downstream end;

a downstream frame, distinct from the upstream frame, and defining a lumen therethrough;

a flexible sheet, shaped to define a conduit, and coupled to the upstream frame and the downstream frame in a manner that provides closed fluid communication between the opening and the lumen; and a plurality of prosthetic leaflets, configured to facilitate downstream movement of liquid through the conduit, and to inhibit upstream movement of liquid through the conduit.

119. The apparatus according to inventive concept 118, wherein the toroid shape is wider at the mid portion than at the upstream end, both with respect to an outer surface of the upstream frame, and with respect to an inner surface of the upstream frame.

120. The apparatus according to inventive concept 118, wherein the opening has a diameter that is greater than a diameter of the lumen.

121. The apparatus according to inventive concept 118, wherein each prosthetic leaflet of the plurality of prosthetic leaflets has an immobilized edge attached to the flexible sheet.

122. The apparatus according to any one of inventive concepts 118-121, wherein an upstream portion of the conduit is wider than a downstream portion of the conduit.

123. The apparatus according to inventive concept 122, wherein the sheet assumes a frustoconical shape.

124. The apparatus according to any one of inventive concepts 118-121, wherein the prosthetic leaflets are attached to at least one element selected from the group consisting of: the flexible sheet, and the downstream frame.

125. The apparatus according to inventive concept 124, wherein the prosthetic leaflets are attached to the flexible sheet.

126. The apparatus according to inventive concept 124, wherein the prosthetic leaflets are attached to the downstream frame.

127. The apparatus according to inventive concept 124, wherein the opening has a diameter that is greater than a diameter of the lumen.

128. The apparatus according to any one of inventive concepts 118-121, wherein the flexible sheet facilitates intracardiac positioning of the downstream frame at least in part independently of intracardiac placement of the upstream frame.

129. The apparatus according to inventive concept 128, wherein the upstream frame has a central longitudinal axis and the downstream frame has a central longitudinal axis, and wherein flexible sheet facilitates lateral movement of the central longitudinal axis of the downstream frame with respect to the central longitudinal axis of the upstream frame.

130. The apparatus according to inventive concept 128, wherein the upstream frame has a central longitudinal axis and the downstream frame has a central longitudinal axis, and wherein flexible sheet facilitates deflection of the central longitudinal axis of the upstream frame with respect to the central longitudinal axis of the downstream frame.

131. The apparatus according to any one of inventive concepts 118-121, wherein the upstream frame is shaped and dimensioned to be placed in an atrium of the heart that is upstream of the native valve, with the downstream end of the upstream frame disposed against an annulus of the native valve.

132. The apparatus according to inventive concept 131, wherein the downstream frame is shaped and dimensioned to be placed in a ventricle of the heart that is downstream of the native valve.

133. The apparatus according to inventive concept 132, wherein the downstream frame is shaped and dimensioned to be placed in the ventricle with an upstream portion of the downstream frame disposed against tissue of the native valve.

134. The apparatus according to inventive concept 131, wherein the upstream frame is shaped and dimensioned to be placed in the atrium with the downstream end of the upstream frame disposed against an annulus of the native valve, and the upstream end of the upstream frame not in contact with a roof of the atrium.

135. The apparatus according to inventive concept 131, wherein the upstream frame has a height between the upstream end and the downstream end, and the height of the upstream frame is smaller than a height of the atrium between the annulus and a roof of the atrium.

136. The apparatus according to any one of inventive concepts 118-121, wherein the apparatus has:

a compressed delivery state in which the apparatus is percutaneously deliverable to the heart, and an expanded state in which:

the upstream frame is in an expanded state in which the upstream frame:

has the generally toroid shape, is wider at the mid portion than at the upstream end or the downstream end, and defines the opening at the downstream end, and the downstream frame is in an expanded state thereof in which the
downstream frame defines the lumen.

137. The apparatus according to inventive concept 136, wherein the apparatus includes an implant including the upstream frame, the downstream frame, the flexible sheet and the prosthetic leaflets, and further includes:
a sheath:
percutaneously-advanceable to the native valve,
via which the implant is percutaneously-deliverable to the native valve in the compressed delivery state, and
configured to constrain at least the downstream frame in the compressed delivery state thereof; and
a rod, configured to be disposed within the lumen, the conduit and the opening while the implant is in the compressed delivery state within the sheath, the upstream frame and the downstream frame being held immobile with respect to the rod while in the compressed delivery state.

138. The apparatus according to inventive concept 137, wherein the implant is configured to be advanced distally out of the sheath such that the upstream frame emerges from the sheath before the downstream frame, and the implant is further configured such that the upstream frame remains in the compressed delivery state thereof subsequently to emerging from the sheath.

139. The apparatus according to inventive concept 137, further including a plurality of control wires extending through the rod and out of the rod, coupled to the upstream frame, and configured to apply a control force to the upstream frame.

140. The apparatus according to inventive concept 139, wherein the control wires are configured to apply an upstream-directed force to the upstream frame while the downstream frame is in the expanded state thereof.

141. The apparatus according to any one of inventive concepts 118-121, wherein the toroid shape is describable as the result of revolving a plane geometrical figure about a central longitudinal axis of the upstream frame, and wherein the plane geometrical figure defines a concavity that faces radially inward toward the central longitudinal axis.

142. The apparatus according to inventive concept 141, wherein the plane geometrical figure is generally U-shaped.

143. The apparatus according to any one of inventive concepts 118-121, wherein the downstream frame includes a generally tubular body and a plurality of snares that protrude radially outward from the body.

144. The apparatus according to inventive concept 143, wherein the snares protrude radially outward from an upstream portion of the body.

145. The apparatus according to inventive concept 143, wherein the snares protrude radially outward from a downstream portion of the body.

146. The apparatus according to any one of inventive concepts 118-121, wherein the upstream frame is elastically coupled to the downstream frame such that, subsequent to application of a force that increases a distance between the upstream frame and the downstream frame, when the force is removed the distance becomes reduced.

147. The apparatus according to inventive concept 146, wherein the flexible sheet is elastic, and provides the elastic coupling.

148. The apparatus according to inventive concept 146, further including at least one tether attached at a first end thereof to the upstream frame and at a second end thereof to the downstream frame.

149. The apparatus according to inventive concept 148, wherein the at least one tether is elastic, and provides the elastic coupling.

150. The apparatus according to inventive concept 146, wherein the upstream frame defines at least one spring that provides the elastic coupling.

151. The apparatus according to inventive concept 150, wherein the at least one spring is coupled to a first end of a respective tether, and a second end of the respective tether is coupled to the downstream frame.

152. The apparatus according to inventive concept 150, wherein the at least one spring is defined by the upstream end of the upstream frame.

153. The apparatus according to inventive concept 150, wherein the shape of the sheet and the coupling of the sheet to the upstream frame and the downstream frame positions the at least one spring with respect to the sheet such that the at least one spring provides the elastic coupling by pulling the sheet in an upstream direction.

154. The apparatus according to inventive concept 150, wherein the at least one spring is defined by the downstream end of the upstream frame.

155. A method for use at a native valve of a heart of a subject, the native valve being disposed between an atrium and a ventricle of the heart, and having an annulus and native leaflets, the method including:
positioning a distal portion of a sheath at the native valve, such that the native leaflets coapt against the sheath, the sheath containing, in a compressed state, an implant including an upstream frame, a downstream frame distinct from the upstream frame, a flexible sheet that couples the upstream frame to the downstream frame, and a plurality of prosthetic leaflets;
exposing a portion of the downstream frame from the sheath such that the portion of the downstream frame expands, and the native leaflets coapt against the portion of the downstream frame;
moving the implant downstream until the leaflets coapt upstream of the portion of the downstream frame;
applying an upstream force to the native leaflets with the downstream frame by moving the implant upstream; and
expanding the upstream frame within the atrium.

156. The method according to inventive concept 155, wherein the portion of the downstream frame includes snares of the downstream frame, and wherein exposing the portion includes exposing the portion such that the snares protrude radially outward.

157. The method according to inventive concept 155, wherein:
the portion of the downstream frame includes snares of the downstream frame,
exposing the portion of the downstream frame includes exposing the portion of the downstream frame such that the snares protrude radially outward, and
applying the upstream force includes applying the upstream force with the snares.

158. The method according to inventive concept 155, wherein the portion of the downstream frame includes an upstream portion of the downstream frame, and wherein exposing the portion of the downstream frame includes exposing the upstream portion of the downstream frame.

159. The method according to inventive concept 155, wherein applying the upstream force with the downstream frame includes applying the upstream force with the portion of the downstream frame.

160. The method according to inventive concept 155, further including, subsequently to moving the step of moving the implant downstream, and prior to the step of applying the upstream force, further expanding the portion of the downstream frame by exposing more of the downstream frame from the sheath.

161. The method according to any one of inventive concepts 155-160, further including, subsequently to the step of expanding, applying a control force to the upstream frame.

162. The method according to inventive concept 161, wherein applying the control force includes applying the control force by adjusting tension on one or more control wires reversibly coupled to the upstream frame.

163. The method according to inventive concept 161, wherein applying the control force includes pulling the upstream frame in an upstream direction.

164. The method according to inventive concept 161, wherein applying the control force includes pulling the upstream frame radially inward.

165. The method according to any one of inventive concepts 155-160, wherein the step of exposing includes exposing the upstream frame, then the sheet, and then the portion of the downstream frame.

166. The method according to inventive concept 165, wherein the step of exposing includes withdrawing the sheath proximally.

167. The method according to any one of inventive concepts 155-160, further including, subsequently to the step of applying the upstream force to the native leaflets, sandwiching tissue of the native valve between the upstream frame and the downstream frame by reducing a distance between the upstream frame and the downstream frame by removing a separating force that maintains a distance between the upstream frame and the downstream frame.

168. The method according to inventive concept 167, further including, prior to removing the separating force, increasing the distance between the upstream frame and the downstream frame by applying the separating force to the implant.

169. The method according to inventive concept 167, wherein the step of expanding the upstream frame includes releasing the upstream frame such that the upstream frame automatically expands and the separating force is removed.

170. The method according to inventive concept 167, wherein the step of expanding the upstream frame includes releasing a restraining element that maintains the upstream frame in the compressed state thereof.

171. The method according to inventive concept 170, wherein releasing the restraining element includes disengaging a retaining member from the restraining element.

172. The method according to inventive concept 171, further including withdrawing the retaining member alongside the implant, and withdrawing the restraining element via the lumen.

173. The method according to any one of inventive concepts 155-160, further including, using imaging, observing coaptation of the native leaflets and the implant juxtaposed with respect to the native leaflets, and wherein the step of positioning includes observing the upstream frame disposed upstream of a level of coaptation of the native leaflets.

174. The method according to inventive concept 173, wherein observing the implant in a position in which the upstream frame is disposed upstream of a level of coaptation of the native leaflets includes observing the portion of the downstream frame disposed at the level of coaptation of the native leaflets.

175. The method according to inventive concept 173, wherein observing the implant in a position in which the upstream frame is disposed upstream of a level of coaptation of the native leaflets includes observing the sheet disposed upstream of a level of coaptation of the native leaflets and downstream of the upstream frame.

176. Apparatus for use at a native valve of a heart of a subject, the native valve being disposed between an atrium and a ventricle of the heart, and having an annulus, the apparatus including:
   an upstream frame, shaped to define an opening, and configured to be placed in the atrium against the annulus;
   a downstream frame, distinct from the upstream frame, and defining a lumen therethrough;
   a flexible sheet, shaped to define a conduit and coupled to the upstream frame and the downstream frame such that, in an expanded state of the apparatus, the sheet is disposed upstream of the downstream frame and downstream of the upstream frame, and provides closed fluid communication between the opening and the lumen; and
   a plurality of prosthetic leaflets:
      each prosthetic leaflet of the plurality of leaflets having an immobilized edge attached to the sheet, and
      configured to facilitate downstream movement of liquid through the conduit, and to inhibit upstream movement of liquid through the lumen.

177. Apparatus for use at a native valve of a heart of a subject, the native valve being disposed between an atrium and a ventricle of the heart, and having an annulus, the apparatus including:
   at least one expandable frame, having a compressed state for percutaneous delivery to the native valve, and intracorporeally expandable into an expanded state;
   a flexible sheet, coupled to the at least one frame, and shaped to define a conduit; and
   a plurality of prosthetic leaflets:
      configured to facilitate downstream movement of liquid through the conduit, and to inhibit upstream movement of liquid through the conduit, and
      attached to the sheet and not sutured to the frame.

178. A method for use at a native valve of a heart of a subject, the native valve being disposed between an atrium and a ventricle of the heart, and having an annulus and native leaflets, the method including:
   percutaneously delivering an implant in a compressed state thereof to the native valve;
   positioning the implant such that:
      a first frame of the implant is disposed upstream of the native valve,
      a second frame of the implant, distinct from the first frame and coupled to the first frame by a flexible sheet, is disposed downstream of the native valve, and
      the flexible sheet traverses the native valve;
   expanding at least a portion of the second frame; and
   subsequently expanding the first frame.

179. The method according to inventive concept 178, wherein the step of expanding at least the portion of the second frame includes expanding at least the portion of the second frame prior to the step of positioning the implant.

180. The method according to inventive concept 178, wherein the step of expanding at least the portion of the second frame includes expanding at least the portion of the second frame subsequently to the step of positioning the implant.

181. The method according to any one of inventive concepts 178-180, wherein the portion of the second frame includes one or more snares of the second frame, and expanding at least the portion of the second frame includes expanding at least the snares.

182. The method according to inventive concept 181, further including, subsequently to expanding at least the snares, and prior to expanding the first frame, moving the implant upstream such that the snares apply an upstream force to tissue of the native valve.

183. The method according to any one of inventive concepts 178-180, further including sandwiching of the native leaflets between the first frame and the second frame by facilitating reduction of a distance between the first frame and the second frame.

184. The method according to inventive concept 183, wherein the second frame is elastically-coupled to the first frame, and facilitating reduction of the distance includes allowing the elastic coupling to reduce the distance.

185. A method for use at a native valve of a heart of a subject, the native valve being disposed between an atrium and a ventricle of the heart, and having an annulus and native leaflets, the method including:

percutaneously delivering to the native valve an implant having an upstream end, a downstream end, and a longitudinal axis therebetween;

subsequently, expanding a longitudinal portion of the implant that does not include the upstream end or the downstream end; and subsequently, expanding the upstream end and the downstream end.

186. The method according to inventive concept 185, wherein the step of expanding the upstream end and the downstream end includes expanding the downstream end and subsequently expanding the upstream end.

187. The method according to any one of inventive concepts 185-186, wherein:

the implant includes an upstream frame, a downstream frame, and a flexible sheet that couples and provides fluid communication between the upstream frame and the downstream frame, the longitudinal portion includes an upstream portion of the downstream frame and a downstream portion of the sheet, and expanding the longitudinal portion includes expanding the upstream portion of the downstream frame and the downstream portion of the sheet.

The present invention will be more fully understood from the following detailed description of applications thereof, taken together with the drawings, in which:

BRIEF DESCRIPTION OF THE DRAWINGS

FIGS. 1A-C and 2 are schematic illustrations of an implant comprising an upstream frame, a downstream frame that is distinct from the upstream frame, and a flexible sheet connecting the upstream and downstream frames, in accordance with some applications of the invention;

FIGS. 4A-J are schematic illustrations of delivery and implantation of the implant, in accordance with some applications of the invention;

FIGS. 12A-C are schematic illustrations of delivery and implantation of an implant, in accordance with some applications of the invention;

FIGS. 13A-C and 14A-C are schematic illustrations of implants that each comprise an upstream frame, a downstream frame, and a flexible sheet connecting the upstream and downstream frames, in accordance with some applications of the invention;

FIGS. 15A-C, 16A-D, and 17 are schematic illustrations of an implant, and implantation thereof, in accordance with some applications of the invention;

FIGS. 20A-C are schematic illustrations of an implant comprising a support frame, a prosthetic valve frame, and a flexible sheet coupling the support frame to the prosthetic valve frame, in accordance with some applications of the invention;

FIGS. 22, 23, 24A-C, and 25A-K are schematic illustrations of an implant, and a system comprising the implant and a delivery tool, in accordance with some applications of the invention.

DETAILED DESCRIPTION OF EMBODIMENTS

Figure 1C:
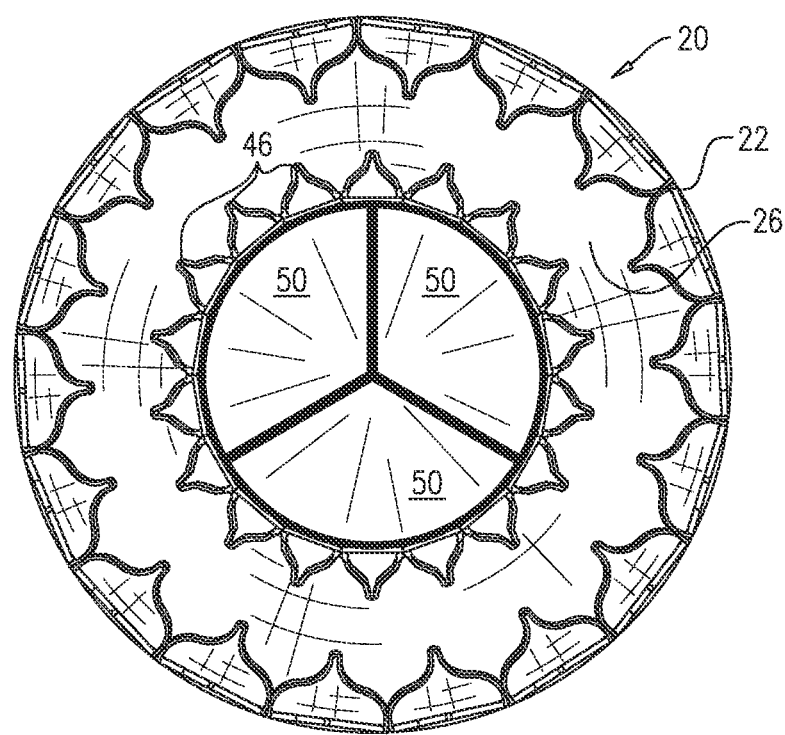

Reference is made to FIGS. 1A-C and 2, which are schematic illustrations of an implant 20 comprising an upstream frame 22, a downstream frame 24 that is distinct from the upstream frame, and a flexible sheet 26 connecting the upstream and downstream frames, in accordance with some applications of the invention. FIGS. 1A-B show respective perspective views of implant 20, FIG. 1C shows an end view of the implant, and FIGS. 2A-B show side views of the implant. Typically upstream frame 22 and downstream frame 24 each define (or are each defined by) a regularly tiled distribution of cells (e.g., a two-dimensional shape) that provides the three-dimensional shape of the frame. Alternatively, the upstream frame and/or the downstream frame may have a different structure, e.g., may comprise a wire frame and/or a braided mesh.

Frame 22 has a generally toroid shape, having an upstream end 32, a downstream end 34, and a mid portion 36 therebetween. Mid portion 36 has a width d1 that is greater than a width d2 of downstream end 34 or a width d3 of upstream end 32. That is, frame 22 is typically wider at mid portion 36 than at upstream end 32 or downstream end 34. Upstream and downstream portions of frame 22 curve radially inward to provide frame 22 with this shape. It is to be noted that, although d2 and d3 are shown as being generally equal, for some applications of the invention these widths are different. For some applications, width d1 is greater than 35 mm and/or less than 75 mm (e.g., 35-75 mm, such as 50-65 mm). For some applications, width d2 and/or width d3 is greater than 35 mm and/or less than 60 mm (e.g., 35-60 mm, such as 40-50 mm). Frame 22 (e.g., downstream end 34 thereof) defines an opening 28 therethrough.

Typically, and as shown, frame 22 is wider at mid portion 36 than at upstream end 32 or downstream end 34, both with respect to an outer surface of the upstream frame, and with respect to an inner surface of the upstream frame. Therefore, the inner surface of the frame typically defines a ring-shaped concavity 52 upstream of downstream end 34 (see FIG. 1A). A toroid is describable as the result of revolving a plane geometrical figure about an axis. Typically, the toroid shape of frame 22 is describable as the result of revolving a plane geometrical figure about a central longitudinal axis ax1 of the upstream frame, the plane geometrical figure defining a concavity 54 that faces radially inward toward axis ax1. For some applications, and as shown, this plane geometric figure is generally U-shaped. Revolution of concavity 54 about axis ax1 results in concavity 52.

For some applications, when viewed from the side, frame 22 appears generally stadium-shaped, and/or as a rectangle with rounded corners.

It is to be noted that, in its expanded state, frame 22 defines at least two layers. That is, a line parallel with and lateral to axis ax1 (i.e., closer to the outer edge of frame 22) will pass through the frame at least twice. For example, in the configuration of frame 22 shown in the figures, upstream end 32 defines a first layer and downstream end 34 defines a second layer. It is hypothesized that such a configuration increases stiffness of frame 22 in its expanded state, in a manner similar to that of a structural channel (known in the construction art), mutatis mutandis. It is to be noted that the scope of the invention includes other configurations (e.g., structures) of frame 22 that define at least two layers.

Frame 24 defines a generally tubular valve body 40 and a lumen 30 therethrough. Frame 24 (e.g., body 40) has an upstream portion 42 (including an upstream end) and a downstream portion 44 (including a downstream end). A plurality of snares (e.g., protrusions) 46 protrude radially outward from tubular body 40, thereby defining a diameter d11 that is greater than a diameter d12 of body 40. Typically, snares 46 protrude outward in an upstream direction (i.e., toward upstream frame 22), e.g., at an angle alpha_1 greater than 10 degrees (e.g., greater than 15 degrees, e.g., greater than 25 degrees) and/or less than 90 degrees (e.g., less than 80 degrees, e.g., less than 55 degrees), such as 10-90 degrees (e.g., 15-80 degrees, e.g., 25-55 degrees), such as about 40 degrees. For some applications, and as shown, snares 46 are disposed at upstream portion 42. Typically, each snare 46 is defined by a cell of frame 24 that is bent out of plane to body 40. Alternatively, snares 46 may be disposed elsewhere on tubular body 40, such as at downstream portion 44 (e.g., as described hereinbelow with reference to FIGS. 8, 13A-C, 14A-C, 15A-17, and/or 20A-C, mutatis mutandis).

Figure 2:
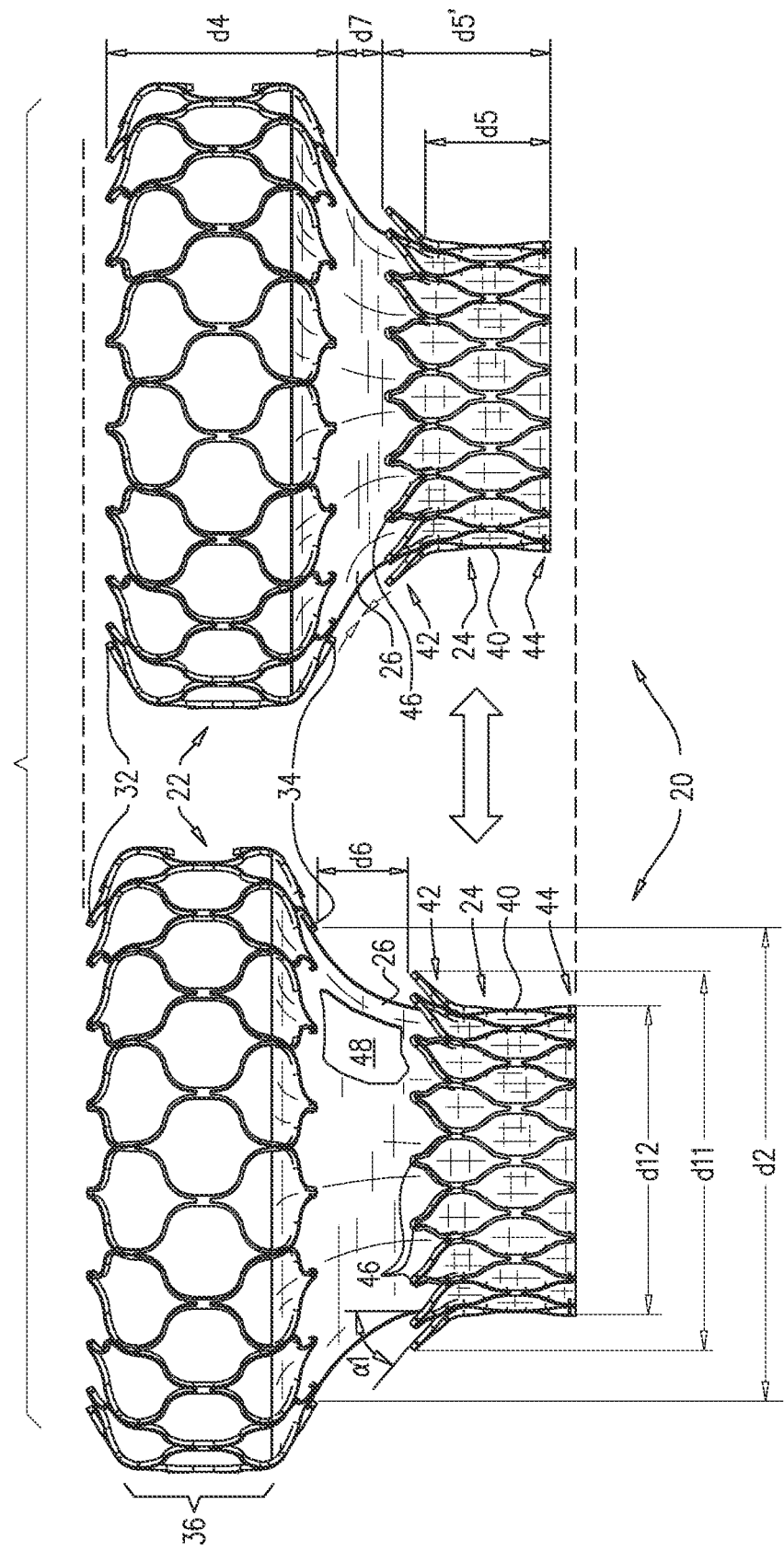

Frame 24 (and lumen 30) has a height that is typically greater than 8 mm and/or less than 40 mm, such as between 8 and 40 mm (e.g., between 12 and 25 mm, such as between 15 and 20 mm). For some applications this height is defined by a height of tubular body 40; this height is represented in FIG. 2 by reference numeral d5. For some applications this height includes additional height provided by snares 46; this height is represented in FIG. 2 by reference numeral d5'. For some applications, the height of frame 24 is greater than 8 mm and/or less than 40 mm (e.g., 8-40 mm, such as 12-25 mm).

Frames 22 and 24 are typically thin-walled (e.g., having a thickness d14 (FIG. 4D) of less than 1.5 mm, greater than 0.2 mm, and/or between 0.2 and 1.5 mm, e.g., 0.4-1.5 mm). Therefore diameter d2 of downstream end 34 of upstream frame 22 is typically similar to the diameter of opening 28, and diameter d12 of body 40 is typically similar to the diameter of lumen 30 (e.g., less than 3 mm, more than 1 mm, and/or between 1 and 3 mm difference in each case).

Sheet 26 is shaped to define a conduit 48, and is coupled to frames 22 and 24 in a manner that provides closed fluid communication between opening 28 and lumen 30. Diameter d2 is typically greater than diameter d12, and the diameter of opening 28 is typically greater than the diameter of the lumen 30. Therefore an upstream portion of conduit 48 (i.e., a portion closer to upstream frame 22) is typically wider than a downstream portion of the conduit (i.e., a portion closer to downstream frame 24). For some applications, sheet 26 assumes a frustoconical or funnel shape, and may in fact serve as a funnel. The shape assumed by sheet 26 is typically at least partly guided by the expansion of frames 22 and 24.

Sheet 26 (i.e., a material thereof) may be a fabric, a film, and/or another sheet-like structure, and may comprise a natural material, a polymer, a biomaterial, and/or any other suitable material. Typically, sheet 214 comprises polyester, PTFE, and/or pericardial tissue.

For some applications, sheet 26 is coupled to frame 22 at a level that is upstream of opening 28, and for some applications the sheet is coupled to frame 24 at a level that is downstream of upstream portion 42. For example, portions of sheet 26 may line and/or cover at least part of (e.g., all of) frame 24, and at least part of frame 22. For example, and as shown, the sheet may line most of frame 22 and at least a downstream portion of frame 22 (including downstream end 34). The flexibility of such portions of the sheet is in effect reduced by being attached to the respective frame. Therefore, throughout this patent application, including the specification and the claims, unless specified otherwise, the term "flexible sheet" refers to portions of the sheet disposed between the frames (e.g., longitudinally between the frames), and typically not to portions of the sheet that line and/or cover the frames. It is to be noted that sheet 26 is not attached to snares 46.

Implant 20 comprises a valve member (e.g., a plurality of prosthetic leaflets) 50, configured to facilitate downstream movement of liquid (e.g., blood) through the apparatus (e.g., through opening 28, conduit 48, and lumen 30), and to inhibit upstream movement of the liquid through the apparatus. Leaflets 50 are shown in FIGS. 1B-C, but for simplicity, not in other figures. Typically, leaflets 50 are at least in part disposed within lumen 30. For some applications, leaflets 50 are alternatively or additionally at least in part disposed within conduit 48. For some applications, at least part of each leaflet is attached (e.g., sutured) to frame 24 (i.e., at least part of an immobilized edge of each leaflet is attached to frame 24).

For some applications, at least part of the immobilized edge of each leaflet is attached (e.g., sutured) to sheet 26 (i.e., within conduit 48). FIG. 1B illustrates an example in which an immobilized edge of each leaflet is attached along an attachment line 56 that extends between frame 24 and sheet 26, i.e., each leaflet is attached within lumen 30 and within conduit 48. Parts of the leaflet that are attached (e.g., sutured) to sheet 26 are thus not attached (e.g., sutured) to frame 24 (snares 46 are not attached to sheet 26, and extend away from the sheet). For some applications, such parts of the leaflet are not attached to a metallic structure. For some applications, a reinforcing wire 58 is provided along attachment line 56, but it is to be noted that the reinforcing wire is typically distinct from frame 24. For some applications, leaflets 50 are coupled only indirectly to frame 24 (e.g. by being attached to sheet 26, which is attached to the frame). Thus, for some applications, leaflets 50 are secured within implant 20 only by being attached to a sheet (e.g., a fabric) that is tensioned by one or both frames.

Implant 20 is configured to be placed at a native heart valve of a subject, such as the mitral valve or tricuspid valve. Upstream frame 22 is shaped and dimensioned to be placed in an atrium of the heart that is upstream of the native valve, such as the left atrium, with downstream end 34 disposed against tissue of the native valve, such as against an annulus of the native valve. Typically, frame 22 is shaped and dimensioned to be placed in this position, with upstream end 32 not in contact with the roof of the atrium (i.e., the superior wall of the atrium). That is, frame 22 typically has a height d4 between upstream end 32 and downstream end 34 that is smaller than the height of the atrium between the annulus and the atrial roof. For some applications, height d4 is greater than 2 mm (e.g., greater than 7 mm) and/or less than 30 mm, e.g., between 2 and 30 mm (e.g., between 7 and 30 mm, such as between 10 and 20 mm). Examples of the positioning described in this paragraph are described in more detail hereinbelow, e.g., with reference to FIGS. 4A-J.

FIGS. 1A-2 show implant 20 in an expanded state thereof. That is, the above description of frames 22 and 24 are descriptions of the frames in respective expanded states. Implant 20 further has a compressed delivery state in which upstream frame 22 and downstream frame 24 are in respective compressed delivery states, and in which the implant is percutaneously deliverable to the heart (e.g., as described hereinbelow). Typically, frames 22 and 24 comprise a shape memory material (e.g., nitinol), are constrained in their expanded states during delivery, and are configured to automatically move toward their expanded shapes when this constraint is removed.

Upstream frame 22 is typically elastically-coupled to downstream frame 24, such that a distance between the two frames is increasable to a distance d6 by applying a force, and in response to subsequent removal of that force, the distance automatically becomes reduced to a distance d7 (see FIG. 2). The overall height of implant 20, from upstream end 32 of upstream frame 22 to downstream portion 44 of downstream frame 24, changes correspondingly to the change in distance between the two frames. Thus the state of implant 20 on the left side of FIG. 2 may be considered an extended state, and the state of the implant on the right side of the figure may be considered a contracted state.

For some applications, distance d6 is greater than 0 mm and/or less than 35 mm (e.g., 0-35 mm, such as 5-18 mm). For some applications, distance d7 is greater than 0 mm and/or less than 25 mm (e.g., 0-25 mm, such as 0-10 mm). For some applications, in the absence of tissue disposed between frames 22 and 24, upstream portion 42 of frame 24 may actually be disposed within a space defined by frame 22 (e.g., may be disposed more than 1 mm and/or less than 10 mm (e.g., 1-10 mm, such as 1-5 mm) upstream of opening 28 of frame 22). For such applications, this distance upstream may be considered a negative value of distance d7, such that, overall, distance d7 may be greater than −10 mm and/or less than 25 mm (e.g., between −10 and 25 mm, such as between −5 and 10 mm).

For implant 20, the elastic coupling is provided by sheet 26. For example, sheet 26 may be a sheet of an elastic material, and/or may comprise one or more elastic threads embedded within, threaded through, and/or attached to the material of the sheet. For other systems similar to implant 20, other elements provide the elastic coupling, such as, but not limited to, those described with reference to FIGS. 5-8.

Figure 3A:
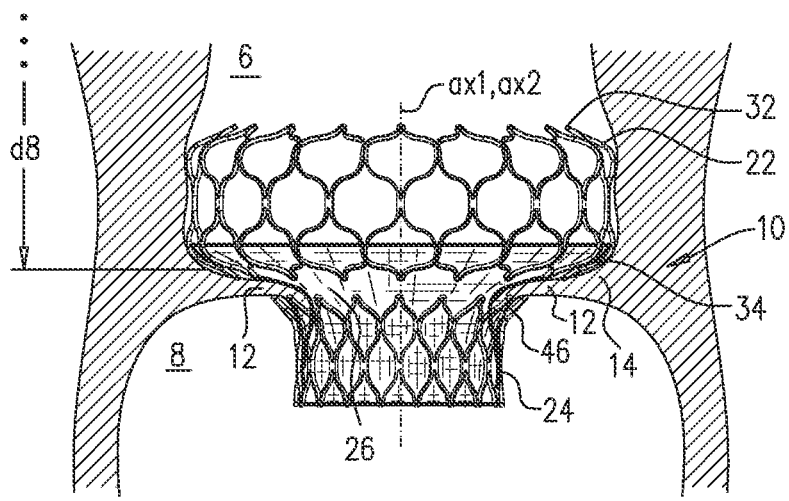
FIGS. 3A-C are schematic illustrations of respective placements of the implant at a native mitral valve of a subject, in accordance with some applications of the invention.
Figure 3B:
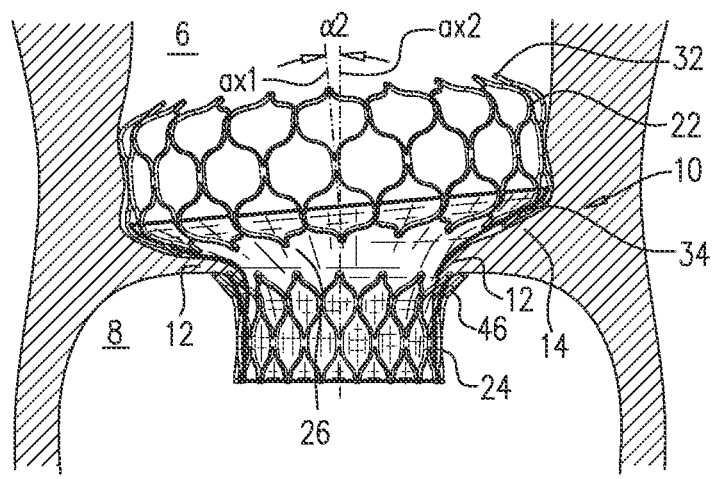
Figure 3C:
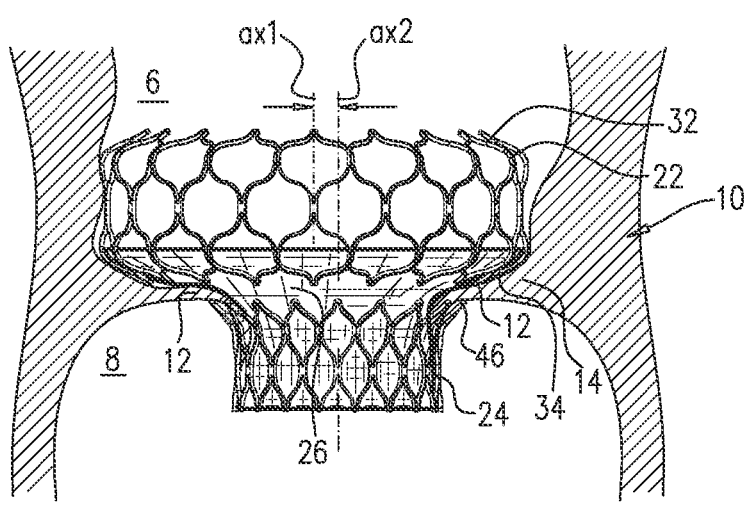

Reference is made to FIGS. 3A-C, which are schematic illustrations of respective placements of implant 20 at a native mitral valve 10 of a subject, in accordance with some applications of the invention. Mitral valve 10 is disposed between left atrium 6 and left ventricle 8 of the subject, and comprises an annulus 14 that supports native valve leaflets 12. As described hereinabove, upstream frame 22 is shaped and dimensioned to be placed in atrium 6, typically with downstream end 34 of the frame disposed against tissue of the native valve, such as against an annulus 14. Typically, in this position, upstream end 32 is not in contact with the roof of the atrium (not shown). That is, height d4 of frame 22 is typically smaller than a height d8 of the atrium between the annulus and the atrial roof. For some applications, upstream frame 22 is shaped and dimensioned to be placed such that downstream end 34 is disposed above (i.e., upstream of) the native annulus. Typically, upstream frame 22 is dimensioned such that, when implanted, any covered and/or lined portion of upstream frame 22 is disposed below a level of the pulmonary vein ostia (i.e., downstream of the ostia) so as not to obstruct blood flow therethrough. For applications in which frame 22 is entirely lined and/or coated, height d4 is less than a height between the valve annulus and the pulmonary vein ostia. For applications in which frame 22 is not entirely lined and/or coated (e.g., the frame is not lined or coated, and/or only a downstream portion of the frame is lined and/or coated), the frame is dimensioned such that at least the lined and/or coated portions of the frame are disposed below the level of the pulmonary vein ostia (whereas uncovered and/or unlined portions of the frame may be disposed at the pulmonary vein ostia).

Downstream frame 24 is shaped and dimensioned to be placed in ventricle 8, typically with upstream portion 42 and/or snares 46 in contact with tissue of the mitral valve, such as leaflets 12.

As described hereinbelow (e.g., with reference to FIGS. 4A-J), implant 20 is secured in place by utilizing the elastic coupling of upstream frame 22 downstream frame 24 to sandwich tissue of the native valve between upstream frame 22 and downstream frame 24 (e.g., snares 46). That is, the elastic coupling provides a sandwiching force which sandwiches the tissue between frames 22 and 24 by drawing the frames closer together along an upstream-downstream axis.

It is to be noted that throughout this application, including the specification and the claims, sandwiching of tissue between apparatus components means reducing a distance between the components while the tissue is disposed between the components (thereby typically increasing coupling to the tissue). Sandwiching does not necessarily require that the components move directly toward each other (e.g., having opposite but collinear vectors). For example, for applications in which diameter d11 is equal to or slightly larger than diameter d12, sandwiching may in fact occur as a result of snares 46 and downstream end 34 of frame 22 moving directly toward each other. However, for applications in which diameter d11 is smaller than diameter d12 (as shown), snares 46 and end 34 may not move directly toward each other, but may instead move as though they would eventually pass each other, nonetheless reducing the distance between these two components.

Inter alia, FIGS. 3A-C illustrate that sheet 26 facilitates intracardiac positioning of downstream frame 24 at least in part independently of intracardiac placement of upstream frame 22.

FIG. 3A shows implant 20 having been implanted at mitral valve 10 with axis ax1 of upstream frame 22 collinear with a central longitudinal axis ax2 of downstream frame 24 (e.g., in a theoretical perfectly symmetrical mitral valve). FIG. 3B shows implant 20 having been implanted at the mitral valve with axis ax1 disposed at a nonzero angle alpha_2 (e.g., deflected) with respect to axis ax2. Sheet 26 (e.g., the flexibility thereof) facilitates such deflection of axis ax1 with respect to axis ax2 while maintaining fluid communication between frames 22 and 24. FIG. 3C shows implant 20 having been implanted at the mitral valve with axis ax1 laterally offset (e.g., translated) with respect to axis ax2. Sheet 26 (e.g., the flexibility thereof) facilitates such lateral movement of axis ax1 with respect to axis ax2 while maintaining fluid communication between frames 22 and 24. It is hypothesized that implant 20 is thereby adaptable to various implantation conditions, such as to anatomical dimensions, while maintaining one-way fluid communication between the atrium and ventricle.

Reference is now made to FIGS. 4A-J, which are schematic illustrations of delivery and implantation of implant 20, in accordance with some applications of the invention. FIGS. 4A-J show transapical delivery and implantation of implant 20, but it is to be noted that the scope of the invention includes transatrial, transfemoral and/or transseptal delivery of the implant, mutatis mutandis.

A trocar 60 is transapically (e.g., intercostally) advanced into ventricle 8, and implant 20, in its compressed delivery state within a sheath 62, is delivered via the trocar (FIG. 4A). In the compressed delivery state of implant 20, frames 22 and 24 are in tandem (i.e., one after the other), coupled via sheet 26. Typically, the distal end of sheath 62 is advanced into atrium 6, and implant 20 is positioned such that upstream portion 42 of downstream frame 24 is disposed at the level of coaptation of leaflets 12, or further into the atrium (i.e., further upstream). Sheath 62 and sheet 26 are typically radiotransparent relative to frames 22 and 24, and the operating physician is typically able to identify this positioning using ultrasound and/or fluoroscopy. In this position leaflets 12 coapt against sheath 62. (That is, central portions (e.g., the a2 and p2 scallops) of the leaflets coapt against the sheath, while portions of the leaflets closer to the commissures (e.g., the a1, a3, p1, and p3 scallops) may coapt against each other.)

Sheath 62 is subsequently partially withdrawn (i.e., moved downstream) such that upstream frame 22, sheet 26, and at least upstream portion 42 and/or snares 46 of downstream frame 24 are exposed from the sheath (FIG. 4B). Although upstream frame 22 emerges from sheath 62 before downstream frame 24, upstream portion 42 of downstream frame 24 automatically expands toward its expanded state, whereas upstream frame 22 is maintained in its compressed delivery state by at least one restraining element 64, such as a restraining filament (described in more detail hereinbelow). Typically, upstream portion 42 expands to greater than 50 percent of its fully expanded diameter (e.g., greater than 50 percent and/or less than 80 percent, such as 50-80 percent, e.g., 60-80%). Following withdrawal of sheath 62, leaflets 12 coapt against implant 20 itself.

Due to the above-described position of implant 20, the leaflets coapt against upstream portion 42, and because of the expansion of this portion, during ventricular systole, a distance d9 between the leaflets at the point of this coaptation (e.g., between scallops a2 and p2) is greater than the distance when they previously coapted against sheath 62. This increased distance is observable by the operating physician using imaging techniques, e.g., as described hereinabove. For some applications, distance d9 is greater than 8 mm and/or less than 18 mm (e.g., 8-18 mm, such as 10-15 mm).

Subsequently, implant 20 and sheath 62 are withdrawn slightly proximally (i.e., downstream), until leaflets 12 coapt above upstream portion 42 and/or snares 46 (e.g., against sheet 26 and/or upstream frame 22). Because frame 22 has not expanded, a distance d10 between the leaflets during systole is now smaller than distance d9. This reduced distance is observable by the operating physician using imaging techniques, e.g., as described hereinabove. For some applications, distance d10 is greater than 5 mm and/or less than 12 mm (e.g., 5-12 mm, such as 6-8 mm). Typically, the withdrawal of implant 20 and sheath 62 is performed slowly, while observing leaflets 12, and withdrawal is stopped as soon as the physician observes a reduction in the systolic distance between them. It is hypothesized that this facilitates identification of a position of implant 20 in which upstream portion 42 of downstream frame 24 is close to, but downstream of, the level of coaptation of leaflets 12.

For some applications, at this stage, sheath 62 is further withdrawn with respect to implant 20, exposing more of downstream frame 24 (e.g., including some of downstream portion 44 thereof), and thereby facilitating further automatic expansion of the downstream frame (FIG. 4D). For example, upstream portion 42 may expand to greater than 70 percent of its fully expanded diameter (e.g., greater than 80 percent, such as greater than 90 percent, e.g., about 100 percent). Alternatively, this further withdrawal of sheath 62 and expansion of downstream frame 24 may be omitted.

It is to be noted that, for some applications, a longitudinal portion of implant 20 other than an end of the implant (e.g., a generally middle portion of the implant—upstream portion 42 and/or snares 46) is expanded prior to expansion of either end of the implant.

Typically, movement of downstream frame 24 with respect to sheath 62 is controlled via a mount 72, which is slidable though the sheath. Mount 72 comprises a body portion 76, and one or more flanges 74 via which it is reversibly coupled to frame 24. Mount 72 is dimensioned such that, while flanges 74 are disposed close to (e.g., touching) the inner wall of sheath 62, a gap 78 having a width d13 exists between body portion 76 and the inner wall of the sheath. Width d13 is greater than thickness d14 of frame 24, e.g., more than twice as great and/or less than 20 times as great, e.g., 2-20 times as great, such as 2-6 times as great. Thus, flanges 74 typically protrude radially outward from body portion 76 by a distance that is greater than thickness d14 (e.g., more than twice as great and/or less than 20 times as great, e.g., 2-20 times as great, such as 2-6 times as great).

Frame 24 is thereby movable radially inward and outward within gap 78, such that when the upstream part of the frame expands radially outward, the downstream end of the frame moves radially inward, frame 24 thereby pivoting about flanges 74. It is hypothesized that this configuration thereby proximal portion 42 and/or snares 46 of frame 24 expanding radially outward further than they would in a similar configuration in which width d13 is generally the same as thickness d14, i.e., in a configuration in which frame 24 fits snugly between body portion 76 and sheath 62.

Implant 20 and sheath 62 are subsequently moved distally (i.e., upstream), such that upstream portion 42 and/or snares 46 contact and apply an upstream force to tissue of the native valve, such as leaflets 12 (FIG. 4E). Because of the technique described hereinabove in which, prior to the step shown in FIG. 4E, upstream portion 42 is close to the level of coaptation of the leaflets, the distance that snares 46 travel upstream during the step shown in FIG. 4E is reduced (e.g., minimized), thereby reducing a probability that the snares might engage and/or damage other anatomical structures, such as chordae tendineae or ventricular walls.

Subsequently, sheath 62 is withdrawn further thereby exposing downstream portion 44 of downstream frame 24, and frame 24 automatically expands fully into its expanded state (FIG. 4F), typically becoming decoupled from mount 72 (described with reference to FIG. 4D).

Upstream frame 22 is subsequently allowed to expand by releasing restraining element 64 while maintaining contact between upstream portion 42 (and/or snares 46) and the tissue of the native valve (FIG. 4G). As shown, restraining element 64 may comprise a single filament wrapped around frame 22 (e.g., wrapped several times around the frame). Alternatively, more than one restraining element may be used. For some applications, restraining element 64 may be held in place by a retaining member 66, such as a wire that passes through one or more eyelets or loops defined by the restraining element. Pulling the retaining member 66 proximally disengages the retaining member, thereby releasing the restraining element, which thereby releases upstream frame 22, which automatically expands (e.g., radially outward).

Restraining element 64 may alternatively or additionally comprise any restraining element configured to reversibly restrain upstream frame 22 in its compressed state. For example, (1) element 64 may comprise a wrapper (e.g., comprising a fabric) that circumscribes upstream frame 22, and retaining member 66 comprises a ripcord that opens the wrapper when pulled, or (2) element 64 may comprise a capsule that is slid off of frame 22.

For some applications, when upstream frame 22 expands, it applies a radially-outward force against the atrial walls, but does not apply a radially-outward force against the annulus (e.g., due to the position of the upstream frame with respect to the native valve). For some applications, when upstream frame 22 expands it does not apply a radially-outward force against the atrial walls (e.g., width d1 may be less than a width of the atrium).

Before release and expansion of upstream frame 22, the upstream frame is disposed around and held immobile with respect to a central rod 68, which provides a separating force that maintains a given distance between frames 22 and 24. Typically, downstream frame 24 is also disposed around and held immobile with respect to rod 68 while in its compressed state within sheath 62. Rod 68 therefore serves as a delivery tool, and/or a component thereof. For some applications, implant 20 is delivered to the heart with frames 22 and 24 separated by that given distance. For some applications, implant 20 is delivered to the heart with frames 22 and 24 closer than that given distance, and prior to release of frame 22 (e.g., subsequently to placement of snares 46 against the tissue of the native valve), the distance is increased by moving frame 22 away from frame 24. For some applications, rod 68 is slidable with respect to (e.g., through) mount 72 (described hereinabove with reference to FIG. 4D). For some such applications, the distance is increased by sliding rod 68 distally through mount 72.

When frame 22 is released, the elastic coupling of frame 22 to frame 24 reduces the distance between the frames generally at the same time that frame 22 expands. The arrows in FIG. 4G show frame 22 expanding and moving closer to frame 24 (i.e., downstream, closer to the native valve). As described hereinabove, this behavior sandwiches tissue of the native valve (e.g., leaflets 12) between upstream frame 22 and downstream frame 24 (e.g., snares 46 thereof), thereby securing implant 20 at the native valve.

Due to the coupling of frame 22 to the upstream portion of sheet 26, expansion of frame 22 pulls the upstream portion of sheet 26 radially outward, typically tensioning the sheet. For some applications, this sandwiches a portion of one or more leaflets 12 between sheet 26 and frame 24 and/or snares 46. For some applications, sheet 26 comprises one or more elastically-deformable wire braces (not shown; e.g., disposed circumferentially around conduit 48) that facilitate the radially-outward movement of the sheet.

For some applications, and as shown, a plurality of control wires 70 are coupled to upstream frame 22 and pass through rod 68 to outside of the body of the subject. For some applications, the operating physician may, by controlling tension on control wires 70, control expansion of frame 22. Alternatively or additionally, the operating physician may adjust positioning of frame 22 subsequently to its expansion, e.g., as shown in FIG. 4H. That is, a control force may be applied to upstream frame 22 via control wires 70. The control force may pull upstream frame 22 radially inward, and/or in an upstream direction.

As described hereinabove, positioning of frame 22 with respect to frame 24, while maintaining fluid communication therethrough, is facilitated by sheet 26. For example, and as shown in FIG. 4H, one side of frame 22 may be pulled upstream and/or radially inward by tensioning one or more of wires 70. For applications in which control wires 70 are used, the control wires are subsequently decoupled from frame 22 and withdrawn via rod 68 (FIG. 4I). For example, each control wire 70 may extend from rod 68, loop around a respective portion of frame 22, and pass back into the rod, and the decoupling may comprise releasing one end of the wire and pulling on the other end, such that the wire unloops from the frame.

FIG. 4J shows the final position of implant 20 following its implantation at the native valve, after rod 68 has been withdrawn proximally through frames 22 and 24 (e.g., via opening 28, conduit 48 and lumen 30), and has been withdrawn, along with sheath 62 and trocar 60, from the body of the subject. For some applications, restraining element 64 is withdrawn via opening 28, conduit 48 and lumen 30, and retaining member 66 is withdrawn alongside implant 20 (i.e., along the outside of the implant).

As described hereinabove, securing of implant 20 at mitral valve 10 is facilitated by the elastic coupling of frame 22 to frame 24 which sandwiches valve tissue between the two frames. It is to be noted that this "sandwiching" is typically possible even when diameter d11 is smaller than width d2 (see FIG. 2). It is to be further noted that, although diameter d11 is shown as being smaller than width d2, it may alternatively be generally equal to, or greater than, width d2. Typically, however, diameter d11 is smaller than width d1. For some applications, and as shown, securing of implant 20 may alternatively or additionally be facilitated by a portion of leaflets 12 becoming sandwiched between upstream portion 42 (e.g., snares 46) and sheet 26, which is pulled radially outward when upstream frame 22 expands.

Reference is again made to FIGS. 4A-J. For some applications, upstream portion 42 of downstream frame 24 is expanded within ventricle 8 (i.e., downstream of the native valve) and moved upstream against the tissue of the native valve without portion 42 having been previously placed at the level of coaptation of leaflets 12 (e.g., the steps described with reference to FIGS. 4B-D are omitted). Thus, at least a portion of downstream frame 24 is expanded prior to positioning the implant such that downstream frame 24 is disposed downstream of the native valve and upstream frame 22 is disposed upstream of the native valve.

It is to be noted that for some applications snares 46 are disposed at a longitudinal portion of downstream frame 24 other than upstream portion 42. For example, snares 46 may be disposed at downstream portion 44 (e.g., as described for implant 140 with reference to FIGS. 8, 13A-C, 14A-C, 15A-17, and/or 20A-C, mutatis mutandis), or between upstream portion 42 and downstream portion 44. For some such applications the method of implantation is adjusted to suit the position of snares 46.

Reference is made to FIGS. 5-8, which are schematic illustrations of respective implants, each comprising an upstream frame elastically coupled to a downstream frame and a flexible sheet that provides fluid communication between the two frames, in accordance with some applications of the invention. Each of the implants (and its components) is typically identical to implant 20 (and its identically-named components), except where noted, and is implanted as described for implant 20, mutatis mutandis. For each figure, the state of the implant on the left side of the figure may be considered an extended state, and the state of the implant on the right side of the figure may be considered a contracted state.

Figure 5:
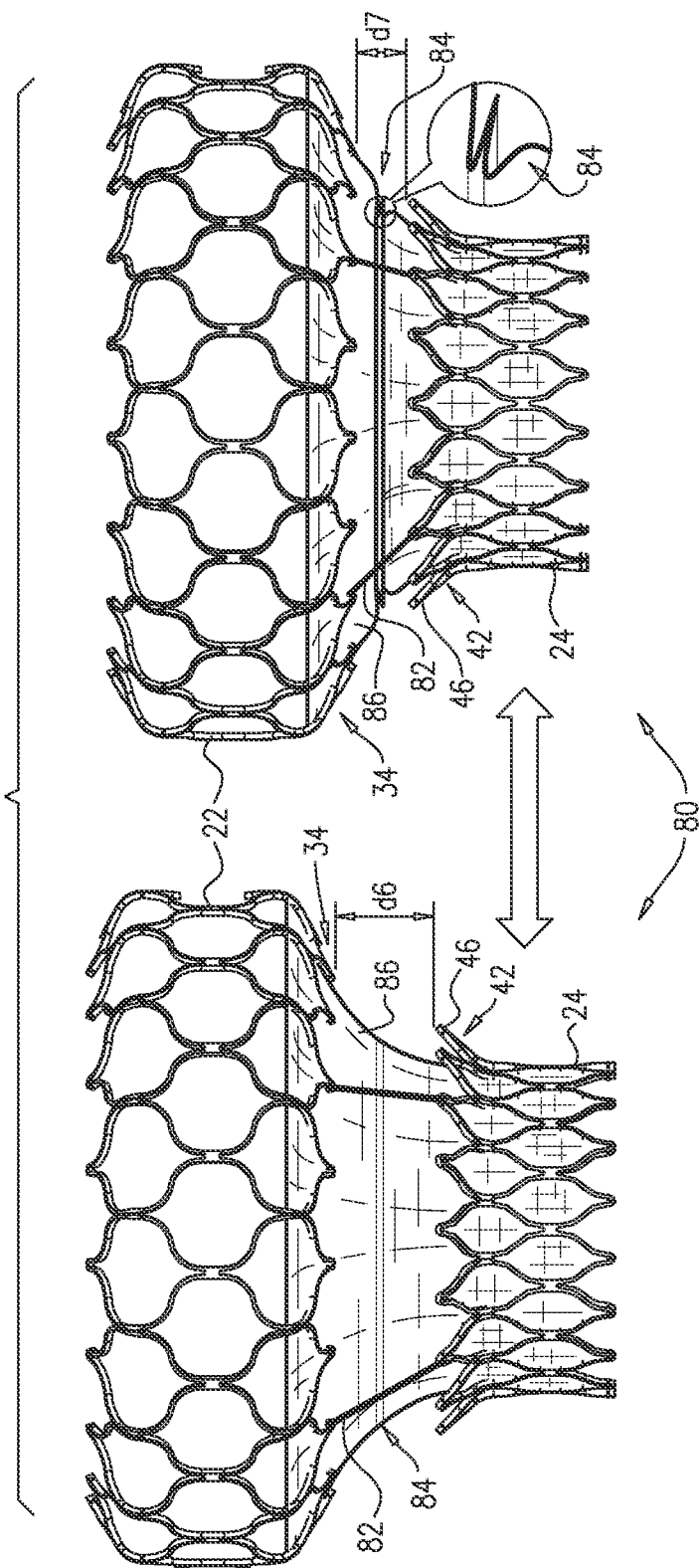
FIGS. 5-8 are schematic illustrations of respective implants each comprising an upstream frame elastically coupled to a downstream frame and a flexible sheet that provides fluid communication between the two frames, in accordance with some applications of the invention.

FIG. 5 shows an implant 80 comprising upstream frame 22, downstream frame 24, and a flexible sheet 86, and is typically identical to implant 20 except that the elastic coupling of frame 22 to frame 24 is provided by one or more elastic tethers 82. Tethers 82 are typically flexible. Each tether is coupled at one end to frame 22 and at the other end to frame 24. Typically, but not necessarily, each tether 82 is coupled to upstream portion 42 of frame 24 and/or to downstream end 34 of frame 22. When tethers 82 reduce the distance between frames 22 and 24 from distance d6 to distance d7, sheet 86, which is typically not elastic itself and therefore has a fixed length (unlike sheet 26 of implant 20), rumples. For some applications, and as shown, sheet 86 is configured to rumple in a pre-determined and/or controlled fashion (e.g., to fold), so as not to interfere with fluid communication through conduit 48 defined by the sheet. For example, at least a portion of the sheet may be pre-creased and/or heat-set such that it folds neatly when the distance between the frames 22 and 24 is reduced. The sheet thereby defines a folding zone 84 in which, for some applications, a first fold of the sheet may touch a second fold of the sheet when the implant is in its contracted state.

Figure 6:
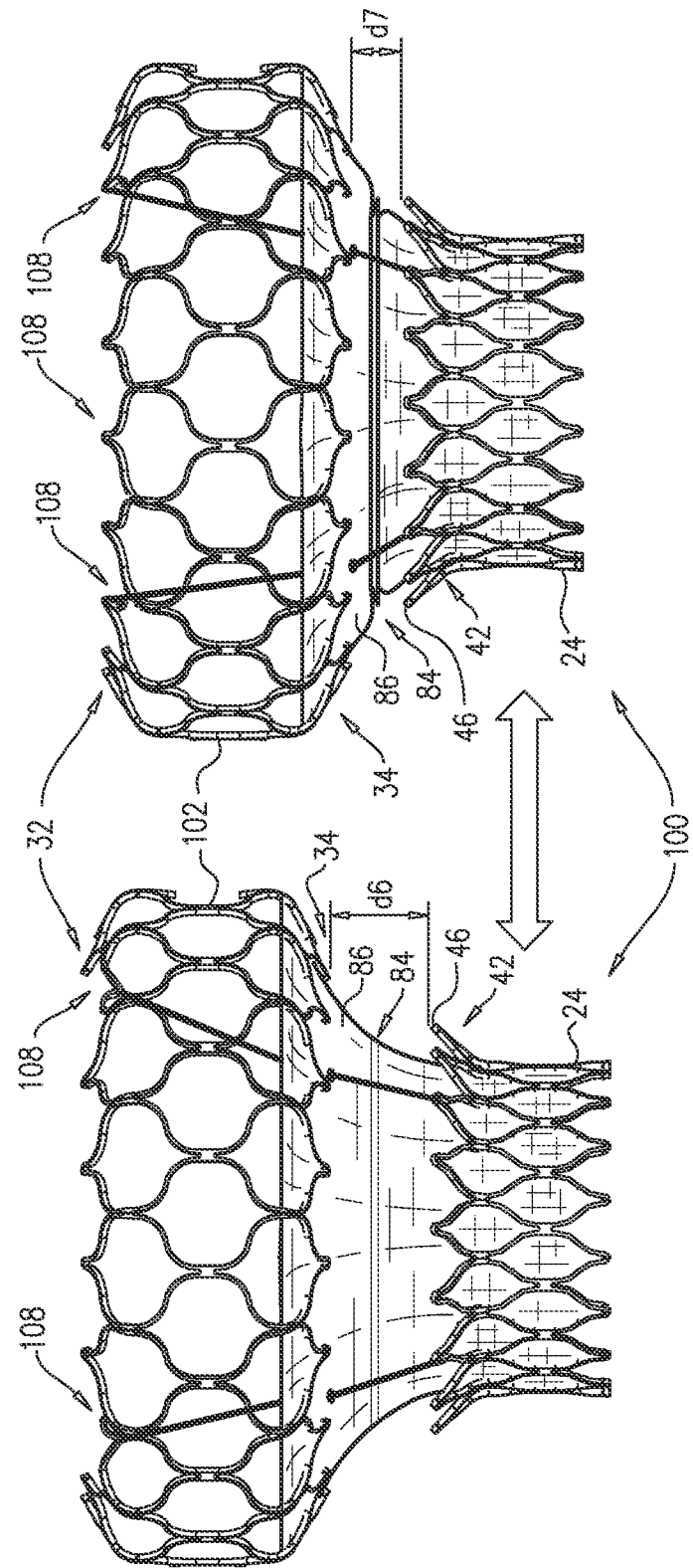

FIG. 6 shows an implant 100 comprising an upstream frame 102, downstream frame 24, and flexible sheet 86, and is typically identical to implant 80 except that the elastic coupling of the upstream frame to the downstream frame is provided by the upstream frame. Upstream frame 102 is configured to provide a plurality of springs 108 (e.g., cantilever springs), which are coupled to downstream frame 24 via a respective plurality of tethers 106. Tethers 106 are typically inelastic, but for some applications may be elastic. Tethers 106 are typically flexible. Typically, springs 108 are defined at upstream end 32 of upstream frame 102 (the reference numeral 32 is used for clarity of reference between frame 102 and frame 22 described hereinabove). For example, and as shown, upstream frame 102 may define a plurality of regularly-tiled cells (e.g., two-dimensional shapes) (e.g., like the other upstream frames described herein), and each spring 108 may be defined by a respective one of the cells, e.g., utilizing the shape-memory property of the material from which the frame is formed. In the extended state of implant 100 (left side of FIG. 6) springs 108 are in an elastically-deformed state, and in the contracted state (right side of FIG. 6) springs 108 are in a less deformed state (e.g., may be in a relaxed state). For some applications, tethers 106 pass through respective holes in sheet 26 as they pass from frame 22 to frame 24. Alternatively, springs 108 may be defined at downstream end 34 of upstream frame 102, or elsewhere on the upstream frame.

Figure 7:
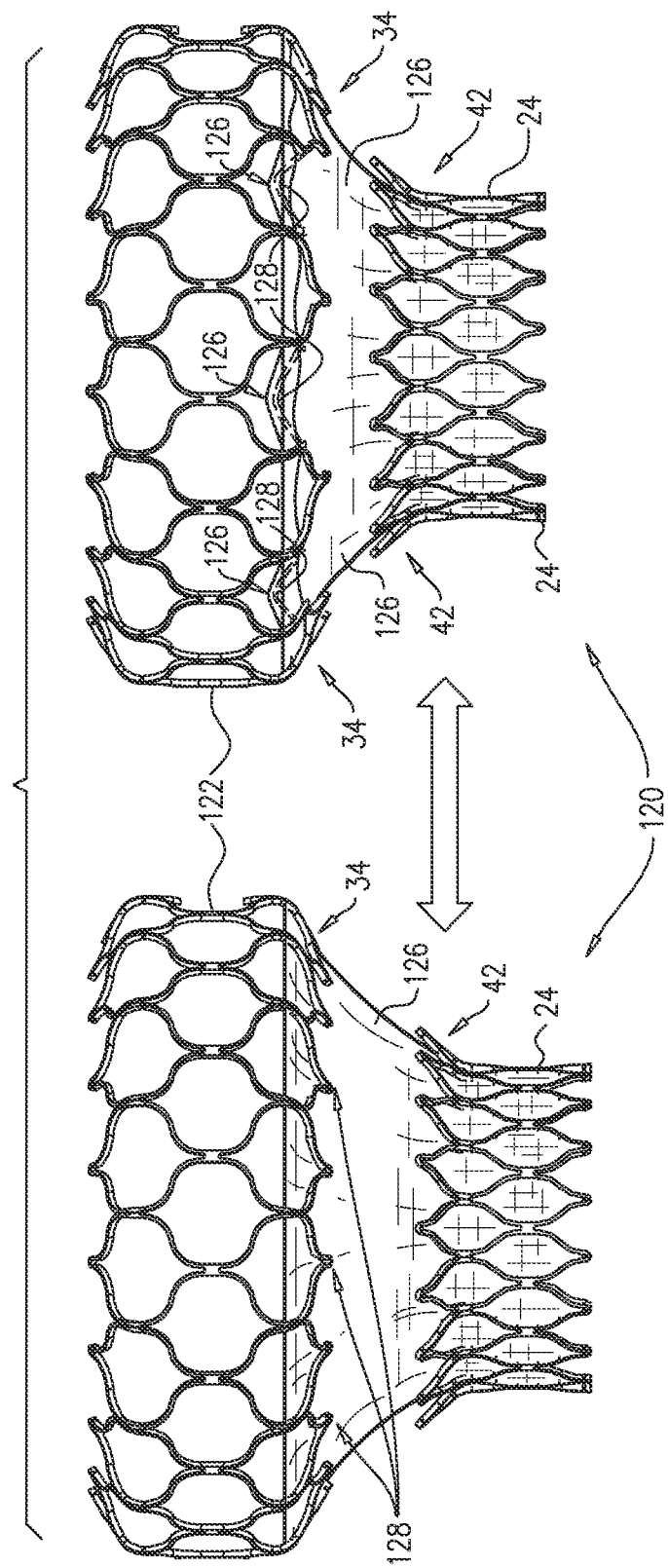

FIG. 7 shows an implant 120 comprising an upstream frame 122, downstream frame 24, and a flexible sheet 126, and is typically identical to implant 100 except that the elastic coupling of the upstream frame to the downstream frame is provided by the upstream frame in a different manner to which the upstream frame of implant 100 provides elastic coupling. Upstream frame 122 is configured to provide a plurality of springs 128 (e.g., cantilever springs), which are not coupled to downstream frame by tethers. Instead, the shape of sheet 126 and its coupling to frames 122 and 24 positions springs 128, which are typically defined at downstream end 34 of frame 122, such that the springs provide the elastic coupling by pulling the sheet in an upstream direction. In the contracted state (right side of FIG. 7) portions of sheet 126 that have been pulled in the upstream direction are visible. In the contracted state, sheet 126 is thereby under tension, and therefore typically does not require folding zone 84.

Figure 8:
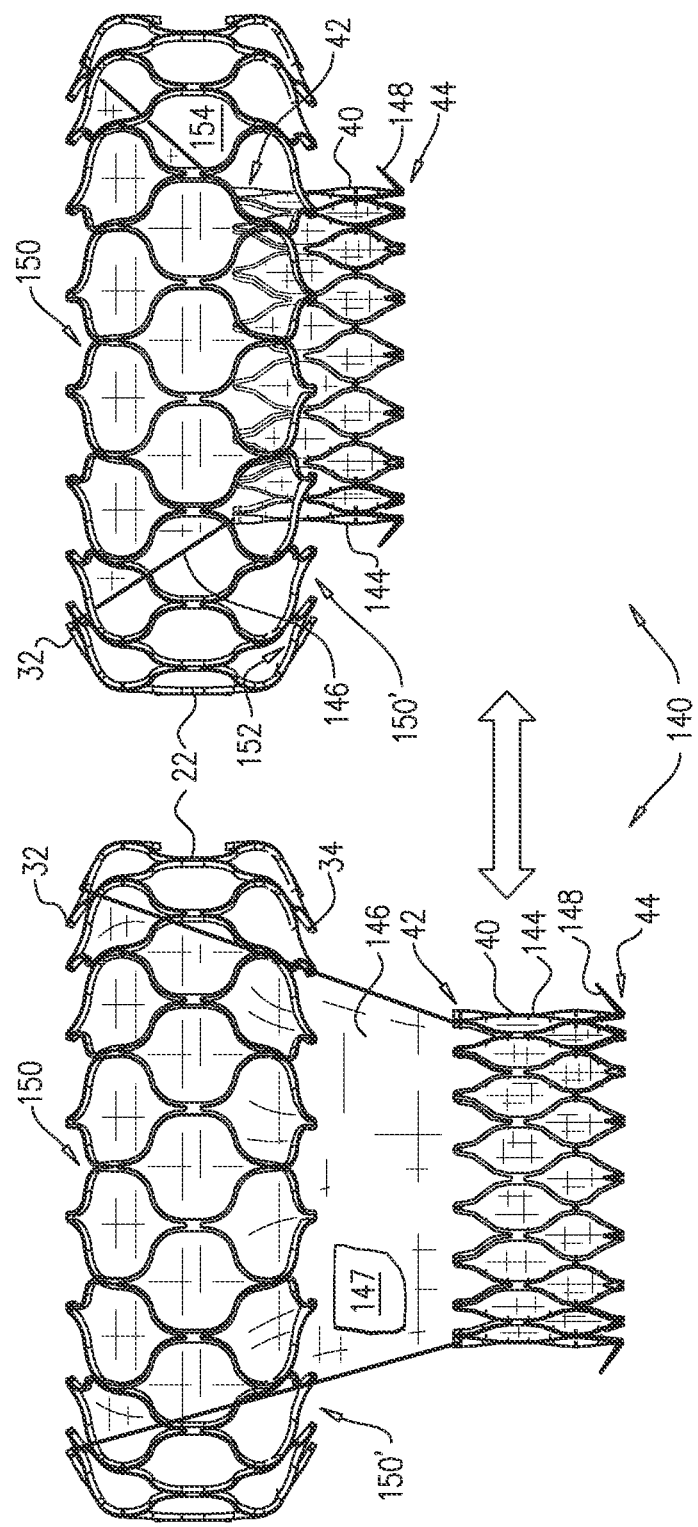

FIG. 8 shows an implant 140 comprising upstream frame 22, a downstream frame 144, and a flexible sheet 146. Frame 144 defines tubular body 40 described hereinabove, which has an upstream portion 42 and a downstream portion 44. A plurality of snares 148 protrude radially outward from downstream portion 44, thereby defining diameter d11 described hereinabove, mutatis mutandis. Snares 148 may alternatively or additionally protrude outward from another longitudinal portion of frame 144, such as upstream portion 42 or a longitudinal portion between portions 42 and 44. Typically, snares 148 protrude outward in an upstream direction (i.e., toward upstream frame 22), which is hypothesized to facilitate capture of native valve leaflets, as described hereinabove, mutatis mutandis. Sheet 146 is coupled to upstream end 32 of upstream frame 22, and defines a conduit 147 that provides fluid communication between an opening 150 defined by frame 22 and lumen 30 defined by body 40. It is to be noted that both upstream end 32 and downstream end 34 of frame 22 may be considered to define a respective opening. Opening 150 is defined by upstream end 32, and a second opening 150' is defined by downstream end 34.

In the contracted state of implant 140, at least upstream portion 42 (e.g., an upstream end) of downstream frame 144 is disposed upstream of second opening 150' (e.g., within a space 154 defined by upstream frame 22). Typically, in the extended state, less (e.g., none) of frame 144 is disposed upstream of opening 150' (e.g., within space 154). During implantation of implant 140, tissue of the native valve becomes sandwiched between snares 148 and upstream frame 22, e.g., using one or more of the mechanisms described herein.

It is hypothesized that the coupling of sheet 146 to upstream end 32 of frame 22 provides improved blood flow compared to a similar device in which the sheet is coupled to downstream end 34 of frame 22, because in the latter a zone 152 may be defined in the vicinity of downstream end 34 in which blood flow is reduced, increasing the likelihood of thrombosis formation. For example, zone 152 may be within space 154, downstream of upstream portion 42 of frame 144, and upstream of downstream end 34 of frame 22. It is to be noted that the scope of the invention includes coupling of sheet 146 to other regions of frame 22, such as slightly downstream of upstream end 32 (e.g., a quarter, a third, halfway, two-thirds, or three-quarters of the way toward downstream end 34).

Figure 9:
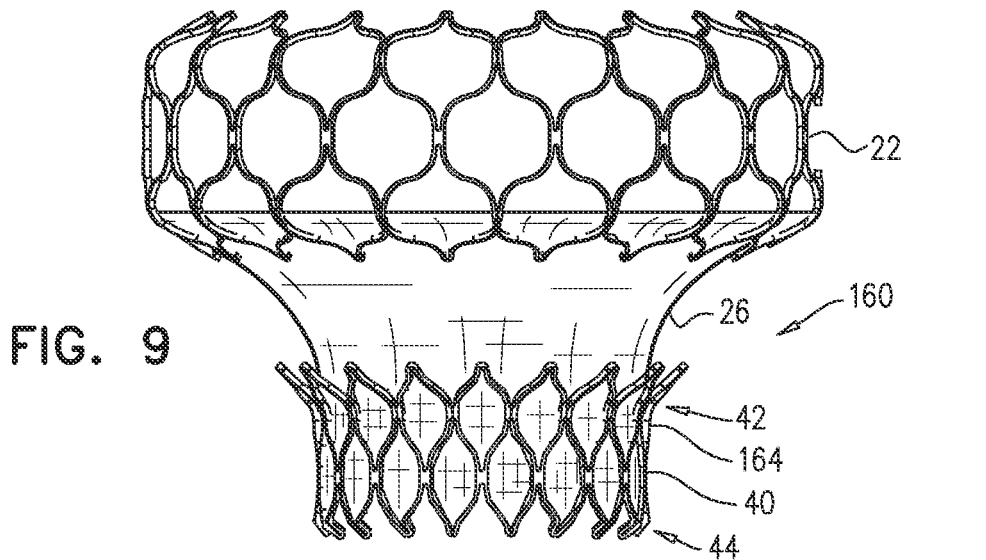
FIGS. 9-10 are schematic illustrations of implants having atraumatic modifications, in accordance with some applications of the invention.
Figure 10:
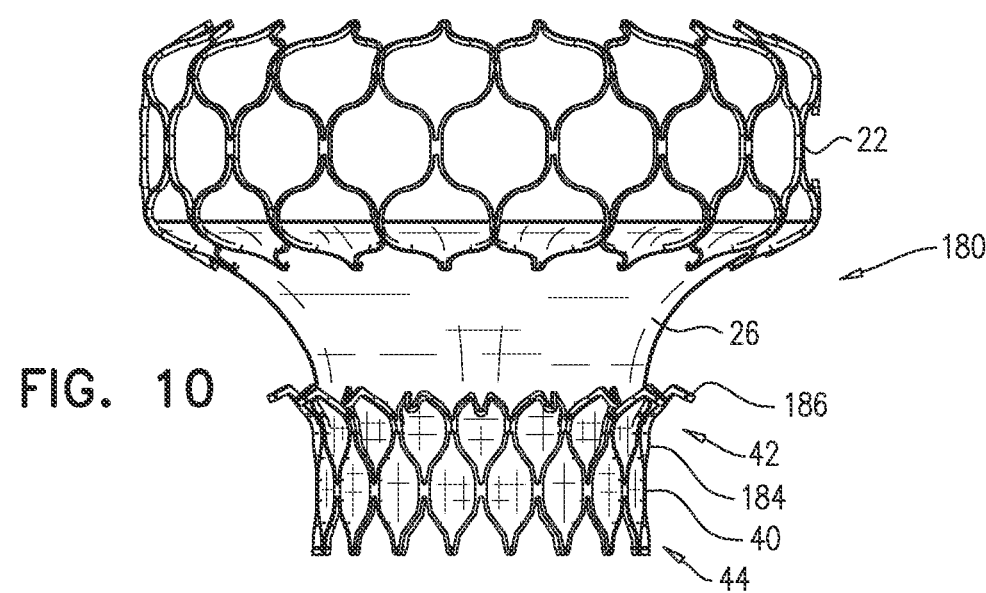

Reference is now made to FIGS. 9-10, which are schematic illustrations of implants 160 and 180, which are typically identical to implant 20, except for the inclusion of atraumatic modifications, in accordance with some applications of the invention. Implant 160 comprises a downstream frame 164 that is typically identical to downstream frame 24, described hereinabove, except that downstream portion 44 is curved inward so as to reduce a likelihood of the downstream portion damaging tissue of the native valve, such as chordae tendineae. Implant 180 comprises a downstream frame 184 that is typically identical to downstream frame 24, except that snares 186 of implant 180 are curved back on themselves so as to reduce a likelihood of damaging tissue of the native valve, such as leaflets or chordae tendineae. For some applications, and as shown, distal ends of snares 186 point downstream. It is to be noted that the atraumatic modifications shown in FIGS. 9-10 may be made (individually or together) to any of the implants described herein.

Figure 11:
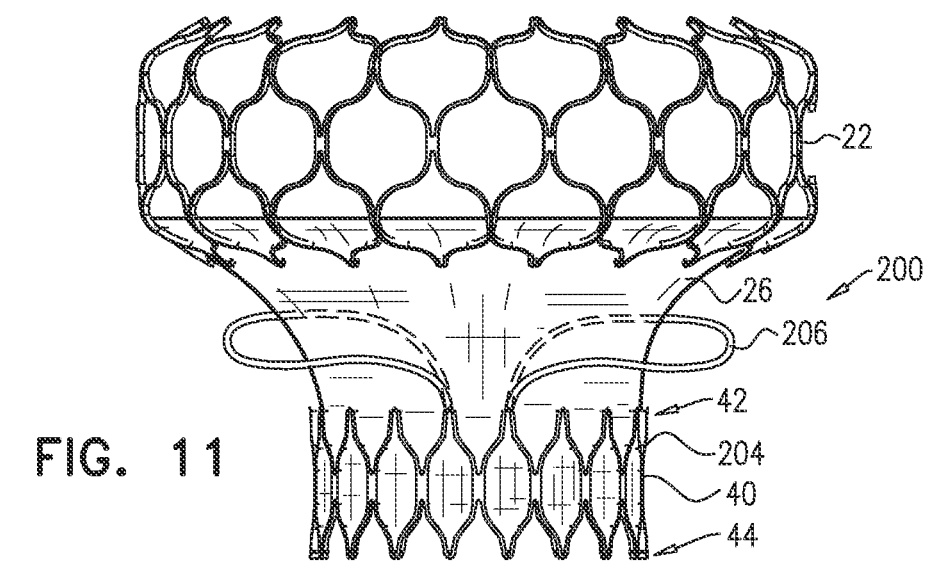
FIG. 11 is a schematic illustration of an implant, in accordance with some applications of the invention.

Reference is now made to FIG. 11, which is a schematic illustration of an implant 200, in accordance with some applications of the invention. Implant 200 is typically identical to implant 20, except where noted. A downstream frame 204 comprises generally tubular body 40, described hereinabove. Snares 206 extend radially outward from body 40, typically from upstream portion 42 (but alternatively may extend from other positions of body 40, such as downstream portion 44). Snares 206 are loops that extend radially away from body 40, circumferentially around body 40, and radially back toward body 40, thereby defining lobes that extend around circumferential portions of body 40. Each snare 206 typically extends from a first cell of the frame of body 40, circumferentially past at least one (e.g., at least two, such as at least three) other cells, and radially back to another cell. Each snare typically extends more than 20 degrees around body 40 (e.g., more than 40 degrees, such as more than 60 degrees). Purely for illustrative purposes, FIG. 11 shows each snare 206 extending about halfway around body 40. Snares 206 facilitate sandwiching of the tissue of the native valve as described hereinabove, mutatis mutandis.

For some applications, snares 206 are used in combination with snares 46, described hereinabove. For example, an implant may comprise one snare 206 and a plurality of snares 46. Typically, when the implant comprises one or more snares 206 (as opposed to solely snares 46), the implant is placed in a particular rotational orientation with respect to the native valve, e.g., before deployment. For example, snares 206 may be aligned with the a2 and/or p2 scallops of leaflets 12 e.g., so as to reduce interaction with chordae tendineae. Typically, for the example in which the implant comprises one snare 206 and a plurality of snares 46, the snare 206 is aligned with the a2 scallop of the anterior leaflet.

Figure 12C:
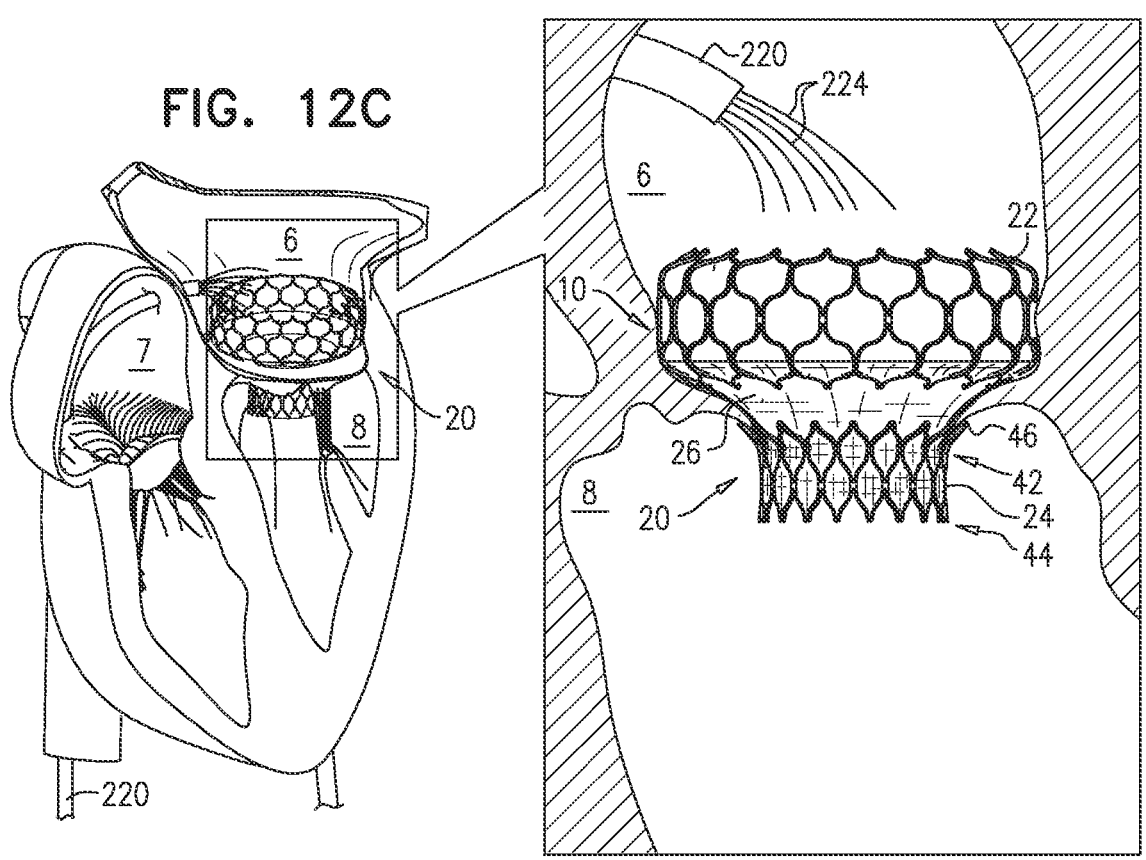

Reference is made to FIGS. 12A-C, which are schematic illustrations of delivery and implantation of implant 20, in accordance with some applications of the invention. As described hereinabove, FIGS. 4A-J show transapical delivery and implantation of implant 20, but the scope of the invention includes other delivery routes. To illustrate this, FIGS. 12A-C show transfemoral transseptal delivery and implantation of implant 20. It is to be understood that the same techniques may be used for other transseptal and transatrial routes, mutatis mutandis.

A catheter 220 (e.g., a sheath) is advanced transfemorally and via the inferior vena cava into right atrium 7 of the heart, and then into left atrium 6 via transseptal puncture, as is known in the art. Compared to the techniques described with reference to FIGS. 4A-J, in its delivery state the orientation of implant 20 is reversed with respect to the catheter through which it is delivered. Whereas for transapical delivery frame 22 is disposed closer to the distal end of the catheter than is frame 24, in FIGS. 12A-C, frame 24 is closer to the distal end.

The step shown in FIG. 12A corresponds generally to the step shown in FIG. 4B, mutatis mutandis. That is, implant 20 has been delivered to between leaflets 12, and upstream portion 42 and/or snares 46 of downstream frame 24 have been exposed and have begun to expand, while upstream frame 22 is maintained in its compressed delivery state. In contrast to FIG. 4B, in FIG. 12A, (1) downstream frame 24 is initially maintained in its compressed delivery state by being disposed in a capsule 222, and upstream portion 42 and/or snares 46 are exposed by moving the capsule distally downstream; and (2) upstream frame 22 is maintained in its compressed delivery state by being disposed within catheter 220.

FIG. 12B corresponds generally to the step shown in FIG. 4F, mutatis mutandis. That is, FIG. 12 shows frame 24 having automatically fully expanded into its expanded state responsively to downstream portion 44 of frame 24 having been fully exposed from capsule 222, subsequently to (1) movement of the implant downstream until leaflets 12 coapt above upstream portion 42 and/or snares 46 (e.g., against sheet 26, frame 24, and/or catheter 220), (2) optional further expansion of upstream portion 42 and/or snares 46 by moving capsule 222 further downstream, and (3) movement of implant 20 upstream such that portion 42 and/or snares 46 contact and apply an upstream force to tissue of the native valve.

FIG. 12C corresponds generally to the step shown in FIG. 4I, mutatis mutandis. That is, subsequently to release and expansion of upstream frame 22 (by deployment out of catheter 220), optionally controlled by a plurality of control wires 224 coupled to frame 22 and passing through the catheter to outside the body of the subject, the control wires are decoupled from frame 22 and withdrawn via the catheter. FIG. 12C also thereby shows the final position of implant 20 at the native valve.

Reference is again made to FIGS. 1A-12C. As described hereinabove, for each implant, the downstream frame is distinct from the upstream frame. For some applications, there is no metallic connection between the upstream and downstream frames. For some applications, there is no metallic connection between the upstream and downstream frames except for flexible tethers, which may be metallic.

For some applications, the upstream frame (e.g., the upstream frame of implant 140, or another upstream frame described herein) may be covered or lined (e.g., partially or entirely) with a covering, such as a fabric. For some applications, the covering may comprise the same material as the flexible sheet. For some such applications, a continuous piece of material may define the covering and the flexible sheet.

For some applications, in addition to or in place of elastic coupling of frame 22 to frame 24, sandwiching may be achieved by the operating physician actively reducing the distance between the frames, such as by tensioning one or more tethers. For some such applications, this may be achieved using apparatus and/or methods described in International Patent Application PCT/IL2014/050087, filed Jan. 23, 2014, which is incorporated herein by reference.

Reference is made to FIGS. 13A-C, and 14A-C, which are schematic illustrations of implants that each comprise an upstream frame (e.g., an upstream support), a downstream frame (e.g., a prosthetic valve frame), and a flexible sheet connecting the upstream and downstream frames, in accordance with some applications of the invention.

FIGS. 13A-C are schematic illustrations of an implant 240, comprising upstream frame 22, a downstream frame 244, and a flexible sheet 246. Downstream frame 244 comprises a plurality of snares 248 at a downstream end of the frame. For some applications, downstream frame 244 is identical to downstream frame 144 described hereinabove, and/or snares 248 are identical to snares 148 described hereinabove.

FIG. 13A shows implant 240 in a compressed state thereof, in which both frame 22 and frame 244 are in respective compressed states thereof (e.g., for percutaneous delivery of the implant). Typically, frame 22 and/or frame 244 are generally cylindrical when in the compressed state. In the compressed state of implant 240, sheet 246 typically extends longitudinally between frames 22 and 244, and articulatably couples the frames to each other, thereby defining an articulation zone 247 between the frames. For some applications this articulation is hypothesized to facilitate percutaneous (e.g., transluminal) delivery of the implant, by allowing the compressed implant to articulate as it passes bends in the percutaneous path to the heart.

FIGS. 13B-C show implant 240 in an expanded state thereof, in which both frame 22 and frame 244 are in respective expanded states thereof (e.g., an implanted state of the implant). FIG. 13B is a perspective view, and FIG. 13C is a cross-sectional view. Frame 244 defines a lumen 250 therethrough, in which prosthetic leaflets 50 (described hereinabove) are disposed and coupled to frame 244, e.g., as described for other implants herein. For clarity, leaflets 50 are not shown in FIGS. 13A-C or 14A-B.

In the expanded state of implant 240, upstream portion (e.g., an upstream end) 42 of downstream frame 244 is disposed longitudinally upstream of opening 150' of upstream frame 22. That is, implant 240 has a central longitudinal axis, and upstream portion 42 is disposed further upstream along the longitudinal axis than is opening 150'. This typically occurs because expansion of upstream frame 22 toward its expanded state pulls valve frame 244 longitudinally in an upstream direction, by pulling sheet 246 radially outward. Typically, in the expanded state of implant 240, a diameter d15 of frame 244 is smaller than diameter d2 of frame 22, and sheet 246 is annular, extending radially inward from frame 22 to frame 244, and is circumferentially attached to frame 244 at a longitudinal site 254 of frame 244. Typically, sheet 246 provides fluid sealing between frames 22 and 244.

Implant 240 is percutaneously advanced, in its compressed state, to the native valve, and is deployed such that snares 248 are disposed downstream of the native valve (i.e., in the ventricle) and upstream frame 22 is disposed upstream of the native valve (i.e., in the atrium), e.g., sandwiching tissue of the native valve between the snares and the upstream frame (and/or between the snares and sheet 246). FIG. 14C illustrates such implantation of a similar implant, mutatis mutandis.

FIGS. 14A-C are schematic illustrations of an implant 260, comprising an upstream frame 262, a downstream frame 264, and two flexible sheets 266a and 266b, which couple the upstream frame to the downstream frame. Downstream frame 264 comprises a plurality of snares 268 at a downstream end of the frame. For some applications, downstream frame 264 is identical to downstream frame 244 and/or downstream frame 144 described hereinabove, and/or snares 266 are identical to snares 248 and/or 148 described hereinabove.

Upstream frame 262 is similar to upstream frame 22 described hereinabove, except that frame 262 is not necessarily widest at a mid-portion thereof (compare to FIG. 1A and description thereof). It is to be noted that for some applications, frame 22 of implant 240 and frame 262 of implant 260 may be substituted for each other.

FIGS. 14A-C show implant 260 in an expanded state thereof, in which both frame 262 and frame 264 are in respective expanded states thereof (e.g., an implanted state of the implant). FIG. 14A is a perspective view, FIG. 14B is a cross-sectional view, and FIG. 14C shows implant 260 having been implanted at native valve 10. Typically, implant 260 is similar to implant 240, except that instead of a single sheet 246, implant 260 comprises a first flexible sheet 266a, which may be identical to sheet 246, and further comprises a second flexible sheet 266b.

In the expanded state of implant 260, upstream portion (e.g., an upstream end) 42 of downstream frame 264 is disposed longitudinally upstream of opening 150' of upstream frame 262. That is, implant 260 has a central longitudinal axis, and upstream portion 42 is disposed further upstream along the longitudinal axis than is opening 150'. This typically occurs because expansion of upstream frame 262 toward its expanded state pulls valve frame 264 longitudinally in an upstream direction, by pulling sheet 266a and/or sheet 266b radially outward. Typically, in the expanded state of implant 260, a diameter of frame 264 is smaller than a diameter d2 of frame 262, e.g., as described for implant 240, mutatis mutandis. That is, the diameter of frame 264 is smaller than the opening defined by the downstream end of frame 262. Sheet 266a extends radially inward from frame 262 to frame 264, and is circumferentially attached to frame 264 at a first longitudinal site 274a of frame 264. For some applications, sheet 266a is identical to sheet 246 described hereinabove, mutatis mutandis.

Sheet 266b also extends radially inward from frame 262 (e.g., from the same or a different point of frame 262), and is circumferentially attached to frame 264 at a second longitudinal site 274b of frame 264. Typically, longitudinal site 274b is closer to upstream portion 42 than is longitudinal site 274b. For example, longitudinal site 274b may be at least 2 mm and/or less than 8 mm closer to upstream portion 42 than is longitudinal site 274b (e.g., 2-12 mm closer, or at least 3 mm closer, such as 3-10 mm closer). Further typically, longitudinal site 274b is at upstream portion 42.

A chamber 276 (e.g., a closed chamber) that circumscribes frame 264 is defined between sheets 266a and 266b (shown in cross-section in FIGS. 14B-C, and also shown by cutaway in FIG. 14A). Chamber 276 is typically toroidal. Subsequently to implantation of implant 260, and as shown in FIG. 14C, tissue formation typically occurs within chamber 276, e.g., due to blood entering the chamber 276 by passing through the flexible sheets (e.g., at least one of the sheets is at least partially blood-permeable). For some applications this tissue formation is hypothesized to gradually increase rigidity of implant 260. It is to be noted that for implant 240 (FIGS. 13A-C), a recessed region 256 circumscribes upstream portion 42 of downstream frame 264. Recessed region 256 is downstream of (i.e., below) upstream portion 42 and upstream of (i.e., above) opening 150'. This recessed region is reduced (e.g., eliminated) in implant 260. The reduction of region 256 is implant 260 is hypothesized to improve blood flow dynamics through the implant, thereby reducing a likelihood of thrombus formation.

Reference is made to FIGS. 15A-C, 16A-D, and 17, which are schematic illustrations of an implant 280, and implantation thereof, in accordance with some applications of the invention. FIG. 15A shows a perspective view of implant 280, FIG. 15B shows a cutaway view of the implant, and FIG. 15C shows an exploded view of frame components of the implant. FIGS. 16A-D and 17 show steps in the implantation of implant 280 at mitral valve 10.

Implant 280 comprises an upstream support 282, a valve frame 284, a snare frame 288, and at least one flexible sheet 286. Sheet 286 couples snare frame 288 to valve frame 284, and as shown, typically further couples upstream support 282 to the valve frame. For some applications, the coupling of upstream support 282 to valve frame 284 via sheet 286 is similar to that of the coupling provided by sheet 266b of implant 260, mutatis mutandis. Sheet 286 typically provides fluid sealing between support 282 (e.g., the frame thereof) and frame 284, and further typically provides fluid sealing between frames 284 and 288. For some applications, a single sheet 286 extends from snare frame 288, along valve frame 284, and to upstream support 282, thereby coupling the three frames together in the configuration shown. The coupling of the frames via sheet 286 advantageously provides some limited movement (e.g., articulation) between the frames, at least in some states of the implant. For example, as described hereinbelow, this coupling facilitates expansion of snare frame 288 while valve frame 284 remains at least in part compressed.

Snare frame 288 typically comprises an annular portion 290 and a plurality of snares 292 that extend from the annular portion. FIG. 15C shows snare frame 288 in an expanded state thereof. In the expanded state of snare frame 288, snares 292 protrude radially outward and in an upstream direction. Typically, annular portion 290 is defined by a repeating pattern of struts, such as in a zig-zag pattern (as shown). Typically, at least annular portion 290 provides shape memory to snare frame 288, which is delivered to the heart constrained in a compressed state, and which automatically moves toward its expanded state when unconstrained (e.g., as described hereinbelow).

Valve frame 284 is a tubular frame that defines a lumen therethrough, e.g., as described herein for other valve frames. For some applications, valve frame 284 is identical to other valve frames described herein.

Upstream support 282 is annular, and defines two annular portions: an upper annular portion 294 and a lower annular portion 296 that is circumferentially coupled to the upper annular portion (e.g., at a perimeter of upstream support 282). Upper annular portion 294 may be considered to be a first layer of support 282, and downstream annular portion 296 may be considered to be a second layer of the support. For some applications, upstream support 282 is cut from a single piece of metal (typically Nitinol), and in a compressed state of the upstream support, struts that form lower annular portion 296 intercalate with struts that form upper annular portion 294. For some applications, and as shown, the struts that define upper annular portion 294 are arranged as chevrons that repeat in a circumferential pattern (e.g., a zigzag pattern). For some applications, and as shown, the struts that define lower annular portion 296 are arranged as chevrons that repeat in a circumferential pattern. For some applications, and as shown, each chevron of upper annular portion 294 is coupled to a chevron of lower annular portion 296 at the perimeter of support 282, and is slightly differently sized to that chevron of the lower annular portion.

As shown in FIG. 15B, upstream support 282 is coupled to valve frame 284 such that (i) upper annular portion 294 extends radially outward from a first longitudinal site 298 of the prosthetic valve frame toward a perimeter 300 of the upstream support, and (ii) lower annular portion 296 extends radially inward from the upper annular portion toward a second longitudinal site 299 of the prosthetic valve frame. Second longitudinal site 299 is downstream of first longitudinal site 298. Typically, and as shown, first longitudinal site 298 is at an upstream end of valve frame 284. Typically, and as shown, lower annular portion 296 does not contact valve frame 284, and an inner perimeter 293 of portion 296 defines a free edge.

For some applications, upstream support 282 is coupled to valve frame 284 such that upper annular portion 294 extends, from first longitudinal site 298, radially outward in a downstream direction (e.g., as shown). For some applications, upstream support 282 is coupled to valve frame 284 such that lower annular portion 296 extends, from the upper annular portion, radially inward in a downstream direction (e.g., as shown).

Lower annular portion 296 is deflectable with respect to upper annular portion 294, and is typically more movable with respect to valve frame 284 than is upper annular portion 296. For example, lower annular portion 296 may be articulatably coupled to upper annular portion 294, and/or may be more flexible than the upper annular portion (e.g., struts that form the lower annular portion may be thinner than those that form the upper annular portion, as shown). As described in more detail hereinbelow, it is hypothesized that this configuration facilitates sealing of support 282 against the upstream surface of mitral valve 10 (e.g., the mitral annulus) by maintaining contact between lower annular portion 296 and the upstream surface of the mitral valve, irrespective of an angle that upper annular portion 294 is disposed with respect to valve frame 284.

For some applications, the struts of upper annular portion 294 have a transverse cross-sectional area 295 of 0.25-1 mm^2. For some applications, the struts of lower annular portion 296 have a transverse cross-sectional area 297 of 0.04-0.2 mm^2. For some applications, support 282 has a diameter (defined by its perimeter) of 50-70 mm.

For some applications, sheet 286 extends over an upper surface of upper annular portion 294, around perimeter 300, and over a lower surface of lower annular portion 296 (thereby serving as a covering of portions 294 & 296). While implant 280 is implanted at mitral valve 10, the above-described configuration of upstream support 282 thereby holds the covering against the upstream surface of the mitral valve, thereby facilitating sealing.

The bubble of FIG. 15B shows an optional arrangement for the coupling of support 282 to frame 284, in accordance with some applications of the invention. A first sheet portion 286a covers at least part of an inner surface of valve frame 284 (e.g., serves as an inner covering, or a liner, of at least part of the valve frame). A second sheet portion 286b covers at least part of an outer surface of valve frame 284 (e.g., serves as an outer covering of at least part of the valve frame). A third sheet portion 286c covers at least part of upstream support 282 (e.g., at least part of upper annular portion 294 thereof). Either portion 286a or portion 286b extends past an upper end of valve frame 284, and covers at least part of upstream support 282, e.g., at least part of upper annular portion 294 thereof (FIG. 15B shows portion 286b doing this). The other one of portion 286a and portion 286b does not extend to the upper end of valve frame 284 (FIG. 15B shows portion 286a doing this). Portion 286c extends past an inner edge of support 282 (e.g., an inner edge of upper annular portion 294), and covers at least part of upstream support 282.

At a connection point 310, portion 286c (i) is connected (e.g., sutured) to portion 286a or 286b (whichever does not extend to the upper end of valve frame 284), and (ii) is typically also connected to the valve frame. (Typically, portion 286a is also connected to valve frame 284 at point 310.) At a connection point 312, portion 286a or 286b (whichever extends to support 282) (i) is connected (e.g., sutured) to portion 286c, and (ii) is typically also connected to support 282. (Typically, portion 286c is also connected to support 282 at point 312.) It is to be noted that such an arrangement results in valve frame 284 being coupled to support 282 via two flexible sheets 286 (each of the sheets being defined by one of the sheet portions).

It is hypothesized that such an arrangement of sheet portions, and such attachment of the sheet portions to the frames and to each other, provides strong and durable coupling of valve frame 284 to support 282 via a flexible sheet.

A technique for implanting implant 280 is now described with reference to FIGS. 16A-D. Implant 280 is percutaneously (e.g., transluminally, such as transfemorally) delivered to mitral valve 10 while the implant is in a compressed state (e.g., within a delivery tube 302, such as a catheter), such that at least snare frame 288 is downstream of the mitral valve (i.e., within ventricle 8). For some applications, in the compressed state, snare frame 288 is inverted inside-out, such that snares 292 are downstream of (e.g., distal to) annular portion 290, and the snare frame is downstream of (e.g., distal to) valve frame 284. FIG. 16A shows implant 280 having been delivered in this manner, and having been partially deployed from delivery tube 302 such that part of snare frame 288 (e.g., part of snares 292) is exposed.

Once snare frame 288 is fully exposed from delivery tube 302, the snare frame automatically expands toward its expanded state, e.g., by re-inverting, such that snares 292 are upstream of annular portion 290 (FIG. 16B). The coupling of snare frame 288 to valve frame 284 via sheet 286 facilitates expansion of the snare frame while the valve frame remains at least partly compressed within delivery tube 302. For example, while valve frame 284 remains at least partly compressed within delivery tube 302, an angle alpha_3 between snare frame 288 (e.g., snares 292 thereof) and a central longitudinal axis of implant 280 is typically greater than of the would be in an otherwise similar implant in which the snare frame is rigidly coupled to the valve frame. Similarly, while an upstream portion of valve frame 284 remains compressed within delivery tube 302, an angle alpha_4 between snare frame 288 (e.g., snares 292 thereof) and a downstream portion of the valve frame is typically greater than it would be in an otherwise similar implant in which the snare frame is rigidly coupled to the valve frame. It can be understood from this that snare frame 288 is typically coupled to valve frame 284 such that angle alpha_3 is independent of angle alpha_4.

These increased angles facilitate engagement of tissue of mitral valve 10 (e.g., leaflets 12) when implant 280 is subsequently moved upstream (FIG. 16C). For example, the increased angles result in snares 292 reaching out further laterally, and/or result in a greater space between the snares and valve frame 284 in which leaflets 12 may become disposed.

Following the upstream movement of implant 280, upstream support 282, in its compressed state within delivery tube 302, is upstream of mitral valve 10 (i.e., in atrium 6). For some applications, the coupling of upstream support 282 to valve frame 284 via sheet 286 facilitates expansion of the valve frame while the upstream support 282 remains compressed. FIG. 16D shows implant 280 fully deployed at mitral valve 10, after upstream support 282 has been deployed from delivery tube 302. Lower annular portion 296 of upstream support 282 is disposed against an upstream surface of the mitral valve and, as described hereinabove, facilitates sealing (i.e., inhibits paravalvular leakage).

It is to be noted that therefore, for some applications, when implanting implant 280 (or another implant in which snares are coupled to the valve frame in the manner described for implant 280), the following steps are performed: (i) The implant is percutaneously delivered via delivery tube 302. (ii) While at least a portion (e.g., an upstream portion) of the valve frame remains disposed within the delivery tube, the snares are deployed from the distal end of the delivery tube such that the snares protrude radially outward and form angle alpha_3 with the axis, and angle alpha_4 with the valve frame. (iii) Subsequently, tissue of the native valve is engaged using the snares (e.g., by moving the implant in an upstream direction). (iv) Subsequently, by deploying more of the valve frame (e.g., the remainder of the valve frame) from the catheter, angle alpha_4 is reduced by at least 30 percent (e.g., by at least 50 percent), while angle alpha_3 is not changed by more than 10 percent (e.g., angle alpha_3 is changed by less than 8 percent, e.g., by less than 5 percent), such as while angle alpha_3 remains constant.

For some applications, in the absence of lower annular portion 296, upstream support 282 would contact the upstream valve surface only at perimeter 300. Lower annular portion 296 increases the contact surface area between upstream support 282 and the upstream valve surface.

Upper annular portion 294 is resilient (e.g., has shape memory) and is thus biased to assume a particular shape. For example, and as shown, upper annular portion 294 may be frustoconical, with its wider base lower than (e.g., downstream of) its narrower base. This characteristic facilitates upstream annular portion 294 serving as a spring that is tensioned by sandwiching of tissue between the upstream annular portion and snare frame 288 during implantation, and thereby facilitates secure anchoring of the implant at the mitral valve. Upstream annular portion facilitates this anchoring via tension on sheet 286.

Tensioning of upper annular portion 294 typically results in deflection of upper annular portion 294 with respect to valve frame 284 (e.g., perimeter 300 becomes more upstream with respect to site 298). This may also occur during the cardiac cycle. The deflectability of lower annular portion 296 with respect to upper annular portion 294 facilitates the lower annular portion remaining in contact with the upstream valve surface despite the deflection of the upper annular portion with respect to the upstream valve surface. Thus, for some applications, an angle alpha_5 between upper annular portion 294 and lower annular portion 296 when the implant is in a rest state (e.g., an unconstrained shape, such as when the implant is on a table-top) (FIG. 15B) is greater than an angle alpha_6 between the annular portions when the implant is implanted and tissue of the native valve is disposed between upstream support 282 and snare frame 288. For some applications, angle alpha_5 is 45-90 degrees.

It is to be noted that for some applications snares 292 (e.g., snare frame 288) may be coupled via a flexible sheet to other prosthetic valves (e.g., to other valve frames described herein), including those comprising a valve frame that is rigidly coupled to an upstream support, and those comprising a valve frame that is not coupled to an upstream support (e.g., prosthetic valves that are configured to be intracorporeally coupled to an upstream support, and prosthetic valves that are configured to be implanted without an upstream support).

It is to be noted that for some applications upstream support 282 may be used in combination with other prosthetic valves (e.g., with other valve frames described herein), including those comprising a valve frame that is rigidly coupled to snares or tissue-engaging elements. It is to be noted that for some applications upstream support 282 may be rigidly coupled to valve frame 284 (or to another valve frame).

Reference is now made to FIG. 17, which shows implant 280, in its compressed state, being delivered to the heart via delivery tube 302 (e.g., a catheter), in accordance with some applications of the invention. In the compressed state of implant 280, valve frame 284 is typically disposed collinearly between upstream support 282 and snare frame 288. The connection of snare frame 288 to valve frame 284 via sheet 286 typically provides articulation between the snare frame and the valve frame while implant 280 is in its compressed state. That is, in the compressed state of implant 280, sheet 286 typically extends longitudinally between frames 288 and 284, thereby defining an articulation zone 289a between these frames. While implant 280 is in its compressed state, sheet 286 further typically defines an articulation zone 289b between valve frame 284 and upstream support 282, e.g., as described hereinabove for implant 240, mutatis mutandis. Therefore, for some applications, in its compressed state, implant 280 has three rigid segments (defined by support 282, frame 284, and frame 288, respectively) in tandem, and two articulation zones separating the rigid segments.

For some applications, articulation zone 289a separates snare frame 288 from valve frame 284 by at least 1.5 mm (e.g., 1.5-10 mm, e.g., 1.5-5 mm, such as 2-5 mm). For some applications, articulation zone 289a separates valve frame 284 from upstream support 282 by at least 1.5 mm (e.g., at least 3 mm, e.g., 3-10 mm, e.g., 3-8 mm, such as 3-5 mm).

For some applications this articulation is hypothesized to facilitate percutaneous (e.g., transluminal) delivery of implant 280, by allowing the compressed implant to articulate as it passes bends in the percutaneous path to the heart. FIG. 17 shows articulation zones 289a and 289b facilitating passage of implant 280 through a bend in delivery tube 302, e.g., in the vicinity of fossa ovalis 5 in the interatrial septum of the heart. For some applications, delivery tube 302 is capable of forming a bend 291 having a radius of curvature of less than 15 mm (e.g., less than 13 mm) and/or more than 5 mm (e.g., 5-15 mm, e.g., 10-15 mm, such as 10-12 mm), and implant 280, in its compressed state, is advanceable through bend 291.

For some applications, in its compressed state, implant 280 has a length of at least 25 mm (e.g., 25-50 mm), such as at least 30 mm. For some applications, in its compressed state, implant 280 has a greatest width that is at least 50 percent (e.g., 50-90 percent), such as at least 75 percent (e.g., 75-98 percent, such as 75-90 percent) of the internal diameter of delivery tube 302. For some applications, in the compressed state of implant 280, upstream support 282, valve frame 284, and snare frame 288, each have a respective width d21 that is at least 50 percent (e.g., 50-90 percent), such as at least 75 percent (e.g., 75-98 percent, such as 75-90 percent) of the internal diameter of delivery tube 302. It is hypothesized that an implant having the same length and width, but not having articulatable coupled segments, would not be advanceable through bend 291.

For some applications, in the compressed state of implant 280, no individual rigid segment has a length (measured along the longitudinal axis of the implant) that is greater than 22 mm. For some applications, in the compressed state of implant 280, a sum of (i) a length d20' of the rigid segment defined by support 282, (ii) a length d20" of the rigid segment defined by frame 284, and a length d20' of the rigid segment defined by frame 288, is at least 35 mm.

Typically, a delivery tool 304, reversibly couplable to implant 280, is used to advance the implant to the heart (e.g., via delivery tube 302). Typically, implant 280 is delivered with snare frame 288 disposed distally to valve frame 284, and upstream support 282 disposed proximally to the valve frame, e.g., such that snare frame 288 emerges from tube 302 first.

For some applications, implant 280 is delivered with frame 288 inverted and folded up against the outside of frame 284. For such applications, it is hypothesized that the coupling of these two frames via sheet 286 facilitates this folding. For example, for some applications frame 288 (e.g., the entire length of frame 288) may be disposed flat against frame 284, thereby resulting in a small maximum width of the implant in its compressed state. In contrast, a different sort of coupling might result in the fold between the frames having a radius of curvature that increases the width of the implant, at least in the area of coupling between frames 288 and 284.

It is to be noted that for some applications the apparatus and techniques described with reference to FIGS. 15A-17 may be used in combination with those described in PCT patent application publication WO 2014/115149 to Hammer et al., which is incorporated herein by reference.

Figure 18:
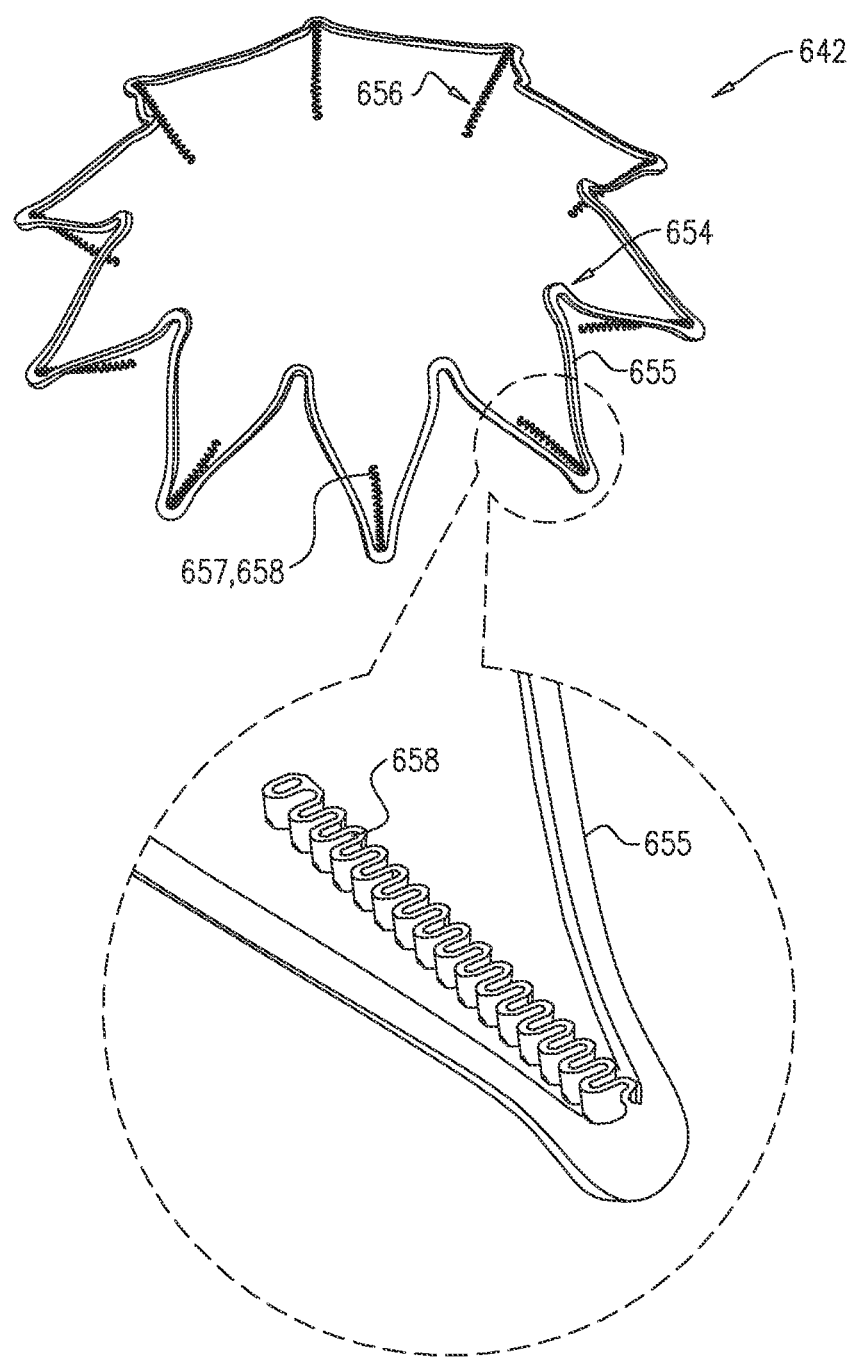
FIGS. 18 and 19A-B are schematic illustrations of frames of upstream supports, in accordance with some applications of the invention.
Figure 19A:
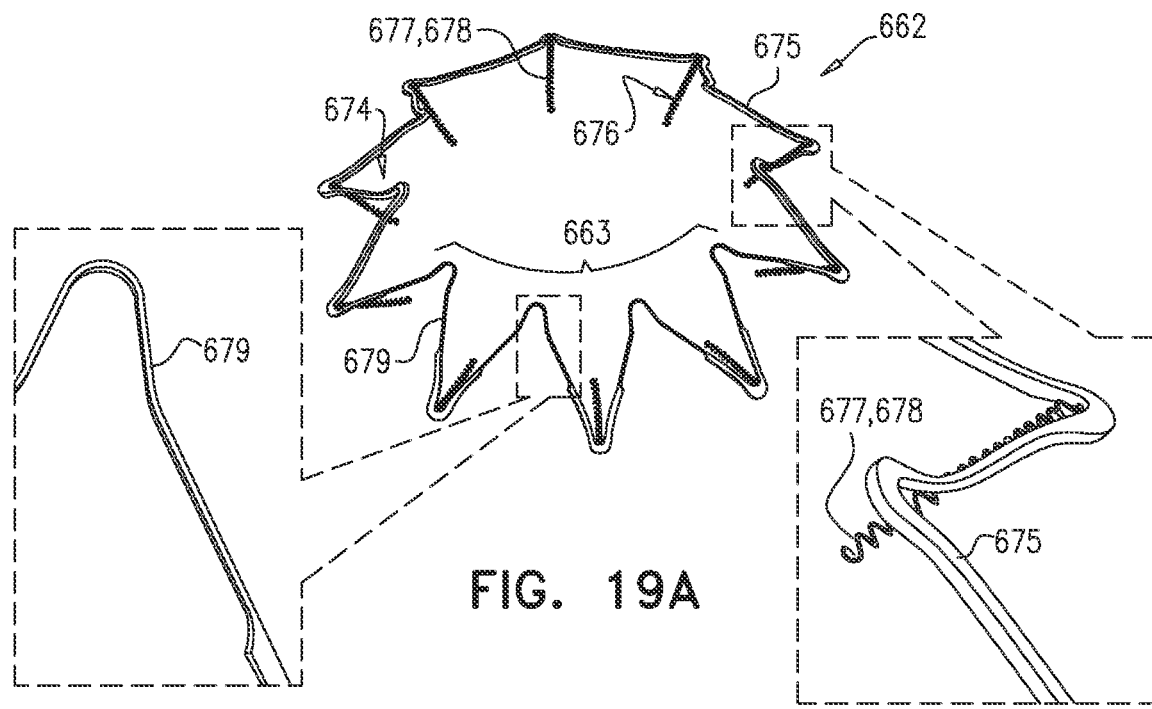
Figure 19B:
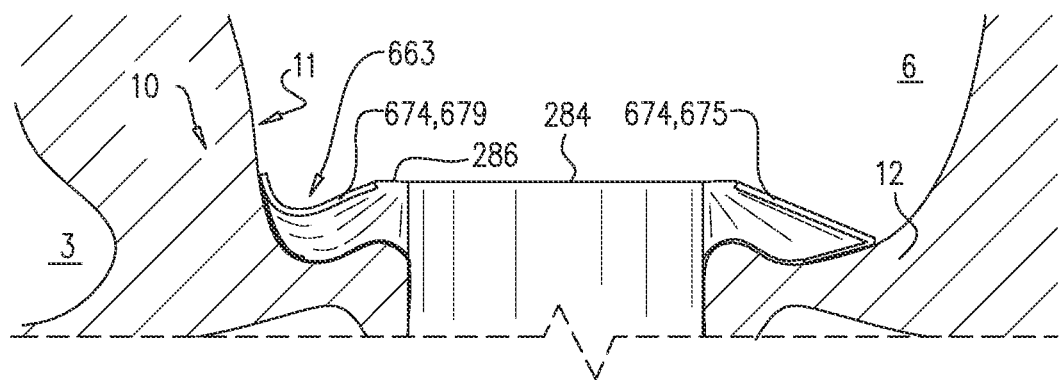

Reference is made to FIGS. 18 and 19A-B, which are schematic illustrations of frames of upstream supports, in accordance with some applications of the invention. FIG. 18 shows a frame of an upstream support 642, and FIGS. 19A-B show a frame of an upstream support 662. Upstream supports 642 and 662 may be used in place of other upstream supports described herein.

Upstream support 642 is typically identical to upstream support 282 except where noted otherwise. Upstream support 642 is annular, and defines two annular portions: an upper annular portion 654 and a lower annular portion 656 that is circumferentially coupled to the upper annular portion (e.g., at a perimeter of upstream support 642). As described for support 282, for some applications struts 655 that form upper annular portion 654 of support 642 are arranged as chevrons that repeat in a circumferential pattern (e.g., a zigzag pattern). In contrast to support 282, struts 657 that form lower annular portion 656 of support 642 are typically individual rods 658 that protrude radially inward from the point at which they are coupled to upper annular portion 654 (e.g., from the perimeter of the frame). It is to be noted that the frame of support 642 (e.g., the struts of its upper and lower annular portions) is typically covered with a covering (e.g., described for support 282), such that the support generally resembles support 282 (e.g., as shown in FIGS. 15A-C), mutatis mutandis.

Support 442 generally functions as described for support 282. It is hypothesized that, for some applications, the different configuration of the lower annular portion of support 642 compared to that of support 282 facilitates independent movement of different regions of lower annular portion 656, thereby improving its conformation to the anatomy and/or sealing against the anatomy. For some applications, this is further facilitated by each rod 658 being shaped as a spring (as shown), thereby increasing flexibility of the rod.

Upstream support 662 is typically identical to upstream support 642 except where noted otherwise. Upstream support 662 is annular, and defines two annular portions: an upper annular portion 674 and a lower annular portion 676 that is circumferentially coupled to the upper annular portion (e.g., at a perimeter of upstream support 662). As described for support 282 and 642, for some applications struts 675 and 679 that form upper annular portion 674 of support 662 are arranged as chevrons that repeat in a circumferential pattern (e.g., a zigzag pattern). For some applications, and as shown, struts 677 that form lower annular portion 676 of support 662 are individual rods 678 that protrude radially inward from the point at which they are coupled to upper annular portion 664 (e.g., as described for support 642). For some applications (not shown), the struts that form lower annular portion 676 are arranged as chevrons that repeat in a circumferential pattern (e.g., as described for support 282). It is to be noted that the frame of support 662 (e.g., the struts of its upper and lower annular portions) is typically covered with a covering (e.g., described for support 282), such that the support generally resembles support 282 (e.g., as shown in FIGS. 15A-C), mutatis mutandis.

Upstream annular portion 674 of support 662 has a flexible sector 663 that is more flexible than other portions of the upstream annular portion. For example, struts 679 that form sector 663 may be more flexible (e.g., by being thinner) than struts 675 that form other portions of upstream annular portion 674. As shown in FIG. 19B, the implant of which support 662 is a component is typically implanted with sector 663 oriented to an anterior side 11 of mitral valve 10. Sector 663 facilitates greater conformation of upstream annular portion 674 to the anatomy (e.g., to the atrial wall separating left atrium 6 from aorta 3), and therefore improved sealing against the anatomy. Support 662 is shown in FIG. 19B as being used with components of implant 280 (e.g., valve frame 284 and sheet 286), but it is to be noted that the scope of the invention includes support 662 being used with components of other implants.

Figure 20A:
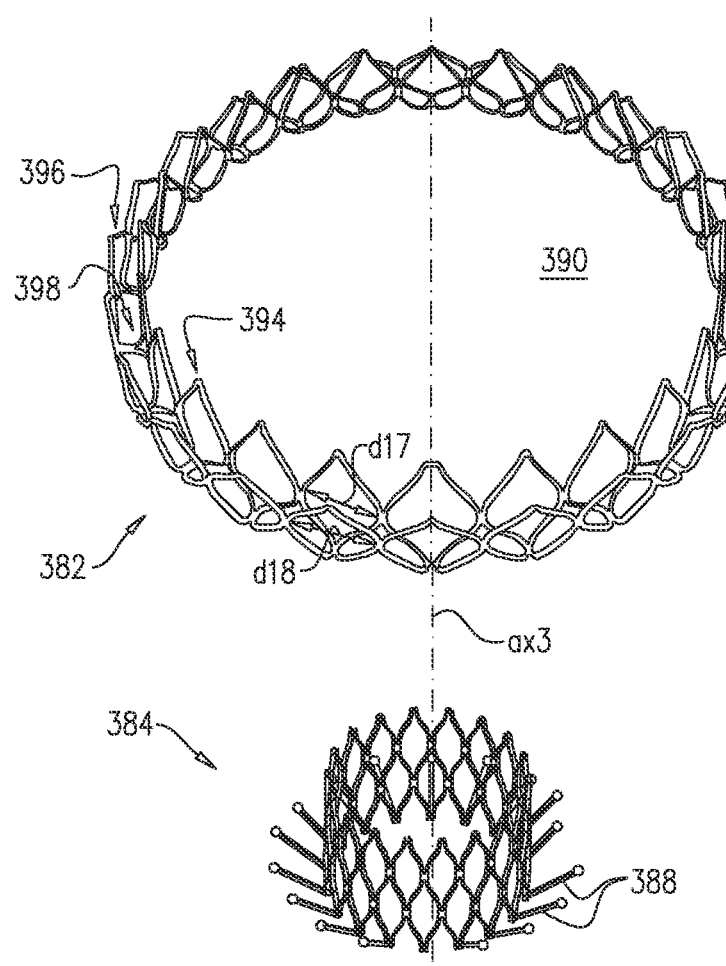

Reference is made to FIGS. 20A-C, which are schematic illustrations of an implant 380 comprising a support frame 382, a prosthetic valve frame 384, and a flexible sheet 386 coupling the support frame to the prosthetic valve frame, in accordance with some applications of the invention. Valve frame 384 may be identical, mutatis mutandis, to another valve frame described herein, such as valve frame 264 or valve frame 284. A plurality of snares 388 protrude radially outward and upstream from valve frame 384, typically from a downstream portion of the valve frame. Snares 388 may be coupled rigidly to valve frame 384 (e.g., as shown) or may be coupled in another fashion, such as via a flexible sheet, as described for implant 280, mutatis mutandis. Snares 388 may be identical to other snares described herein, mutatis mutandis.

A valve member (e.g., a plurality of prosthetic leaflets) is disposed within the lumen defined by valve frame 384, so as to facilitate one-way downstream movement of blood through the lumen, e.g., as described herein for other valve members. For clarity, the valve member is not shown in FIGS. 20A-C.

Implant 380 has a compressed state for percutaneous (e.g., transluminal) delivery to the heart, and is intracorporeally expandable into an expanded state. In the compressed state of implant 380, frames 382 and 384 are in respective compressed states thereof. FIGS. 20A-C show implant 380 in its expanded state, with frames 382 and 384 in respective expanded states thereof, and the descriptions herein refer to implant 380 in its expanded state, unless stated otherwise.

FIG. 20A shows support frame 382 and valve frame 384, with the support frame in a relaxed state. FIG. 20B shows implant 380 with support frame 382 in its relaxed state, and FIG. 20C shows the implant with the support frame in a constrained state thereof. The relaxed and constrained states of implant 380 (and of support frame 382) are described in more detail hereinbelow.

Support frame 382 has a generally toroid shape, defining an opening 390 through the support frame, and dimensioned to be placed against an upstream surface of the native heart valve such that the support frame circumscribes the valve orifice. Typically, support frame 382 is dimensioned to be placed on the annulus of the native valve. It is to be noted that the term toroid (including the specification and the claims) is describable as the result of revolving a plane geometric figure about a central longitudinal axis. The generally toroid shape of support frame 382 is describable as the result of revolving a plane geometric figure about a central longitudinal axis ax3 of the support frame (and/or of implant 380 as a whole). That is, an axis of revolution ax4 of the toroid shape circumscribes axis ax3, and the toroid shape is describable as the result of moving the plane geometric figure along the axis of revolution. It is to be noted that the position of axis of revolution ax4 is merely an illustrative example, and may pass through another part of the plane geometric figure.

For some applications, and as shown, the plane geometric figure is U-shaped or V-shaped (e.g., as shown in the cross-sections of FIGS. 20B-C). However, the plane geometric figure may alternatively or additionally have a different shape.

FIG. 20B shows implant 380 in its relaxed state (e.g., in a relaxed state of support frame 382). Valve frame 384 is held by sheet 386 at a given height with respect to support frame 382. For some applications, and as shown, in the relaxed state of implant 380, at least part of the lumen defined by valve frame 384 is disposed within opening 390 of the support frame.

When valve frame 384 is moved in a downstream direction, a force is applied to support frame 382 via sheet 386, and the support frame 382 responsively rolls inward (e.g., about axis of revolution ax4) such that an orientation of the plane geometric figure with respect to opening 390 changes (e.g., the plane geometric figure deflects and/or rotates). For example, in FIG. 20B the U-shape is oriented such that the arms of the U-shape point at right angles to opening 390, whereas in FIG. 20C, the arms point more toward the opening.

Support frame 382 is biased to assume its relaxed state, such that removal of the force (e.g., releasing of valve frame 384) results in implant 380 returning to the state shown in FIG. 20B. During implantation at the native valve (e.g., using techniques similar to those described elsewhere herein) such that snares 388 are disposed downstream of the native valve and support frame 382 is disposed upstream of the native valve, the force is applied such that implant 380 is in its constrained state. When the force is removed, the implant moves toward its relaxed state, thereby sandwiching tissue of the native valve between snares 388 and support frame 382. For some applications, and as shown, in the constrained state, at least part of the lumen defined by valve frame 384 is disposed within opening 390 of the support frame. Alternatively, the lumen defined by the valve frame may be disposed entirely downstream of opening 390.

For some applications support frame 382 defines an inner ring 394 and an outer ring 396, each ring defined by a circumferential arrangement of cells, each cell of the inner ring coupled to adjacent cells of the inner ring, and to a corresponding cell of the outer ring. The inner ring defines one arm of the U-shape, the outer ring defines the other arm of the U-shape, and the inner ring cells are coupled to the outer ring cells at a trough 398 of the U-shape. The rolling of frame 382 in response to the applied force compresses the inner ring cells and outer ring cells, at least in part, i.e., reducing a width d17 of the inner ring cells and a width d18 of the outer ring cells. Upon removal of the force, the cells re-widen, thereby causing support frame 382 to roll back toward its relaxed state.

The mechanics described in the above paragraph may be alternatively described as follows: The rolling of the frame moves at least part of inner ring 394 and at least part of outer ring 396 radially inward, such that a diameter of each ring becomes smaller. Upon removal of the force each ring re-expands toward its original diameter, thereby causing support frame 382 to roll back toward its relaxed state. That is, support frame 382 defines at least one ring that is compressed as the frame rolls inward, and expands as the frame rolls outward. This is illustrated in the cross-sections of FIGS. 20B-C. A diameter of inner ring 394, measured at the point of coupling between cells of the inner ring, is greater when support frame 382 is in its relaxed state (diameter d22 of FIG. 20B) than when the support frame is in its constrained state (diameter d23 of FIG. 20C).

The biasing of support frame 382 to assume its relaxed state is typically achieved by forming the support frame from a shape-memory material such as Nitinol.

For some applications, and as shown, sheet 386 extends over the lip of inner ring 394, and covers at least part of the inner ring. For some such applications, sheet 386 is circumferentially attached to support frame 382 at least at trough 398.

The rolling inward of support frame 382 typically involves a most-radially-inward point of contact between the support frame and sheet 386 moving in a downstream direction, and further typically involves the most-radially-inward point of contact moving radially inward. For example, and as shown in the cross-sections of FIGS. 20B-C, for some applications the most-radially-inward point of contact between support frame 382 and sheet 386 is the lip of inner ring 394, and the rolling inwards involves the lip of the inner ring moving in a downstream and radially-inward direction.

Figure 21A:
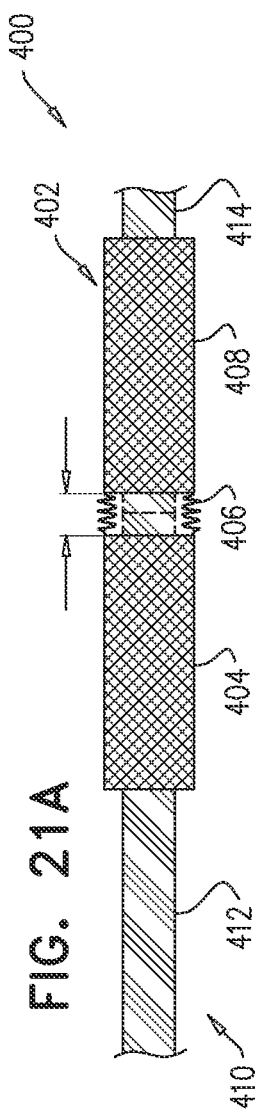
FIGS. 21A-C are schematic illustrations of a system for stretching an elastic coupling between frames of an implant, in accordance with some applications of the invention.
Figure 21B:
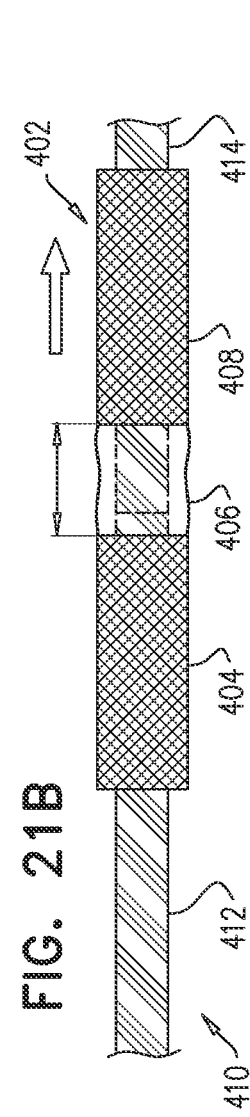
Figure 21C:
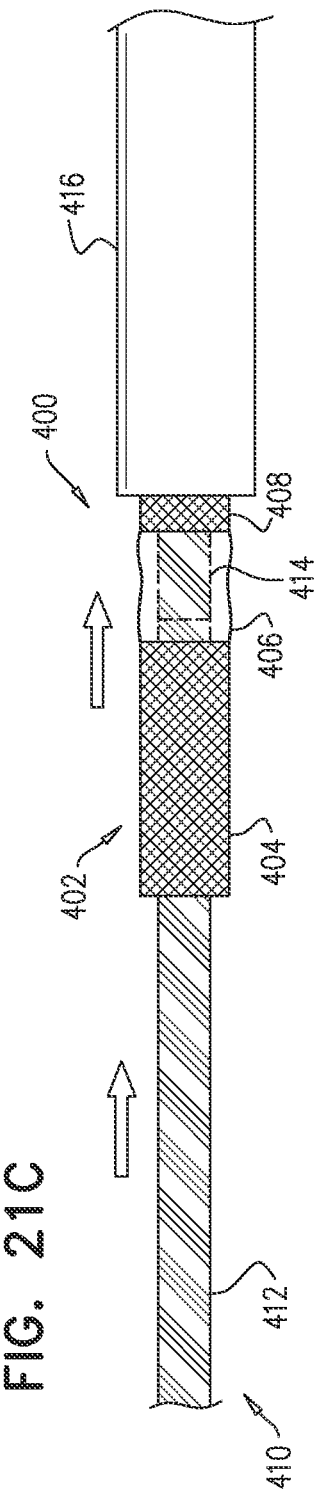

Reference is made to FIGS. 21A-C, which are schematic illustrations of a system 400 for stretching an elastic coupling between frames of an implant, in accordance with some applications of the invention. For some applications, an implant 402 comprises a first frame 404 elastically coupled to a second frame 408. For some such applications, implant 402 comprises a flexible sheet 406 that extends between frame 404 and frame 408, and provides fluid sealing and/or fluid communication between the frames once the implant is implanted. The elastic coupling may be provided by the flexible sheet, and/or may be provided by another mechanism. The elastic coupling typically facilitates sandwiching of tissue of a subject between the two frames upon implantation of the implant. Moving frames 404 and 408 away from each other (thereby stretching the elastic coupling between the frames) prior to implantation facilitates positioning of the frames (or parts thereof) on either side of the tissue, such that upon release of the stretching force, the elastic coupling draws the frames closer together, thereby sandwiching the tissue between the frames (or parts thereof).

FIGS. 21A-C are general schematic illustrations. Implant 402 may comprise any of the implants described herein in which a flexible sheet couples two frames, or implant 402 may comprise another implant. For example, implant 402 may comprise implant 20, implant 80, implant 100, implant 120, implant 140, implant 160, implant 180, implant 200, implant 240, implant 260, or implant 380, mutatis mutandis.

Prior to implantation, implant 402 is coupled to a delivery tool 410, which typically comprises a central rod (e.g., as described elsewhere herein, mutatis mutandis). For some applications, implant 402 is provided pre-coupled to the delivery tool (e.g., by being compressed, or "crimped", onto the delivery tool, as is known in the art, mutatis mutandis). For some applications, part or all of implant 402 is coupled to delivery tool 410 soon before implantation (e.g., by the operating physician, or by a technician at the operating institution). For example, for applications in which one of the frames (e.g., frame 408) comprises a prosthetic valve frame that comprises prosthetic leaflets, it may be desirable that the prosthetic valve frame not remain compressed for an extended period, and so at least that frame is compressed against the delivery tool soon before implantation. FIG. 21A shows implant 402 after both frame 404 and frame 408 have been coupled to tool 410, and are in tandem with each other.

Once frames 404 and 408 are coupled to the delivery tool (e.g., to respective connectors of the delivery tool), the elastic coupling between the frames is stretched by increasing a distance between the frames, such as by increasing a distance between the connectors to which the frames are coupled (FIG. 21B). For example, and as shown, tool 410 may comprise a first portion 412 (which may comprise a first connector, not shown) and a second portion 414 (which may comprise a second connector, not shown), and movement of portion 414 axially with respect to portion 412 (e.g., increasing an overall length of tool 410).

FIG. 21C shows implant 402 being advanced into a delivery tube 416 (e.g., a catheter) subsequently to the above-described stretching. However it is to be noted that the scope of the invention includes performing the stretching after the implant has been advanced into delivery tube 416 (e.g., while the implant is in a vicinity of the implantation site).

Reference is now made to FIGS. 22, 23, 24A-C, and 25A-K, which are schematic illustrations of an implant 460, and a system 500 comprising implant 460 and a delivery tool 502, in accordance with some applications of the invention. Implant 460 is similar, and comprises similar elements, to other implants described hereinabove. In particular implant 460 is typically identical to implant 260, except where noted, and components of implant 460 share similar structure and/or function with identically-named elements of implant 260, except where noted.

Implant 460 comprises an upstream frame 462, a downstream frame 464, and at least one flexible sheet 466 that couples the upstream frame to the downstream frame. Typically, implant 460 comprises two flexible sheets 466, such as a flexible sheet 466a and a flexible sheet 466b, which each couple upstream frame 462 to downstream frame 464. Downstream frame 464 comprises a tubular body that defines a lumen therethrough (e.g., as described hereinabove for other downstream frames), and a plurality of snares 468. As shown, snares 468 typically meet the valve body defined by frame 464 toward a downstream end of the valve body, and do not extend in an upstream direction as far as the upstream end of frame 464. Implant 460 comprises a valve member (e.g., a plurality of prosthetic leaflets) 50 disposed within the lumen defined by downstream frame 464, e.g., as described hereinabove, mutatis mutandis.

As described for upstream frame 22, mutatis mutandis, upstream frame 462 (and other upstream frames described herein, such as upstream frame 262) may be considered to define an upstream opening 150 (i.e., an opening defined by an upstream end of the upstream frame) and a downstream opening 150' (i.e., an opening defined by a downstream end of the upstream frame). An upstream end 492 of frame 462 defines upstream opening 150 of frame 462, and a downstream end 494 of frame 462 defines downstream opening 150' of frame 462. It is to be noted that throughout this application (including the specification and the claims), in the absence of further definition, the "opening" of any of the upstream frames typically refers to the downstream opening of the upstream frame.

FIG. 22 shows implant 460 in its expanded state, in which an upstream portion (e.g., an upstream end) of downstream frame 464 is disposed longitudinally upstream of opening 150' of upstream frame 462 (e.g., as described for implant 260, mutatis mutandis). That is, implant 460 has a central longitudinal axis, and the upstream portion of downstream frame 464 is disposed further upstream along the longitudinal axis than is opening 150'. The position of frames 464 with respect to frame 462 is due to the nature of coupling of the frames to each other via sheet(s) 466. As described hereinbelow, implant 460 is transluminally delivered in a compressed state in which frames 462 and 464 are both compressed, and are disposed in tandem. At the implantation site, expansion of upstream frame 462 toward its expanded state pulls valve frame 464 longitudinally into frame 462 (i.e., into opening 150') by pulling sheet 466a and/or sheet 466b radially outward (i.e., tensioning the sheet(s)).

As described for implant 260, mutatis mutandis, in the expanded state of implant 460, a diameter of frame 464 is smaller than a diameter of opening 150' defined by downstream end 494 of frame 462. Sheet 466a extends radially inward from frame 462 to frame 464, and is circumferentially attached to frame 464 at a first longitudinal site 474a of frame 464. For some applications, sheet 466a is identical to sheet 266a described hereinabove, mutatis mutandis. Sheet 466b also extends radially inward from frame 462, and is circumferentially attached to frame 464 at a second longitudinal site 474b of frame 464.

Typically, longitudinal site 474b is closer to upstream portion 42 than is longitudinal site 474b. For example, longitudinal site 474b may be at least 4 mm and/or less than 10 mm closer to an upstream end of frame 464 than is longitudinal site 474b (e.g., 4-10 mm closer, or at least 3 mm closer, such as 3-10 mm closer, e.g., about 6 mm closer). For some applications, longitudinal site 474b is at the upstream end of frame 464, although is shown in FIG. 22 as slightly downstream of this.

Typically, sheet 466b is attached to upstream frame 462 further upstream than is sheet 466a. For example, and as shown, sheet 466a may be attached to (i.e., may extend from) downstream end 494 of frame 462, whereas sheet 466b may be attached to (i.e., may extend from) upstream end 492 of frame 462. The sites of attachment of sheets 466 to frames 462 and 464 (i) facilitates the longitudinal pulling of frame 464 into frame 462 (e.g., via opening 150') by the radial expansion of frame 462, (ii) facilitate smooth blood-flow from opening 150 into the lumen of downstream frame 464, and/or (iii) defines, between sheets 466a and 466b, a chamber 476 (e.g., a closed chamber) that circumscribes frame 464. Chamber 476 is typically toroidal. Subsequently to implantation of implant 460, tissue formation typically occurs within chamber 476, e.g., due to blood entering the chamber 476 by passing through the flexible sheets (e.g., at least one of the sheets is at least partially blood-permeable). For some applications this tissue formation is hypothesized to gradually increase rigidity of implant 460.

Therefore, as described with reference to implants 260 and 460, percutaneously-implantable apparatus is provided, comprising (i) a first frame; (ii) a second frame; and (iii) a plurality of flexible sheets comprising at least a first flexible sheet and a second flexible sheet, at least the first sheet coupling the first frame to the second frame, and the plurality of flexible sheets being coupled to the first frame and the second frame such that a closed chamber is disposed between the first sheet and the second sheet, and at least one of the sheets being at least partially blood-permeable.

As described hereinabove for other implants, mutatis mutandis, frames 462 and 464 (or at least portions thereof) are typically covered and/or lined, and flexible sheets 466a and 466b may extend over portions of the frames so as to perform this function. For example, and as shown, sheet 466a typically extends from longitudinal site 474a of frame 464, to downstream end 494 of frame 462, and over an outer surface of frame 462. Sheet 466a may continue to extend around upstream end 492 of frame 462 and line part of an inner surface of frame 462, as shown. Frame 464 is typically at least partly lined, e.g., with a fabric, which may be the same material as sheet(s) 466. For some applications, and as shown, frame 464 has unlined zones, e.g., positioned where leaflets 50 deflect outward to allow fluid flow.

FIG. 23 shows system 500, including several sub-views, with implant 460, in a compressed delivery state, loaded onto delivery tool 502, in accordance with some applications of the invention. Delivery tool 502 comprises one or more steerable catheters, such as a first catheter 504 (having a distal steerable portion 505) and a second catheter 506, which extends through catheter 504 such that a steerable distal portion 507 of catheter 506 is disposed out of the distal end of catheter 504. Catheter 504 has an external diameter d24 that is typically 7-10 mm (e.g., 8-9 mm), and catheter 506 has an external diameter d25 that is typically 5-8 mm (e.g., 6-7 mm), and is smaller than an internal diameter of catheter 504. Tool 502 further comprises a rod 508 (e.g., a central rod), which has an external diameter d27 that is smaller than an internal diameter of catheter 506. Rod 508 extends through catheter 506 such that a steerable distal portion 509 of rod 508 is disposed out of the distal end of catheter 506. For some applications, a width (e.g., a greatest width) d27 of implant 460 in its compressed state is greater than the internal diameter of catheter 504. This is possible because, as described hereinbelow, implant 460 is not advanced through catheters 504 and 506, but instead is advanced with the catheters, while disposed distally to them. Typically, catheter 504, catheter 506 and rod 508 each comprise a polymer. The arrangement of catheter 504, catheter 506 and rod 508 is most clearly shown in sub-view D.

There is therefore provided, in accordance with some applications of the invention, apparatus comprising: (i) a first catheter (e.g., catheter 504), dimensioned for transfemoral and transseptal advancement into a left atrium of a heart of a subject, and having a lumen that has an internal diameter; (ii) a second catheter (e.g., catheter 506), having an external diameter that is smaller than the internal diameter, the second catheter being sufficiently long to extend through the first catheter such that a steerable distal portion (e.g., portion 507) of the second catheter extends out of a distal end of the first catheter; and (iii) an implant (e.g., implant 460), having a compressed state in which the implant is transfemorally and transseptally advanceable into the left atrium by the first catheter and the second catheter, and in which a width of the implant is greater than the internal diameter of the first catheter.

It is to be noted that the term "steerable" (including the specification and the claims) means actively steerable, e.g., by using an extracorporeal controller to effect bending. (This is in contrast to a flexible but non-steerable element, which may bend in response to encountering forces during advancement through the body of the subject.) Bending of portion 505 of catheter 504 is performed by actuating a controller 565 (e.g., on a handle 555 at a proximal end of catheter 504) that is operably coupled (e.g., via pull-wires) to portion 505. Bending of portion 507 of catheter 506 is performed by actuating a controller 567 (e.g., on a handle 557 at a proximal end of catheter 506) that is operably coupled (e.g., via pull-wires) to portion 507. Bending of portion 509 of rod 508 is performed by actuating a controller 569 (e.g., on a handle 559 at a proximal end of rod 508) that is operably coupled (e.g., via pull-wires) to portion 509. Typically, a bending plane of portion 507 is orthogonal to a bending plane of portion 505. Thereby together catheters 504 and 506 provide movement in two dimensions. Portion 509 of rod 508 may be steerable on one or more bending planes (e.g., on two bending planes). As well as being steerable, rod 508 is typically slidable longitudinally with respect to the catheters (e.g., by sliding handle 559, such as along a track 558).

As shown in sub-views C and B, implant 460, in its compressed state, is disposed around steerable distal portion 509 of rod 508, with frames 464 and 462 in tandem with each other. Sub-view C shows implant 460 including sheets 466 (which also serve as coverings for the frames of implant 460, e.g., as described elsewhere hereinabove, mutatis mutandis), and sub-view B shows the implant in the absence of sheets 466, thereby more clearly showing the positions of frames 462 and 464. Frame 462 is disposed around rod 508 (e.g., around distal portion 509 thereof) at a first longitudinal site 560a, sheet 466 is disposed around rod 508 at a second longitudinal site 560b, and frame 464 is disposed around rod 508 at a third longitudinal site 560c. Distal portion 509 is bendable at least at second longitudinal site 560b, which serves as an articulation zone.

As shown in sub-view A (as well as the primary view), a sheath 510 is disposed over at least implant 460 (and typically over at least portions 507 and 509 of catheters 506 and 508). Sheath 510 is thin (e.g., greater than 100 microns and/or less than 300 microns, e.g., 100-300 microns, such as about 200 microns thick), typically has insignificant compressive, torsional, or deflective strength, and is sufficiently flexible to passively bend in response to the bending of rod 508 and the articulation between frames 462 and 464. Sheath 510 comprises a low-friction material (e.g., is formed from the low-friction material, or is coated in the low-friction material) such as polytetrafluoroethylene (PTFE).

Figure 24A:
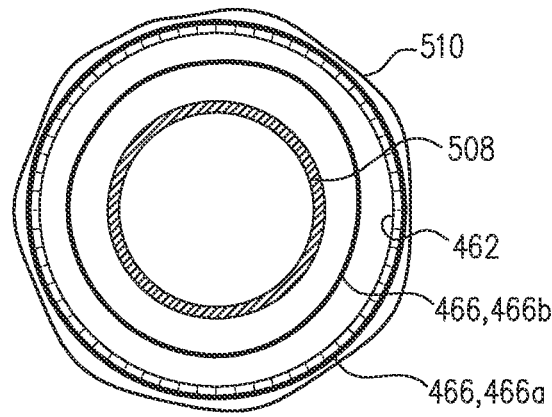
Figure 24B:
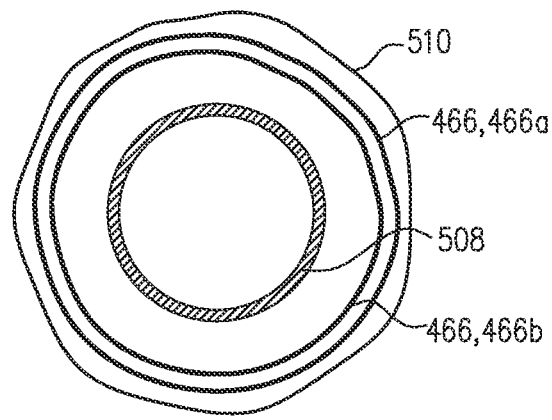
Figure 24C:
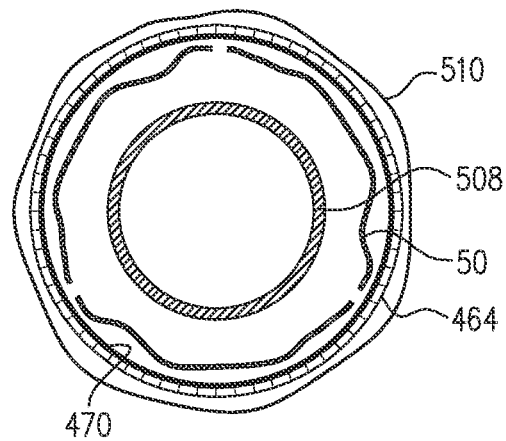

FIGS. 24A-C show transverse cross-sections through system 500 (i.e., cross-sections transverse to a longitudinal axis of system 500), the location of each cross-section being indicated in sub-view A of FIG. 23. Each of the cross-sections shows concentric layers. A first cross-section (FIG. 24A) shows concentric layers comprising, respectively, from inside outwardly: polymer (of rod 508), fabric (of sheet 466b), metal (of frame 462), and PTFE (of sheath 510). Typically, another layer of fabric (the covering of frame 462, typically part of sheet 466a) is disposed between the metal and PTFE layers.

A second cross-section (FIG. 24B) shows concentric layers comprising, respectively, from inside outwardly: polymer (of rod 508), fabric (of sheet(s) 466), and PTFE (of sheath 510), without a metal layer between the polymer and the fabric, or between the fabric and the PTFE. Typically, and as shown, there are also no struts (e.g., struts of a frame) between the polymer and the fabric, or between the fabric and the PTFE. Typically, and as shown, there is no metal at all between the polymer and the fabric, or between the fabric and the PTFE.

A third cross-section (FIG. 24C) shows concentric layers comprising, respectively, from inside outwardly: polymer (of rod 508), pericardial tissue (of leaflets 50), metal (of frame 464), and PTFE (of sheath 510). Typically, another layer 470 of fabric (which lines the lumen of frame 464) is disposed between the pericardial tissue layer and the metal layer. The second cross-section is disposed longitudinally between the first and third cross-sections.

It is to be noted that in this context, the term "layer" (including in the specification and in the claims) may refer to a continuous layer (such as that defined by sheath 510) or an interrupted layer (such as that which might defined by the struts of frames 462 and 464, when viewed in cross-section).

Figure 25A:
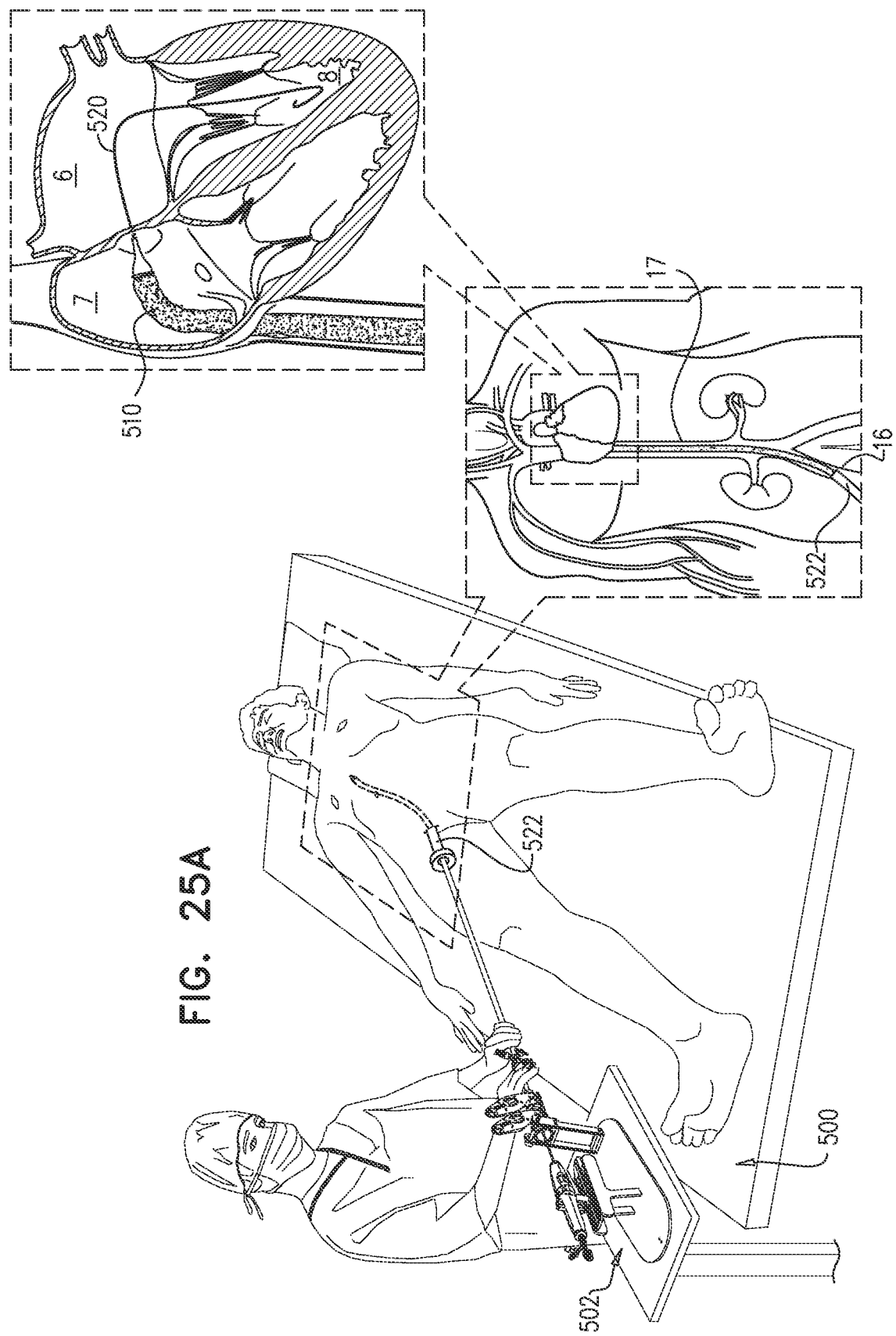

FIGS. 25A-K show system 500 in use, with delivery tool 502 being used to implant implant 460, in accordance with some applications of the invention. The femoral vein 16 is punctured (e.g., using the Seldinger technique), and a guidewire 520 is transfemorally and transseptally advanced to the left side of the heart of the subject (at least into left atrium 6, and typically into left ventricle 8). A trocar 522 (e.g., a standard, commercially-available trocar) is used to provide access to the femoral vein. A distal portion of system 500 (comprising implant 460, and distal portions of catheter 504, catheter 506, rod 508 and sheath 510) is advanced through trocar 522 into femoral vein 16, along inferior vena cava 17, into right atrium 7 (FIG. 25A). For some applications (and as shown), system 500 is advanced along guidewire 520. Alternatively, guidewire 520 is used to facilitate septal puncture, and is removed prior to advancing system 500.

It is to be noted that no guide catheter is advanced to the heart prior to advancing implant 460. Rather, system 500 is advanced as-is, through the vasculature. Rather, sheath 510 slides through the vasculature simultaneously with implant 460, and reduces friction between implant 460 and the vasculature.

It is to be further noted, that implant 460 is not disposed within a steerable (i.e., actively bendable) catheter for any part of the implantation process. Rather, and as can be understood from FIG. 23, and FIGS. 25A-K, implant 460 is disposed distally to steerable catheters 504 and 508.

System 500 is advanced transseptally into left atrium 6 (FIG. 25B). As shown, the steerability of catheters 504 and 508, and of rod 508, facilitates this. Furthermore, the steerability of rod 508 facilitates articulation of implant 460 down toward mitral valve 10, immediately after the implant clears the interatrial septum (or even before implant 460 has completely traversed the septum). It is hypothesized that, inter alia, (i) the articulatable coupling between frames 462 and 464 provided by sheet(s) 466, and (ii) the exploitation of this articulation by steerable rod 508, facilitates transfemoral and transseptal implantation, at the mitral valve, of an implant having a greater length (in its compressed state) than would be possible for a non-articulatable implant, or using a delivery system that does not actively articulate the implant during delivery.

System 500 is then advanced between leaflets 12 of mitral valve 10, typically such that (within sheath 510) at least part of frame 464 is disposed in left ventricle 8, and at least part of frame 462 is disposed within left atrium 6 (FIG. 25C). For some applications, the transition between the stage shown in FIG. 25B and that shown in 25C involves (i) advancing system 500 distally, (ii) increasing bending of catheter 504 and/or of catheter 506, and (iii) reducing the bending of rod 508 (and therefore the articulation of implant 460).

There is therefore provided, in accordance with some applications of the invention, a method comprising (i) using a delivery tool, percutaneously advancing toward a heart of a subject a prosthetic valve implant coupled to a distal portion of the delivery tool, the implant comprising a first frame coupled to a second frame; (ii) subsequently, articulating the first frame with respect to the second frame by bending the distal portion of the delivery tool; (iii) subsequently, reducing the articulation of the first frame with respect to the second frame by reducing the bending of the distal portion of the delivery tool; and (iv) subsequently, implanting the implant in the heart of the subject. For some applications, between the step of articulating the first frame and the step of implanting, another portion of the delivery tool, proximal to the distal portion, is bent.

There is therefore also provided, in accordance with some applications of the invention, apparatus, comprising: (i) a delivery tool (e.g., tool 502) comprising: (a) a first catheter (e.g., catheter 504), (b) a second catheter (e.g., catheter 506) extending through the first catheter, and (c) one or more extracorporeal controllers (e.g., controllers 565, 567, and 569), coupled to a proximal end of at least one of the first catheter and the second catheter; and (ii) an implant (e.g., implant 460), comprising a first frame (e.g., frame 462) articulatably coupled to a second frame (e.g., frame 464), and coupled to a distal portion of the delivery tool, distal to a distal end of the first catheter and to a distal end of the second catheter, and the one or more extracorporeal controllers are actuatable to transition the apparatus between: (i) a first state in which the first catheter and the second catheter are straight, and the first frame is articulated with respect to the second frame, and (ii) a second state in which a distal portion of at least one of the first catheter and the second catheter is bent, and the first frame is collinear with the second frame.

Figure 25D:
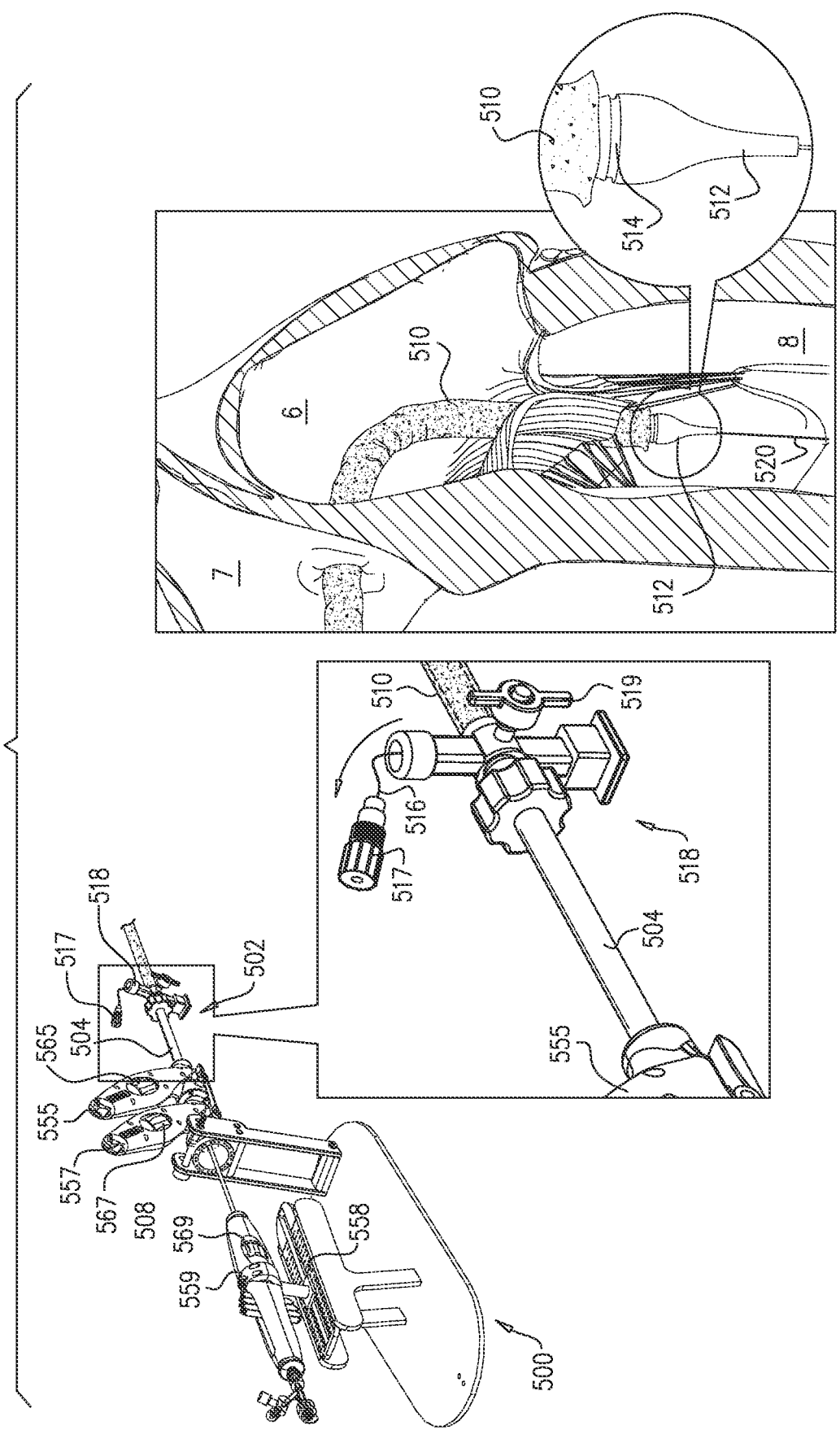
Figure 25E:
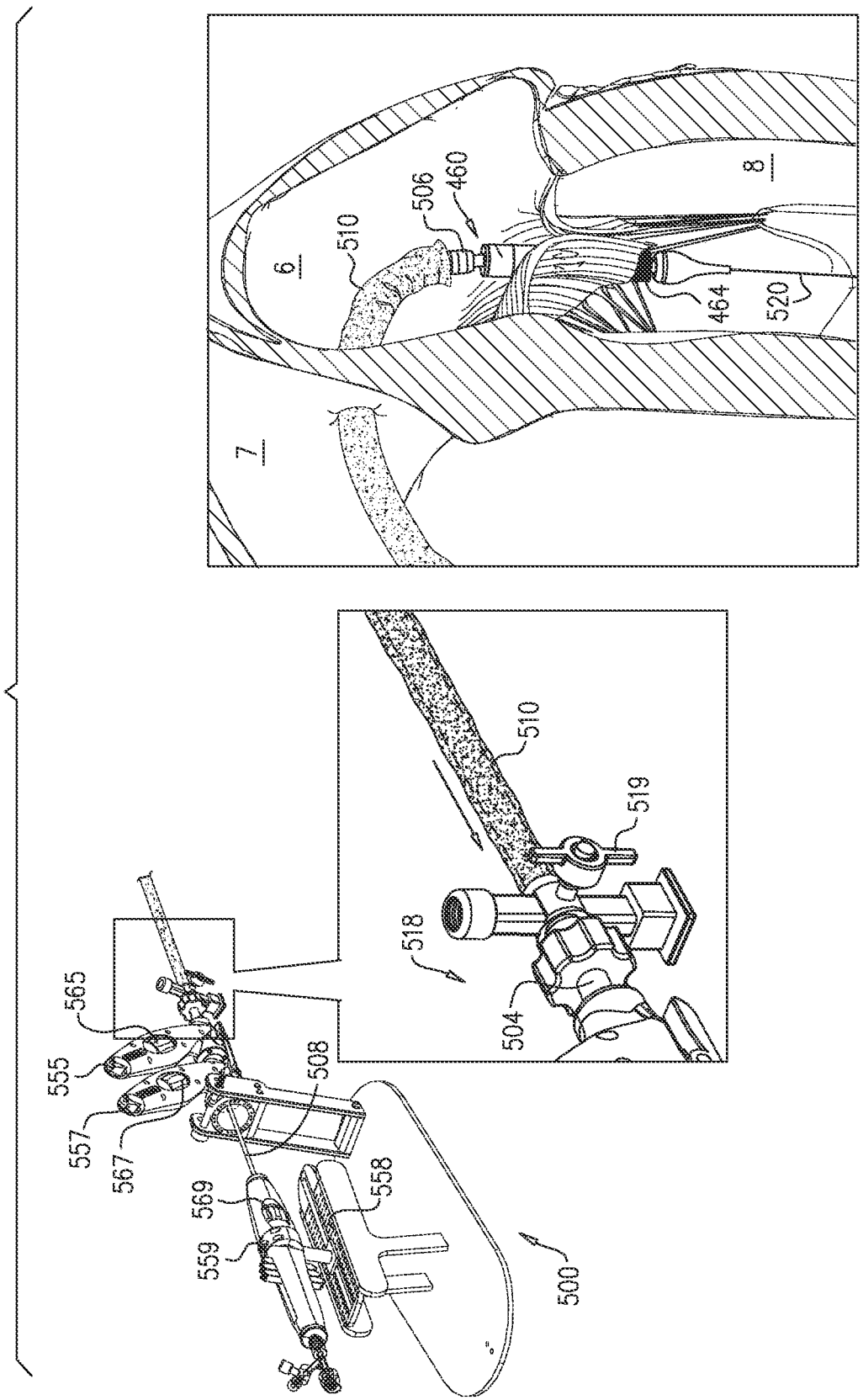

Subsequently, implant 460 is unsheathed (FIGS. 25D-E). A distal portion of sheath 510 is typically reversibly secured to a distal portion of rod 508. For example, and as shown, rod 508 may have a bulbous distal end 512 with a circumferential groove 514, and a loop of a wire 516 may secure the distal portion of the sheath within the groove. The unsheathing is performed using an extracorporeal controller 518. An example of such a controller is shown. Controller 518 has a tab 517 which is attached to wire 516. Sheath 510 is released from distal end 512 by pulling tab 517, which disengages wire 516 from groove 514 (FIG. 25D). Controller 518 is attached to a proximal portion of sheath 510, and sliding of the controller proximally (e.g., with respect to catheter 504) draws sheath 510 proximally, thereby unsheathing implant 460 (FIG. 25E). For some applications, controller 518 comprises a lock 519 (e.g., comprising a set screw), which, while locked, prevents movement of sheath 510 (e.g., by gripping an outer surface of catheter 504).

As shown in FIG. 25E, despite the unsheathing of implant 460, the implant remains in its compressed state. A plurality of restraints 530 restrain the implant in its compressed state. Typically, restraints 530 are coupled to, and actuated via, rod 508. Typically, a first restraint 530a restrains snares 468, a second restraint 530b restrains downstream frame 464 (e.g., the valve body thereof), and a third restraint 530c restrains upstream frame 462. Further typically, restraints 530 are disengaged using one or more extracorporeal restraint controllers 532 (e.g., respective controllers 532a, 532b, and 532c), such as switches, on handle 559. For some applications, and as shown, each restraint 530 comprises a respective loop of wire, which circumscribes a respective portion of implant 460 (most clearly shown in FIG. 23 sub-view B). However, restraints 530 may comprise another type of restraint, such as a latch or detent that protrudes radially from rod 508.

First restraint 530a, which restrains snares 468 in their compressed state, is disengaged, thereby allowing the snares to extend radially away from frame 464 (e.g., from the valve body thereof) (FIG. 25F). Snares 468 are shown in the figures as (i) being disposed against the valve body defined by frame 464 when in their compressed state, and (ii) moving through an acute angle when released. However, snares 468 may have a different configuration, such as (i) being disposed distal/downstream to the valve body defined by frame 464 when in their compressed state, and (ii) moving through an obtuse angle when released.

Second restraint 530b remains in place, restraining frame 464 (e.g., the valve body thereof) in its compressed state, and third restraint 530c remains in place, restraining frame 462 in its compressed state. Typically, at this stage, one or more imaging techniques (e.g., fluoroscopy) are used to determine, and optionally adjust, the position of implant 460, and in particular of snares 468 thereof. FIG. 25G illustrates the use of an imaging machine (e.g., a fluoroscope) to provide an image on a display 540, while the position of implant 460 is adjusted. Once the desired position is achieved, restraint 530b is disengaged (e.g., using restraint controller 532b), thereby allowing downstream frame 464 to expand toward its expanded state (FIG. 25H).

There is therefore provided (e.g., as described with reference to FIGS. 25A-H) a method, comprising (i) transluminally advancing an implant to a heart of a subject while the implant is disposed within a sheath, the implant including (a) an expandable valve frame in a compressed state, (b) a valve member disposed within the valve frame, and (c) a plurality of snares coupled to the valve frame; (ii) subsequently, entirely unsheathing the valve frame and the snares from the sheath; (iii) subsequently (i.e., not instantaneously), extending the snares radially outward from the valve frame while retaining the valve frame in the compressed state; and (iv) subsequently, expanding the valve frame radially outward.

Figure 25H:
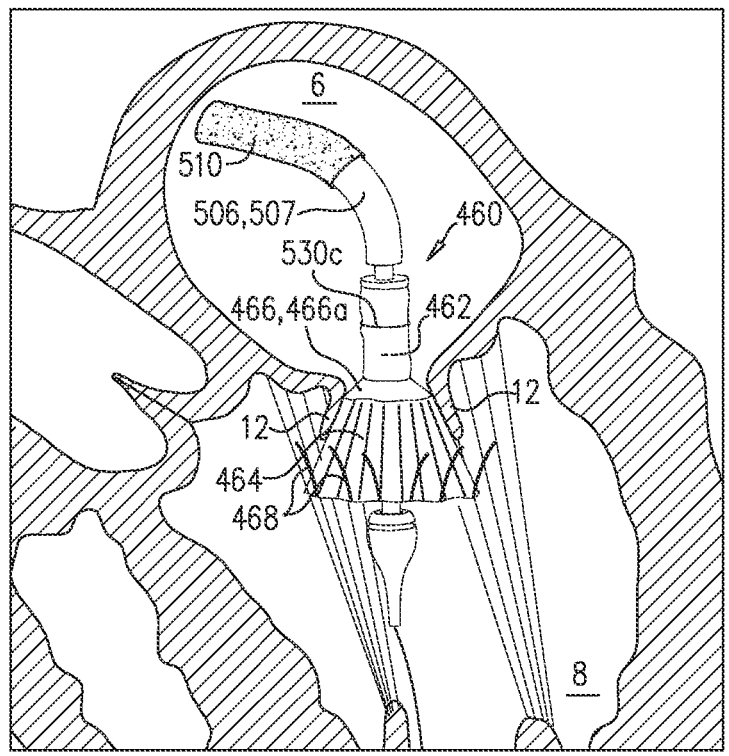

As shown in FIG. 25H, upstream frame 462 continues to be restrained in its compressed state by restraint 530c. For some applications, the dimension of sheet(s) 466 are such that, while frame 462 remains in its compressed state, the upstream frame limits expansion of the upstream portion of frame 464 via tension on the sheet(s). Expansion of the upstream portion of frame 464 is typically limited more than is expansion of a downstream portion of frame 464. Typically, in such a state, frame 464 (e.g., the valve body thereof) and/or sheet(s) 466 are frustoconical. For example, and as shown, sheet 466a may define a first conical frustum, and frame 464 may form a second conical frustum, e.g., with steeper sides than the first conical frustum.

There is therefore provided, in accordance with some applications of the invention, a method, comprising: (i) transluminally advancing an implant to a heart of a subject, the implant including (a) a valve frame at a downstream portion of the implant, (b) a valve member disposed within the valve frame, (c) a flexible sheet, and (d) a support frame at an upstream portion of the implant, coupled to the valve frame via the flexible sheet, wherein the valve frame and the support frame are constrained in respective compressed states during the advancing; and (ii) within the heart, (a) releasing the valve frame such that the valve frame automatically expands from its compressed state, while (b) maintaining the support frame in its compressed state such that the support frame limits expansion of an upstream portion of the valve frame via tension on the sheet.

Figure 25I:
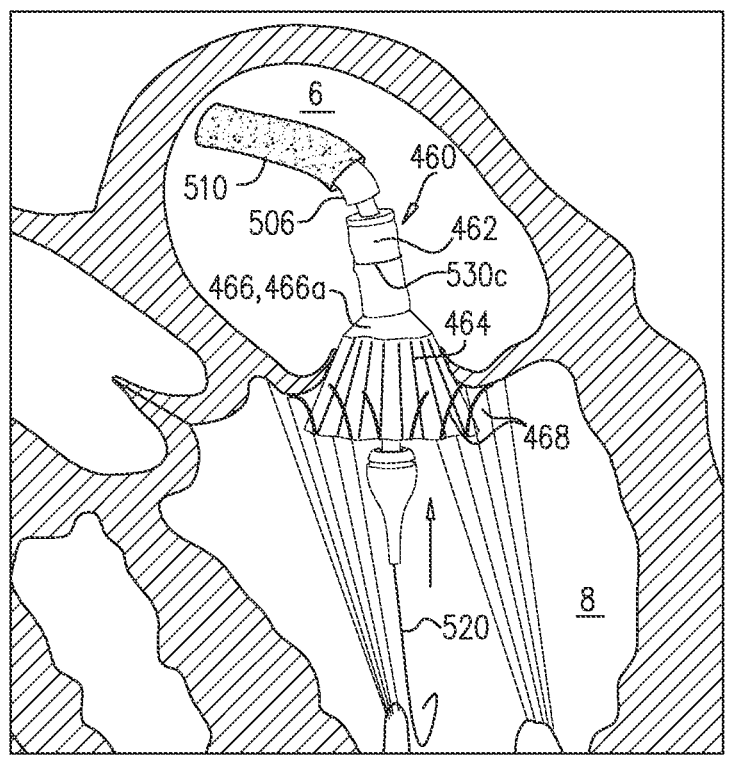

Tissue of the native valve (e.g., leaflet tissue) is engaged using snares 468 by moving implant 460 upstream (e.g., by withdrawing rod 508 into catheter 506) (FIG. 25I). This also moves frame 462 into (or further into) atrium 6. This step is typically performed after the step shown in FIG. 25H, but may alternatively be performed before the step shown in FIG. 25H.

Figure 25J:
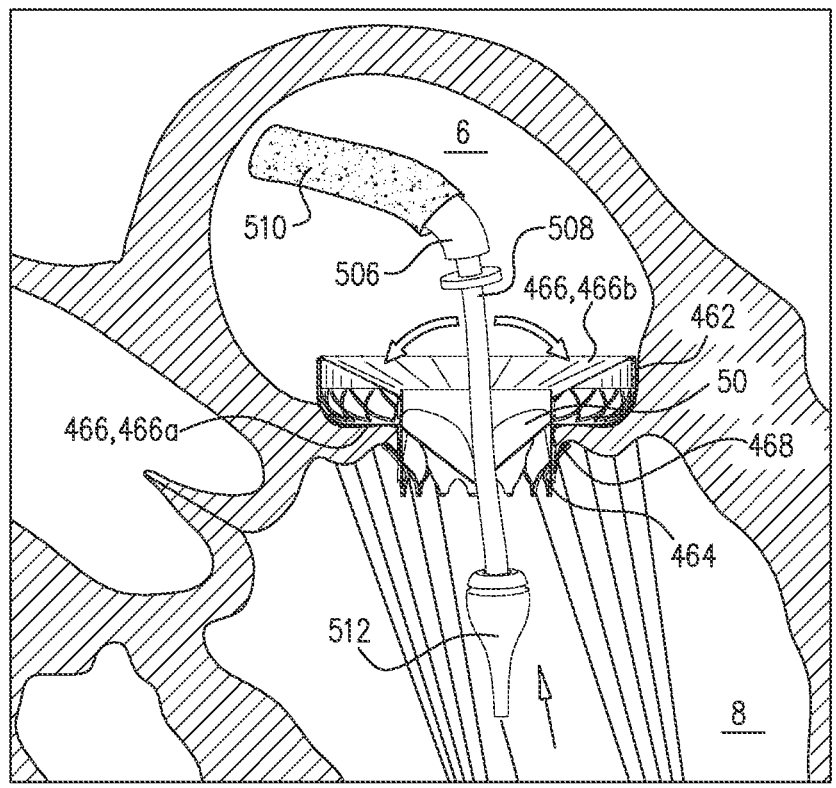

Subsequently, restraint 530*c* is disengaged (e.g., using restraint controller 532*c*), thereby allowing upstream frame 462 to expand toward its expanded state (FIG. 25J). As described hereinabove, the radial expansion of frame 462 pulls sheet(s) 466 radially outward, such that frame 464 is pulled into frame 462, and snares 468 become closer to frame 462. It is to be noted that this description relates to the relative movement between frames 462 and 464, independent of their position with respect to the anatomy. Therefore, although frame 464 may remain stationary with respect to the anatomy while frame 462 expands, the effect on the implant is the same—frame 464 is pulled into frame 462. The movement of snares 468 closer to frame 462 sandwiches tissue of the native valve (e.g., leaflets 12), thereby securing implant 460 at the native valve, e.g., as described hereinabove, mutatis mutandis.

Figure 25K:
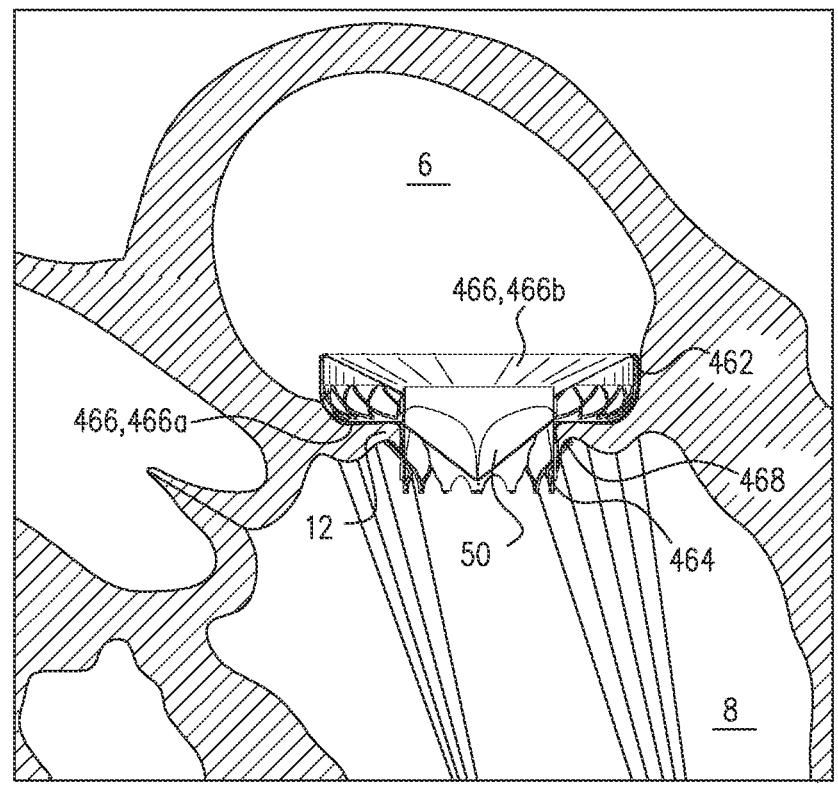

Subsequently, delivery tool 502 is withdrawn from the subject, leaving implant 460 implanted at the native valve, and serving as a prosthetic valve (FIG. 25K).

There is therefore provided, in accordance with some applications of the invention, a method comprising (i) transfemorally advancing to the heart a rod (e.g., rod 508) and an implant (e.g., implant 460) compressed around a distal portion of the rod, the implant including a first frame (e.g., frame 462), a second frame (e.g., frame 464), a valve member (e.g., leaflets 50) disposed within the second frame, and a flexible sheet (e.g., sheet 466*a*) coupling the first frame to the second frame, wherein the first frame and the second frame are in tandem; (ii) subsequently, articulating the second frame with respect to the first frame by bending the distal portion of the rod by operating an extracorporeal controller (e.g., controller 569); and (iii) subsequently, implanting the implant at the valve such that at least part of the first frame is disposed on a first side of the valve and at least part of the second frame is disposed on a second side of the valve.

As described for implant 460, and for other implants, there is also provided, in accordance with some applications of the invention, a method, comprising (i) percutaneously delivering into the body an implant in a compressed state, the implant (a) having a longitudinal axis, and (b) including a first frame, a flexible sheet, and a second frame coupled, via the flexible sheet, to the first frame in tandem along the longitudinal axis; and (ii) subsequently, radially expanding the first frame such that the first frame pulls the second frame longitudinally into the first frame by pulling the sheet radially outward.

There is also provided, in accordance with some applications of the invention, apparatus comprising (i) a first frame having a compressed state in which the frame is transluminally advanceable into the subject, and having a tendency to radially expand from the compressed state toward an expanded state; and (ii) a second frame distinct from the first frame, and coupled to the first frame in tandem with the first frame along a longitudinal axis of the implant, and the coupling of the second frame to the first frame is such that a radially outward force of the first frame during its expansion is converted into a longitudinal force that pulls the second frame into the first frame.

Although transfemoral and transseptal delivery is described, for some applications a retrograde approach (i.e., via the aortic valve) is used, mutatis mutandis. For such applications, as well as other differences, implant 460 is disposed on delivery tool 502 in the inverse orientation (i.e., with frame 464 disposed proximally to frame 462).

It is to be noted that delivery tool 502 may be used to deliver prosthetic heart valves other than implant 460. For some applications, tool 502 is used to deliver a prosthetic valve that, in its delivery state, does not have an articulation zone between two frames. For some applications, tool 502 is used to deliver a prosthetic valve that, in its delivery state, is rigid. For such applications, rod 508 is typically used to orient the compressed prosthetic valve with respect to the native valve.

Reference is again made to FIGS. 8, 13A-C, 14A-C, 20A-C, 22, and 25A-K. It is to be noted that, for some applications, implants described herein are implanted such that at least part of the valve frame (e.g., at least part of the lumen defined by the valve frame) is disposed within the opening defined by the support frame, without placing the valve frame (or at least not the tubular body thereof) in contact with the support frame. For such applications, the valve frame typically does not apply a radially-expansive force to the support frame. For some such applications, the valve frame (e.g., the tubular body thereof) has a diameter that is less than 80 percent as great (e.g., 50-80 percent), such as less than 75 percent (e.g., 50-75 percent, such as 60-75 percent) as the diameter of the opening of the support frame. For some such applications, during delivery, the valve frame and the support frame are arranged collinearly, e.g., with the flexible sheet providing an articulation zone therebetween, e.g., as described with reference to FIG. 17, mutatis mutandis.

Therefore apparatus is provided, in accordance with some applications of the invention, comprising (i) a support frame, having a compressed state, and an expanded state in which the support frame defines an opening therethrough, and is dimensioned to be placed against an upstream surface of the native valve such that the opening is disposed over an orifice defined by the native valve; (ii) a flexible sheet; and (i) a valve frame that (a) has a compressed state, and an expanded state in which the valve frame defines a lumen therethrough, (b) comprises a valve member disposed within the lumen, and (c) is coupled to the support frame via the flexible sheet such that when the support frame is in its expanded state, and the valve frame is in its expanded state, at least part of the lumen is disposed within the opening, and the valve frame is not in contact with the support frame.

Reference is again made to FIGS. 14A-C and 22. As described hereinabove, both implant 260 and implant 460 define a closed toroidal chamber (276, 476), defined by the flexible sheets that couple the frames of the implant. On at least one surface of the chamber the fabric does not contact either of the frames. There is therefore provided, in accordance with some applications of the invention, a percutaneously-implantable implant, comprising (i) a metallic frame; and (ii) a closed chamber (a) having a toroid shape, and (b) defined by a fabric that is at least partially blood-permeable, and is coupled to the metallic frame. The toroid shape is describable as a result of revolving, about an axis, a cross-section of the chamber in which (a) the chamber is delimited by a boundary of the fabric (for both implant 260 and implant 460 the boundary is shown roughly as an irregular quadrilateral), and (b) at least a portion of the boundary does not contact the metallic frame (e.g., the portions where the flexible sheets extend from one of the frames to the other one of the frames). For some applications, at least one position of the revolution, at least part of the boundary contacts the metallic frame (e.g., the part of the boundary where a frame is covered in the fabric that defines the chamber). For some applications, at every position of the revolution, at least part of the boundary contacts the metallic frame.

Reference is again made to FIGS. 1A-25K. Throughout the present application, including the specification and the claims, frames are described as being coupled to each other "by a flexible sheet" or "via a flexible sheet". It is to be noted that, in this context, the coupling is primarily provided by the flexible sheet. That is, the frames are primarily mechanically coupled via the sheet. For example, if other elements were to extend between the two frames, but were to provide minor mechanical coupling (e.g., minor restriction of movement of the frames relative to each other), the frames should still be understood as being coupled by/via the flexible sheet. In contrast, where other elements provide the primary coupling, and a flexible sheet also extends between the two frames (e.g., merely to provide sealed fluid communication), the frames should not be understood as being coupled by/via the flexible sheet.

Reference is again made to FIGS. 1A-25K. Typically, the implants described herein are provided (e.g., in a sealed product container) with their downstream frame/valve frame in its expanded state to increase the shelf-life of the valve member disposed within. Typically, the implants are provided with their upstream frame also in its expanded state. However, for some applications, the implants are provided with their downstream frame in its expanded state, but its upstream frames in its compressed state. For some such applications, a method is provided, for use with an implant that includes a first frame coupled to a second frame, and a valve member disposed within the second frame, the method comprising (i) while the second frame is coupled to the first frame, compressing the second frame into a compressed state for percutaneous advancement into a subject; (ii) without compressing the first frame, percutaneously advancing the implant into the subject; and (iii) expanding the first frame and the second frame inside the subject. For some such applications, a crimping tool is provided with the implant, for compressing the second frame into its compressed state.

For some applications, the apparatus and techniques described herein may be used in combination with apparatus and techniques described in one or more of the following references, which are incorporated herein by reference:

US patent application publication 2013/0172992 to Gross et al.;
U.S. Pat. No. 8,852,272 to Gross et al.;
US patent application publication 2014/0324164 to Gross et al.;
US patent application publication 2014/0257475 to Gross et al.;
US patent application publication 2014/0207231 to HaCohen et al.; and
PCT patent application publication 2014/115149 to Hammer et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with a native valve of a heart of a subject, the native valve being disposed between an atrium and a ventricle of the heart, and having an annulus and leaflets, the method comprising:
   advancing a prosthetic valve to the heart while the prosthetic valve is in a compressed state thereof, the prosthetic valve including a tubular valve body, snares, and an upstream support;
   positioning the prosthetic valve within the heart such that the snares are disposed upstream of the annulus and leaflets, and expanding the snares radially outwardly upstream of the leaflets;
   subsequently, moving the prosthetic valve in a downstream direction such that the snares become disposed downstream of the leaflets; and
   while the snares remain downstream of the leaflets, expanding the upstream support within the atrium and placing the upstream support against an upstream surface of the annulus and expanding the downstream portion of the valve body subsequently to expanding the snares.

2. The method according to claim 1, wherein expanding the snares comprises expanding the snares while a downstream portion of the tubular valve body remains compressed.

3. The method according to claim 2, wherein moving the prosthetic valve in the downstream direction comprises moving the prosthetic valve in the downstream direction while the downstream portion of the tubular valve body remains compressed.

4. The method according to claim 1, wherein expanding the downstream portion of the valve body subsequently to expanding the snares comprises expanding the downstream portion of the valve body subsequently to expanding the upstream support portion within the atrium.

5. The method according to claim 4, wherein expanding the downstream portion of the valve body comprises exposing the downstream portion of the valve body from a sheath such that the downstream portion of the valve body automatically expands.

6. The method according to claim 1, further comprising, subsequently to moving the prosthetic valve in the downstream direction, and prior to expanding the upstream support within the atrium, moving the prosthetic valve back in an upstream direction such that the snares apply an upstream force to the leaflets.

7. The method according to claim 6, wherein moving the prosthetic valve back in the upstream direction comprises placing the snares against the leaflets such that the snares inhibit further movement of the prosthetic valve in the upstream direction through the native valve.

8. The method according to claim 1, wherein expanding the snares comprises expanding the snares such that the snares extend further upstream than the tubular valve body.

9. The method according to claim 1, wherein positioning the prosthetic valve comprises identifying a position of the prosthetic valve within the heart using an imaging technique selected from the group consisting of: ultrasonography and fluoroscopy.

10. The method according to claim 1, wherein expanding the upstream support within the atrium comprises expanding the upstream support while the tubular valve body is disposed between the leaflets.

11. The method according to claim 1, wherein expanding the snares comprises exposing the snares from a sheath such that the snares automatically expand.

12. The method according to claim 1, wherein advancing the prosthetic valve to the heart comprises transapically advancing the prosthetic valve to the heart.

13. The method according to claim 1, wherein advancing the prosthetic valve to the heart comprises transfemorally advancing the prosthetic valve to the heart.

* * * * *